United States Patent
Haq et al.

(10) Patent No.: US 11,852,631 B2
(45) Date of Patent: Dec. 26, 2023

(54) BIOMARKERS PREDICTIVE OF ANTI-IMMUNE CHECKPOINT RESPONSE

(71) Applicant: Dana-Farber Cancer Institute, Inc., Boston, MA (US)

(72) Inventors: Rizwan Haq, Boston, MA (US); Cecile Marie Gstalder, Boston, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 262 days.

(21) Appl. No.: 16/771,802

(22) PCT Filed: Jan. 18, 2019

(86) PCT No.: PCT/US2019/014117
§ 371 (c)(1),
(2) Date: Jun. 11, 2020

(87) PCT Pub. No.: WO2019/143880
PCT Pub. Date: Jul. 25, 2019

(65) Prior Publication Data
US 2021/0072248 A1   Mar. 11, 2021

Related U.S. Application Data

(60) Provisional application No. 62/619,524, filed on Jan. 19, 2018.

(51) Int. Cl.

| | |
|---|---|
| *G01N 33/574* | (2006.01) |
| *A61P 35/04* | (2006.01) |
| *A61K 39/395* | (2006.01) |
| *A61K 45/06* | (2006.01) |
| *C07K 16/28* | (2006.01) |
| *C12N 9/22* | (2006.01) |
| *C12N 15/113* | (2010.01) |
| *G01N 33/50* | (2006.01) |
| *A61K 39/00* | (2006.01) |

(52) U.S. Cl.
CPC ... *G01N 33/57492* (2013.01); *A61K 39/3955* (2013.01); *A61K 45/06* (2013.01); *A61P 35/04* (2018.01); *C07K 16/2818* (2013.01); *C12N 9/22* (2013.01); *C12N 15/113* (2013.01); *G01N 33/5017* (2013.01); *A61K 2039/505* (2013.01); *A61K 2039/507* (2013.01); *A61K 2039/545* (2013.01); *C07K 2317/24* (2013.01); *C07K 2317/76* (2013.01); *C12N 2310/20* (2017.05); *C12N 2800/80* (2013.01)

(58) Field of Classification Search
CPC .............. G01N 33/57492; A61P 35/04; A61K 39/3955; C07K 16/2818
See application file for complete search history.

(56) References Cited

FOREIGN PATENT DOCUMENTS

| WO | WO-2015/116868 A3 | 11/2015 |
|---|---|---|
| WO | WO-2017/103086 A1 | 6/2017 |
| WO | WO-2019/143880 A1 | 7/2019 |

OTHER PUBLICATIONS

Sato et al., MYC is a critical target of FBXW7, Oncotarget, vol. 6, No. 5, p. 3292-3305, Publication Date: Dec. 26, 2014 (Year: 2014).*
Akhoondi et al., "FBXW7/hCDC4 is a general tumor suppressor in human cancer," Cancer Res, 67(19):9006-9012 (2007).
International Search Report for International Application No. PCT/US2019/014117 dated Apr. 8, 2019.
Shin et al., "Primary Resistance to PD-1 Blockade Mediated by JAK1/2 Mutations," Cancer Discov, 7(2):188-201 (2016).
Yumimoto et al., "Fbxw7 suppresses cancer metastasis by inhibiting niche formation," Oncoimmunology, 4(8):1-3 (2015).
Zhao et al., "MAGEA1 interacts with FBXW7 and regulates ubiquitin ligase-mediated turnover of NICD1 in breast and ovarian cancer cells," Oncogene, 36(35):5023-5034 (2017).
Sato et al., "MYC is a critical target of FBXW7", Oncotarget, 6(5): 3292-3305, (2014).
Mlecnik et al., "The tumor microenvironment and immunoscore are critical determinants of dissemination to distant metastasis," Sci. Transl. Med., 8(327):327ra26 (2016).
Shou et al., "P3.07-009 PI3K/mTOR pathway alterations may mediate PD-1/PD-L1 blockade resistance in non-small cell lung cancer," J. Thorac. Oncol. 12(11):S2301 (2017).
Song et al., "E3 ligase FBXW7 is critical for RIG-I stabilization during antiviral responses," Nat. Commun. 8:14654 (2017).
You et al., "Shp-2 tyrosine phosphatase functions as a negative regulator of the interferon-stimulated Jak/STAT Pathway," Mol. Cell. Biol. 19(3):2416-2424 (1999).

* cited by examiner

*Primary Examiner* — Peter J Reddig
*Assistant Examiner* — Cheng Lu
(74) *Attorney, Agent, or Firm* — Foley Hoag LLP

(57) ABSTRACT

The present invention is based in part on the identification of Fbxw7 as a biomarker predictive of responsiveness to anti-immune checkpoint therapies.

6 Claims, 38 Drawing Sheets

Specification includes a Sequence Listing.

● Signature 1: Associated with UV exposure
○ Signature 2: Unknown etiology

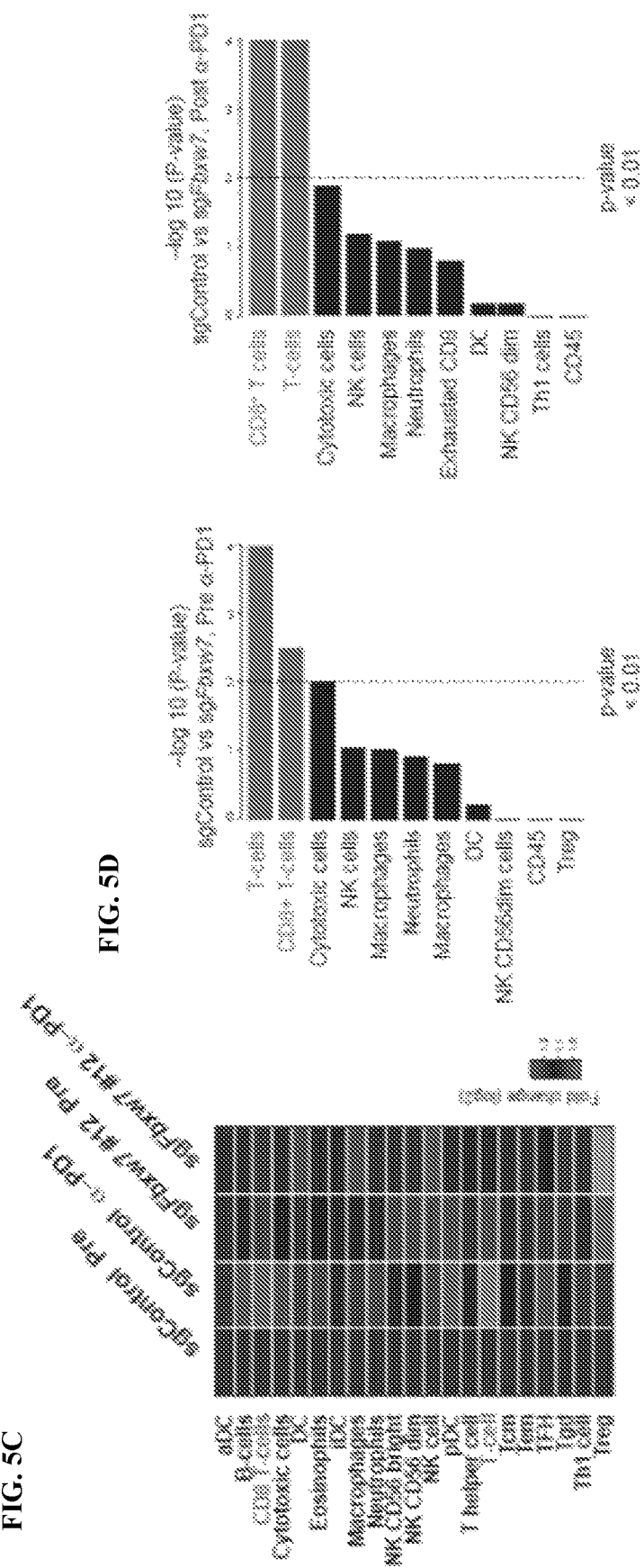

| Hallmark Gene Set | NES | FDR q-val |
|---|---|---|
| MYC_TARGETS_V1 | 3.22 | ~0 |
| E2F_TARGETS | 3.16 | ~0 |
| G2M_CHECKPOINT | 3.05 | ~0 |
| MYC_TARGETS_V2 | 2.47 | ~0 |
| SPERMATOGENESIS | 1.67 | 0.01 |
| MITOTIC_SPINDLE | 1.67 | 0.00 |
| DNA_REPAIR | 1.61 | 0.01 |
| UNFOLDED_PROTEIN_RESPONSE | 1.33 | 0.07 |
| GLYCOLYSIS | 1.25 | 0.11 |
| OXIDATIVE_PHOSPHORYLATION | 0.93 | 0.68 |

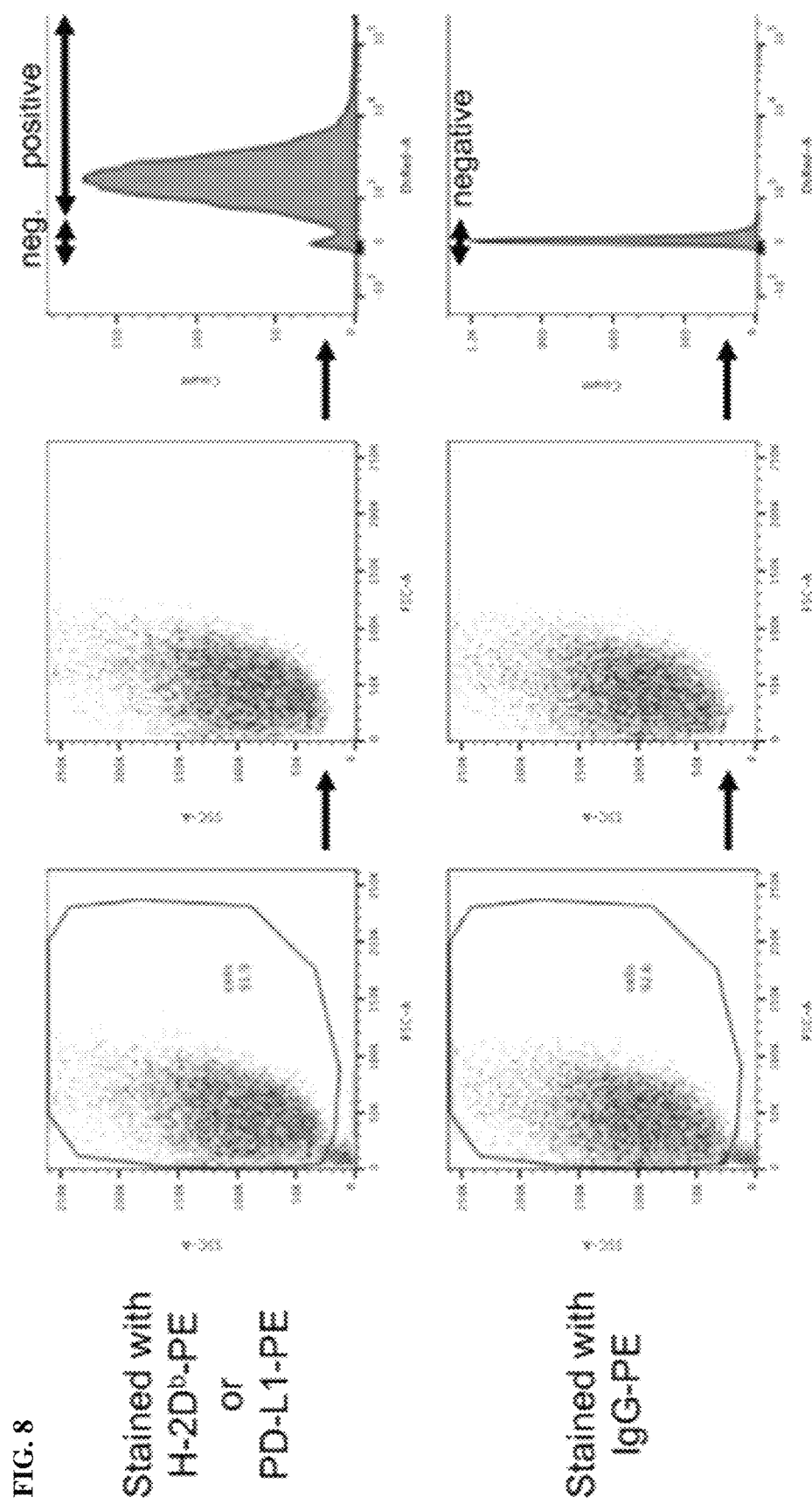

SEQUENCE LISTING

```
<160> NUMBER OF SEQ ID NOS: 23

<210> SEQ ID NO 1
<211> LENGTH: 3927
<212> TYPE: DNA
<213> ORGANISM: Homo sapiens

<400> SEQUENCE: 1
taccgcgccg gagccttccg cagctgccgc ttcagtccga aggaggaagg gaaccaaccc      60
actttctcgg cgccgcggct cttttctaaa agtaatgtga aaacctttgc atcttctgat     120
agtctagcca aggtccaaga agtagcaagc tggcttttgg aaatgaatca ggaactgctc     180
tctgtgggca gcaaaagacg acgaactgga ggctctctga gaggtaaccc ttcctcaagc     240
caggtagatg aagaacagat gaatcgtgtg gtagaggagg aacagcaaca gcaactcaga     300
caacaagagg aggagcacac tgcaaggaat ggtgaagttg ttggagtaga acctagacct     360
ggaggccaaa atgattccca gcaaggacag ttggaagaaa acaataatag atttatttcg     420
gtagatgagg actcctcagg aaaccaagaa gaacaagagg aagatgaaga acatgctggt     480
gaacaagatg aggaggatga ggaggaggag gagatggacc aggagagtga cgattttgat     540
cagtctgatg atagtagcag agaagatgaa catacacata ctaacagtgt cacgaactcc     600
agtagtattg tggacctgcc cgttcaccaa ctctcctccc cattctatac aaaaacaaca     660
aaaatgaaaa gaaagttgga ccatggttct gaggtccgct cttttctttt gggaaagaaa     720
ccatgcaaag tctcagaata tacaagtacc actgggcttg taccatgttc agcaacacca     780
acaacttttg gggacctcag agcagccaat ggccaagggc aacaacgacg ccgaattaca     840
tctgtccagc cacctacagg cctccaggaa tggctaaaaa tgtttcagag ctggagtgga     900
ccagagaaat tgcttgcttt agatgaactc attgatagtt gtgaaccaac acaagtaaaa     960
catatgatgc aagtgataga accccagttt caacgagact tcatttcatt gctccctaaa    1020
```

```
gagttggcac tctatgtgct ttcattcctg gaacccaaag acctgctaca agcagctcag   1080
acatgtcgct actggagaat tttggctgaa gacaaccttc tctggagaga gaaatgcaaa   1140
gaagagggga ttgatgaacc attgcacatc aagagaagaa aagtaataaa accaggtttc   1200
atacacagtc catggaaaag tgcatacatc agacagcaca gaattgatac taactggagg   1260
cgaggagaac tcaaatctcc taaggtgctg aaaggacatg atgatcatgt gatcacatgc   1320
ttacagtttt gtggtaaccg aatagttagt ggttctgatg acaacacttt aaaagtttgg   1380
tcagcagtca caggcaaatg tctgagaaca ttagtgggac atacaggtgg agtatggtca   1440
tcacaaatga gagacaacat catcattagt ggatctacag atcggacact caaagtgtgg   1500
aatgcagaga ctggagaatg tatacacacc ttatatgggc atacttccac tgtgcgttgt   1560
atgcatcttc atgaaaaaag agttgttagc ggttctcgag atgccactct tagggtttgg   1620
gatattgaga caggccagtg tttacatgtt ttgatgggtc atgttgcagc agtccgctgt   1680
gttcaatatg atggcaggag ggttgttagt ggagcatatg atttatggt aaaggtgtgg   1740 gatccagaga ctgaaacctg tctacacacg ttgcagggc atactaatag agtctattca   1800
ttacagtttg atggtatcca tgtggtgagt ggatctcttg atacatcaat ccgtgtttgg   1860
gatgtggaga cagggaattg cattcacacg ttaacagggc accagtcgtt aacaagtgga   1920
atggaactca agacaatat tcttgtctct gggaatgcag attctacagt taaaatctgg   1980
gatatcaaaa caggacagtg tttacaaaca ttgcaaggtc ccaacaagca tcagagtgct   2040
gtgacctgtt tacagttcaa caagaacttt gtaattacca gctcagatga tggaactgta   2100
aaactatggg acttgaaaac gggtgaattt attcgaaacc tagtcacatt ggagagtggg   2160
gggagtgggg gagttgtgtg gcggatcaga gcctcaaaca caaagctggt gtgtgcagtt   2220
gggagtcgga atgggactga agaaaccaag ctgctggtgc tggactttga tgtggacatg   2280
aagtgaagag cagaaaagat gaatttgtcc aattgtgtag acgatatact ccctgccctt   2340 cccctgcaa aagaaaaaa agaaagaaa agaaaaaaa tcccttgttc tcagtggtgc   2400
aggatgttgg cttggggcaa cagattgaaa agacctacag actaagaagg aaaagaagaa   2460
gagatgacaa accataactg acaagagagg cgtctgctgt ctcatcacat aaaaggcttc   2520
acttttgact gagggcagct ttgcaaaatg agactttcta aatcaaacca ggtgcaatta   2580
tttctttatt ttcttctcca gtggtcattg ggcagtgtta atgctgaaac atcattacag   2640
attctgctag cctgttcttt taccactgac agctagacac ctagaaagga actgcaataa   2700
tatcaaaaca agtactggtt gactttctaa ttagagagca tctgcaacaa aaagtcattt   2760
ttctggagtg gaaaagctta aaaaaattac tgtgaattgt ttttgtacag ttatcatgaa   2820 aagcttttt ttttttttt ttgccaacca ttgccaatgt caatcaatca cagtattagc   2880
ctctgttaat ctatttactg ttgcttccat atacattctt caatgcatat gttgctcaaa   2940
ggtggcaagt tgtcctgggt tctgtgagtc ctgagatgga tttaattctt gatgctggtg   3000
ctagaagtag gtcttcaaat atgggattgt tgtcccaacc ctgtactgta ctcccagtgg   3060
ccaaacttat ttatgctgct aaatgaaaga agaaaaaag caaattattt ttttttattt   3120
tttttctgct gtgacgtttt agtcccagac tgaattccaa atttgctcta gtttggttat   3180 ggaaaaaga cttttgcca ctgaaacttg agccatctgt gcctctaaga ggctgagaat   3240
ggaagagttt cagataataa agagtgaagt ttgcctgcaa gtaaagaatt gagagtgtgt   3300
gcaaagctta ttttctttta tctgggcaaa aattaaaaca cattccttgg aacagagcta   3360
```

```
ttacttgcct gttctgtgga gaaacttttc tttttgaggg ctgtggtgaa tggatgaacg    3420
tacatcgtaa aactgacaaa atattttaaa aatatataaa acacaaaatt aaaataaagt    3480
tgctggtcag tcttagtgtt ttacagtatt tgggaaaaca actgttacag ttttattgct    3540
ctgagtaact gacaaagcag aaactattca gtttttgtag taaaggcgtc acatgcaaac    3600
aaacaaaatg aatgaaacag tcaaatggtt tgcctcattc tccaagagcc acaactcaag    3660
ctgaactgtg aaagtggttt aacactgtat cctaggcgat ctttttttcct ccttctgttt    3720 atttttttgt ttgttttatt tatagtctga tttaaaacaa tcagattcaa gttggttaat    3780
tttagttatg taacaacctg acatgatgga ggaaaacaac cttttaaggg attgtgtcta    3840
tggtttgatt cacttagaaa ttttattttc ttataactta agtgcaataa aatgtgtttt    3900
ttcatgttaa aaaaaaaaaa aaaaaaa                                        3927

<210> SEQ ID NO 2
<211> LENGTH: 3751
<212> TYPE: DNA
<213> ORGANISM: Homo sapiens

<400> SEQUENCE: 2
cttacgggtt ccctggagcg gatcaccata taattgatgt gcagtctgca ttgctgaatc      60
ctggactgca ccattctgtg ttcaagggaa gatgtaatct gatccctctg ctgctgaggg     120
aggaatctgt tcagtcaagg ctttgacagg gcatagtctc ctccaataat cttctccgtt     180
ctctctcatt attccctcga gttcttctca gtcaagctgc atgtatgtat gtgtgtcccg     240
agaagcggtt tgatactgag ctgcatttgc ctttactgtg gagttttgtt gccggttctg     300
ctccctaatc ttccttttct gacgtgcctg agcatgtcca cattagaatc tgtgacatac     360
ctacctgaaa aaggtttata ttgtcagaga ctgccaagca gccggacaca cgggggcaca     420
gaatcactga aggggaaaaa tacagaaaat atgggtttct acggcacatt aaaaatgatt     480
ttttacaaaa tgaaagaaa gttggaccat ggttctgagg tccgctcttt ttctttggga     540
aagaaaccat gcaaagtctc agaatataca agtaccactg ggcttgtacc atgttcagca     600
acaccaacaa cttttgggga cctcagcagc gccaatggcc aagggcaaca acgacgccga     660
attacatctg tccagccacc tacaggcctc caggaatggc taaaaatgtt tcagagctgg     720
agtggaccag agaaattgct tgctttagat gaactcattg atagttgtga accaacacaa     780
gtaaaacata tgatgcaagt gatagaaccc cagtttcaac gagacttcat ttcattgctc     840
cctaaagagt tggcactcta tgtgctttca ttcctggaac ccaaagacct gctacaagca     900
gctcagacat gtcgctactg gagaattttg gctgaagaca accttctctg gagagagaaa     960
tgcaaagaag aggggattga tgaaccattg cacatcaaga aagaaaagt aataaaacca    1020 ggtttcatac acagtccatg gaaagtgca tacatcagac agcacagaat tgatactaac    1080
tggaggcgag gagaactcaa atctcctaag gtgctgaaag acatgatga tcatgtgatc    1140 acatgcttac agttttgtgg taaccgaata gttagtggtt ctgatgacaa cactttaaaa    1200
gtttggtcag cagtcacagg caaatgtctg agaacattag tgggacatac aggtggagta    1260
tggtcatcac aaatgagaga caacatcatc attagtggat ctacagatcg gacactcaaa    1320
gtgtggaatg cagagactgg agaatgtata cacaccttat atgggcatac ttccactgtg    1380
cgttgtatgc atcttcatga aaaagagtt gttagcggtt ctcgagatgc cactcttagg    1440
gtttgggata ttgagacagg ccagtgttta catgttttga tgggtcatgt tgcagcagtc    1500
cgctgtgttc aatatgatgg caggagggtt gttagtggag catatgattt tatggtaaag    1560
```

```
gtgtgggatc cagagactga aacctgtcta cacacgttgc aggggcatac taatagagtc    1620
tattcattac agtttgatgg tatccatgtg gtgagtggac ctcttgatac atcaatccgt    1680
gtttgggatg tggagacagg gaattgcatt cacacgttaa cagggcacca gtcgttaaca    1740
agtggaatgg aactcaaaga caatattctt gtctctggga atgcagattc tacagttaaa    1800
atctgggata tcaaaacagg acagtgttta caaacattgc aaggtcccaa caagcatcag    1860
agtgctgtga cctgtttaca gttcaacaag aactttgtaa ttaccagctc agatgatgga    1920
actgtaaaac tatgggactt gaaaacgggt gaatttattc gaaacctagt cacattggag    1980
agtgggggga gtgggggagt tgtgtggcgg atcagagcct caaacacaaa gctggtgtgt    2040
gcagttggga gtcggaatgg gactgaagaa accaagctgc tggtgctgga ctttgatgtg    2100
gacatgaagt gaagagcaga aaagatgaat ttgtccaatt gtgtagacga tatactccct    2160
gcccttcccc ctgcaaaaag aaaaaaagaa aagaaaaaga aaaaatccc ttgttctcag    2220 tggtgcagga tgttgccttg ggcaacaga ttgaaaagac ctacagacta agaaggaaaa    2280
gaagaagaga tgacaaacca taactgacaa gagaggcgtc tgctgtctca tcacataaaa    2340
ggcttcactt ttgactgagg gcagcttttgc aaaatgagac tttctaaatc aaaccaggtg    2400
caattatttc tttatttttct tctccagtgg tcattgggca gtgttaatgc tgaaacatca    2460
ttacagattc tgctagcctg ttcttttacc actgacagct agacacctag aaaggaactg    2520
caataatatc aaaacaagta ctggttgact ttctaattag agagcatctg caacaaaaag    2580
tcatttttct ggagtggaaa agcttaaaaa aattactgtg aattgttttt gtacagttat    2640
catgaaaagc tttttttttt tttttttgc caaccattgc caatgtcaat caatcacagt    2700
attagcctct gttaatctat ttactgttgc ttccatatac attcttcaat gcatatgttg    2760
ctcaaaggtg gcaagttgtc ctgggttctg tgagtcctga gatggattta attcttgatg    2820
ctggtgctag aagtaggtct tcaaatatgg gattgttgtc ccaaccctgt actgtactcc    2880
cagtggccaa acttatttat gctgctaaat gaaagaaaga aaaagcaaa ttattttttt    2940 ttattttttt tctgctgtga cgttttagtc ccagactgaa ttccaaattt gctctagttt    3000
ggttatggaa aaaagacttt ttgccactga aacttgagcc atctgtgcct ctaagaggct    3060
gagaatggaa gagtttcaga ataaaagag tgaagtttgc ctgcaagtaa agaattgaga    3120
gtgtgtgcaa agcttatttt ctttttatctg ggcaaaaatt aaaacacatt ccttggaaca    3180
gagctattac ttgcctgttc tgtggagaaa cttttcttt tgagggctgt ggtgaatgga    3240
tgaacgtaca tcgtaaaact gacaaaatat tttaaaaata tataaaacac aaaattaaaa    3300
taaagttgct ggtcagtctt agtgttttac agtatttggg aaaacaactg ttacagtttt    3360
attgctctga gtaactgaca aagcagaaac tattcagttt ttgtagtaaa ggcgtcacat    3420
gcaaacaaac aaaatgaatg aaacagtcaa atggtttgcc tcattctcca agagccacaa    3480
ctcaagctga actgtgaaag tggtttaaca ctgtatccta ggcgatcttt tttcctcctt    3540
ctgtttattt ttttgtttgt tttatttata gtctgattta aaacaatcag attcaagttg    3600 gttaattttta gttatgtaac aacctgacat gatggaggaa acaacccttt aaagggattg    3660
tgtctatggt ttgattcact tagaaatttt attttcttat aacttaagtg caataaaatg    3720 tgtttttttca tgttaaaaaa aaaaaaaaaa a                                  3751
```

<210> SEQ ID NO 3
<211> LENGTH: 3570
<212> TYPE: DNA

<213> ORGANISM: Homo sapiens

<400> SEQUENCE: 3

| | | | | | |
|---|---|---|---|---|---|
| agacaggtca | ggacatttgg | taggggaagg | ttgaaagaca | aaagcagcag | gccttgggtt | 60 |
| ctcagccttt | taaaaactat | tattaaatat | atattttaa | aatttagtgg | ttagagcttt | 120 |
| tagtaatgtg | cctgtattac | atgtagagag | tattcgtcaa | ccaagaggag | ttttaaaatg | 180 |
| tcaaaaccgg | gaaaacctac | tctaaaccat | ggcttggttc | ctgttgatct | taaaagtgca | 240 |
| aaagagcctc | taccacatca | aactgtgatg | aagatattta | gcattagcat | cattgcccaa | 300 |
| ggcctccctt | tttgtcgaag | acggatgaaa | agaaagttgg | accatggttc | tgaggtccgc | 360 |
| tcttttcctt | tgggaaagaa | accatgcaaa | gtctcagaat | atacaagtac | cactgggctt | 420 |
| gtaccatgtt | cagcaacacc | aacaactttt | ggggacctca | gagcagccaa | tggccaaggg | 480 |
| caacaacgac | gccgaattac | atctgtccag | ccacctacag | gcctccagga | tggctaaaa | 540 |
| atgtttcaga | gctggagtgg | accagagaaa | ttgcttgctt | tagatgaact | cattgatagt | 600 |
| tgtgaaccaa | cacaagtaaa | acatatgatg | caagtgtatag | aaccccagtt | tcaacgagac | 660 |
| ttcatttcat | tgctccctaa | agagttggca | ctctatgtgc | tttcattcct | ggaacccaaa | 720 |
| gacctgctac | aagcagctca | gacatgtcgc | tactggagaa | ttttggctga | agacaacctt | 780 |
| ctctggagag | agaaatgcaa | agaagagggg | attgatgaac | cattgcacat | caagagaaga | 840 |
| aaagtaataa | aaccaggttt | catacacagt | ccatggaaaa | gtgcatacat | cagacagcac | 900 |
| agaattgata | ctaactggag | gcgaggagaa | ctcaaatctc | ctaaggtgct | gaaaggacat | 960 |
| gatgatcatg | tgatcacatg | cttacagttt | tgtggtaacc | gaatagttag | tggttctgat | 1020 |
| gacaacactt | taaagtttg | gtcagcagtc | acaggcaaat | gtctgagaac | attagtggga | 1080 |
| catacaggtg | gagtatggtc | atcacaaatg | agagacaaca | tcatcattag | tggatctaca | 1140 |
| gatcggacac | tcaaagtgtg | gaatgcagag | actggagaat | gtatacacac | cttatatggg | 1200 |
| catacttcca | ctgtgcgttg | tatgcatctt | catgaaaaaa | gagttgttag | cggttctcga | 1260 |
| gatgccactc | ttagggtttg | ggatattgag | acaggccagt | gtttacatgt | tttgatgggt | 1320 |
| catgttgcag | cagtccgctg | tgttcaatat | gatggcagga | gggttgttag | tggagcatat | 1380 |
| gattttatgg | taaaggtgtg | ggatccagag | actgaaacct | gtctacacac | gttgcagggg | 1440 |
| catactaata | gagtctattc | attacagttt | gatggtatcc | atgtggtgag | tggatctctt | 1500 |
| gatacatcaa | tccgtgtttg | ggatgtggag | acagggaatt | gcattcacac | gttaacaggg | 1560 |
| caccagtcgt | taacaagtgg | aatggaactc | aaagacaata | ttcttgtctc | tgggaatgca | 1620 |
| gattctacag | ttaaaatctg | ggatatcaaa | acaggacagt | gtttacaaac | attgcaaggt | 1680 |
| cccaacaagc | atcagagtgc | tgtgacctgt | ttacagttca | acaagaactt | tgtaattacc | 1740 |
| agctcagatg | atggaactgt | aaaactatgg | gacttgaaaa | cgggtgaatt | tattcgaaac | 1800 |
| ctagtcacat | tggagagtgg | ggggagtggg | ggagttgtgt | ggcggatcag | agcctcaaac | 1860 |
| acaaagctgg | tgtgtgcagt | tgggagtcgg | aatgggactg | aagaaaccaa | gctgctggtg | 1920 |
| ctggactttg | atgtggacat | gaagtgaaga | gcagaaaaga | tgaatttgtc | caattgtgta | 1980 |
| gacgatatac | tccctgccct | tccccctgca | aaaagaaaaa | aagaaagaa | aaagaaaaaa | 2040 |
| atcccttgtt | ctcagtggtg | caggatgttg | gcttgggca | acagattgaa | aagacctaca | 2100 |
| gactaagaag | gaaaagaaga | agagatgaca | aaccataact | gacaagagag | gcgtctgctg | 2160 |
| tctcatcaca | taaaaggctt | cacttttgac | tgagggcagc | tttgcaaaat | gagactttct | 2220 |
| aaatcaaacc | aggtgcaatt | atttcttat | tttcttctcc | agtggtcatt | gggcagtgtt | 2280 |

```
aatgctgaaa catcattaca gattctgcta gcctgttctt ttaccactga cagctagaca    2340
cctagaaagg aactgcaata atatcaaaac aagtactggt tgactttcta attagagagc    2400
atctgcaaca aaaagtcatt tttctggagt ggaaaagctt aaaaaaatta ctgtgaattg    2460
tttttgtaca gttatcatga aaagcttttt tttttttttt tttgccaacc attgccaatg    2520
tcaatcaatc acagtattag cctctgttaa tctatttact gttgcttcca tatacattct    2580
tcaatgcata tgttgctcaa aggtggcaag ttgtcctggg ttctgtgagt cctgagatgg    2640
atttaattct tgatgctggt gctagaagta ggtcttcaaa tatgggattg ttgtcccaac    2700
cctgtactgt actcccagtg gccaaactta tttatgctgc taaatgaaag aaagaaaaaa    2760
gcaaattatt ttttttttatt tttttctgc tgtgacgttt tagtcccaga ctgaattcca    2820
aatttgctct agtttggtta tggaaaaaag acttttttgcc actgaaactt gagccatctg    2880
tgcctctaag aggctgagaa tggaagagtt tcagataata aagagtgaag tttgcctgca    2940
agtaaagaat tgagagtgtg tgcaaagctt atttttcttt atctgggcaa aaattaaaac    3000
acattccttg aacagagct attacttgcc tgttctgtgg agaaactttt cttttttgagg    3060 gctgtggtga atggatgaac gtacatcgta aaactgacaa atatttttaa aaatatataa    3120
aacacaaaat taaaataaag ttgctggtca gtcttagtgt tttacagtat ttgggaaaac    3180
aactgttaca gttttattgc tctgagtaac tgacaaagca gaaactattc agttttgta    3240 gtaaaggcgt cacatgcaaa caaacaaaat gaatgaaaca gtcaaatggt ttgcctcatt    3300
ctccaagagc cacaactcaa gctgaactgt gaaagtggtt taacactgta tcctaggcga    3360
tcttttttcc tccttctgtt tatttttttg tttgttttat ttatagtctg atttaaaaca    3420
atcagattca agttggttaa ttttagttat gtaacaacct gacatgatgg aggaaaacaa    3480
cctttaaagg gattgtgtct atggtttgat tcacttagaa attttatttt cttataactt    3540
aagtgcaata aaatgtgttt tttcatgtta                                    3570
```

<210> SEQ ID NO 4
<211> LENGTH: 989
<212> TYPE: DNA
<213> ORGANISM: Homo sapiens

<400> SEQUENCE: 4

```
ggaaacttta caaaaacaaa atccggagtc tcccaaacct gactgtcccg ggagaagtgg      60
ccctggacgg gcagaagccg cagcctgaaa agacccagga agaggaaaag aggagtaccg     120
cgccggagcc ttccgcagct gccgcttcag tccgaaggag gaagggaacc aacccacttt     180
ctcggcgccg cggctctttt ctaaaagtga ttacttcctt aggatagatt gccagaagtg     240
gagttactgg gtcagaggaa tgtgaaaacc tttgcatctt ctgatagtct agccaaggtc     300
caagaagtag caagctggct tttggaaatg aatcaggaac tgctctctgt gggcagcaaa     360
agacgacgaa ctggaggctc tctgagaggt aacccttcct caagccaggt agatgaagaa     420
cagatgaatc gtgtggtaga ggaggaacag caacagcaac tcagacaaca agaggaggag     480
cacactgcaa ggaatggtga agttgttgga gtagaaccta gacctggagg ccaaaatgat     540
tcccagcaag gacagttgga agaaaacaat aatagattta tttcggtaga tgaggactcc     600
tcaggaaacc aagaagaaca agaggaagat gaagaacatg ctggtgaaca agatgaggag     660
gatgaggagg aggaggagat ggaccaggag agtgacgatt tgatcagtc tgatgatagt     720 agcagagaag atgaacatac acatactaac agtgtcacga actccagtag tattgtggac     780
```

| | |
|---|---|
| ctgcccgttc caactctc ctccccattc tatacaaaaa caacaaaagt gagtatattc | 840 |
| aatatattgt taacctgaga aactttacat atctatttta attgtaatga aactttcctc | 900 |
| acagtctttg tattactaaa aattaatctt aagatgtgta ataataaaat gaactagttt | 960 |
| tttgtcttac aaaaaaaaaa aaaaaaaaa | 989 |

<210> SEQ ID NO 5
<211> LENGTH: 4945
<212> TYPE: DNA
<213> ORGANISM: Homo sapiens
<400> SEQUENCE: 5

| | |
|---|---|
| cctctctctg gagtgaggcg agagcccgc acagagcgag ggagacagcg agctgagctc | 60 |
| cgggcgctgc cgctgccgct gccgccgccg ccgccgctga gactgagagc gaaggagcat | 120 |
| ccgagagatc cagtccccct gcactggccg ccgccgagac cttcgctctc acctgggcca | 180 |
| gcgggagccg cggccgcact cctttccccc cctcaccttc ccggccggca gcggcggctg | 240 |
| cacacgccgg agccggagcc agagccggag cccgagcctg agccggagcc ggcggcttgg | 300 |
| ggggcaggga ggcggctacc acgggccggg agtgggtagc tgctccgcgg tgagagaacg | 360 |
| ctgaggaggc gccagagctt ctgcctcgtc ccgtggggcg tggggcgaga cccccaaggt | 420 |
| gtagggaggg gggtcccagc cgcagcgaca catgcgggag ccgggagcgg gggcggcgcc | 480 |
| gagcggagcc ggccgggtcc ctcgccttgc cgccgactcg gccacccgcc cggggccgta | 540 |
| gcatcttgcc ccggagtgta tgaaccgggg ccccaaccaa gctcggcaac cacccccgg | 600 |
| ccggggggc ggggacccccg atgtgaagcg gcggctgggg cggcggagag aacaggaccg | 660 |
| acgccgccgt cctttcctca ccttccccct cccctcagcc cctccgggg gtcttctccc | 720 |
| ttggccagtc gccggccccc cggctccttg gctggactcc gggaggagtt cctagagccc | 780 |
| ccctcccccg ccccagtccc gagggcggcg gggccggggg ggacccgggg ggccggccgc | 840 |
| agcctccacc cagaggaaac tttacaaaaa caaaatccgg agtctcccaa acctgactgt | 900 |
| cccgggagaa gtggccctgg acgggcagaa gccgcagcct gaaaagaccc aggaagagga | 960 |
| aaagaggagt accgcgccgg agccttccgc agctgccgct tcagtccgaa ggaggaaggg | 1020 |
| aaccaaccca ctttctcggc gccgcggctc ttttctaaaa gtgattactt ccttaggata | 1080 |
| gattgccaga agtggagtta ctgggtcaga ggaatgtgaa aacctttgca tcttctgata | 1140 |
| gtctagccaa ggtccaagaa gtagcaagct ggcttttgga aatgaatcag gaactgctct | 1200 |
| ctgtgggcag caaagacga cgaactggag gctctctgag aggtaaccct tcctcaagcc | 1260 |
| aggtagatga agaacagatg aatcgtgtgg tagaggagga acagcaacag caactcagac | 1320 |
| aacaagagga ggagcacact gcaaggaatg gtgaagttgt tggagtagaa cctagacctg | 1380 |
| gaggccaaaa tgattcccag caaggacagt tggaagaaaa caataataga tttatttcgg | 1440 |
| tagatgagga ctcctcagga aaccaagaag aacaagagga agatgaagaa catgctggtg | 1500 |
| aacaagatga ggaggatgag gaggaggagg agatggacca ggagagtgac gattttgatc | 1560 |
| agtctgatga tagtagcaga gaagatgaac atacacatac taacagtgtc acgaactcca | 1620 |
| gtagtattgt ggacctgccc gttcaccaac tctcctcccc attctataca aaacaacaa | 1680 |
| aaatgaaaag aaagttggac catggttctg aggtccgctc tttttctttg ggaaagaaac | 1740 |
| catgcaaagt ctcagaatat acaagtacca ctgggcttgt accatgttca gcaacaccaa | 1800 |
| caactttgg ggaccccaga gcagccaatg gccaagggac acaacgacgc gaattacat | 1860 |
| ctgtccagcc acctacaggc ctccaggaat ggctaaaaat gtttcagagc tggagtggac | 1920 |

-continued

```
cagagaaatt gcttgcttta gatgaactca ttgatagttg tgaaccaaca caagtaaaac   1980
atatgatgca agtgatagaa ccccagtttc aacgagactt catttcattg ctccctaaag   2040
agttggcact ctatgtgctt tcattcctgg aacccaaaga cctgctacaa gcagctcaga   2100
catgtcgcta ctggagaatt ttggctgaag acaaccttct ctggagagag aaatgcaaag   2160 aagagggat tgatgaacca ttgcacatca agagaagaaa agtaataaaa ccaggtttca   2220
tacacagtcc atggaaaagt gcatacatca gacagcacag aattgatact aactggaggc   2280
gaggagaact caaatctcct aaggtgctga aggacatga tgatcatgtg atcacatgct   2340
tacagttttg tggtaaccga atagttagtg gttctgatga caacacttta aaagtttggt   2400
cagcagtcac aggcaaatgt ctgagaacat tagtgggaca tacaggtgga gtatggtcat   2460
cacaaatgag agacaacatc atcattagtg gatcctacaga tcggacactc aaagtgtgga   2520
atgcagagac tggagaatgt atacacacct tatatgggca tacttccact gtgcgttgta   2580
tgcatcttca tgaaaaaaga gttgttagcg gttctcgaga tgccactctt agggtttggg   2640
atattgagac aggccagtgt ttacatgttt tgatgggtca tgttgcagca gtccgctgtg   2700
ttcaatatga tggcaggagg gttgttagtg gagcatatga ttttatggta aaggtgtggg   2760
atccagagac tgaaacctgt ctacacacgt tgcagggca tactaataga gtctattcat   2820
tacagtttga tggtatccat gtggtgagtg gatctcttga tacatcaatc cgtgtttggg   2880
atgtggagac agggaattgc attcacacgt taacagggca ccagtcgtta caagtggaaa   2940
tggaactcaa agacaatatt cttgtctctg ggaatgcaga ttctacagtt aaaatctggg   3000
atatcaaaac aggacagtgt ttacaaacat tgcaaggtcc caacaagcat cagagtgctg   3060
tgacctgttt acagttcaac aagaactttg taattaccag ctcagatgat ggaactgtaa   3120
aactatggga cttgaaaacg ggtgaattta ttcgaaacct agtcacattg gagagtgggg   3180
ggagtggggg agttgtgtgg cggatcagag cctcaaacac aaagctggtg tgtgcagttg   3240
ggagtcggaa tgggactgaa gaaaccaagc tgctggtgct ggactttgat gtggacatga   3300
agtgaagagc agaaaagatg aatttgtcca attgtgtaga cgatatactc cctgcccttc   3360
cccctgcaaa aagaaaaaaa gaaagaaaa agaaaaaaat cccttgttct cagtggtgca   3420
ggatgttggc ttggggcaac agattgaaaa gacctacaga ctaagaagga aaagaagaag   3480
agatgacaaa ccataactga caagagaggc gtctgctgtc tcatcacata aaaggcttca   3540
cttttgactg agggcagctt tgcaaaatga gactttctaa atcaaaccag gtgcaattat   3600
ttctttattt tcttctccag tggtcattgg gcagtgttaa tgctgaaaca tcattacaga   3660
ttctgctagc ctgttctttt accactgaca gctagacacc tagaaaggaa ctgcaataat   3720
atcaaaacaa gtactggttg actttctaat tagagagcat ctgcaacaaa aagtcatttt   3780
tctggagtgg aaaagcttaa aaaaattact gtgaattgtt tttgtacagt tatcatgaaa   3840
agcttttttt tttttttttt tgccaaccat tgccaatgtc aatcaatcac agtattagcc   3900
tctgttaatc tatttactgt tgcttccata tacattcttc aatgcatatg ttgctcaaag   3960
gtggcaagtt gtcctgggtt ctgtgagtcc tgagatggat ttaattcttg atgctggtgc   4020
tagaagtagg tcttcaaata tgggattgtt gtcccaaccc tgtactgtac tcccagtggc   4080
caaacttatt tatgctgcta aatgaaagaa agaaaaaagc aaattatttt tttttatttt   4140
ttttctgctg tgacgtttta gtcccagact gaattccaaa tttgctctag tttggttatg   4200
gaaaaaagac ttttttgccac tgaaacttga gccatctgtg cctctaagag gctgagaatg   4260
```

-continued

```
gaagagtttc agataataaa gagtgaagtt tgcctgcaag taaagaattg agagtgtgtg    4320
caaagcttat tttctttttat ctgggcaaaa attaaaacac attccttgga acagagctat    4380
tacttgcctg ttctgtggag aaacttttct ttttgagggc tgtggtgaat ggatgaacgt    4440
acatcgtaaa actgacaaaa tattttaaaa atatataaaa cacaaaatta aaataaagtt    4500
gctggtcagt cttagtgttt tacagtattt gggaaaacaa ctgttacagt tttattgctc    4560
tgagtaactg acaaagcaga aactattcag ttttgtagt aaaggcgtca catgcaaaca    4620
aacaaaatga atgaaacagt caaatggttt gcctcattct ccaagagcca caactcaagc    4680
tgaactgtga aagtggttta acactgtatc ctaggcgatc ttttttcctc cttctgttta    4740
tttttttgtt tgtttttattt atagtctgat ttaaaacaat cagattcaag ttggttaatt    4800
ttagttatgt aacaacctga catgatggag gaaaacaacc tttaaaggga ttgtgtctat    4860
ggtttgattc acttagaaat tttattttct tataacttaa gtgcaataaa atgtgttttt    4920
tcatgttaaa aaaaaaaaa aaaaa                                            4945
```

<210> SEQ ID NO 6
<211> LENGTH: 707
<212> TYPE: PRT
<213> ORGANISM: Homo sapiens

<400> SEQUENCE: 6

```
Met Asn Gln Glu Leu Leu Ser Val Gly Ser Lys Arg Arg Arg Thr Gly
1               5                   10                  15

Gly Ser Leu Arg Gly Asn Pro Ser Ser Ser Gln Val Asp Glu Glu Gln
            20                  25                  30

Met Asn Arg Val Val Glu Glu Glu Gln Gln Gln Gln Leu Arg Gln Gln
        35                  40                  45

Glu Glu Glu His Thr Ala Arg Asn Gly Glu Val Val Gly Val Glu Pro
    50                  55                  60

Arg Pro Gly Gly Gln Asn Asp Ser Gln Gln Gly Gln Leu Glu Glu Asn
65                  70                  75                  80

Asn Asn Arg Phe Ile Ser Val Asp Glu Asp Ser Ser Gly Asn Gln Glu
                85                  90                  95

Glu Gln Glu Glu Asp Glu Glu His Ala Gly Glu Gln Asp Glu Glu Asp
            100                 105                 110

Glu Glu Glu Glu Met Asp Gln Glu Ser Asp Asp Phe Asp Gln Ser
        115                 120                 125

Asp Asp Ser Ser Arg Glu Asp Glu His Thr His Thr Asn Ser Val Thr
    130                 135                 140

Asn Ser Ser Ser Ile Val Asp Leu Pro Val His Gln Leu Ser Ser Pro
145                 150                 155                 160

Phe Tyr Thr Lys Thr Thr Lys Met Lys Arg Lys Leu Asp His Gly Ser
                165                 170                 175

Glu Val Arg Ser Phe Ser Leu Gly Lys Lys Pro Cys Lys Val Ser Glu
            180                 185                 190

Tyr Thr Ser Thr Thr Gly Leu Val Pro Cys Ser Ala Thr Pro Thr Thr
        195                 200                 205

Phe Gly Asp Leu Arg Ala Ala Asn Gly Gln Gly Gln Gln Arg Arg Arg
    210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255
```

```
Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
            275                 280                 285

Ala Leu Tyr Val Leu Ser Phe Leu Glu Pro Lys Asp Leu Leu Gln Ala
            290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                325                 330                 335

Lys Arg Arg Lys Val Ile Lys Pro Gly Phe Ile His Ser Pro Trp Lys
            340                 345                 350

Ser Ala Tyr Ile Arg Gln His Arg Ile Asp Thr Asn Trp Arg Arg Gly
            355                 360                 365

Glu Leu Lys Ser Pro Lys Val Leu Lys Gly His Asp Asp His Val Ile
            370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
            435                 440                 445

Glu Thr Gly Glu Cys Ile His Thr Leu Tyr Gly His Thr Ser Thr Val
            450                 455                 460

Arg Cys Met His Leu His Glu Lys Arg Val Val Ser Gly Ser Arg Asp
465                 470                 475                 480

Ala Thr Leu Arg Val Trp Asp Ile Glu Thr Gly Gln Cys Leu His Val
                485                 490                 495

Leu Met Gly His Val Ala Ala Val Arg Cys Val Gln Tyr Asp Gly Arg
            500                 505                 510

Arg Val Val Ser Gly Ala Tyr Asp Phe Met Val Lys Val Trp Asp Pro
            515                 520                 525

Glu Thr Glu Thr Cys Leu His Thr Leu Gln Gly His Thr Asn Arg Val
            530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
                565                 570                 575

Leu Thr Gly His Gln Ser Leu Thr Ser Gly Met Glu Leu Lys Asp Asn
            580                 585                 590

Ile Leu Val Ser Gly Asn Ala Asp Ser Thr Val Lys Ile Trp Asp Ile
            595                 600                 605

Lys Thr Gly Gln Cys Leu Gln Thr Leu Gln Gly Pro Asn Lys His Gln
            610                 615                 620

Ser Ala Val Thr Cys Leu Gln Phe Asn Lys Asn Phe Val Ile Thr Ser
625                 630                 635                 640

Ser Asp Asp Gly Thr Val Lys Leu Trp Asp Leu Lys Thr Gly Glu Phe
                645                 650                 655

Ile Arg Asn Leu Val Thr Leu Glu Ser Gly Gly Ser Gly Gly Val Val
            660                 665                 670
```

Trp Arg Ile Arg Ala Ser Asn Thr Lys Leu Val Cys Ala Val Gly Ser
            675                 680                 685

Arg Asn Gly Thr Glu Glu Thr Lys Leu Leu Val Leu Asp Phe Asp Val
690                 695                 700

Asp Met Lys
705

<210> SEQ ID NO 7
<211> LENGTH: 627
<212> TYPE: PRT
<213> ORGANISM: Homo sapiens

<400> SEQUENCE: 7

Met Cys Val Pro Arg Ser Gly Leu Ile Leu Ser Cys Ile Cys Leu Tyr
1               5                   10                  15

Cys Gly Val Leu Leu Pro Val Leu Leu Pro Asn Leu Pro Phe Leu Thr
            20                  25                  30

Cys Leu Ser Met Ser Thr Leu Glu Ser Val Thr Tyr Leu Pro Glu Lys
        35                  40                  45

Gly Leu Tyr Cys Gln Arg Leu Pro Ser Ser Arg Thr His Gly Gly Thr
    50                  55                  60

Glu Ser Leu Lys Gly Lys Asn Thr Glu Asn Met Gly Phe Tyr Gly Thr
65                  70                  75                  80

Leu Lys Met Ile Phe Tyr Lys Met Lys Arg Lys Leu Asp His Gly Ser
                85                  90                  95

Glu Val Arg Ser Phe Ser Leu Gly Lys Lys Pro Cys Lys Val Ser Glu
            100                 105                 110

Tyr Thr Ser Thr Thr Gly Leu Val Pro Cys Ser Ala Thr Pro Thr Thr
        115                 120                 125

Phe Gly Asp Leu Arg Ala Ala Asn Gly Gln Gly Gln Gln Arg Arg Arg
    130                 135                 140

Ile Thr Ser Val Gln Pro Pro Thr Gly Leu Gln Glu Trp Leu Lys Met
145                 150                 155                 160

Phe Gln Ser Trp Ser Gly Pro Glu Lys Leu Leu Ala Leu Asp Glu Leu
                165                 170                 175

Ile Asp Ser Cys Glu Pro Thr Gln Val Lys His Met Met Gln Val Ile
            180                 185                 190

Glu Pro Gln Phe Gln Arg Asp Phe Ile Ser Leu Leu Pro Lys Glu Leu
        195                 200                 205

Ala Leu Tyr Val Leu Ser Phe Leu Glu Pro Lys Asp Leu Leu Gln Ala
    210                 215                 220

Ala Gln Thr Cys Arg Tyr Trp Arg Ile Leu Ala Glu Asp Asn Leu Leu
225                 230                 235                 240

Trp Arg Glu Lys Cys Lys Glu Glu Gly Ile Asp Glu Pro Leu His Ile
                245                 250                 255

Lys Arg Arg Lys Val Ile Lys Pro Gly Phe Ile His Ser Pro Trp Lys
            260                 265                 270

Ser Ala Tyr Ile Arg Gln His Arg Ile Asp Thr Asn Trp Arg Arg Gly
        275                 280                 285

Glu Leu Lys Ser Pro Lys Val Leu Lys Gly His Asp Asp His Val Ile
    290                 295                 300

Thr Cys Leu Gln Phe Cys Gly Asn Arg Ile Val Ser Gly Ser Asp Asp
305                 310                 315                 320

Asn Thr Leu Lys Val Trp Ser Ala Val Thr Gly Lys Cys Leu Arg Thr
                325                 330                 335

Leu Val Gly His Thr Gly Gly Val Trp Ser Ser Gln Met Arg Asp Asn
                340                 345                 350

Ile Ile Ile Ser Gly Ser Thr Asp Arg Thr Leu Lys Val Trp Asn Ala
            355                 360                 365

Glu Thr Gly Glu Cys Ile His Thr Leu Tyr Gly His Thr Ser Thr Val
        370                 375                 380

Arg Cys Met His Leu His Glu Lys Arg Val Ser Gly Ser Arg Asp
385                 390                 395                 400

Ala Thr Leu Arg Val Trp Asp Ile Glu Thr Gly Gln Cys Leu His Val
                405                 410                 415

Leu Met Gly His Val Ala Ala Val Arg Cys Val Gln Tyr Asp Gly Arg
            420                 425                 430

Arg Val Val Ser Gly Ala Tyr Asp Phe Met Val Lys Val Trp Asp Pro
        435                 440                 445

Glu Thr Glu Thr Cys Leu His Thr Leu Gln Gly His Thr Asn Arg Val
    450                 455                 460

Tyr Ser Leu Gln Phe Asp Gly Ile His Val Val Ser Gly Ser Leu Asp
465                 470                 475                 480

Thr Ser Ile Arg Val Trp Asp Val Glu Thr Gly Asn Cys Ile His Thr
                485                 490                 495

Leu Thr Gly His Gln Ser Leu Thr Ser Gly Met Glu Leu Lys Asp Asn
            500                 505                 510

Ile Leu Val Ser Gly Asn Ala Asp Ser Thr Val Lys Ile Trp Asp Ile
        515                 520                 525

Lys Thr Gly Gln Cys Leu Gln Thr Leu Gln Gly Pro Asn Lys His Gln
    530                 535                 540

Ser Ala Val Thr Cys Leu Gln Phe Asn Lys Asn Phe Val Ile Thr Ser
545                 550                 555                 560

Ser Asp Asp Gly Thr Val Lys Leu Trp Asp Leu Lys Thr Gly Glu Phe
                565                 570                 575

Ile Arg Asn Leu Val Thr Leu Glu Ser Gly Gly Ser Gly Gly Val Val
            580                 585                 590

Trp Arg Ile Arg Ala Ser Asn Thr Lys Leu Val Cys Ala Val Gly Ser
        595                 600                 605

Arg Asn Gly Thr Glu Glu Thr Lys Leu Leu Val Leu Asp Phe Asp Val
    610                 615                 620

Asp Met Lys
625

<210> SEQ ID NO 8
<211> LENGTH: 589
<212> TYPE: PRT
<213> ORGANISM: Homo sapiens

<400> SEQUENCE: 8

Met Ser Lys Pro Gly Lys Pro Thr Leu Asn His Gly Leu Val Pro Val
1               5                   10                  15

Asp Leu Lys Ser Ala Lys Glu Pro Leu Pro His Gln Thr Val Met Lys
            20                  25                  30

Ile Phe Ser Ile Ser Ile Ile Ala Gln Gly Leu Pro Phe Cys Arg Arg
        35                  40                  45

Arg Met Lys Arg Lys Leu Asp His Gly Ser Glu Val Arg Ser Phe Ser
    50                  55                  60

Leu Gly Lys Lys Pro Cys Lys Val Ser Glu Tyr Thr Ser Thr Thr Gly

-continued

```
                65                  70                  75                  80
Leu Val Pro Cys Ser Ala Thr Pro Thr Thr Phe Gly Asp Leu Arg Ala
                    85                  90                  95
Ala Asn Gly Gln Gly Gln Gln Arg Arg Arg Ile Thr Ser Val Gln Pro
                100                 105                 110
Pro Thr Gly Leu Gln Glu Trp Leu Lys Met Phe Gln Ser Trp Ser Gly
                115                 120                 125
Pro Glu Lys Leu Leu Ala Leu Asp Glu Leu Ile Asp Ser Cys Glu Pro
            130                 135                 140
Thr Gln Val Lys His Met Met Gln Val Ile Glu Pro Gln Phe Gln Arg
145                 150                 155                 160
Asp Phe Ile Ser Leu Leu Pro Lys Glu Leu Ala Leu Tyr Val Leu Ser
                165                 170                 175
Phe Leu Glu Pro Lys Asp Leu Leu Gln Ala Ala Gln Thr Cys Arg Tyr
                180                 185                 190
Trp Arg Ile Leu Ala Glu Asp Asn Leu Leu Trp Arg Glu Lys Cys Lys
            195                 200                 205
Glu Glu Gly Ile Asp Glu Pro Leu His Ile Lys Arg Arg Lys Val Ile
        210                 215                 220
Lys Pro Gly Phe Ile His Ser Pro Trp Lys Ser Ala Tyr Ile Arg Gln
225                 230                 235                 240
His Arg Ile Asp Thr Asn Trp Arg Arg Gly Glu Leu Lys Ser Pro Lys
                245                 250                 255
Val Leu Lys Gly His Asp Asp His Val Ile Thr Cys Leu Gln Phe Cys
                260                 265                 270
Gly Asn Arg Ile Val Ser Gly Ser Asp Asp Asn Thr Leu Lys Val Trp
            275                 280                 285
Ser Ala Val Thr Gly Lys Cys Leu Arg Thr Leu Val Gly His Thr Gly
        290                 295                 300
Gly Val Trp Ser Ser Gln Met Arg Asp Asn Ile Ile Ile Ser Gly Ser
305                 310                 315                 320
Thr Asp Arg Thr Leu Lys Val Trp Asn Ala Glu Thr Gly Glu Cys Ile
                325                 330                 335
His Thr Leu Tyr Gly His Thr Ser Thr Val Arg Cys Met His Leu His
                340                 345                 350
Glu Lys Arg Val Val Ser Gly Ser Arg Asp Ala Thr Leu Arg Val Trp
            355                 360                 365
Asp Ile Glu Thr Gly Gln Cys Leu His Val Leu Met Gly His Val Ala
        370                 375                 380
Ala Val Arg Cys Val Gln Tyr Asp Gly Arg Arg Val Val Ser Gly Ala
385                 390                 395                 400
Tyr Asp Phe Met Val Lys Val Trp Asp Pro Glu Thr Glu Thr Cys Leu
                405                 410                 415
His Thr Leu Gln Gly His Thr Asn Arg Val Tyr Ser Leu Gln Phe Asp
                420                 425                 430
Gly Ile His Val Val Ser Gly Ser Leu Asp Thr Ser Ile Arg Val Trp
            435                 440                 445
Asp Val Glu Thr Gly Asn Cys Ile His Thr Leu Thr Gly His Gln Ser
        450                 455                 460
Leu Thr Ser Gly Met Glu Leu Lys Asp Asn Ile Leu Val Ser Gly Asn
465                 470                 475                 480
Ala Asp Ser Thr Val Lys Ile Trp Asp Ile Lys Thr Gly Gln Cys Leu
                485                 490                 495
```

```
Gln Thr Leu Gln Gly Pro Asn Lys His Gln Ser Ala Val Thr Cys Leu
            500                 505                 510
Gln Phe Asn Lys Asn Phe Val Ile Thr Ser Ser Asp Gly Thr Val
        515                 520                 525
Lys Leu Trp Asp Leu Lys Thr Gly Glu Phe Ile Arg Asn Leu Val Thr
530                 535                 540
Leu Glu Ser Gly Gly Ser Gly Gly Val Val Trp Arg Ile Arg Ala Ser
545                 550                 555                 560
Asn Thr Lys Leu Val Cys Ala Val Gly Ser Arg Asn Gly Thr Glu Glu
                565                 570                 575
Thr Lys Leu Leu Val Leu Asp Phe Asp Val Asp Met Lys
            580                 585
```

<210> SEQ ID NO 9
<211> LENGTH: 176
<212> TYPE: PRT
<213> ORGANISM: Homo sapiens

<400> SEQUENCE: 9

```
Met Asn Gln Glu Leu Leu Ser Val Gly Ser Lys Arg Arg Arg Thr Gly
1               5                   10                  15
Gly Ser Leu Arg Gly Asn Pro Ser Ser Ser Gln Val Asp Glu Glu Gln
                20                  25                  30
Met Asn Arg Val Val Glu Glu Gln Gln Gln Gln Leu Arg Gln Gln
            35                  40                  45
Glu Glu Glu His Thr Ala Arg Asn Gly Glu Val Val Gly Val Glu Pro
    50                  55                  60
Arg Pro Gly Gly Gln Asn Asp Ser Gln Gln Gly Gln Leu Glu Glu Asn
65                  70                  75                  80
Asn Asn Arg Phe Ile Ser Val Asp Glu Asp Ser Ser Gly Asn Gln Glu
                85                  90                  95
Glu Gln Glu Glu Asp Glu Glu His Ala Gly Gln Glu Glu Asp
            100                 105                 110
Glu Glu Glu Glu Met Asp Gln Glu Ser Asp Asp Phe Asp Gln Ser
        115                 120                 125
Asp Asp Ser Ser Arg Glu Asp Glu His Thr His Thr Asn Ser Val Thr
130                 135                 140
Asn Ser Ser Ser Ile Val Asp Leu Pro Val His Gln Leu Ser Ser Pro
145                 150                 155                 160
Phe Tyr Thr Lys Thr Thr Lys Val Ser Ile Phe Asn Ile Leu Leu Thr
                165                 170                 175
```

<210> SEQ ID NO 10
<211> LENGTH: 707
<212> TYPE: PRT
<213> ORGANISM: Homo sapiens

<400> SEQUENCE: 10

```
Met Asn Gln Glu Leu Leu Ser Val Gly Ser Lys Arg Arg Arg Thr Gly
1               5                   10                  15
Gly Ser Leu Arg Gly Asn Pro Ser Ser Ser Gln Val Asp Glu Glu Gln
                20                  25                  30
Met Asn Arg Val Val Glu Glu Glu Gln Gln Gln Gln Leu Arg Gln Gln
            35                  40                  45
Glu Glu Glu His Thr Ala Arg Asn Gly Glu Val Val Gly Val Glu Pro
    50                  55                  60
```

```
Arg Pro Gly Gly Gln Asn Asp Ser Gln Gln Gly Gln Leu Glu Glu Asn
 65                  70                  75                  80

Asn Asn Arg Phe Ile Ser Val Asp Glu Asp Ser Ser Gly Asn Gln Glu
                 85                  90                  95

Glu Gln Glu Glu Asp Glu Glu His Ala Gly Glu Gln Asp Glu Glu Asp
            100                 105                 110

Glu Glu Glu Glu Glu Met Asp Gln Glu Ser Asp Asp Phe Asp Gln Ser
        115                 120                 125

Asp Asp Ser Ser Arg Glu Asp Glu His Thr His Thr Asn Ser Val Thr
130                 135                 140

Asn Ser Ser Ser Ile Val Asp Leu Pro Val His Gln Leu Ser Ser Pro
145                 150                 155                 160

Phe Tyr Thr Lys Thr Thr Lys Met Lys Arg Lys Leu Asp His Gly Ser
                165                 170                 175

Glu Val Arg Ser Phe Ser Leu Gly Lys Lys Pro Cys Lys Val Ser Glu
            180                 185                 190

Tyr Thr Ser Thr Thr Gly Leu Val Pro Cys Ser Ala Thr Pro Thr Thr
        195                 200                 205

Phe Gly Asp Leu Arg Ala Ala Asn Gly Gln Gly Gln Gln Arg Arg Arg
210                 215                 220

Ile Thr Ser Val Gln Pro Pro Thr Gly Leu Gln Glu Trp Leu Lys Met
225                 230                 235                 240

Phe Gln Ser Trp Ser Gly Pro Glu Lys Leu Leu Ala Leu Asp Glu Leu
                245                 250                 255

Ile Asp Ser Cys Glu Pro Thr Gln Val Lys His Met Met Gln Val Ile
            260                 265                 270

Glu Pro Gln Phe Gln Arg Asp Phe Ile Ser Leu Leu Pro Lys Glu Leu
        275                 280                 285

Ala Leu Tyr Val Leu Ser Phe Leu Glu Pro Lys Asp Leu Leu Gln Ala
290                 295                 300

Ala Gln Thr Cys Arg Tyr Trp Arg Ile Leu Ala Glu Asp Asn Leu Leu
305                 310                 315                 320

Trp Arg Glu Lys Cys Lys Glu Glu Gly Ile Asp Glu Pro Leu His Ile
                325                 330                 335

Lys Arg Arg Lys Val Ile Lys Pro Gly Phe Ile His Ser Pro Trp Lys
            340                 345                 350

Ser Ala Tyr Ile Arg Gln His Arg Ile Asp Thr Asn Trp Arg Arg Gly
        355                 360                 365

Glu Leu Lys Ser Pro Lys Val Leu Lys Gly His Asp Asp His Val Ile
370                 375                 380

Thr Cys Leu Gln Phe Cys Gly Asn Arg Ile Val Ser Gly Ser Asp Asp
385                 390                 395                 400

Asn Thr Leu Lys Val Trp Ser Ala Val Thr Gly Lys Cys Leu Arg Thr
                405                 410                 415

Leu Val Gly His Thr Gly Gly Val Trp Ser Ser Gln Met Arg Asp Asn
            420                 425                 430

Ile Ile Ile Ser Gly Ser Thr Asp Arg Thr Leu Lys Val Trp Asn Ala
        435                 440                 445

Glu Thr Gly Glu Cys Ile His Thr Leu Tyr Gly His Thr Ser Thr Val
450                 455                 460

Arg Cys Met His Leu His Glu Lys Arg Val Val Ser Gly Ser Arg Asp
465                 470                 475                 480
```

```
Ala Thr Leu Arg Val Trp Asp Ile Glu Thr Gly Gln Cys Leu His Val
                485                 490                 495

Leu Met Gly His Val Ala Ala Val Arg Cys Val Gln Tyr Asp Gly Arg
            500                 505                 510

Arg Val Val Ser Gly Ala Tyr Asp Phe Met Val Lys Val Trp Asp Pro
            515                 520                 525

Glu Thr Glu Thr Cys Leu His Thr Leu Gln Gly His Thr Asn Arg Val
            530                 535                 540

Tyr Ser Leu Gln Phe Asp Gly Ile His Val Val Ser Gly Ser Leu Asp
545                 550                 555                 560

Thr Ser Ile Arg Val Trp Asp Val Glu Thr Gly Asn Cys Ile His Thr
                565                 570                 575

Leu Thr Gly His Gln Ser Leu Thr Ser Gly Met Glu Leu Lys Asp Asn
            580                 585                 590

Ile Leu Val Ser Gly Asn Ala Asp Ser Thr Val Lys Ile Trp Asp Ile
            595                 600                 605

Lys Thr Gly Gln Cys Leu Gln Thr Leu Gln Gly Pro Asn Lys His Gln
            610                 615                 620

Ser Ala Val Thr Cys Leu Gln Phe Asn Lys Asn Phe Val Ile Thr Ser
625                 630                 635                 640

Ser Asp Asp Gly Thr Val Lys Leu Trp Asp Leu Lys Thr Gly Glu Phe
                645                 650                 655

Ile Arg Asn Leu Val Thr Leu Glu Ser Gly Ser Gly Ser Gly Val Val
            660                 665                 670

Trp Arg Ile Arg Ala Ser Asn Thr Lys Leu Val Cys Ala Val Gly Ser
            675                 680                 685

Arg Asn Gly Thr Glu Glu Thr Lys Leu Leu Val Leu Asp Phe Asp Val
            690                 695                 700

Asp Met Lys
705

<210> SEQ ID NO 11
<211> LENGTH: 4092
<212> TYPE: DNA
<213> ORGANISM: Mus musculus

<400> SEQUENCE: 11
atttcttctc tttatatctt ttgtgatccc tctacacatt gtgtctagac aatcagtttg      60
aattagtgct tggatttttg cctagacaaa aggagtaact tggaatgaag aaaatggact     120
caaacttaaa gagctgcaca ctaatcaatc cttcgaacgc acatggaaac cagagaccac     180
ccctactgtc ctcttagtta cacaagtggc tgagaatgtg aaaacctttg catcttctga     240
tagtctagcc aaggtccaag aagtagcaag ctggcttttg gaaatgaatc aggaactgct     300
ctctgtgggc agcaaaagac gacgaactgg aggctctctg agagggaatg cttcctcaag     360
ccaggttgat gagggacaga tgaatcgcgt ggttgaggag gatccacagc agcaagcgag     420
acatcaagag gaggagcaca ctgcgcggaa tggtgaactt gtgggtgcaa accctaggcc     480
tggagaccag aacgataccc agcaaggaca agtggaggaa ataataaacc gctttatttc     540
agtagatgag gactcttcgg gaaatcagga agagcaagag gaagatgaag agcatgctgg     600
ggaacaggag gaggaagagg aggaagagga agaggaggag gagatggacc aggagagtga     660
tgattttgat ccgtctgatg acagtagcag agaagatgaa catacgcaca atagcaatgt     720
cacaaactgc agtagtgtct cggacctgcc cgctcaccag ctctcctctc cattctatac     780
```

```
aaagacaaca aaaatgaaaa gaaagttgga ccatggttct gaagttcgtt ccttttcttt    840
gggaaagaaa ccatgcaaag tctcagatta taccagtacc actggccttg taccatgttc    900
agcaacacca acaacttttg gggacctgag agcagccaat gggcaagggc agcagcggcg    960
gaggattaca tctgtccaac cacccacagg ccttcaagag tggctgaaaa tgtttcagag   1020
ctggagcgga ccagagaagt tgctggcttt agatgagctc attgacagct gtgaaccaac   1080
acaagtgaag catatgatgc aagtgataga gccccagttc cagcgagact tcatctcctt   1140
gcttcctaaa gagttggcac tctatgtgct ttcattcctg gaacccaaag acctgctgca   1200
agcggctcag acttgtcgat actggagaat tttggctgag gataaccttc tctggagaga   1260
gaaatgtaaa gaagagggga ttgatgaacc gttgcacatc aagagaagaa aaataataaa   1320
accaggtttc atacacagcc catggaagag tgcgtatatc agacagcaca gaattgatac   1380
aaactggaga cgaggagaac tcaaatctcc taaggtgctg aaagggcatg atgaccatgt   1440
gatcacatgc ctacagtttt gtggcaaccg catagttagt ggttctgatg acaacacttt   1500
aaaagtttgg tcagcggtca cgggcaagtg tctgagaacg ttagtgggac atacaggtgg   1560
agtgtggtca tcacagatga gagacaatat catcatcagt ggatcgactg accggactct   1620
caaagtgtgg aatgctgaaa ctggagagtg tatacatact ttatatgggc acacttctac   1680
tgtacggtgt atgcatctcc atgaaaaaag ggttgtaagc ggttctcgag atgccactct   1740 cagggttttgg gatattgaga ccggccagtg tttacacgtc ctgatgggtc acgtagcagc   1800
ggtccgctgc gttcagtatg atggcaggag ggttgttagt ggagcttatg attttatggt   1860
gaaggtgtgg gatccagaga ctgagacctg tctacacacg ttacagggac acactaatag   1920
agtctattca ttacagtttg atggcatcca tgtggtgagt ggatctcttg atacatcaat   1980
ccgagtctgg gatgtggaga cagggaattg tattcacacg ctaacaggac accagtcatt   2040
aacgagtgga atggaactca agacaatat tcttgtctct gggaatgcag attctacagt   2100
taagatctgg gatatcaaaa caggacagtg tttacaaact ttgcaaggtc ccagcaagca   2160
tcagagcgct gtgacctgct tacagttcaa caagaacttc gtaattacca gctcagacga   2220
cggaacggtc aaactctggg acttgaaaac gggtgaattt atccgaaacc tcgtcacatt   2280
ggagagtggg gggagcgggg gagttgtgtg gcggatcagg gcctcaaaca caaagctggt   2340
gtgtgcagtc gggagtcgga atggaactga ggaaaccaag ctcctggtgc tggactttga   2400
tgtggacatg aaatgaaaag cagacatgat gaattttgtc caactgtgta gacaatatac   2460
tccctaccct tccccctgcg caaaaaacaa aacaaacaa acaaaaaaat gaaaaaaaaa   2520
aacagaaaaa aaaaagaga aaaagaaaa ggaaaaaaat cccttgtact cagtggtgca   2580
ggatgttggc ttgggacaac agactgaaaa gacctacaga ctaagaaggc aagaagagac   2640
aagagaccgt aactgacagg aggcggcagc tgtcgcatct cgcaaaggcc tcacttgtga   2700 ctgagggggca gcttggcaag acgactctct aaatccaacc aggtgcaatt attctttgtt   2760
ttcttctcca gtggtcattg agcagagcta catcagcgtt gttaccgtca cctagaaagg   2820
agtggcagta atatccaaac acgggctgct tatcttctaa tcagagcatc tgcaacaaac   2880
cgtcattttt ctgaagtgga aaagcttaaa acaattactg tgaattgttt ttgtacagtt   2940
atcatgaagc tttcttttt ctcttttcc tgtttctctt cttttctttt ttcttttttt   3000 ttttgccaa ccattgccaa tgtcaatcaa tcacagtatt agcctctgtt aatctatctc   3060
tttactgttg cttctactct tcaatgcata tgttgctcaa aggtggcaag ttgtcctggg   3120
ttgtgtgagt cctgagatgg atataattct tgatgctggt gctagaagta ggtcttcaaa   3180
```

-continued

| | |
|---|---|
| tccggggtcg ttgtcccacc cctgtactgt actcccagtg gccaaactta tttatgctgc | 3240 |
| taaatgaaag aaagaaaaag caaattattt tttttttatt tttttctgc tgtgacgttt | 3300 |
| tagtcccaga ctgaattcca aatttgctct agtttggtta cagaaaaaaa agactttttt | 3360 |
| gccactgaaa cttgagccat ctgtgcctct aagaggctga gaatggaaaa gtttcagata | 3420 |
| ataaagagtg aagtttgcct gcaaataaag aattgagagt gtgtgcaaag cttattttct | 3480 |
| tttatctggg caaaaattaa aacacattcc ttgggacaga gcctgaggtg cctgttctgt | 3540 |
| ggagaaactt cttttgagg gctgtggtga atggaagaac atacatagca aaactgacaa | 3600 |
| gatattttaa agatatataa aacacaaagg aaaaggaggt tgctggtcag tcgtagcatc | 3660 |
| ttacagtatt ggggaaaaca actgttacag tttcattgct ctgagtgact gacgtgagag | 3720 |
| gaattcgctc tgcagtgacg ctgtctgtca ctcgcctacc agctcgacga gcaagagagc | 3780 |
| gggagtcaga tggtccgcct cattcaccag gagccgtaac tcaagctgaa ctgtgaaagt | 3840 |
| ggttaacact gtatcctagg ccgtctttt tttcctcctc ctgtttattt tttgtttgtt | 3900 |
| ttatttatag tctgatttaa aacaatcaga ttcaagttgg ttaattttag ttatgtaaca | 3960 |
| acctgacgtg atggaggaaa caacctgtaa agggattgtg tctatggttt gattcactta | 4020 |
| gaaattttat tttcttataa cttaagtgca ataaaatgtg tttttcatg ttaaaaaaaa | 4080 |
| aaaaaaaaaa aa | 4092 |

<210> SEQ ID NO 12
<211> LENGTH: 4183
<212> TYPE: DNA
<213> ORGANISM: Mus musculus

<400> SEQUENCE: 12

| | |
|---|---|
| gagcgagcgg ggccgccacc gccgcctcta tcccagcagc gcggaagaga cccgggtagc | 60 |
| tgcttggtgg agcgacgcta gcaccgcttc ttcctcagtt ccgcgcctag ccagccttcc | 120 |
| gcagctgccc gcctcagccc gaaggaggaa gggagccagc cacattgtca gcgccaccgc | 180 |
| tcgactctga agcgaaatct cagctatcaa ggagactttt aaaaggctct ctaaatattt | 240 |
| ggtacgagaa tttcttctct ttatatcttt tgtgatccct ctacacattg tgtctagaca | 300 |
| atcagaatgt gaaaaccttt gcatcttctg atagtctagc caaggtccaa gaagtagcaa | 360 |
| gctggctttt ggaaatgaat caggaactgc tctctgtggg cagcaaaaga cgacgaactg | 420 |
| gaggctctct gagagggaat gcttcctcaa gccaggttga tgagggacag atgaatcgcg | 480 |
| tggttgagga ggatccacag cagcaagcga gacatcaaga ggaggagcac actgcgcgga | 540 |
| atggtgaact tgtgggtgca aaccctaggc ctggagacca gaacgatacc cagcaaggac | 600 |
| aagtggagga aaataataac cgctttattt cagtagatga ggactcttcg ggaaatcagg | 660 |
| aagagcaaga ggaagatgaa gagcatgctg gggaacagga ggaggaagag gaggaagagg | 720 |
| aagaggagga ggagatggac caggagagtg atgattttga tccgtctgat gacagtagca | 780 |
| gagaagatga acatacgcac aatagcaatg tcacaaactg cagtagtgtc tcggacctgc | 840 |
| ccgctcacca gctctcctct ccattctata caaagacaac aaaaatgaaa agaaagttgg | 900 |
| accatggttc tgaagttcgt tccttttctt tgggaaagaa accatgcaaa gtctcagatt | 960 |
| ataccagtac cactggcctt gtaccatgtt cagcaacacc aacaactttt ggggacctga | 1020 |
| gagcagccaa tggcaaggg cagcagcggc ggaggattac atctgtccaa ccacccacag | 1080 |
| gccttcaaga gtggctgaaa atgtttcaga gctggagcgg accagagaag ttgctggctt | 1140 |

-continued

```
tagatgagct cattgacagc tgtgaaccaa cacaagtgaa gcatatgatg caagtgatag    1200
agccccagtt ccagcgagac ttcatctcct tgcttcctaa agagttggca ctctatgtgc    1260
tttcattcct ggaacccaaa gacctgctgc aagcggctca gacttgtcga tactggagaa    1320
ttttggctga ggataaccTt ctctggagag agaaatgtaa agaagagggg attgatgaac    1380
cgttgcacat caagagaaga aaaataataa aaccaggttt catacacagc ccatggaaga    1440
gtgcgtatat cagacagcac agaattgata caaactggag acgaggagaa ctcaaatctc    1500
ctaaggtgct gaaagggcat gatgaccatg tgatcacatg cctacagttt tgtggcaacc    1560
gcatagttag tggttctgat gacaacactt taaaagtttg gtcagcggtc acgggcaagt    1620
gtctgagaac gttagtggga catacaggtg gagtgtggtc atcacagatg agagacaata    1680
tcatcatcag tggatcgact gaccggactc tcaaagtgtg gaatgctgaa actggagagt    1740
gtatacatac tttatatggg cacacttcta ctgtacggtg tatgcatctc catgaaaaaa    1800
gggttgtaag cggttctcga gatgccactc tcagggtttg ggatattgag accggccagt    1860
gtttacacgt cctgatgggt cacgtagcag cggtccgctc cgttcagtat gatggcagga    1920
gggttgttag tggagcttat gattttatgg tgaaggtgtg ggatccagag actgagacct    1980
gtctacacac gttacaggga cacactaata gagtctattc attacagttt gatggcatcc    2040
atgtggtgag tggatctctt gatacatcaa tccgagtctg ggatgtggag acagggaatt    2100
gtattccacc gctaacagga caccagtcat taacgagtgg aatggaactc aaagacaata    2160
ttcttgtctc tgggaatgca gattctacag ttaagatctg ggatatcaaa acaggacagt    2220
gtttacaaac tttgcaaggt cccagcaagc atcagagcgc tgtgacctgc ttacagttca    2280
acaagaactt cgtaattacc agctcagacg acggaacggt caaactctgg gacttgaaaa    2340
cgggtgaatt tatccgaaac ctcgtcacat tggagagtgg ggggagcggg ggagttgtgt    2400
ggcggatcag ggcctcaaac acaaagctgg tgtgtgcagt cgggagtcgg aatggaactg    2460
aggaaaccaa gctcctggtg ctggactttg atgtggacat gaaatgaaaa gcagacatga    2520
tgaattttgt ccaactgtgt agacaatata ctccctaccc ttcccctgc gcaaaaaaca     2580
aaacaaaca  aacaaaaaaa tgaaaaaaaa aaacagaaaa aaaaaagag aaaaaagaaa    2640
aggaaaaaaa tcccttgtac tcagtggtgc aggatgttgg cttgggacaa cagactgaaa   2700
agacctacag actaagaagg caagaagaga caagagaccg taactgacag gaggcggcag   2760
ctgtcgcatc tcgcaaaggc ctcacttgtg actgaggggc agcttggcaa gacgactctc   2820
taaatccaac caggtgcaat tattctttgt tttcttctcc agtggtcatt gagcagagct    2880
acatcagcgt tgttaccgtc acctagaaag gagtggcagt aatatccaaa cacgggctgc    2940
ttatcttcta atcagagcat ctgcaacaaa ccgtcatttt tctgaagtgg aaaagcttaa    3000
aacaattact gtgaattgtt tttgtacagt tatcatgaag ctttctttt tctcttttc     3060
ctgtttctct tcttttcttt tttctttttt tttttgcca accattgcca atgtcaatca     3120
atcacagtat tagcctctgt taatctatct ctttactgtt gcttctactc ttcaatgcat   3180
atgttgctca aaggtggcaa gttgtcctgg gttgtgtgag tcctgagatg gatataattc   3240
ttgatgctgg tgctagaagt aggtcttcaa atccggggtc gttgtcccac ccctgtactg   3300
tactcccagt ggccaaactt atttatgctg ctaaatgaaa gaaagaaaaa gcaaattatt    3360
ttttttttat ttttttttctg ctgtgacgtt ttagtcccag actgaattcc aaattttgctc  3420
tagtttggtt acagaaaaaa aagacttttt tgccactgaa acttgagcca tctgtgcctc    3480
taagaggctg agaatggaaa agtttcagat aataaagagt gaagtttgcc tgcaaataaa    3540
```

```
gaattgagag tgtgtgcaaa gcttattttc ttttatctgg gcaaaaatta aaacacattc    3600
cttgggacag agcctgaggt gcctgttctg tggagaaact tcttttttgag ggctgtggtg    3660 aatggaagaa catacatagc aaaactgaca agatatttta agatatata aaacacaaag     3720 gaaaaggagg ttgctggtca gtcgtagcat cttacagtat tggggaaaac aactgttaca    3780
gtttcattgc tctgagtgac tgacgtgaga ggaattcgct ctgcagtgac gctgtctgtc    3840
actcgcctac cagctcgacg agcaagagag cgggagtcag atggtccgcc tcattcacca    3900
ggagccgtaa ctcaagctga actgtgaaag tggttaacac tgtatcctag gccgtctttt    3960
ttttcctcct cctgtttatt ttttgtttgt tttatttata gtctgattta aaacaatcag    4020
attcaagttg gttaatttta gttatgtaac aacctgacgt gatggaggaa acaacctgta    4080
aagggattgt gtctatggtt tgattcactt agaaatttta ttttcttata acttaagtgc    4140
aataaaatgt gttttttcat gttaaaaaaa aaaaaaaaaa aaa                      4183

<210> SEQ ID NO 13
<211> LENGTH: 3728
<212> TYPE: DNA
<213> ORGANISM: Mus musculus

<400> SEQUENCE: 13
accctggact gcaccattct gtgttcaagg gaagatgtaa tctgatccct ctgctgctga     60
gggaggaatc tgttcagtca aggctttgac agggcatagt ctcctccaat aatcttgtgg    120
gttctcgctc attattcccc gagttctcct cagtggagct gcatgcgtgt gtgcgtcccg    180
agcagcgttc tggttctgag ctgcgtctgc tggtgctggg gagttttgct gccggttccg    240
ctgcctaatc ttcctttcct ggcgtgcctg agcatgtcca cgttagaatc tgtgacatac    300
ctacctgaaa aggggttata ttgtcagaga ctgccaagca gccggacaca cgggggcaca    360
gaatccctga aggggaaaaa tacagaaaat atgggtttct acggcacatt aaaaatgatt    420
ttttacaaaa tgaaagaaa gttggaccat ggttctgaag ttcgttcctt ttctttggga     480
aagaaaccat gcaaagtctc agattatacc agtaccactg gccttgtacc atgttcagca    540
acaccaacaa cttttgggga cctgagagca gccaatgggc aagggcagca gcggcggagg    600
attacatctg tccaaccacc cacaggcctt caagagtggc tgaaaatgtt tcagagctgg    660
agcggaccag agaagttgct ggcttttagat gagctcattg acagctgtga accaacacaa    720
gtgaagcata tgatgcaagt gatagagccc cagttccagc gagacttcat ctccttgctt    780
cctaaagagt tggcactcta tgtgctttca ttcctggaac ccaaagacct gctgcaagcg    840
gctcagactt gtcgatactg gagaattttg gctgaggata accttctctg gagagagaaa    900
tgtaaagaag aggggattga tgaaccgttg cacatcaaga gaagaaaaat aataaaacca    960
ggtttcatac acagcccatg gaagagtgcg tatatcagac agcacagaat tgatacaaac    1020
tggagacgag gagaactcaa atctcctaag gtgctgaaag gcatgatga ccatgtgatc     1080 acatgcctac agttttgtgg caaccgcata gttagtggtt ctgatgacaa cactttaaaa    1140
gtttggtcag cggtcacggg caagtgtctg agaacgttag tgggacatac aggtggagtg    1200
tggtcatcac agatgagaga caatatcatc atcagtggat cgactgaccg gactctcaaa    1260
gtgtggaatg ctgaaactgg agagtgtata catactttat atgggcacac ttctactgta    1320
cggtgtatgc atctccatga aaaagggtt gtaagcggtt ctcgagatgc cactctcagg    1380
gtttgggata ttgagaccgg ccagtgttta cacgtcctga tgggtcacgt agcagcggtc    1440
```

```
cgctgcgttc agtatgatgg caggagggtt gttagtggag cttatgattt tatggtgaag    1500
gtgtgggatc cagagactga gacctgtcta cacacgttac agggacacac taatagagtc    1560
tattcattac agtttgatgg catccatgtg gtgagtggat ctcttgatac atcaatccga    1620
gtctgggatg tggagacagg gaattgtatt cacacgctaa caggacacca gtcattaacg    1680
agtggaatgg aactcaaaga caatattctt gtctctggga atgcagattc tacagttaag    1740
atctgggata tcaaaacagg acagtgttta caaactttgc aaggtcccag caagcatcag    1800
agcgctgtga cctgcttaca gttcaacaag aacttcgtaa ttaccagctc agacgacgga    1860
acggtcaaac tctgggactt gaaaacgggt gaatttatcc gaaacctcgt cacattggag    1920
agtgggggga gcggggagt tgtgtggcgg atcagggcct caaacacaaa gctggtgtgt    1980
gcagtcggga gtcggaatgg aactgaggaa accaagctcc tggtgctgga ctttgatgtg    2040
gacatgaaat gaaaagcaga catgatgaat tttgtccaac tgtgtagaca atatactccc    2100
tacccttccc cctgcgcaaa aaacaaaaac aaacaaacaa aaaaatgaaa aaaaaaaaca    2160
gaaaaaaaaa aagagaaaaa agaaaaggaa aaaaatccct tgtactcagt ggtgcaggat    2220
gttggcttgg gacaacagac tgaaaagacc tacagactaa gaaggcaaga agagacaaga    2280
gaccgtaact gacaggaggc ggcagctgtc gcatctcgca aaggcctcac ttgtgactga    2340
ggggcagctt ggcaagacga ctctctaaat ccaaccaggt gcaattattc tttgttttct    2400
tctccagtgg tcattgagca gagctacatc agcgttgtta ccgtcaccta gaaggagtg    2460 gcagtaatat ccaaacacgg gctgcttatc ttctaatcag agcatctgca acaaaccgtc    2520 attttctga agtggaaaag cttaaaacaa ttactgtgaa ttgttttgt acagttatca    2580 tgaagctttc ttttttctct ttttcctgtt tctcttcttt tcttttttct tttttttttt    2640
tgccaaccat tgccaatgtc aatcaatcac agtattagcc tctgttaatc tatctcttta    2700
ctgttgcttc tactcttcaa tgcatatgtt gctcaaaggt ggcaagttgt cctgggttgt    2760
gtgagtcctg agatggatat aattcttgat gctggtgcta gaagtaggtc ttcaaatccg    2820
gggtcgttgt cccaccctg tactgtactc ccagtggcca aacttattta tgctgctaaa    2880
tgaaagaaag aaaaagcaaa ttatttttt tttatttttt ttctgctgtg acgttttagt    2940
cccagactga attccaaatt tgctctagtt tggttacaga aaaaaaagac tttttttgcca    3000 ctgaaacttg agccatctgt gcctctaaga ggctgagaat ggaaaagttt cagataataa    3060
agagtgaagt ttgcctgcaa ataaagaatt gagagtgtgt gcaaagctta ttttcttta    3120 tctgggcaaa aattaaaaca cattccttgg gacagagcct gaggtgcctg ttctgtggag    3180
aaacttcttt ttgagggctg tggtgaatgg aagaacatac atagcaaaac tgacaagata    3240
ttttaaagat atataaaaca caaggaaaa ggaggttgct ggtcagtcgt agcatcttac    3300
agtattgggg aaaacaactg ttacagtttc attgctctga gtgactgacg tgagaggaat    3360
tcgctctgca gtgacgctgt ctgtcactcg cctaccagct cgacgagcaa gagagcggga    3420
gtcagatggt ccgcctcatt caccaggagc cgtaactcaa gctgaactgt gaaagtggtt    3480
aacactgtat cctaggccgt cttttttttc ctcctcctgt ttatttttg tttgttttat    3540 ttatagtctg atttaaaaca atcagattca agttggttaa ttttagttat gtaacaacct    3600
gacgtgatgg aggaaacaac ctgtaaaggg attgtgtcta tggtttgatt cacttagaaa    3660
ttttattttc ttataactta agtgcaataa aatgtgtttt ttcatgttaa aaaaaaaaa    3720 aaaaaaaa                                                            3728
```

```
<210> SEQ ID NO 14
<211> LENGTH: 710
<212> TYPE: PRT
<213> ORGANISM: Mus musculus

<400> SEQUENCE: 14
```

| | | | | | | | | | | | | | | |
|---|---|---|---|---|---|---|---|---|---|---|---|---|---|---|
| Met | Asn | Gln | Glu | Leu | Leu | Ser | Val | Gly | Ser | Lys | Arg | Arg | Thr | Gly |
| 1 | | | | 5 | | | | | 10 | | | | | 15 |
| Gly | Ser | Leu | Arg | Gly | Asn | Ala | Ser | Ser | Gln | Val | Asp | Glu | Gly | Gln |
| | | | 20 | | | | | 25 | | | | | 30 | |
| Met | Asn | Arg | Val | Val | Glu | Glu | Asp | Pro | Gln | Gln | Ala | Arg | His | Gln |
| | | | | 35 | | | | | 40 | | | | | 45 |
| Glu | Glu | Glu | His | Thr | Ala | Arg | Asn | Gly | Glu | Leu | Val | Gly | Ala | Asn | Pro |
| | 50 | | | | | | 55 | | | | | 60 | | |
| Arg | Pro | Gly | Asp | Gln | Asn | Asp | Thr | Gln | Gln | Gly | Gln | Val | Glu | Asn |
| 65 | | | | | 70 | | | | | 75 | | | | 80 |
| Asn | Asn | Arg | Phe | Ile | Ser | Val | Asp | Glu | Asp | Ser | Ser | Gly | Asn | Gln | Glu |
| | | | | 85 | | | | | 90 | | | | | 95 |
| Glu | Gln | Glu | Glu | Asp | Glu | Glu | His | Ala | Gly | Glu | Gln | Glu | Glu | Glu |
| | | | | 100 | | | | | 105 | | | | | 110 |
| Glu | Glu | Glu | Glu | Glu | Glu | Glu | Met | Asp | Gln | Glu | Ser | Asp | Asp | Phe |
| | | | 115 | | | | | 120 | | | | | 125 | |
| Asp | Pro | Ser | Asp | Ser | Ser | Arg | Glu | Asp | Glu | His | Thr | His | Asn | Ser |
| | 130 | | | | | 135 | | | | | 140 | | | |
| Asn | Val | Thr | Asn | Cys | Ser | Ser | Val | Ser | Asp | Leu | Pro | Ala | His | Gln | Leu |
| 145 | | | | 150 | | | | | 155 | | | | | 160 |
| Ser | Ser | Pro | Phe | Tyr | Thr | Lys | Thr | Thr | Lys | Met | Lys | Arg | Lys | Leu | Asp |
| | | | | 165 | | | | | 170 | | | | | 175 |
| His | Gly | Ser | Glu | Val | Arg | Ser | Phe | Ser | Leu | Gly | Lys | Lys | Pro | Cys | Lys |
| | | | 180 | | | | | 185 | | | | | 190 | |
| Val | Ser | Asp | Tyr | Thr | Ser | Thr | Thr | Gly | Leu | Val | Pro | Cys | Ser | Ala | Thr |
| | | | 195 | | | | | 200 | | | | | 205 | |
| Pro | Thr | Thr | Phe | Gly | Asp | Leu | Arg | Ala | Ala | Asn | Gly | Gln | Gly | Gln | Gln |
| | 210 | | | | | 215 | | | | | 220 | | | |
| Arg | Arg | Arg | Ile | Thr | Ser | Val | Gln | Pro | Thr | Gly | Leu | Gln | Glu | Trp |
| 225 | | | | | 230 | | | | | 235 | | | | 240 |
| Leu | Lys | Met | Phe | Gln | Ser | Trp | Ser | Gly | Pro | Glu | Lys | Leu | Leu | Ala | Leu |
| | | | | 245 | | | | | 250 | | | | | 255 |
| Asp | Glu | Leu | Ile | Asp | Ser | Cys | Glu | Pro | Thr | Gln | Val | Lys | His | Met | Met |
| | | | 260 | | | | | 265 | | | | | 270 | |
| Gln | Val | Ile | Glu | Pro | Gln | Phe | Gln | Arg | Asp | Phe | Ile | Ser | Leu | Leu | Pro |
| | | | 275 | | | | | 280 | | | | | 285 | |
| Lys | Glu | Leu | Ala | Leu | Tyr | Val | Leu | Ser | Phe | Leu | Glu | Pro | Lys | Asp | Leu |
| | 290 | | | | | 295 | | | | | 300 | | | |
| Leu | Gln | Ala | Ala | Gln | Thr | Cys | Arg | Tyr | Trp | Arg | Ile | Leu | Ala | Glu | Asp |
| 305 | | | | | 310 | | | | | 315 | | | | 320 |
| Asn | Leu | Leu | Trp | Arg | Glu | Lys | Cys | Lys | Glu | Gly | Ile | Asp | Glu | Pro |
| | | | | 325 | | | | | 330 | | | | | 335 |
| Leu | His | Ile | Lys | Arg | Arg | Lys | Ile | Ile | Lys | Pro | Gly | Phe | Ile | His | Ser |
| | | | 340 | | | | | 345 | | | | | 350 | |
| Pro | Trp | Lys | Ser | Ala | Tyr | Ile | Arg | Gln | His | Arg | Ile | Asp | Thr | Asn | Trp |
| | | | 355 | | | | | 360 | | | | | 365 | |
| Arg | Arg | Gly | Glu | Leu | Lys | Ser | Pro | Lys | Val | Leu | Lys | Gly | His | Asp | Asp |
| | 370 | | | | | 375 | | | | | 380 | | | |

-continued

```
His Val Ile Thr Cys Leu Gln Phe Cys Gly Asn Arg Ile Val Ser Gly
385                 390                 395                 400

Ser Asp Asp Asn Thr Leu Lys Val Trp Ser Ala Val Thr Gly Lys Cys
            405                 410                 415

Leu Arg Thr Leu Val Gly His Thr Gly Gly Val Trp Ser Ser Gln Met
        420                 425                 430

Arg Asp Asn Ile Ile Ile Ser Gly Ser Thr Asp Arg Thr Leu Lys Val
    435                 440                 445

Trp Asn Ala Glu Thr Gly Glu Cys Ile His Thr Leu Tyr Gly His Thr
450                 455                 460

Ser Thr Val Arg Cys Met His Leu His Glu Lys Arg Val Val Ser Gly
465                 470                 475                 480

Ser Arg Asp Ala Thr Leu Arg Val Trp Asp Ile Glu Thr Gly Gln Cys
            485                 490                 495

Leu His Val Leu Met Gly His Val Ala Ala Val Arg Cys Val Gln Tyr
        500                 505                 510

Asp Gly Arg Arg Val Val Ser Gly Ala Tyr Asp Phe Met Val Lys Val
    515                 520                 525

Trp Asp Pro Glu Thr Glu Thr Cys Leu His Thr Leu Gln Gly His Thr
530                 535                 540

Asn Arg Val Tyr Ser Leu Gln Phe Asp Gly Ile His Val Val Ser Gly
545                 550                 555                 560

Ser Leu Asp Thr Ser Ile Arg Val Trp Asp Val Glu Thr Gly Asn Cys
            565                 570                 575

Ile His Thr Leu Thr Gly His Gln Ser Leu Thr Ser Gly Met Glu Leu
        580                 585                 590

Lys Asp Asn Ile Leu Val Ser Gly Asn Ala Asp Ser Thr Val Lys Ile
    595                 600                 605

Trp Asp Ile Lys Thr Gly Gln Cys Leu Gln Thr Leu Gln Gly Pro Ser
610                 615                 620

Lys His Gln Ser Ala Val Thr Cys Leu Gln Phe Asn Lys Asn Phe Val
625                 630                 635                 640

Ile Thr Ser Ser Asp Asp Gly Thr Val Lys Leu Trp Asp Leu Lys Thr
            645                 650                 655

Gly Glu Phe Ile Arg Asn Leu Val Thr Leu Glu Ser Gly Gly Ser Gly
        660                 665                 670

Gly Val Val Trp Arg Ile Arg Ala Ser Asn Thr Lys Leu Val Cys Ala
    675                 680                 685

Val Gly Ser Arg Asn Gly Thr Glu Glu Thr Lys Leu Leu Val Leu Asp
690                 695                 700

Phe Asp Val Asp Met Lys
705                 710

<210> SEQ ID NO 15
<211> LENGTH: 710
<212> TYPE: PRT
<213> ORGANISM: Mus musculus

<400> SEQUENCE: 15

Met Asn Gln Glu Leu Leu Ser Val Gly Ser Lys Arg Arg Thr Gly
1               5                   10                  15

Gly Ser Leu Arg Gly Asn Ala Ser Ser Gln Val Asp Glu Gly Gln
            20                  25                  30

Met Asn Arg Val Val Glu Glu Asp Pro Gln Gln Ala Arg His Gln
        35                  40                  45
```

-continued

```
Glu Glu Glu His Thr Ala Arg Asn Gly Glu Leu Val Gly Ala Asn Pro
        50                  55                  60

Arg Pro Gly Asp Gln Asn Asp Thr Gln Gln Gly Gln Val Glu Glu Asn
 65                  70                  75                  80

Asn Asn Arg Phe Ile Ser Val Asp Glu Asp Ser Ser Gly Asn Gln Glu
                85                  90                  95

Glu Gln Glu Glu Asp Glu Glu His Ala Gly Glu Gln Glu Glu Glu Glu
            100                 105                 110

Glu Glu Glu Glu Glu Glu Glu Met Asp Gln Glu Ser Asp Asp Phe
            115                 120                 125

Asp Pro Ser Asp Asp Ser Ser Arg Glu Asp Glu His Thr His Asn Ser
        130                 135                 140

Asn Val Thr Asn Cys Ser Ser Val Ser Asp Leu Pro Ala His Gln Leu
145                 150                 155                 160

Ser Ser Pro Phe Tyr Thr Lys Thr Thr Lys Met Lys Arg Lys Leu Asp
                165                 170                 175

His Gly Ser Glu Val Arg Ser Phe Ser Leu Gly Lys Lys Pro Cys Lys
            180                 185                 190

Val Ser Asp Tyr Thr Ser Thr Thr Gly Leu Val Pro Cys Ser Ala Thr
            195                 200                 205

Pro Thr Thr Phe Gly Asp Leu Arg Ala Ala Asn Gly Gln Gly Gln Gln
    210                 215                 220

Arg Arg Arg Ile Thr Ser Val Gln Pro Pro Thr Gly Leu Gln Glu Trp
225                 230                 235                 240

Leu Lys Met Phe Gln Ser Trp Ser Gly Pro Glu Lys Leu Leu Ala Leu
                245                 250                 255

Asp Glu Leu Ile Asp Ser Cys Glu Pro Thr Gln Val Lys His Met Met
            260                 265                 270

Gln Val Ile Glu Pro Gln Phe Gln Arg Asp Phe Ile Ser Leu Leu Pro
        275                 280                 285

Lys Glu Leu Ala Leu Tyr Val Leu Ser Phe Leu Glu Pro Lys Asp Leu
290                 295                 300

Leu Gln Ala Ala Gln Thr Cys Arg Tyr Trp Arg Ile Leu Ala Glu Asp
305                 310                 315                 320

Asn Leu Leu Trp Arg Glu Lys Cys Lys Glu Glu Gly Ile Asp Glu Pro
                325                 330                 335

Leu His Ile Lys Arg Arg Lys Ile Ile Lys Pro Gly Phe Ile His Ser
            340                 345                 350

Pro Trp Lys Ser Ala Tyr Ile Arg Gln His Arg Ile Asp Thr Asn Trp
        355                 360                 365

Arg Arg Gly Glu Leu Lys Ser Pro Lys Val Leu Lys Gly His Asp Asp
370                 375                 380

His Val Ile Thr Cys Leu Gln Phe Cys Gly Asn Arg Ile Val Ser Gly
385                 390                 395                 400

Ser Asp Asp Asn Thr Leu Lys Val Trp Ser Ala Val Thr Gly Lys Cys
                405                 410                 415

Leu Arg Thr Leu Val Gly His Thr Gly Gly Val Trp Ser Ser Gln Met
            420                 425                 430

Arg Asp Asn Ile Ile Ile Ser Gly Ser Thr Asp Arg Thr Leu Lys Val
        435                 440                 445

Trp Asn Ala Glu Thr Gly Glu Cys Ile His Thr Leu Tyr Gly His Thr
450                 455                 460
```

```
Ser Thr Val Arg Cys Met His Leu His Glu Lys Arg Val Val Ser Gly
465                 470                 475                 480

Ser Arg Asp Ala Thr Leu Arg Val Trp Asp Ile Glu Thr Gly Gln Cys
                485                 490                 495

Leu His Val Leu Met Gly His Val Ala Ala Val Arg Cys Val Gln Tyr
            500                 505                 510

Asp Gly Arg Arg Val Val Ser Gly Ala Tyr Asp Phe Met Val Lys Val
        515                 520                 525

Trp Asp Pro Glu Thr Glu Thr Cys Leu His Thr Leu Gln Gly His Thr
    530                 535                 540

Asn Arg Val Tyr Ser Leu Gln Phe Asp Gly Ile His Val Val Ser Gly
545                 550                 555                 560

Ser Leu Asp Thr Ser Ile Arg Val Trp Asp Val Glu Thr Gly Asn Cys
                565                 570                 575

Ile His Thr Leu Thr Gly His Gln Ser Leu Thr Ser Gly Met Glu Leu
            580                 585                 590

Lys Asp Asn Ile Leu Val Ser Gly Asn Ala Asp Ser Thr Val Lys Ile
        595                 600                 605

Trp Asp Ile Lys Thr Gly Gln Cys Leu Gln Thr Leu Gln Gly Pro Ser
    610                 615                 620

Lys His Gln Ser Ala Val Thr Cys Leu Gln Phe Asn Lys Asn Phe Val
625                 630                 635                 640

Ile Thr Ser Ser Asp Asp Gly Thr Val Lys Leu Trp Asp Leu Lys Thr
                645                 650                 655

Gly Glu Phe Ile Arg Asn Leu Val Thr Leu Glu Ser Gly Gly Ser Gly
            660                 665                 670

Gly Val Val Trp Arg Ile Arg Ala Ser Asn Thr Lys Leu Val Cys Ala
        675                 680                 685

Val Gly Ser Arg Asn Gly Thr Glu Glu Thr Lys Leu Leu Val Leu Asp
    690                 695                 700

Phe Asp Val Asp Met Lys
705                 710

<210> SEQ ID NO 16
<211> LENGTH: 629
<212> TYPE: PRT
<213> ORGANISM: Mus musculus

<400> SEQUENCE: 16

Met Arg Val Cys Val Pro Ser Ser Val Leu Val Leu Ser Cys Val Cys
1               5                   10                  15

Trp Cys Trp Gly Val Leu Leu Pro Val Pro Leu Pro Asn Leu Pro Phe
                20                  25                  30

Leu Ala Cys Leu Ser Met Ser Thr Leu Glu Ser Val Thr Tyr Leu Pro
            35                  40                  45

Glu Lys Gly Leu Tyr Cys Gln Arg Leu Pro Ser Arg Thr His Gly
        50                  55                  60

Gly Thr Glu Ser Leu Lys Gly Lys Asn Thr Glu Asn Met Gly Phe Tyr
65                  70                  75                  80

Gly Thr Leu Lys Met Ile Phe Tyr Lys Met Lys Arg Lys Leu Asp His
                85                  90                  95

Gly Ser Glu Val Arg Ser Phe Ser Leu Gly Lys Lys Pro Cys Lys Val
            100                 105                 110

Ser Asp Tyr Thr Ser Thr Thr Gly Leu Val Pro Cys Ser Ala Thr Pro
        115                 120                 125
```

```
Thr Thr Phe Gly Asp Leu Arg Ala Ala Asn Gly Gln Gly Gln Gln Arg
    130                 135                 140
Arg Arg Ile Thr Ser Val Gln Pro Pro Thr Gly Leu Gln Glu Trp Leu
145                 150                 155                 160
Lys Met Phe Gln Ser Trp Ser Gly Pro Glu Lys Leu Leu Ala Leu Asp
                165                 170                 175
Glu Leu Ile Asp Ser Cys Glu Pro Thr Gln Val Lys His Met Met Gln
                180                 185                 190
Val Ile Glu Pro Gln Phe Gln Arg Asp Phe Ile Ser Leu Leu Pro Lys
            195                 200                 205
Glu Leu Ala Leu Tyr Val Leu Ser Phe Leu Glu Pro Lys Asp Leu Leu
        210                 215                 220
Gln Ala Ala Gln Thr Cys Arg Tyr Trp Arg Ile Leu Ala Glu Asp Asn
225                 230                 235                 240
Leu Leu Trp Arg Glu Lys Cys Lys Glu Glu Gly Ile Asp Glu Pro Leu
                245                 250                 255
His Ile Lys Arg Arg Lys Ile Ile Lys Pro Gly Phe Ile His Ser Pro
                260                 265                 270
Trp Lys Ser Ala Tyr Ile Arg Gln His Arg Ile Asp Thr Asn Trp Arg
            275                 280                 285
Arg Gly Glu Leu Lys Ser Pro Lys Val Leu Lys Gly His Asp Asp His
290                 295                 300
Val Ile Thr Cys Leu Gln Phe Cys Gly Asn Arg Ile Val Ser Gly Ser
305                 310                 315                 320
Asp Asp Asn Thr Leu Lys Val Trp Ser Ala Val Thr Gly Lys Cys Leu
                325                 330                 335
Arg Thr Leu Val Gly His Thr Gly Gly Val Trp Ser Ser Gln Met Arg
            340                 345                 350
Asp Asn Ile Ile Ile Ser Gly Ser Thr Asp Arg Thr Leu Lys Val Trp
            355                 360                 365
Asn Ala Glu Thr Gly Glu Cys Ile His Thr Leu Tyr Gly His Thr Ser
        370                 375                 380
Thr Val Arg Cys Met His Leu His Glu Lys Arg Val Val Ser Gly Ser
385                 390                 395                 400
Arg Asp Ala Thr Leu Arg Val Trp Asp Ile Glu Thr Gly Gln Cys Leu
                405                 410                 415
His Val Leu Met Gly His Val Ala Ala Val Arg Cys Val Gln Tyr Asp
                420                 425                 430
Gly Arg Arg Val Val Ser Gly Ala Tyr Asp Phe Met Val Lys Val Trp
            435                 440                 445
Asp Pro Glu Thr Glu Thr Cys Leu His Thr Leu Gln Gly His Thr Asn
450                 455                 460
Arg Val Tyr Ser Leu Gln Phe Asp Gly Ile His Val Val Ser Gly Ser
465                 470                 475                 480
Leu Asp Thr Ser Ile Arg Val Trp Asp Val Glu Thr Gly Asn Cys Ile
                485                 490                 495
His Thr Leu Thr Gly His Gln Ser Leu Thr Ser Gly Met Glu Leu Lys
            500                 505                 510
Asp Asn Ile Leu Val Ser Gly Asn Ala Asp Ser Thr Val Lys Ile Trp
            515                 520                 525
Asp Ile Lys Thr Gly Gln Cys Leu Gln Thr Leu Gln Gly Pro Ser Lys
530                 535                 540
```

```
His Gln Ser Ala Val Thr Cys Leu Gln Phe Asn Lys Asn Phe Val Ile
545                 550                 555                 560

Thr Ser Ser Asp Asp Gly Thr Val Lys Leu Trp Asp Leu Lys Thr Gly
                565                 570                 575

Glu Phe Ile Arg Asn Leu Val Thr Leu Glu Ser Gly Ser Gly Gly
                580                 585                 590

Val Val Trp Arg Ile Arg Ala Ser Asn Thr Lys Leu Val Cys Ala Val
            595                 600                 605

Gly Ser Arg Asn Gly Thr Glu Glu Thr Lys Leu Leu Val Leu Asp Phe
        610                 615                 620

Asp Val Asp Met Lys
625

<210> SEQ ID NO 17
<211> LENGTH: 31
<212> TYPE: DNA
<213> ORGANISM: Artificial Sequence
<220> FEATURE:
<223> OTHER INFORMATION: /note="Description of Artificial Sequence:
      Synthetic primer sequence"

<400> SEQUENCE: 17
agcggtctgc tgcgttcagt atgatggcag g                                      31

<210> SEQ ID NO 18
<211> LENGTH: 27
<212> TYPE: DNA
<213> ORGANISM: Artificial Sequence
<220> FEATURE:
<223> OTHER INFORMATION: /note="Description of Artificial Sequence:
      Synthetic primer sequence"

<400> SEQUENCE: 18
acgcagcaga ccgctgctac gtgaccc                                           27

<210> SEQ ID NO 19
<211> LENGTH: 18
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 19
ctccaaagga cttgtacg                                                     18

<210> SEQ ID NO 20
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 20
tgaacatggt acaaggccag                                                   20

<210> SEQ ID NO 21
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"
```

```
<400> SEQUENCE: 21
gcaaagtctc agattatacc                                              20

<210> SEQ ID NO 22
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 22
cacccacagg ccttcaagag                                              20

<210> SEQ ID NO 23
<211> LENGTH: 20
<212> TYPE: DNA
<213> ORGANISM: Artificial Sequence
<220> FEATURE:
<223> OTHER INFORMATION: /note="Description of Artificial Sequence:
      Synthetic sgRNA targeting sequence"

<400> SEQUENCE: 23
ccaggtaacg ttgaatagag                                              20
```

BIOMARKERS PREDICTIVE OF ANTI-IMMUNE CHECKPOINT RESPONSE

CROSS-REFERENCE TO RELATED APPLICATION

This application is the U.S. national phase of International Patent Application No. PCT/US2019/014117, filed on Jan. 18, 2019, which claims the benefit of priority to U.S. Provisional Application Ser. No. 62/619,524, filed on Jan. 19, 2018; the entire contents of each of said applications are incorporated herein in their entirety by this reference.

STATEMENT OF RIGHTS

This invention was made with government support under grant numbers R01CA227388 and P50CA101942 awarded by The National Institutes of Health. The government has certain rights in the present invention.

BACKGROUND OF THE INVENTION

Immunotherapies, such as PD-1 inhibitors and CTLA-4 inhibitors, have revolutionized the treatment of many cancers. However, a key challenge to optimize the opportunity provided by these therapies is the dramatically varied responses among different patients, or even among different tumors in the same patient (Hamid et al. (2013) *N. Engl. J. Med.* 369:134-144; Topalian et al. (2012) *N. Engl. J. Med.* 366:2443-2454; Topalian et al. (2014) *J. Clin. Oncol.* 32:1020-1030; Hodi et al. (2010) *N. Engl. J. Med.* 363:711-723). For example, only a minority of melanoma patients benefit from PD-1 inhibitors, whereas the remainder of patients have either incomplete or no response. Various studies have identified T-cell infiltration (Tumeh et al. (2014) *Nature* 515:568-5715), mutational load/neo-antigen expression (Snyder et al. (2014) *N. Engl. J. Med.* 371:2189-2199; Van Allen et al. (2015) *Science* 350:207-211; Le et al. (2015) *N. Engl. Med.* 372:2509-2520; Rizvi et al. (2015) *Science* 348:124-128) and mutations in antigen-presentation and interferon-γ signaling pathway (Hugo et al. (2016) *Cell* 165:35-44; Wang et al. (2017) *Cancer Res.* 77:839-850; Gao et al. (2016) *Cell* 167:397-404) as determinants of immunotherapy response and resistance. Thus, although some cancers can initially respond to anti-immune checkpoint therapy, even these cancers generally become resistant to such therapies. Accordingly, there is a great need to identify the mechanisms of de novo and acquired resistance in cancers in order to develop improved diagnostic, prognostic, and therapeutic strategies.

SUMMARY OF THE INVENTION

The present invention is based, at least in part, on the discovery of a biomarker (i.e. Fbxw7), the mutation of which predicts the resistance to therapy with an immune checkpoint therapy, such as a PD-1 inhibitor, in cancers. Accordingly, the present invention relates, in part, to methods for stratifying patients who are predicted to be resistant to an immune checkpoint therapy based upon a determination and analysis of Fbxw7 according to amount (e.g., copy number or level of expression) and/or activity, such as loss or gain of function, relative to a control. Such analyses can be used to perform a number of diagnostic and prognostic assays described herein either alone or in combination with useful therapeutic regimens (e.g., based on predictions of clinical response, subject survival or relapse, timing of adjuvant or neoadjuvant treatment, etc.). In addition, methods of treating cancers, such as those that are resistant to an immune checkpoint therapy, are described herein.

In one aspect, a method of identifying the likelihood of a cancer in a subject to be resistant to an immune checkpoint therapy is provided, the method comprising a) obtaining or providing a sample comprising cancer cells from a subject having the cancer; b) measuring the presence, copy number, amount, and/or activity of Fbxw7 in the subject sample; and c) comparing the presence, copy number, amount, and/or activity of Fbxw7 in a control, wherein the absence of or a significantly decreased amount or activity of Fbxw7 in the subject sample and/or the presence of or a significantly increased amount or activity of Fbxw7 having a loss of function mutation in the subject sample relative to the control sample identifies the cancer as being less likely to be responsive to the immune checkpoint therapy; and wherein the presence of or a significantly increased amount or activity of Fbxw7 in the subject sample and/or the absence of or a decreased amount or activity of Fbxw7 having a loss of function mutation in the subject sample relative to the control sample identifies the cancer as being more likely to be responsive to the immune checkpoint therapy.

Numerous embodiments are further provided that can be applied to any aspect of the present invention and/or combined with any other embodiment described herein. For example, in one embodiment, the method further comprises recommending, prescribing, or administering the immune checkpoint therapy if the cancer is determined likely to be responsive to the immune checkpoint therapy or administering an anti-cancer therapy other than the immune checkpoint therapy as a single agent if the cancer is determined be less likely to be responsive to the immune checkpoint therapy. In another embodiment, the anti-cancer therapy other than the immune checkpoint therapy as a single agent comprises the immune checkpoint therapy. In still another embodiment, the anti-cancer therapy is selected from the group consisting of an anti-SHP2 therapy, anti-CD47 therapy, anti-MYC therapy, interferon-gamma therapy, IRF1 therapy, JAK/STAT therapy, targeted therapy, chemotherapy, radiation therapy, and/or hormonal therapy. In yet another embodiment, the anti-cancer therapy is administered to the subject in combination with the immune checkpoint therapy, optionally wherein the anti-cancer therapy is administered before, after, or concurrently with the immune checkpoint therapy. In another embodiment, the targeted therapy is an immunotherapy, such as cell-based immunotherapy, a cancer vaccine, and/or a virus. In still another embodiment, the immune checkpoint therapy inhibits an immune checkpoint, such as CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, A2Ar, and/or any combination thereof. In yet another embodiment, the immune checkpoint is PD-1, or a combination of PD-1 and CTLA-4. In another embodiment, the immune checkpoint therapy comprises an anti-PD-1 antibody, such as pembrolizumab, nivolumab, pidilizumab, AMP-224, AMP-514, and/or PDR001. In still another embodiment, the immune checkpoint therapy comprises an antibody against a PD-1 ligand, optionally wherein the PD-1 ligand is PD-L1 and/or PD-L2, such as atezolizumab, avelumab, durvalumab, and/or BMS-936559. In yet another embodiment, the control is determined from a cancerous or non-cancerous sample from the subject or a member of the same species to which the subject belongs. In another embodiment, the control is determined from a cancerous or non-cancerous sample from a member of the same species to which the subject belongs. In still another embodiment, the control does not comprise cells. In yet another embodiment, the control is a sample that comprises cells or does not comprise cells. In another embodiment, the control sample comprises cancer cells that are resistant to the immune checkpoint therapy or are not resistant to the immune checkpoint therapy. In another embodiment, the method further comprises comparing the activity and/or phosphorylation of the JAK/STAT signaling pathway in the subject sample and control sample, optionally wherein the phosphorylation of the JAK/STAT signaling pathway is determined using phosphorylation of JAK1 and/or STAT1.

In another aspect, a method of assessing the efficacy of an agent for treating a cancer in a subject, comprising a) detecting in a first subject sample comprising cancer cells maintained in the presence of the agent the presence, copy number, amount, and/or activity of Fbxw7 in the first subject sample; b) detecting the presence, copy number, amount, and/or activity of Fbxw7 in a second subsequent subject sample comprising cancer cells maintained in the absence of the test compound; and c) comparing the presence, copy number, amount and/or activity of Fbxw7 from steps a) and b), wherein the absence of or a significantly decreased amount or activity of Fbxw7 in the cancer cells of first subject sample and/or the presence of or a significantly increased amount or activity of Fbxw7 having a loss of function mutation in the cancer cells of the first subject sample, relative to at least one subsequent subject sample, indicates that the agent does not treat the cancer in the subject; and wherein the presence of or a significantly increased amount or activity of Fbxw7 in the cancer cells of the first subject sample and/or the absence of or a decreased amount or activity of Fbxw7 having a loss of function mutation in the cancer cells of the first subject sample, relative to at least one subsequent subject sample indicates that the agent treats the cancer in the subject, is provided. In one embodiment, the method further comprises comparing the activity and/or phosphorylation of the JAK/STAT signaling pathway in the first subject sample and the second subject sample, optionally wherein the phosphorylation of the JAK/STAT signaling pathway is determined using phosphorylation of JAK1 and/or STAT1.

In still another aspect, a method of assessing the efficacy of an agent for treating a cancer in a subject or prognosing progression of a cancer in a subject, comprising a) detecting in a subject sample comprising cancer cells at a first point in time the presence, copy number, amount, and/or activity of Fbxw7; b) repeating step a) during at least one subsequent point in time after administration of the agent; and c) comparing the presence, copy number, amount, and/or activity of Fbxw7 from steps a) and b), wherein the absence of or a significantly decreased amount or activity of Fbxw7 in the cancer cells of the subsequent sample and/or the presence of or a significantly increased amount or activity of Fbxw7 having a loss of function mutation in the cancer cells of the subsequent sample, relative to the sample at the first point in time, indicates that the agent does not treat the cancer in the subject; and wherein the presence of or a significantly increased amount or activity of Fbxw7 in the subsequent sample and/or the absence of or a decreased amount or activity of Fbxw7 having a loss of function mutation in the cancer cells in the subsequent sample, relative to the sample at the first point in time, indicates that the agent treats the cancer or has progressed in the subject, is provided.

As described above, numerous embodiments are contemplated for any aspect of the present invention described herein. For example, in one embodiment, the subject has undergone treatment, completed treatment, and/or is in remission for the cancer in between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject. In another embodiment, the sample comprises cells, serum, peritumoral tissue, and/or intratumoral tissue obtained from the subject. In still another embodiment, the method further comprises determining responsiveness to the therapy and/or agent by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In another embodiment, the method further comprises comparing the activity and/or phosphorylation of the JAK/STAT signaling pathway in subject sample of the first point in time, and in the subject sample of the subsequent point in time, optionally wherein the phosphorylation of the JAK/STAT signaling pathway is determined using phosphorylation of JAK1 and/or STAT1.

In yet another aspect, a cell-based assay for screening for agents that have a cytotoxic or cytostatic effect on cancer cells that are resistant to an immune checkpoint therapy comprising, contacting the cancer cell with a test agent, and determining the ability of the test agent to increase the copy number, amount, and/or activity of Fbxw7 and/or decrease the copy number, amount, and/or activity of Fbxw7 having a loss of function mutation, is provided.

As described above, numerous embodiments are contemplated for any aspect of the present invention described herein. For example, in one embodiment, the step of contacting occurs in vivo, ex vivo, or in vitro. In another embodiment, the cancer cells that are resistant to the immune checkpoint therapy are contacted with the test agent in combination with the immune checkpoint therapy, optionally wherein the test agent is administered before, after, or concurrently with the immune checkpoint therapy. In still another embodiment, a reduction in the viability or proliferation of the cancer cells is further determined. In another embodiment, the method further comprises determining an increase in the activity and/or phosphorylation of the JAK/STAT signaling pathway; optionally wherein the phosphorylation of the JAK/STAT signaling pathway is determined using phosphorylation of JAK1 and/or STAT1.

In another aspect, a method of treating a subject afflicted with a cancer that is resistant to an immune checkpoint inhibitor therapy comprising administering to the subject a therapeutically effective amount of the immune checkpoint therapy in combination with a therapeutically effective amount of an agent that increases the copy number, amount, and/or activity of Fbxw7 and/or decreases the copy number, amount, and/or activity of Fbxw7 having a loss of function mutation, thereby treating the subject afflicted with the cancer that is resistant to the immune checkpoint inhibitor therapy, is provided.

As described above, numerous embodiments are contemplated for any aspect of the present invention described herein. For example, in one embodiment, the agent is administered before, after, or concurrently with the immune checkpoint inhibitor therapy. In another embodiment, the agent comprises a nucleic acid, protein, RNA interfering agent, CRISPR guide RNA (gRNA), oligonucleotide, peptide, peptidomimetic, aptamer, antibody, or intrabody. In still another embodiment, the nucleic acid is an mRNA or cDNA. In yet another embodiment, the agent comprises wild-type Fbxw7, or a biologically active portion thereof, and/or an agent that inhibits Fbxw7 having a loss of function mutation. In another embodiment, the agent reduces the number of proliferating cells in the cancer and/or reduces the volume or size of a tumor of the cancer. In still another embodiment, the agent is administered in a pharmaceutically acceptable formulation. In yet another embodiment, anti-cancer therapy other than an immune checkpoint therapy as a single agent, optionally wherein the anti-cancer therapy is administered before, after, or concurrently with the agent and/or the immune checkpoint therapy is administered. In another embodiment, the anti-cancer therapy is selected from the group consisting of an anti-SHP2 therapy, anti-CD47 therapy, anti-MYC therapy, interferon-gamma therapy, IRF1 therapy, JAK/STAT therapy targeted therapy, chemotherapy, radiation therapy, and/or hormonal therapy. In still another embodiment, the targeted therapy is an immunotherapy, such as a cell-based immunotherapy, a cancer vaccine, and/or virus. In yet another embodiment, the immunotherapy inhibits an immune checkpoint, such as CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-1BB, OX-40, BTLA, SIRPalpha (CD47), CD48, 2B4 (CD244), B7.1, B7.2, ILT-2, ILT-4, TIGIT, HHLA2, butyrophilins, A2Ar, and/or any combination thereof. In another embodiment, the immune checkpoint is PD-1, or a combination of PD-1 and CTLA-4. In still another embodiment, the immune checkpoint therapy comprises an anti-PD-1 antibody pembrolizumab, nivolumab, pidilizumab, AMP-224, AMP-514, and/or PDR001. In yet another embodiment, the immune checkpoint therapy comprises an antibody against a PD-1 ligand, optionally wherein the PD-1 ligand is PD-L1 and/or PD-L2, such as atezolizumab, avelumab, durvalumab, and/or BMS-936559. In another embodiment, the cancer has an Fbxw7 loss of function mutation, optionally wherein the cancer is selected from the group consisting of melanoma, colorectal cancer, and uterine cancer. In still another embodiment, the subject is an animal model of cancer, such as a mouse model. In yet another embodiment, the subject is a mammal, such as a mouse or a human.

BRIEF DESCRIPTION OF FIGURES

FIG. 2A shows CT scans from a patient with metastatic melanoma who developed acquired resistance to the combination of PD-1 inhibitor nivolumab and a CTLA-4 inhibitor ipilumumab. The patient had diffuse metastatic disease (Apr. 19, 2015), all which responded to treatment except for the right adrenal mass (Mar. 24, 2016). The patient's tumor was biopsied prior to treatment and upon the development of adrenal resistance. FIG. 2B shows a comparison of inferred copy number of pre-treatment and resistant tumor. There were no significant copy number changes. FIG. 2C shows that the number of somatic mutations in pre-treatment ("primary") lesion and resistant ("metastatic") lesions are not significantly different. FIG. 2D shows that an inactivating mutation in FBXW7 is associated with resistance to PD-1 blockade. FIG. 2D shows that mutational signatures (Shukla et al. (2015) Nat Biotechnol 33:1152-1158) of pre-treatment (left) and resistant (right) are not significantly different. The mutation is strongly enriched in the resistant tumor, but is absent in the pre-treatment tumor. FIG. 2E shows a comparison of whole exome sequencing of pre-treatment and resistant (right adrenal) lesion. Two patients who developed resistance to PD-1 inhibitor had identical R505 mutations in the Fbxw7 gene. FIG. 2F shows the frequency of Fbxw7 mutations in cancer (from cBioportal.org) and the location of the Fbxw7 mutations in The Cancer Genome Atlas Project (data extracted from cBioPortal). R505 and R465 are known oncogenic, loss-of-function mutations in Fbxw7. Green: missense mutations; black: nonsense mutations. cBioPortal, 1483 samples. FIG. 2G shows that Fbxw7 is infrequently mutated in melanoma. FIG. 2H shows that Fbxw7 mutation and loss is relatively common among cancers. FIG. 2I-FIG. 2K show that an inactivating mutation in FBXW7 is associated with resistance to PD-1 blockade. FIG. 2I show CT scans from a patient with metastatic melanoma who developed acquired resistance to the PD-1 inhibitor pembrolizumab. The patient presented with diffuse metastatic disease, which responded to treatment (yellow circle; top panels) with the exception of a right adrenal mass. The patient's cervical lymph node tumor was biopsied prior to treatment and right adrenal gland (red circle; bottom panels) was biopsied upon the development of adrenal resistance. FIG. 2J shows the phylogic analysis of the somatic mutations identified by whole exome sequencing of the pre-treatment and resistant (right adrenal) biopsies. FIG. 2K shows intersection of clonal, deleterious somatic changes identified by SIFT or PolyPhen analysis with clonal somatic mutations listed in the COSMIC database.

FIG. 3A-FIG. 3C show the results of D4M3A-Cas9 (D4C9) cells implanted in C57BL/6 or nude mice followed by treatment with anti-PD1 (29F.1A12) (FIG. 3A) or control IgG antibodies (FIG. 3B) and MC38 cells were similarly implanted in C57BL/6 mice or nude mice (FIG. 3C) (given at days 9, 12, 15; depicted with black arrows for each experiment). Tumor volume was measured by calipers. FIG. 3D shows overall survival of C57BL/6 or nude mice injected with D4C9 cells treated with PD-1 inhibitor or control antibodies. $p<0.01$ compared to control IgG in the top left sub-panel. Survival of C57BL/6 (bottom left panel) or nu/nu mice (bottom right panel) inoculated with D4C9-sgCtrl cells following treatment with control IgG and anti-PD-1. For C57BL/6, n=13; nu/nu, n=3. Log-rank (Mantel-Cox) test was used to determine statistical significance (****, $P<0.0001$). FIG. 3E shows PD-L1 (CD274) surface expression in D4C9 cells edited with control or CD274 sgRNAs. FACS was performed following treatment with murine interferon gamma (100 ng/μL, 24 h). Data shown are representative of 4 independent control or PD-L1 targeting sgRNAs. FIG. 3F shows growth of D4C9 control and sgPD-L1 cells following treatment with anti-PD-1 or control antibodies. *, $p<0.05$ compared to control IgG. ns, not significant compared to control IgG.

FIG. 4A and FIG. 4B show results from a Western blot evaluating the effect of sgRNA targeting Fbxw7 on c-Myc expression in D4C9 cells. The Western blot results of D4C9 cells transduced with sgRNA targeting Fbxw7 were confirmed with 3 additional sgRNAs. In particular, Fbxw7 was deleted in D4C9 cells using CRISPR/Cas9 using the indicated sgRNAs. Deletion of Fbxw7 was confirmed by immunoprecipitation of Fbxw7 followed by Western blot with Fbxw7 antibodies (top). sgRNAs #9, 10, 11, 12 efficiently suppressed the expression of Fbxw7. FIG. 4B shows that efficient knockout of Fbxw7 was associated with an increase in the expression of the Fbxw7 target c-Myc. FIG. 4B shows a Western blot of c-Myc and COX IV (loading control) expression performed on cell lysates (WCL). FIG. 4F presents graphs showing viable cell number of D4C9 derivatives transduced with sgRNAs targeting Fbxw7. Graphs show mean values. Error bars, s.e.m. (n=4 biologically independent samples per group). FIG. 4G shows the growth of D4C9 derivatives transduced with sgRNAs targeting Fbxw7 in C57BL/6 animals. Anti-PD-1 or control immunoglobulin (Ctrl IgG) were administered at Days 9, 12, 15 (black arrowheads) after implantation. Graphs show mean values, with error bars depicting s.e.m. (n≥20 biologically independent samples per group). Significant differences between groups were calculated by one-way ANOVA with correction with Tukey's multiple comparison test. **, $P<0.0001$; *, $P<0.001$; *, $P<0.05$. FIG. 4H shows survival of C57BL/6 mice implanted with D4C9 derivatives (n=10 per group). Significant differences between groups were calculated by Log-rank (MantelCox) tests with Bonferroni correction. *, $P<0.001$. FIG. 4I shows Western blot of D4C9 cells transduced with empty vector, wild-type Fbxw7 or Fbxw7(R505C). FIG. 4J shows the growth of D4C9 derivatives transduced with empty vector, wild-type Fbxw7 or Fbxw7(R505C) in C57BL/6 animals. Anti-PD-1 or control immunoglobulin (Ctrl IgG) were administered at Days 9, 12, 15 (black arrowheads) after implantation. Graphs show mean values, with error bars depicting s.e.m. (n=20 per group). Significant differences between groups were calculated by one-way ANOVA with correction with Tukey's multiple comparison test. , $P<0.0001$; , $P<0.01$. *, $P<0.05$. FIG. 4K shows survival of C57BL/6 mice implanted with D4C9 derivatives (n=10 per group). Significant differences between groups were calculated by Log-rank (Mantel-Cox) tests with Bonferroni correction. *, $P<0.05$; ***, $P<0.001$. FIG. 4L and FIG. 4M show the tumor volume after treatment of C57BL/6 (FIG. 4L) or nu/nu (FIG. 4M) mice following control IgG and anti-PD-1 treatment (black arrowheads). To permit direct comparison of growth in C57BL/6 and nu/nu mice, data are represented as the percentage of change in tumor volume relative to day 9 (first injection of anti-PD-1). Graphs show mean values, with error bars depicting s.e.m. (n=5 biologically independent samples per group). Significant differences between groups were calculated by t-test. *, $P<0.05$. FIG. 4O shows survival of C57BL/6 mice inoculated with control or Fbxw7-deficient MC38 cells following treatment with control IgG and anti-PD-1 treatment (black arrowheads). **, $P<0.01$ by log-rank (Mantel-Cox) test (n=10 per group).

FIG. 5A-FIG. 5H show that loss of Fbxw7 is associated with altered immune microenvironment. FIG. 5A shows the identification of immune cells significantly altered in Fbxw7-mutant versus wild-type tumors prior to anti-PD-1 antibodies using the NanoString Immune Profiling Panel. CD8+ T cells were significantly depleted in Fbxw7-mutant tumors. FIG. 5B shows that Fbxw7 is required for induction of T-cell signatures by PD-1 antibodies. FIG. 5C-FIG. 5H show that loss of Fbxw7 is associated with diminished T cell infiltration and decreased interferon γ signaling. FIG. 5C shows a heat map showing relative expression (log 2 fold change of D4C9-sgCtrl pretreatment) of Nanostring immune cell population transcriptional signatures in Fbxw7 deficient and control D4C9 tumors prior (Day 9) or after (Day 16) treatment with antiPD-1 (n=3-5 per group). FIG. 5D shows statistical significance of differences between D4C9 sgControl and sgFbxw7 tumors pre- or post-treatment with anti-PD-1. P-value calculated using a permutation test, as described in the nCounter Advanced Analysis Plugin for nSolver Software User Manual (n=3-5 per group). FIG. 5E shows Cd3e, Cd3g, Cd8a, Cd8b1 and Gzmk transcript counts in Fbxw7-deficient and control D4C9 tumors pre- or post-treatment with anti-PD-1. Each dot represents an independent biologic replicate. One-way ANOVA followed by Sidak's multiple comparison test was used to statistical significance (, $P<0.01$, *, $P<0.001$). FIG. 5F shows representative immunohistochemical staining sections from wild-type and Fbxw7-deficient D4C9 tumors with anti-CD3 and anti-CD8 antibodies. FIG. 5G shows the number of CD3 or CD8 positive cells per square mm of D4C9 tumors obtained from C57BL/6 mice prior (Day 9) or after (Day 16) treatment with antiPD-1. Each dot represents a different biological replicate (n=3-6 per condition/drug treatment). Error bars depict s.e.m. Significant differences between groups were calculated by one way ANOVA with the Sidak's multiple comparison test correction. **, $P<0.01$; *, $P<0.05$.

FIG. 5H shows a heat map showing expression of IFNγ responsive genes in Fbxw7-deficient and control D4C9 tumors pre- or post-treatment with anti-PD-1.

FIG. 6A shows the effect of Fbxw7 deletion on induction of MHC Class I (H-2d$^b$) expression by interferon α, β and γ. Expression of MHC class I (H-2db) in D4C9sgFbxw7#12 cells and D4C9-sgCtrl cells treated with IFNα, β or γ (250 pM) for 24 h. rMFI (median fluorescent intensity) was measured relative to sgCtrl (n=3-4 per group). Oneway ANOVA was used to determine statistical significance (*, P<0.05, , P<0.01). FIG. 6D-FIG. 6O show that Fbxw7 is necessary for interferon γ signaling. FIG. 6D and FIG. 6E show RNA-seq analysis of Fbxw7-deficient and control D4C9 cells treated with IFNγ (10 ng/ml) for 24 h. FIG. 6D presents Venn diagram showing significantly altered genes (false discovery rate q<0.25) in D4C9-sgFbxw7#9 and D4C9-sgFbxw7#12 cells compared to control cells in presence of IFNg (n=3). FIG. 6E shows the most significantly downregulated gene sets in D4C9-sgFbxw7#9 cells compared to control cells in presence of IFNγ (n=3; reported q value is based on Wald statistical test). FIG. 6F shows Western blot of Jak/STAT signaling pathway components in D4C9 cells transduced with control or Fbxw7 sgRNAs following IFNγ (10 ng/ml) treatment for indicated time points. For phosphorylated and total Jak1 detection, Jak1 was immunoprecipitated followed by blotting. Whole cell lysates (WCL) were used to evaluate other proteins. FIG. 6G shows Western blot of control and Fbxw7-deficient D4C9 cells transduced with IRF1 expressing virus. Cells were treated with IFNγ (10 ng/mL) or vehicle control for 24 h as indicated. FIG. 6H shows growth of control and Fbxw7-deficient D4C9 derivatives in C57BL/6 mice treated with control IgG or anti-PD-1 (black arrowheads). Graphs show mean values. Error bars, s.e.m. (n=10 per group). Statistical significance was calculated using oneway ANOVA with Sidak's multiple comparison tests. *, P<0.001. FIG. 6I shows survival of C57BL/6 mice with D4C9 tumors after anti-PD-1 treatment. Statistical significance was calculated using the Log-rank (Mantel-Cox) test with Bonferroni multiple comparison correction. n=5 per group. ***, P<0.001. FIG. 6J-FIG. 6O show that Fbxw7 is necessary for interferon γ signaling. FIG. 6J shows the top downregulated gene sets in D4C9-sgFbxw7#12 cells compared to control cells in presence of IFNg (n=3 each condition). FIG. 6K shows PD-L1 cell surface expression in Fbxw7 deficient and control D4C9 cells treated with vehicle or IFNg (10 ng/ml) for 24 h. Data were normalized to D4C9-sgCtrl. t test was used to determine statistical significance of Fbxw7-deficient cells relative to sgControl cells (*, P<0.05, , P<0.01, **, P<0.0001, n=4 per condition). FIG. 6L shows CD47 cell surface expression in Fbxw7-deficient and control D4C9 cells treated with vehicle or IFNγ (10 ng/ml) for 24 h. Data were normalized to D4C9-sgCtrl. t test was used to determine statistical significance of Fbxw7-deficient cells relative to control transduced cells (n=5 per condition). FIG. 6M shows expression of PD-L1 and MHC class I (H-2db) in Fbxw7-deficient and control D4C9 cells following expression of IRF1. Where indicated, cells are treated with IFNγ (long/ml) for 24 h. (n=3 per condition). Median fluorescent intensity (rMFI) of 3 biologically independent experiments are shown at right panel. FIG. 6N shows Western blot of D4C9 cells transduced with empty vector or Fbxw7(R505C) upon treatment with IFNγ (10 ng/mL) for the indicated time. FIG. 6O shows surface expression of MHC class I (H-2db) following IFNγ (10 ng/mL) treatment of D4C9 cells transduced with empty vector or Fbxw7(R505C) (n=3 per condition). rMFI (median fluorescent intensity) was measured relative to vector (n=3 per group). t test was used to determine statistical significance (*, P<0.05).

FIG. 7A shows Spearman correlation of FBXW7 mRNA levels with CD8A mRNA levels across TCGA cancers. Each dot represents a cancer type in TCGA, red dots indicate significant correlation with P<0.05. SKCM, skin cutaneous melanoma; BRCA, breast cancer. FIG. 7B shows survival of melanoma patients in TCGA (n=425 patients) divided into highest expressing tumors (50%) vs lowest expressing tumors (50%). Statistical comparison was done with log-rank test. FIG. 7C shows gene set enrichment analysis comparing gene expression of FBXW7-mutant and wild-type tumors. Highlighted in red are the expected increases of the interferon response and inflammatory signatures in FBXW7-mutated cancer. NES: Normalized Enrichment Score. FIG. 7D shows enrichment score plots for the indicated gene sets. Vertical bars refer to individual genes in a gene set and their position reflects the contribution of each gene to the ES. FIG. 7E shows association between FBXW7 status (wild-type or mutant) and response to immune checkpoint blockade or clinical benefit. Using RECIST criteria, "responders" and "non-responders" were defined as individuals having a best radiographic response of complete or partial response, or progressive disease, respectively. "Clinical benefit" was defined as a best radiographic response of partial or complete response, or stable disease and a PFS of ≥180 days. Fisher's Exact test was used to determine statistical significance OR: odds ratio. FIG. 7F shows Kaplan-Meier curves representing the overall survival of melanoma patients harboring wild-type FBXW7 or mutant FBXW7. Log-rank (Mantel-Cox) test was used to determine statistical significance. FIG. 7G and FIG. 7H show that Fbxw7 mutations are associated with diminished interferon signaling and resistance to immunotherapy. FIG. 7G shows hallmark gene sets enriched in TCGA melanoma samples with FBXW7 mutations relative to non-mutated samples. NES, normalized enrichment score. FDR, false discovery rate. Highlighted in red are the expected increase of the Myc signatures in FBXW7 mutated cancer. FIG. 7H shows enrichment score plots for the Myc target gene set. Vertical bars refer to individual genes in a gene set and their position reflects the contribution of each gene to the ES.

FIG. 8 shows gating strategy used to detect anti-PD-L1 and MHC class I. Cells were gated on the basis of cell size (FSC-A) and scatter (SSC-A) as depicted.

Figure 1:
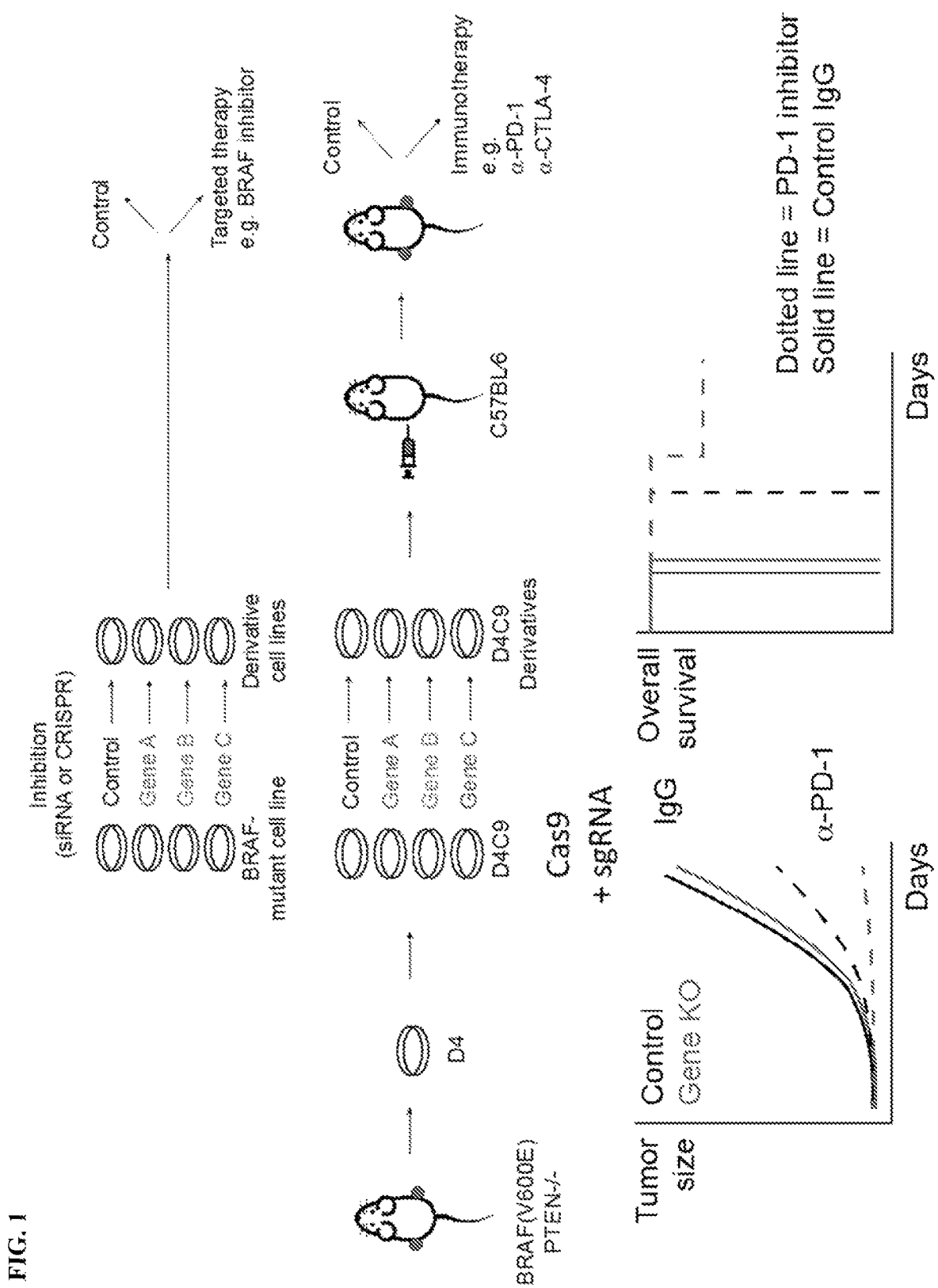
FIG. 1 shows a schematic of a CRISPR/Cas9 model to functionally evaluate genes associated with immune checkpoint therapy response and resistance. In general, biopsies are obtained from cancer patients, such as melanoma patients, prior to immunotherapy or at time of resistance. Mutations associated with treatment response or resistance are knocked out by CRISPR/Cas9 in cells. The response of formed tumors to immune checkpoint therapy, such as anti-PD-1 antibody treatment, or control therapy, such as control antibodies, can be determined measuring tumor size or comparing overall mouse survival. In one embodiment, a murine melanoma cell line was obtained from BRAF (V600E) PTEN−/− mice bred on a C57BL/6 background. Cells were modified by the introduction of Cas9, generating D4C9 cells, which are genetically identical to C57BL/6 mice. Derivative cell lines lacking candidate treatment resistance genes are then created by the introduction of specific sgRNAs into D4C9 cells. The response of wild-type and mutant tumors to anti-PD-1 or control antibodies is determined by measuring tumor size or comparing overall mouse survival.

For any figure showing a bar histogram, curve, or other data associated with a legend, the bars, curve, or other data presented from left to right for each indication correspond directly and in order to the boxes from top to bottom, or from left to right, of the legend.

In addition, the anti-PD1 blocking antibody used in the experiments was clone 29F.1A12 kindly donated by Dr. Gordon Freeman (Dana-Farber Cancer Institute).

DETAILED DESCRIPTION OF THE INVENTION

The present invention is based, at least in part, on the discovery that FBXW7 is a biomarker, the mutation of which predicts the resistance of cancers (e.g., melanoma, colorectal cancer, uterine cancer, and the like) to treatment with an immune checkpoint therapy (e.g., PD-1 inhibitor), and the resistance is reversible with various modalities, such as wild-type Fbxw7, a SHP2 inhibitor, and the like. Accordingly, the present invention relates, in part, to methods for stratifying patients who are predicted to be resistant to an immune checkpoint therapy based upon a determination and analysis of Fbxw7 and/or loss of function mutants of Fbxw7 according to amount (e.g., copy number or level of expression) and/or activity, relative to a control. Such analyses can be used to perform a number of diagnostic and prognostic assays described herein either alone or in combination with useful therapeutic regimens (e.g., based on predictions of clinical response, subject survival or relapse, timing of adjuvant or neoadjuvant treatment, etc.). The present invention also relates, in part, to methods for treating a subject afflicted with an Fbxw7$^{mut}$ cancer, such as a cancer that is resistant to an immune checkpoint therapy like a PD-1 inhibitor, such as by administering to the subject a therapeutically effective amount of the PD-1 inhibitor in combination with a therapeutically effective amount of an agent that increases the copy number, amount, and/or activity of functional Fbxw7 and/or an agent that restores downstream functions of functional Fbxw7, such as SHP2 inhibitors, CD47 inhibitors, and/or MYC inhibitors.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or even greater than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl.*

Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of resistance to an immune checkpoint therapy in a cancer. Biomarkers can include, without limitation, nucleic acids (e.g., genomic nucleic acids and/or transcribed nucleic acids) and proteins, including those shown in Table 1, the Examples, and the Figures. Many biomarkers listed in Table 1 are also useful as therapeutic targets. In one embodiment, such targets are Fbxw7 members shown in Table 1.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. As used herein, the term "cancer" includes premalignant as well as malignant cancers. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer whose phenotype is determined by the method of the present invention is an epithelial cancer such as, but not limited to, bladder cancer, breast cancer, cervical cancer, colon cancer, colorectal cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of melanoma and its subtypes.

In some embodiment, the cancer is melanoma. The term "melanoma" generally refers to cancers derived from melanocytes. Although melanocytes are predominantly located in skin, they are also found in other parts of the body, including the eye and bowel. Although cutaneous melanoma is most common, melanoma can originate from any melanocyte in the body. Though melanoma is less than five percent of the skin cancers, it is the seventh most common malignancy in the U.S. and is responsible for most of the skin cancer related deaths. The incidence has increased dramatically in the last several decades due to altered sun exposure habits of the population. Several hereditary risk factors are also known. Other important risk factors are the number of pigment nevi, the number dysplastic nevi, and skin type. An increased risk is coupled to many nevi, both benign and dysplastic, and fair skin. Familial history of malignant melanomas is a risk factor, and approximately 8-12% of malignant melanoma cases are familial. Additional details are well known, such as described in US Pat. Publs. 2012-0269764 and 2013-0237445.

Malignant melanomas are clinically recognized based on the ABCD(E) system, where A stands for asymmetry, B for border irregularity, C for color variation, D for diameter >5 mm, and E for evolving. Further, an excision biopsy can be performed in order to corroborate a diagnosis using microscopic evaluation. Infiltrative malignant melanoma is traditionally divided into four principal histopathological subgroups: superficial spreading melanoma (SSM), nodular malignant melanoma (NMM), lentigo maligna melanoma (LMM), and acral lentiginous melanoma (ALM). Other rare types also exists, such as desmoplastic malignant melanoma. A substantial subset of malignant melanomas appear to arise from melanocytic nevi and features of dysplastic nevi are often found in the vicinity of infiltrative melanomas. Melanoma is thought to arise through stages of progression from normal melanocytes or nevus cells through a dysplastic nevus stage and further to an in situ stage before becoming invasive. Some of the subtypes evolve through different phases of tumor progression, which are called radial growth phase (RGP) and vertical growth phase (VGP).

Malignant melanomas are staged according to the American Joint Committee on Cancer (AJCC) TNM-classification system, where Clark level is considered in T-classification. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ.

Stages I and II represent no metastatic disease and for stage I (T1a/b-2a,N0,M0) prognosis is very good. The 5-year survival for stage I disease is 90-95%, for stage II (T2b-4-b,N0,M0) the corresponding survival rate ranges from 80 to 45%. Stages III (T1a-4-b,N1a-3,M0) and IV (T(aII),N(aII),M1a-c) represent spread disease, and for these stages 5-year survival rates range from 70 to 24%, and from 19 to 7%, respectively. "Clark's level" is a measure of the layers of skin involved in a melanoma and is a melanoma prognostic factor. For example, level I involves the epidermis. Level II involves the epidermis and upper dermis. Level III involves the epidermis, upper dermis, and lower dermis.

Level IV involves the epidermis, upper dermis, lower dermis, and subcutis. When the primary tumor has a thickness of >1 mm, ulceration, or Clark level IV-V, sentinel node biopsy (SNB) is typically performed. SNB is performed by identifying the first draining lymph node/s (i.e., the SN) from the tumour. This is normally done by injection of radiolabelled colloid particles in the area around the tumour, followed by injection of Vital Blue dye. Rather than dissection of all regional lymph nodes, which was the earlier standard procedure, only the sentinel nodes are generally removed and carefully examined. Following complete lymph node dissection is only performed in confirmed positive cases.

In addition to staging and diagnosis, factors like T-stage, Clark level, SNB status, Breslow's depth, ulceration, and the like can be used as endpoints and/or surrogates for analyses according to the present invention. For example, patients who are diagnosed at an advanced stage with metastases generally have a poor prognosis. For patients diagnosed with a localized disease, the thickness of the tumor measured in mm (Breslow) and ulceration can be endpoints for prognosis. Breslow's depth is determined by using an ocular micrometer at a right angle to the skin. The depth from the granular layer of the epidermis to the deepest point of invasion to which tumor cells have invaded the skin is directly measured. Clark level is important for thin lesions (<1 mm). Other prognostic factors include age, anatomic site of the primary tumor and gender. The sentinel node (SN) status can also be a prognostic factor, especially since the 5-year survival of SN-negative patients has been shown to be as high as 90%. Similarly, overall survival (OS) can be used as a standard primary endpoint. OS takes in to account time to death, irrespective of cause, e.g. if the death is due to cancer or not. Loss to follow-up is censored and regional recurrence, distant metastases, second primary malignant melanomas and second other primary cancers are ignored. Other surrogate endpoints for survival can be used, as described further herein, such as disease-free survival (DFS), which includes time to any event related to the same cancer, i.e. all cancer recurrences and deaths from the same cancer are events.

In addition to endpoints, certain diagnostic and prognostic markers can be analyzed in conjunction with the methods described herein. For example, lactate dehydrogenase (LDH) can be measured as a marker for disease progression. Patients with distant metastases and elevated LDH levels belong to stage IV Mlc. Another serum biomarker of interest is S100B. High S100B levels are associated with disease progression, and a decrease in the S100B level is an indicator of treatment response. Melanoma-inhibiting activity (MIA) is yet another serum biomarker that has been evaluated regarding its prognostic value. Studies have shown that elevated MIA levels are rare in stage I and II disease, whereas in stage III or IV, elevation in MIA levels can be seen in 60-100% of cases. Additional useful biomarkers include RGS1 (associated with reduced relapse-free survival (RFS)), osteopontin (associated with both reduced RFS and disease-specific survival (DSS), and predictive of SLN metastases), HER3 (associated with reduced survival), and NCOA3 (associated with poor RFS and DSS, and predictive of SLN metastases). In addition, HMB-45, Ki-67 (MD31), MITF and MART-1/Melan-A or combinations of any described marker may be used for staining (Ivan & Prieto, 2010, Future Oncol. 6(7), 1163-1175; Linos et al., 2011, Biomarkers Med. 5(3) 333-360). In a literature review Rothberg et al. report that melanoma cell adhesion molecule (MCAM)/MUC18, matrix metalloproteinase-2, Ki-67, proliferating cell nuclear antigen (PCNA) and p16/INK4A are predictive of either all-cause mortality or melanoma specific mortality (Rothberg et al., 2009 J. Nat. Canc. Inst. 101(7) 452-474).

Currently, the typical primary treatment of malignant melanoma is radical surgery. Even though survival rates are high after excision of the primary tumour, melanomas tend to metastasize relatively early, and for patients with metastatic melanoma the prognosis is poor, with a 5-year survival rate of less than 10%. Radical removal of distant metastases with surgery can be an option and systemic chemotherapy can be applied, but response rates are normally low (in most cases less than 20%), and most treatment regiments fail to prolong overall survival. The first FDA-approved chemotherapeutic agent for treatment of metastatic melanoma was dacarbazine (DTIC), which can give response rates of approximately 20%, but where less than 5% may be complete responses. Temozolamid is an analog of DTIC that has the advantage of oral administration, and which have been shown to give a similar response as DTIC. Other chemotherapeutic agents, for example different nitrosureas, cisplatin, carboplatin, and vinca alkaloids, have been used, but without any increase in response rates. Since chemotherapy is an inefficient treatment method, immunotherapy agents have also been proposed. Most studied are interferon-alpha and interleukin-2. As single agents they have not been shown to give a better response than conventional treatment, but in combination with chemotherapeutic agents higher response rates have been reported. For patients with resected stage IIB or III melanoma, some studies have shown that adjuvant interferon alfa has led to longer disease free survival. For first- or second-line stage III and IV melanoma systemic treatments include: carboplatin, cisplatin, dacarbazine, interferon alfa, high-dose interleukin-2, paclitaxel, temozolomide, vinblastine or combinations thereof (NCCN Guidelines, ME-D, MS-9-13). Recently, the FDA approved Zelboraf™ (vemurafenib, also known as INN, PLX4032, RG7204 or R05185426) for unresectable or metastatic melanoma with the BRAF V600E mutation (Bollag et al. (2010) *Nature* 467:596-599 and Chapman et al. (2011) *New Eng. J. Med.* 364:2507-2516). Another recently approved drug for unresectable or metastatic melanoma is Yervoy® (ipilimumab) an antibody which binds to cytotoxic T-lymphocyte-associated antigen 4 (CTLA-4) (Hodi et al. (2010) *New Eng. J. Med.* 363:711-723). Others recently reported that patients with KIT receptor activating mutations or over-expression responded to Gleevac® (imatinib mesylate) (Carvajal et al. (2011) *JAMA* 305:2327-2334). In addition, radiation treatment may be given as an adjuvant after removal of lymphatic metastases, but malignant melanomas are relatively radioresistant. Radiation treatment might also be used as palliative treatment. Melanoma oncologists have also noted that BRAF mutations are common in both primary and metastatic melanomas and that these mutations are reported to be present in 50-70% of all melanomas. This has led to an interest in B-raf inhibitors, such as sorafenib, as therapeutic agents.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-off point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer. Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

The term "Fbxw7" refers to F-box/WD repeat-containing protein 7 protein as well as the Fbxw7 gene (also known as F-Box Protein FBX30, SEL-10, HCdc4, FBW7, and HAgo), depending on the context. Fbxw7 is a member of the F-box protein family, which is characterized by an approximately 40 amino acid motif, the F-box and 7 tandem WD40 repeats. Mutations in this gene are detected in ovarian and breast cancer cell lines, implicating the gene's potential role in the pathogenesis of human cancers. Multiple transcript variants encoding different isoforms, and orthologues in different species can been found, and are exemplified herein, without limitation, in Table 1.

The term "loss of function mutation" for a biomarker, such as Fbxw7, refers to any mutation in the biomarker, such as an Fbxw7-related nucleic acid or protein, that results in reduced or eliminated biomarker protein amounts and/or function. For example, nucleic acid mutations include single-base substitutions, multi-base substitutions, insertion mutations, deletion mutations, frameshift mutations, missesnse mutations, nonsense zmutations, splice-site mutations, epigenetic modifications (e.g., methylation, phosphorylation, acetylation, ubiquitylation, sumoylation, histone acetylation, histone deacetylation, and the like), and combinations thereof. In some embodiments, the mutation is a "nonsynonymous mutation," meaning that the mutation alters the amino acid sequence of the biomarker. Such mutations reduce or eliminate biomarker protein amounts and/or function by eliminating proper coding sequences required for proper biomarker protein translation and/or coding for biomarker proteins that are non-functional or have reduced function (e.g., deletion of enzymatic and/or structural domains, reduction in protein stability, alteration of sub-cellular localization, and the like). Such mutations are well-known in the art. In addition, a representative list describing a wide variety of structural mutations correlated with the functional result of reduced or eliminated biomarker protein amounts and/or function is described in the Tables and the Examples.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "JAK/STAT therapy" encompasses any therapy that modulates the presence, copy number, amount, and/or activity of the JAK/STAT signaling pathway. The term also encompasses any therapy that modulates the phosphorylation level of any member of the JAK/STAT signaling pathway. For example, the term includes a therapy that modulates the phosphorylation level of JAK1 and/or STAT1. In some embodiments, JAK/STAT therapy may increase the presence, copy number, amount, and/or activity of the JAK/STAT signaling pathway.

The term "interferon-gamma therapy" encompasses any therapy that modulates the presence, copy number, amount, and/or activity of IFNγ. In some embodiments, the interferon-gamma therapy may increase the presence, copy number, amount, and/or activity of IFNγ.

The term "IRF1 therapy" encompasses any therapy that modulates the presence, copy number, amount, and/or activity of IRF1 (Interferon Regulatory Factor 1). In some embodiments, the IRF1 therapy may increase the presence, copy number, amount, and/or activity of IRF1.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, A2Ar, and/or any combination thereof (see, for example, WO 2012/177624). The term further encompasses biologically active protein fragments, as well as nucleic acids encoding full-length immune checkpoint proteins and biologically active protein fragments thereof. In some embodiment, the term further encompasses any fragment according to homology descriptions provided herein.

The term "immune checkpoint inhibitor" or "immune checkpoint therapy" refers to the use of agents that inhibit immune checkpoint nucleic acids and/or proteins. Inhibition of one or more immune checkpoints can block or otherwise neutralize inhibitory signaling to promote immunomodulation. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins that block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to immune checkpoint proteins and its natural receptor(s); nucleic acid molecules that block immune checkpoint nucleic acid transcription or translation; and the like. Such agents can directly block the interaction between the one or more immune checkpoint proteins and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "PD-1 inhibitor" refers to certain PD-1 agents that can bind to PD-1 and/or one or more of its ligands and inhibit and/or block its interactions with one ore more of its ligands. For example, PD-1 inhibitors can inhibit and/or block PD-1 binding with one or both of its ligands. Direct PD-1 combination inhibitors are well-known in the art, especially since the natural binding partners of PD-1 (e.g., PD-L1 and PD-L2), PD-L1 (e.g., PD-1 and B7-1), and PD-L2 (e.g., PD-1 and RGMb) are known. In some embodiments, an anti-PD-1 antibody is selected from the group consisting of: anti-PD-1 antibodies that inhibit and/or block the interaction between PD-1 and PD-L1 without inhibiting and/or blocking the interaction between PD-1 and PD-L2; anti-PD-1 antibodies that inhibit and/or block the interaction between PD-1 and PD-L2 without inhibiting and/or blocking the interaction between PD-1 and PD-L1; and anti-PD-1 antibodies that inhibit and/or block both the interaction between PD-1 and PD-L1 and the interaction between PD-L1 and PD-L2. Examples of inhibitors include, without limitation, pembrolizumab, nivolumab, pidilizumab, AMP-224, AMP-514, and PDR001. In some embodiments the inhibitor is an antibody against a PD-1 ligand, such as PD-L1. In some such embodiments the inhibitor is, for example and without limitation, atezolizumab, avelumab, durvalumab, or BMS-936559. In some embodiments the inhibitor is an antibody against PD-L2.

The term "PD-1" refers to a member of the immunoglobulin gene superfamily that functions as a coinhibitory receptor having PD-L1 and PD-L2 as known ligands. PD-1 was previously identified using a subtraction cloning based approach to select for proteins involved in apoptotic cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). Through such mechanisms, PD-1 inhibits the immune system, preventing autoimmune diseases, but it also inhibits the immune system from responding to cancer cells. In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker are available to the public at the GenBank database under NM_005018.2 and NP_005009.2 (see also Ishida et al. (1992) 20 EMBO J 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) Genomics 23:704; and U.S. Pat. No. 5,698,520). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6): 285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), monkey PD-1 (NM_001114358.1 and NP_001107830.1), dog PD-1 (XM_543338.4 and XP_543338.3), cow PD-1 (NM_001083506.1 and NP_001076975.1), and chicken PD-1 (XM_422723.3, XP_422723.2, XM_004943337.1, and XP_004943394.1).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. PD-1 transmits an inhibitory signal to an immune cell in a manner similar to CTLA4. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) J. Exp. Med. 192:1027 for sequence data) and PD-L2 (See Latchman et al. (2001) Nat. Immunol. 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see, Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1 (CD80), B7-2 (CD86), inducible costimulatory ligand (ICOS-L), B7-H3, B7-H4, VISTA, B7-H6, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (see the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the Cl-set within the Ig superfamily. Other IgC domains fall within other sets. IgV domains also share sequence patterns and are called V set domains. IgV domains are longer than IgC domains and contain an additional pair of β strands.

The term "PD-L1" refers to a specific PD-1 ligand. Two forms of human PD-L1 molecules have been identified. One form is a naturally occurring PD-L1 soluble polypeptide, i.e., having a short hydrophilic domain at the COOH-terminal end and no transmembrane domain, and is referred to herein as PD-L1S. The second form is a cell-associated polypeptide, i.e., having a transmembrane and cytoplasmic domain, referred to herein as PD-L1M. The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and X_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two B sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the Cl set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, PD-L2 polypeptides can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a biological function, such as the function of a protein and/or binding of one protein to another, is inhibited if it is decreased as compared to a reference state, such as a control like a wild-type state or a state in the absence of an applied agent. For example, the binding of a PD-1 protein to one or more of its ligands, such as PD-L1 and/or PD-L2, and/or resulting PD-1 signaling and immune effects is inhibited or deficient if the binding, signaling, and other immune effects are decreased due to contact with an agent, such as an anti-PD-1 antibody, in comparison to when the PD-1 protein is not contacted with the agent. Such inhibition or deficiency can be induced, such as by application of agent at a particular time and/or place, or can be constitutive, such as by continual administration. Such inhibition or deficiency can also be partial or complete (e.g., essentially no measurable activity in comparison to a reference state, such as a control like a wild-type state). Essentially complete inhibition or deficiency is referred to as blocked. In some embodiments, inhibition that is incomplete, such as partial blocking, is determined to have at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, 2×, 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 105×, 110×, 120×, 125×, 150×, 200×, 250×, 300×, 350×, 400×, 450×, 500×, 600×, 700×, 800×, 900×, 1000×, or greater, or any range in between, inclusive, less binding, signaling, immune effect, etc. in the experimental state, such as the presence of an anti-PD-1 antibody, as compared to a reference state, such as the absence of the anti-PD-1 antibody. Such percentage changes apply equally well to other relevant metrics, such as an anti-PD-1 antibody of interest relative to a reference anti-PD-1 antibody of interest, competition assay kinetic metrics, binding affinity metrics, and the like. Similarly, such percentage changes apply equally well when comparing among hosts, such as mouse versus mouse or human versus human proteins and/or cells, or when comparing between hosts, such as human antibody against mouse proteins, human antibody against mouse proteins having human epitopes, and the like.

Similarly, a biological function, such as the function of a protein, is inhibited if it is decreased as compared to a reference state, such as a control like a wild-type state. For example, activity of a mutant Fbxw7 and/or wild type Fbxw7 that is contacted with an inhibitor is inhibited or deficient if the activity is decreased due to the mutation and/or contact with the inhibitor, in comparison to the wild-type Fbxw7 and/or Fbxw7 not contacted with the inhibitor. Such inhibition or deficiency can be induced, such as by application of agent at a particular time and/or place, or can be constitutive, such as by a heritable mutation. Such inhibition or deficiency can also be partial or complete (e.g., essentially no measurable activity in comparison to a reference state, such as a control like a wild-type state). Essentially complete inhibition or deficiency is referred to as blocked.

Inhibitors of biomarkers of the present invention are well-known in the art. For example, representative examples of Myc inhibitors include 7-nitro-N-(2-phenylphenyl)-2,1,3-benzoxadiazol-4-amine (10074-G5) (Clausen D M et al, (2010) J. Pharmacol. Exp. Ther. 335(3):715-27), thioxothiazolidinone [Z-]-5-[4-ethylbenzylidene]-2-thioxo-1,3-thiazolidin-4-one (10058-F4) (Clausen et al (2010) J. Pharmacol. Exp. Ther. 335(3):715-27; Lin C P et al (2007) Anticancer Drugs, 18(2): 161-70; Huang et al (2006) Exp. Hematol. 34(11): 1480-9), 4-phenylbutyrate (phenylbutyrate) (Engelhard et al (1998) J. Neurooncol. 37(2):97-108), Compound 0012 (Hurley et al (2010) J. Vasc. Res. 47(1): 80-90), curcumin (Aggarwal et al (2005) Clin. Cancer Res. 11(20):7490-8), magnesium hydroxide (Mori et al (1997) J. Cell. Biochem. Suppl. 27:35-41), BP-1-102 (Zhang et al (2012) Proc. Natl. Acad. Sci. U.S.A. 109(24): 9623-8), WP1 193 (Sai et al (2012) J. Neurooncol. 107(3): 487-501), BP-1-107 (Page et al (2012) J. Med. Chem. 55(3): 1047-55), BP-1-108 (Page et al (2012) J. Med. Chem. 55(3): 1047-55), SF-1-087 (Page et al (2012) J. Med. Chem. 55(3): 1047-55), SF-1-088 (Page et al (2012) J. Med. Chem. 55(3): 1047-55), STX-0119 (Ashizawa et al (2011) Int. J. Oncol. 38(5): 1245-52), substituted thiazol-4-one compounds (U.S. Pat. No. 7,872,027), (Z,E)-5-(4-ethylbenzylidene)-2-thioxothiazolidin-4-one (10058-F4) (U.S. Pat. No. 7,026,343), S2T1-60TD (U.S. Publication No. 20120107317A1), Quarfloxin (CX-3543) (U.S. Publication No. 20120107317A1), benzoylanthranilic acid (U.S. Publication No. 20120107317A1), cationic porphyrin TMPyP4 (U.S. Publication No. 20120107317A1), tyrphostin and tryphostin-like compounds (European Patent No. EP2487156A1), AG490 (European Patent No. EP2487156A1), FBXW-7 expression vectors (Ishikawa Y et al, supra), and siRNAs targeting Myc transcript (Id.).

Similarly, representative examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "overexpression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as a PD-1 pathway inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or underactivity, emergence, expression, growth, remission, recurrence or resistance of tumors before, during or after therapy, for determining the likelihood of response of a cancer to an IL3-conjugated toxin. Such predictive use of the biomarker may be confirmed by, e.g., (1) increased or decreased copy number (e.g., by FISH, FISH plus SKY, single-molecule sequencing, e.g., as described in the art at least at Augustin et al. (2001) *J. Biotechnol.*, 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular IL3-conjugated toxin treatment or non-IL3-conjugated toxin treatment or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., $FBW7^{mut}$ cancers), development of one or more clinical factors, or recovery from the disease.

The term "response to anti-cancer therapy" relates to any response of the hyperproliferative disorder (e.g., cancer) to an anti-cancer agent, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., an anti-SHP2 therapy, anti-CD47 therapy, interferon-gamma therapy, IRF1 therapy, JAK/STAT therapy, and/or anti-MYC therapy in combination with an immune checkpoint therapy, such as an anti-PD-1 agent) is able to produce a significant decrease in tumor volume at a level of statistical significance (e.g., $p<0.05$) when compared to tumor volume of untreated tumor in the circumstance where the primary cancer therapy (e.g., an immune checkpoint therapy alone or in combination with an anti-SHP2 therapy, anti-CD47 therapy, interferon-gamma therapy, IRF1 therapy, JAK/STAT therapy, and/or anti-MYC therapy) alone is unable to produce a statistically significant decrease in tumor volume compared to tumor volume of untreated tumor. This generally applies to tumor volume measurements made at a time when the untreated tumor is growing log logarithmically. In some embodiments, the combination allows for a dose defined as a "sub-cytotoxic dose" of one or more of the agents of the combination. A "sub-cytotoxic dose" is a dose that does not necessarily induce cell death (CD) but still has a negative effect on cell growth.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G et al. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

In addition to RNAi, genome editing can be used to modulate the copy number or genetic sequence of a biomarker of interest, such as constitutive or induced knockout or mutation of a biomarker of interest, such as Fbxw7 or an Fbxw7 pathway component like SHP2, CD47, and/or MYC. For example, the CRISPR-Cas system can be used for precise editing of genomic nucleic acids (e.g., for creating non-functional or null mutations). In such embodiments, the CRISPR guide RNA and/or the Cas enzyme may be expressed. For example, a vector containing only the guide RNA can be administered to an animal or cells transgenic for the Cas9 enzyme. Similar strategies may be used (e.g., designer zinc finger, transcription activator-like effectors (TALEs) or homing meganucleases). Such systems are well-known in the art (see, for example, U.S. Pat. No. 8,697,359; Sander and Joung (2014) *Nat. Biotech.* 32:347-355; Hale et al. (2009) *Cell* 139:945-956; Karginov and Hannon (2010) *Mol. Cell* 37:7; U.S. Pat. Publ. 2014/0087426 and 2012/0178169; Boch et al. (2011) *Nat. Biotech.* 29:135-136; Boch et al. (2009) *Science* 326:1509-1512; Moscou and Bogdanove (2009) *Science* 326:1501; Weber et al. (2011) *PLoS One* 6:e19722; Li et al. (2011) *Nucl. Acids Res.* 39:6315-6325; Zhang et al. (2011) *Nat. Biotech.* 29:149-153; Miller et al. (2011) *Nat. Biotech.* 29:143-148; Lin et al. (2014) *Nucl. Acids Res.* 42:e47). Such genetic strategies can use constitutive expression systems or inducible expression systems according to well-known methods in the art.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., chemotherapeutic, and/or radiation therapy). In some embodiments, normal cells are not affected to an extent that causes the normal cells to be unduly injured by the IL3-conjugated toxin or non-IL3-conjugated toxin treatment. An increased sensitivity or a reduced sensitivity to a therapeutic treatment is measured according to a known method in the art for the particular treatment and methods described herein below, including, but not limited to, cell proliferative assays (Tanigawa, N et al. (9821) *Cancer Res* 42: 2159-2164), cell death assays (Weisenthal, L et al. (1984) *Cancer Res* 94: 161-173; Weisenthal, L et al. (1985) *Cancer Treat Rep* 69: 615-632; Weisenthal, L et al. Harwood Academic Publishers, 1993: 415-432; Weisenthal, L (1994) *Contrib Gynecol Obstet* 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-cancer agents (e.g., combination of IL3-conjugated toxin with an agent that increases copy number, amount and/or activity of Fbxw7) can be greater than the sum of the separate effects of the anticancer agents alone. In some embodiments, a cancer that is resistant to the IL3-conjugated toxin is significantly or synergistically more responsive when treated with a combination of IL3-conjugated toxin and an agent that increases copy number, amount and/or activity of Fbxw7, such as anti-SHP2 therapy, anti-CD47 therapy, interferon-gamma therapy, IRF1 therapy, JAK/STAT therapy, and/or anti-MYC therapy, in combination.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "SHP-2" or "SHP2" refers to a member of non-membrane tyrosine phosphatases. SHP-1 and SHP-2 bind to phosphorylated tyrosine residues on receptors or Jaks, and inactivate signaling by dephosphorylating them (Hague et al. (1998) *J. Biol. Chem.* 273:33898-33896: You et al. (1999) *Mol. Cell. Biol.* 19:2416-2424). SHP-1, also known as PTPN6, and SHP-2, also known as Syp, SHPTP2, PTP2C, PTPN11, PTP1D, and BPTP3, are members of the family of non-membrane tyrosine phosphatases (U.S. Pat. Nos. 5,589,375, and 5,831,009). The SHP proteins contain two src homology 2 (SH2) domains, conserved regions of approximately 100 amino acids originally identified in Src protein tyrosine kinases, that promote protein-protein interactions through phosphotyrosyl residue binding (Neel (1993) *Semin. Cell. Biol.* 4: 419-432). These two domains have been shown to display differential functions in the regulation of the phosphatase activity and consequently affect different signaling pathways. The N-terminal SH2 domain serves as a regulatory and recruiting domain, producing an autoinhibitory effect through intramolecular interactions with the internal catalytic phosphatase domain. While the C-terminal SH2 domain acts merely to recruit other proteins for intermolecular interactions necessary for signal transduction (Pei et al. (1996) *Proc. Natl. Acad. Sci. USA*. 93:1141-1145). The phosphorylation state of the SHP molecule regulates its phosphatase activity. Protein-tyrosine phosphatases, including SH2-containing phosphatases, are highly conserved among eukaryotes from such diverse species as mammals, including humans, to yeast and *Xenopus*. SHP-2 has been shown to play a critical role in aberrant immunological responses (e.g., in the allergic response. (Pazdrak et al. (1997) *J. Exp. Med.* 186:561-568). SHP phosphorylation is easily detectable by methods known in the art, including, without limitation, the detection of altered mobility of the SHP molecule on a PAGE gel, phosphorylation assays, and assays which measure the activity of the SHP molecule. Detection of SHP phosphorylation may be direct, or alternatively may be indirect, e.g., detection of a downstream activity or event.

Representative human SHP-2 cDNA and protein sequences are well-known in the art and are publicly available from the National Center for Biotechnology Information (NCBI). For example, SHP-2 isoform 1 is available under accession numbers NM_002834.3 and NP_002825.3. Transcript variant 1 encoding isoform 1 represents the longer transcript and encodes the longer isoform. Transcript variant 2 (NM_080601.1) differs in the 3' untranslated region (UTR) and coding sequence as compared to transcript variant 1 resulting in a SHP-2 isoform 2 (NP_542168.1) with a shorter and distinct N-terminus as compared to isoform 1. Nucleic acid and polypeptide sequences of SHP-2 orthologs in organisms other than humans are well known and include, for example, chimpanzee SHP-2 (XM 522535.4 and XP 522535.3), monkey SHP-2 (NM_001261109.1 and NP_001248038.1), dog SHP-2 (XM_005636251.1, XP_005636308.1, XM_005636250.1, and XP_005636307.1), cow SHP-2 (XM_002694590.3 and XP_002694636.2), mouse SHP-2 (NM_011202.3, NP_035332.1, NM_001109992.1, and NP_001103462.1), rat SHP-2 (NM_013088.2, NP_037220.2, NM_001177593.1, and NP_001171064.1), and chicken SHP-2 (NM_204968.1 and NP_990299.1). In addition, many modulators of SHP-2 are known, including, for example, CRISPR guide RNAs (OriGene KN220029 and KN314207), small molecule inhibitors (SHP099 (TNO155), sodium stibogluconate, dodecane-trimehtylamine, BVT-948, NSC 87877, sodium orthovanadate, TCS 401, VO-OHpic, etidronate, and others known in the art, such as described in U.S. Pat. Publs. 20170204080, 20170015680, 20170001975 and U.S. Pat. No. 9,815,813, which are hereby incorporated in their entireties by this reference), shRNAs (ViGene Biosciences SH896948), siRNAs (Santa Cruz sc-36488), and the like.

The term "subject" refers to any healthy animal, mammal or human, or any animal, mammal or human afflicted with a cancer. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

In one embodiment, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

As used herein, the term "unresponsiveness" includes refractivity of cancer cells to therapy or refractivity of therapeutic cells, such as immune cells, to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below. It is to be noted that the terms described above can further be used to refer to any combination of features described herein regarding the biomarkers. For example, any combination of sequence composition, percentage identify, sequence length, domain structure, functional activity, etc. can be used to describe a biomarker of the present invention.

Human Fbxw7 nucleic acid (NM_033632.3, NM_018315.4, NM_001013415.1, NM_001257069.1, and NM_001349798.1) and amino acid (NP_361014.1, NP_060785.2, NP_001013433.1, NP_001243998.1, and NP_001336727.1) sequences are publicly available on the GenBank database maintained by the U.S. National Center for Biotechnology Information. Nucleic acid and polypeptide sequences of FBXW7 orthologs in species other than humans are also well known and include, for example, mouse FBXW7 (NM_001177774.1 and NP_001171245.1), chimpanzee FBXW7 (XM_016952377.1 and XP_016807866.1), monkey FBXW7 (NM_001257948.2 and NP_001244877.1), frog FBXW7 (XM_004911148.3 and XP_004911205.1), cattle FBXW7 (NM_001076249.1 and NP_001069717.1), rat FBXW7 (XM_002729089.5 and XP_002729135.3), and chicken FBXW7 (NM_001349722.1 and NP_001336651.1).

Representative sequences of Fbxw7 orthologs are presented below in Table 1. Fbxw7 agents, including antibodies, nucleic acids, and the like are well-known in the art. It is to be noted that the term can further be used to refer to any combination of features described herein regarding Fbxw7 molecules. For example, any combination of sequence composition, percentage identify, sequence length, domain structure, functional activity, etc. can be used to describe an Fbxw7 molecule of the present invention.

TABLE 1

SEQ ID NO: 1 Homo sapiens F-box and WD repeat domain containing 7
(FBXW7) cDNA, transcript variant 1 (NM_0336323)

```
   1   taccgcgccg gagccttccg cagctgccgc ttcagtccga aggaggaagg gaaccaaccc 61   actttctcgg cgccgcggct cttttctaaa agtaatgtga aaacctttgc atcttctgat 121   agtctagcca aggtccaaga agtagcaagc tggcttttgg aaatgaatca ggaactgctc 181   tctgtgggca gcaaaagacg acgaactgga ggctctctga gaggtaaccc ttcctcaagc 241   caggtagatg aagaacagat gaatcgtgtg gtagaggagg aacagcaaca gcaactcaga 301   caacaagagg aggagcacac tgcaaggaat ggtgaagttg ttggagtaga acctagacct 361   ggaggccaaa atgattccca gcaaggacag ttggaagaaa acaataatag atttatttcg 421   gtagatgagg actcctcagg aaaccaagaa gaacaagagg aagatgaaga acatgctggt 481   gaacaagatg aggaggatga ggaggaggag gagatggacc aggagagtga cgattttgat
```

TABLE 1-continued

```
 541  cagtctgatg atagtagcag agaagatgaa catacacata ctaacagtgt cacgaactcc
 601  agtagtattg tggacctgcc cgttccaccaa ctctcctccc cattctatac aaaaacaaca
 661  aaaatgaaaa gaaagttgga ccatggttct gaggtccgct cttttctttt gggaaagaaa
 721  ccatgcaaag tctcagaata tacaagtacc actgggcttg taccatgttc agcaacacca
 781  acaacttttg gggacctcag agcagccaat ggccaagggc aacaacgacg ccgaattaca
 841  tctgtccagc cacctacagg cctccaggaa tggctaaaaa tgtttcgagg ctggagtgga
 901  ccagagaaat tgcttgcttt agatgaactc attgatagtt gtgaaccaac acaagtaaaa
 961  catatgatgc aagtgataga accccagttt caacgagact tcatttcatt gctccctaaa
1021  gagttggcac tctatgtgct ttcattcctg gaacccaaag acctgctaca agcagctcag
1081  acatgtcgct actggagaat tttggctgaa gacaaccttc tctggagaga gaaatgcaaa
1141  gaagagggga ttgatgaacc attgcacatc aagagaagaa agtaataaa accaggtttc
1201  atacacagtc catggaaaag tgcatacatc agacagcaca gaattgatac taactggagg
1261  cgaggagaac tcaaatctcc taaggtgctg aaaggacatg atgatcatgt gatcacatgc
1321  ttacagtttt gtggtaaccg aatagttagt ggttctgatg acaacacttt aaaagtttgg
1381  tcagcagtca caggcaaatg tctgagaaca ttagtgggac atacaggtgg agtatggtca
1441  tcacaaatga gagacaacat catcattagt ggatctacag atcggacact caaagtgtgg
1501  aatgcagaga ctggagaatg tatacacacc ttatatgggc atacttccac tgtgcgttgt
1561  atgcatcttc atgaaaaaag agttgttagc ggttctcgag atgccactct tagggtttgg
1621  gatattgaga caggccagtg tttacatgtt ttgatgggtc atgttgcagc agtccgctgt
1681  gttcaatatg atggcaggag ggttgttagt ggagcatatg attttatggt aaaggtgtgg
1741  gatccagaga ctgaaacctg tctacacacg ttgcaggggc atactaatag agtctattca
1801  ttacagtttg atggtatcca tgtggtgagt ggatctcttg atacatcaat ccgtgtttgg
1861  gatgtggaga cagggaattg cattcacacg ttaacagggc accagtcgtt aacaagtgga
1921  atggaactca agacaatat tcttgtctct gggaatgcag attctacagt taaaatctgg
1981  gatatcaaaa caggacagtg tttacaaaca ttgcaaggtc ccaacaagca tcagagtgct
2041  gtgacctgtt tacagttcaa caagaacttt gtaattacca gctcagatga tggaactgta
2101  aaactatggg acttgaaaac gggtgaattt attcgaaacc tagtcacatt ggagagtggg
2161  gggagtgggg gagttgtgtg gcggatcaga gcctcaaaca caaagctggt gtgtgcagtt
2221  gggagtcgga atgggactga agaaccaag ctgctggtgc tggactttga tgtggacatg
2281  aagtgaagag cagaaaagat gaatttgtcc aattgtgtag acgatatact ccctgcccctt
2341  cccctgcaa aaagaaaaaa agaaaagaa aagaaaaaa tcccttgttc tcagtggtgc
2401  aggatgttgg cttggggcaa cagattgaaa agacctacag actaagaagg aaaagaagaa
2461  gagatgacaa accataactg acaagagagg cgtctgctgt ctcatcacat aaaaggcttc
2521  acttttgact gagggcagct ttgcaaaatg agactttcta aatcaaacca ggtgcaatta
2581  tttctttatt ttcttctcca gtggtcattg gcagtgtta atgctgaaac atcattacag
2641  attctgctag cctgttcttt taccactgac agctagacac ctagaaagga actgcaataa
2701  tatcaaaaca agtactggtt gactttctaa ttagagagca tctgcaacaa aaagtcattt
2761  ttctggagtg gaaaagctta aaaaaattac tgtgaattgt ttttgtacag ttatcatgaa
2821  aagcttttt ttttttttt ttgccaacca ttgccaatgt caatcaatca cagtattagc
2881  ctctgttaat ctatttactg ttgcttccat atacattctt caatgcatat gttgctcaaa
```

TABLE 1-continued

```
2941    ggtggcaagt tgtcctgggt tctgtgagtc ctgagatgga tttaattctt gatgctggtg
3001    ctagaagtag gtcttcaaat atgggattgt tgtcccaacc ctgtactgta ctcccagtgg
3061    ccaaacttat ttatgctgct aaatgaaaga aagaaaaaag caaattattt tttttttattt
3121    tttttctgct gtgacgtttt agtcccagac tgaattccaa atttgctcta gtttggttat
3181    ggaaaaaaga cttttttgcca ctgaaacttg agccatctgt gcctctaaga ggctgagaat
3241    ggaagagttt cagataataa agagtgaagt ttgcctgcaa gtaaagaatt gagagtgtgt
3301    gcaaagctta ttttctttta tctgggcaaa aattaaaaca cattccttgg aacagagcta
3361    ttacttgcct gttctgtgga gaaactttc tttttgaggg ctgtggtgaa tggatgaacg
3421    tacatcgtaa aactgacaaa atattttaaa aatatataaa acacaaaatt aaaataaagt
3481    tgctggtcag tcttagtgtt ttacagtatt tgggaaaaca actgttacag ttttattgct
3541    ctgagtaact gacaaagcag aaactattca gtttttgtag taaaggcgtc acatgcaaac
3601    aaacaaaatg aatgaaacag tcaaatggtt tgcctcattc tccaagagcc acaactcaag
3661    ctgaactgtg aaagtggttt aacactgtat cctaggcgat cttttttcct ccttctgttt
3721    atttttttgt ttgttttatt tatagtctga tttaaaacaa tcagattcaa gttggttaat
3781    tttagttatg taacaacctg acatgatgga ggaaaacaac ctttaaaggg attgtgtcta
3841    tggtttgatt cacttagaaa tttatttttc ttataactta agtgcaataa aatgtgtttt
3901    ttcatgttaa aaaaaaaaa aaaaaaa
```

SEQ ID NO: 2 *Homo sapiens* F-box and WD repeat domain containing 7
(FBXW7) cDNA, transcript variant 2 (NM_018315.4)

```
1       cttacggggtt ccctggagcg gatcaccata taattgatgt gcagtctgca ttgctgaatc
61      ctggactgca ccattctgtg ttcaagggaa gatgtaatct gatccctctg ctgctgaggg
121     aggaatctgt tcagtcaagg ctttgacagg gcatagtctc ctccaataat cttctccgtt
181     ctctctcatt attccctcga gttcttctca gtcaagctgc atgtatgtat gtgtgtcccg
241     agaagcggtt tgatactgag ctgcatttgc ctttactgtg gagttttgtt gccggttctg
301     ctccctaatc ttccttttct gacgtgcctg agcatgtcca cattagaatc tgtgacatac
361     ctacctgaaa aaggtttata ttgtcagaga ctgccaagca gccggacaca cggggggcaca
421     gaatcactga aggggaaaaa tacagaaaat atgggtttct acggcacatt aaaaatgatt
481     ttttacaaaa tgaaaagaaa gttggaccat ggttctgagg tccgctcttt ttctttggga
541     aagaaaccat gcaaagtctc agaatataca agtaccactg ggcttgtacc atgttcagca
601     acaccaacaa cttttgggga cctcagagca gccaatggcc aagggcaaca acgacgccga
661     attacatctg tccagccacc tacaggcctc caggaatggc taaaaatgtt tcagagctgg
721     agtggaccag agaaattgct tgctttagat gaactcattg atagttgtga accaacacaa
781     gtaaaacata tgatgcaagt gatagaaccc cagtttcaac gagacttcat ttcattgctc
841     cctaaagagt tggcactcta tgtgctttca ttcctggaac ccaaagacct gctacaagca
901     gctcagacat gtcgctactg agaattttg gctgaagaca accttctctg gagagagaaa
961     tgcaaagaag aggggattga tgaaccattg cacatcaaga gaagaaaagt aataaaacca
1021    ggtttcatac acagtccatg gaaaagtgca tacatcagac agcacagaat tgatactaac
1081    tggaggcgag agaactcaa atctcctaag gtgctgaaag gacatgatga tcatgtgatc
1141    acatgcttac agttttgtgg taaccgaata gttagtggtt ctgatgacaa cactttaaaa
1201    gtttggtcag cagtcacagg caaatgtctg agaacattag tgggacatac aggtggagta
1261    tggtcatcac aaatgagaga caacatcatc attagtggat ctacagatcg gacactcaaa
```

TABLE 1-continued

```
1321   gtgtggaatg cagagactgg agaatgtata cacaccttat atgggcatac ttccactgtg
1381   cgttgtatgc atcttcatga aaaaagagtt gttagcggtt ctcgagatgc cactcttagg
1441   gtttgggata ttgagacagg ccagtgttta catgttttga tgggtcatgt tgcagcagtc
1501   cgctgtgttc aatatgatgg caggagggtt gttagtggag catatgattt tatggtaaag
1561   gtgtgggatc cagagactga aacctgtcta cacacgttgc aggggcatac taatagagtc
1621   tattcattac agtttgatgg tatccatgtg gtgagtggat ctcttgatac atcaatccgt
1681   gtttgggatg tggagacagg gaattgcatt cacacgttaa cagggcacca gtcgttaaca
1741   agtggaatgg aactcaaaga caatattctt gtctctggga atgcagattc tacagttaaa
1801   atctgggata tcaaaacagg acagtgttta caaacattgc aaggtcccaa caagcatcag
1861   agtgctgtga cctgtttaca gttcaacaag aactttgtaa ttaccagctc agatgatgga
1921   actgtaaaac tatgggactt gaaaacgggt gaatttattc gaaacctagt cacattggag
1981   agtgggggga gtgggggagt tgtgtggcgg atcagagcct caaacacaaa gctggtgtgt
2041   gcagttggga gtcggaatgg gactgaagaa accaagctgc tggtgctgga ctttgatgtg
2101   gacatgaagt gaagagcaga aaagatgaat ttgtccaatt gtgtagcgaa tatactccct
2161   gcccttcccc ctgcaaaaag aaaaaagaa aagaaaaaga aaaaatccc ttgttctcag
2221   tggtgcagga tgttggcttg gggcaacaga ttgaaaagac ctacagacta agaaggaaaa
2281   gaagaagaga tgacaaacca taactgacaa gagaggcgtc tgctgtctca tcacataaaa
2341   ggcttcactt ttgactgagg gcagctttgc aaaatgagac tttctaaatc aaaccaggtg
2401   caattatttc tttattttct tctccagtgg tcattgggca gtgttaatgc tgaaacatca
2461   ttacagattc tgctagcctg ttcttttacc actgacagct agacacctag aaaggaactg
2521   caataatatc aaaacaagta ctggttgact ttctaattag agagcatctg caacaaaaag
2581   tcatttttct ggagtggaaa agcttaaaaa aattactgtg aattgttttt gtacagttat
2641   catgaaaagc ttttttttt tttttttgc caaccattgc caatgtcaat caatcacagt
2701   attagcctct gttaatctat ttactgttgc ttccatatac attcttcaat gcatatgttg
2761   ctcaaaggtg gcaagttgtc ctgggttctg tgagtcctga gatggattta attcttgatg
2821   ctggtgctag aagtaggtct tcaaatatgg gattgttgtc ccaaccctgt actgtactcc
2881   cagtggccaa acttatttat gctgctaaat gaaagaaaga aaaaagcaaa ttatttttt
2941   ttatttttt tctgctgtga cgttttagtc ccagactgaa ttccaaattt gctctagttt
3001   ggttatggaa aaagactttt ttgccactga aacttgagcc atctgtgcct ctaagaggct
3061   gagaatggaa gagtttcaga taataaagag tgaagtttgc ctgcaagtaa agaattgaga
3121   gtgtgtgcaa agcttatttt cttttatctg ggcaaaaatt aaaacacatt ccttggaaca
3181   gagctattac ttgcctgttc tgtggagaaa cttttctttt tgagggctgt ggtgaatgga
3241   tgaacgtaca tcgtaaaact gacaaaatat tttaaaaata tataaaacac aaaattaaaa
3301   taaagttgct ggtcagtctt agtgttttac agtatttggg aaaacaactg ttacagtttt
3361   attgctctga gtaactgaca aagcagaaac tattcagttt ttgtagtaaa ggcgtcacat
3421   gcaaacaaac aaaatgaatg aaacagtcaa atggtttgcc tcattctcca agagccacaa
3481   ctcaagctga actgtgaaag tggtttaaca ctgtatccta ggcgatcttt tttcctcctt
3541   ctgtttattt ttttgtttgt tttatttata gtctgattta aaacaatcag attcaagttg
3601   gttaatttta gttatgtaac aacctgacat gatggaggaa aacaaccttt aaagggattg
```

TABLE 1-continued

```
3661    tgtctatggt ttgattcact tagaaatttt attttcttat aacttaagtg caataaaatg 3721    tgttttttca tgttaaaaaa aaaaaaaaaa a SEQ ID NO: 3 Homo sapiens F-box and WD repeat domain containing 7
(FBXW7) cDNA, transcript variant 3 (NM_001013415.1)
   1    agacaggtca ggacatttgg taggggaagg ttgaaagaca aaagcagcag gccttgggtt 61    ctcagccttt taaaaactat tattaaatat atatttttaa aatttagtgg ttagagcttt 121    tagtaatgtg cctgtattac atgtagagag tattcgtcaa ccaagaggag ttttaaaatg 181    tcaaaaccgg gaaaacctac tctaaaccat ggcttggttc ctgttgatct taaaagtgca 241    aaagagcctc taccacatca aactgtgatg aagatattta gcattagcat cattgcccaa 301    ggcctccctt tttgtcgaag acggatgaaa agaaagttgg accatggttc tgaggtccgc 361    tcttttttctt tgggaaagaa accatgcaaa gtctcagaat atacaagtac cactgggctt 421    gtaccatgtt cagcaacacc aacaacttttt ggggacctca gagcagccaa tggccaaggg 481    caacaacgac gccgaattac atctgtccag ccacctacag gcctccagga atggctaaaa 541    atgtttcaga gctggagtgg accagagaaa ttgcttgctt tagatgaact cattgatagt 601    tgtgaaccaa cacaagtaaa acatatgatg caagtgatag accccagtt tcaacgagac 661    ttcatttcat tgctccctaa agagttggca ctctatgtgc tttcattcct ggaacccaaa 721    gacctgctac aagcagctca gacatgtcgc tactggagaa ttttggctga agacaacctt 781    ctctggagag agaaatgcaa agaagagggg attgatgaac cattgcacat caagagaaga 841    aaagtaataa aaccaggttt catacacagt ccatggaaaa gtgcatacat cagacagcac 901    agaattgata ctaactggag gcgaggagaa ctcaaatctc ctaaggtgct gaaaggacat 961    gatgatcatg tgatcacatg cttacagttt tgtggtaacc gaatagttag tggttctgat 1021    gacaacactt taaaagtttg gtcagcagtc acaggcaaat gtctgagaac attagtggga 1081    catacaggtg gagtatggtc atcacaaatg agagacaaca tcatcattag tggatctaca 1141    gatcggacac tcaaagtgtg gaatgcagag actggagaat gtatacacac cttatatggg 1201    catacttcca ctgtgcgttg tatgcatctt catgaaaaaa gagttgttag cggttctcga 1261    gatgccactc ttagggtttg ggatattgag acaggccagt gtttacatgt tttgatgggt 1321    catgttgcag cagtccgctg tgttcaatat gatggcagga gggttgttag tggagcatat 1381    gattttatgg taaaggtgtg ggatccagag actgaaacct gtctacacac gttgcagggg 1441    catactaata gagtctattc attacagttt gatggtatcc atgtggtgag tggatctctt 1501    gatacatcaa tccgtgtttg ggatgtggag acagggaatt gcattcacac gttaacaggg 1561    caccagtcgt taacaagtgg aatggaactc aaagacaata ttcttgtctc tgggaatgca 1621    gattctacag ttaaaatctg ggatatcaaa acaggacagt gtttacaaac attgcaaggt 1681    cccaacaagc atcagagtgc tgtgacctgt ttacagttca acaagaactt tgtaattacc 1741    agctcagatg atggaactgt aaaactatgg gacttgaaaa cgggtgaatt tattcgaaac 1801    ctagtcacat ggagagtgg ggggagtggg ggagttgtgt ggcggatcag agcctcaaac 1861    acaaagctgg tgtgtgcagt tgggagtcga atgggactg aagaaaccaa gctgctggtg 1921    ctggactttg atgtggacat gaagtgaaga gcagaaaaga tgaatttgtc caattgtgta 1981    gacgatatac tccctgccct tccccctgca aaagaaaaa aagaaaagaa aagaaaaaa 2041    atcccttgtt ctcagtggtg caggatgttg gcttggggca acagattgaa aagacctaca 2101    gactaagaag gaaagaagaa agagatgaca aaccataact gacaagagag gcgtctgctg 2161    tctcatcaca taaaaggctt cacttttgac tgagggcagc tttgcaaaat gagactttct
```

TABLE 1-continued

```
2221    aaatcaaacc aggtgcaatt atttctttat tttcttctcc agtggtcatt gggcagtgtt 2281    aatgctgaaa catcattaca gattctgcta gcctgttctt ttaccactga cagctagaca 2341    cctagaaagg aactgcaata atatcaaaac aagtactggt tgactttcta attagagagc 2401    atctgcaaca aaaagtcatt tttctggagt ggaaaagctt aaaaaaatta ctgtgaattg 2461    tttttgtaca gttatcatga aaagcttttt tttttttttt tttgccaacc attgccaatg 2521    tcaatcaatc acagtattag cctctgttaa tctatttact gttgcttcca tatacattct 2581    tcaatgcata tgttgctcaa aggtggcaag ttgtcctggg ttctgtgagt cctgagatgg 2641    atttaattct tgatgctggt gctagaagta ggtcttcaaa tatgggattg ttgtcccaac 2701    cctgtactgt actcccagtg gccaaactta tttatgctgc taaatgaaag aaagaaaaaa 2761    gcaaattatt tttttttatt tttttctgc tgtgacgttt tagtcccaga ctgaattcca 2821    aatttgctct agtttggtta tggaaaaaag acttttgcc actgaaactt gagccatctg 2881    tgcctctaag aggctgagaa tggaagagtt tcagataata aagagtgaag tttgcctgca 2941    agtaaagaat tgagagtgtg tgcaaagctt attttctttt atctgggcaa aaattaaaac 3001    acattccttg gaacagagct attacttgcc tgttctgtgg agaaactttt cttttttgagg 3061    gctgtggtga atggatgaac gtacatcgta aaactgacaa atatttttaa aaatatataa 3121    aacacaaaat taaaataaag ttgctggtca gtcttagtgt tttacagtat ttgggaaaac 3181    aactgttaca gttttattgc tctgagtaac tgacaaagca gaaactattc agttttttgta 3241    gtaaaggcgt cacatgcaaa caaacaaaat gaatgaaaca gtcaaatggt ttgcctcatt 3301    ctccaagagc cacaactcaa gctgaactgt gaaagtggtt taacactgta tcctaggcga 3361    tctttttttcc tccttctgtt tatttttttg tttgtttttat ttatagtctg atttaaaaca 3421    atcagattca agttggttaa ttttagttat gtaacaaacct gacatgatgg aggaaaacaa 3481    ccttttaaagg gattgtgtct atggtttgat tcacttagaa attttatttt cttataactt 3541    aagtgcaata aaatgtgttt tttcatgtta
```

SEQ ID NO: 4 Homo sapiens F-box and WD repeat domain containing 7
(FBXW7) cDNA, transcript variant 4 (NM_001257069.1)

```
  1     ggaaacttta caaaaacaaa atccggagtc tcccaaacct gactgtcccg ggagaagtgg 61     ccctggacgg gcagaagccg cagcctgaaa agacccagga agaggaaaag aggagtaccg 121     cgccggagcc ttccgcagct gccgcttcag tccgaaggag gagggaaacc aacccacttt 181     ctcggcgccg cggctctttt ctaaaagtga ttacttcctt aggatagatt gccagaagtg 241     gagttactgg gtcagaggaa tgtgaaaacc tttgcatctt ctgatagtct agccaaggtc 301     caagaagtag caagctggct tttggaaatg aatcaggaac tgctctctgt gggcagcaaa 361     agacgacgaa ctggaggctc tctgagaggt aacccttcct caagccaggt agatgaagaa 421     cagatgaatc gtgtggtaga ggaggaacag caacagcaac tcagacaaca agaggaggag 481     cacactgcaa ggaatggtga agttgttgga gtagaaccta gacctggagg ccaaaatgat 541     tcccagcaag gacagttgga agaaaacaat aatagattta tttcggtaga tgaggactcc 601     tcaggaaacc aagaagaaca agaggaagat gaagaacatg ctggtgaaca agatgaggag 661     gatgaggagg aggaggagat ggaccaggag agtgacgatt tgatcagtc tgatgatagt 721     agcagagaag atgaacatac acatactaac agtgtcacga actccagtag tattgtggac 781     ctgcccgttc accaactctc ctccccattc tatacaaaaa caacaaaagt gagtatattc 841     aatatattgt taacctgaga aactttacat atctatttta attgtaatga aactttcctc
```

TABLE 1-continued

```
 901    acagtctttg tattactaaa aattaatctt aagatgtgta ataataaaat gaactagttt
 961    tttgtcttac aaaaaaaaaa aaaaaaaa
```

SEQ ID NO: 5 Homo sapiens F-box and WD repeat domain containing 7
(FBXW7) cDNA, transcript variant 5 (NM_001349798.1)

```
   1    cctctctctg gagtgaggcg agagccccgc acagagcgag ggagacagcg agctgagctc
  61    cgggcgctgc cgctgccgct gccgccgccg ccgccgctga gactgagagc gaaggagcat
 121    ccgagagatc cagtccccct gcactggccg ccgccgagac cttcgctctc acctgggcca
 181    gcgggagccg cggccgcact cctttccccc cctcaccttc ccggccggca gcggcggctg
 241    cacacgccgg agccggagcc agagccggag cccgagcctg agccggagcc ggcggcttgg
 301    ggggcaggga gcggctacc acgggccggg agtgggtagc tgctccgcgg tgagagaacg
 361    ctgaggaggc gccagagctt ctgcctcgtc ccgtggggcg tggggcgaga ccccaaggt
 421    gtagggaggg gggtcccagc cgcagcgaca catgcgggag ccgggagcgg gggcggcgcc
 481    gagcggagcc ggccgggtcc ctcgccttgc cgccgactcg gccacccgcc cggggccgta
 541    gcatcttgcc ccggagtgta tgaaccgggg ccccaaccaa gctcggcaac caccccccgg
 601    ccggggggc ggggacccg atgtgaagcg gcggctgggg cggcggagag aacaggaccg
 661    acgccgccgt cctttcctca ccttccccct ccctcagcc ccctccgggg gtcttctccc
 721    ttggccagtc gccggccccc cggctccttg gctggactcc gggaggagtt cctagagccc
 781    ccctcccccg ccccagtccc gagggcggcg gggccggggg gacccgggg ggccggccgc
 841    agcctccacc cagaggaaac tttacaaaaa caaatccgg agtctcccaa acctgactgt
 901    cccgggagaa gtggccctgg acgggcagaa gccgcagcct gaaaagaccc aggaagagga
 961    aaagaggagt accgcgccgg agccttccgc agctgccgct tcagtccgaa ggaggaaggg
1021    aaccaaccca ctttctcggc gccgcggctc ttttctaaaa gtgattactt ccttaggata
1081    gattgccaga agtggagtta ctgggtcaga ggaatgtgaa aacctttgca tcttctgata
1141    gtctagccaa ggtccaagaa gtagcaagct ggcttttgga aatgaatcag gaactgctct
1201    ctgtgggcag caaaagacga cgaactggag gctctctgag aggtaaccct tcctcaagcc
1261    aggtagatga agaacagatg aatcgtgtgg tagaggagga acagcaacag caactcagac
1321    aacaagagga ggagcacact gcaaggaatg gtgaagttgt tggagtagaa cctagacctg
1381    gaggccaaaa tgattcccag caaggacagt tggaagaaaa caataataga tttatttcgg
1441    tagatgagga ctcctcagga aaccaagaag aacaagagga agatgaagaa catgctggtg
1501    aacaagatga ggaggatgag gaggaggagg agatggacca ggagagtgac gattttgatc
1561    agtctgatga tagtagcaga gaagatgaac atacacatac taacagtgtc acgaactcca
1621    gtagtattgt ggacctgccc gttcaccaac tctcctcccc attctataca aaaacaacaa
1681    aaatgaaaag aaagttggac catggttctg aggtccgctc tttttctttg ggaaagaaac
1741    catgcaaagt ctcagaatat acaagtacca ctgggcttgt accatgttca gcaacaccaa
1801    caacttttgg ggacctcaga gcagccaatg gccaagggca caacgacgc cgaattacat
1861    ctgtccagcc acctacaggc ctccaggaat ggctaaaaat gtttcagagc tggagtggac
1921    cagagaaatt gcttgcttta gatgaactca ttgatagttg taaccaaca caagtaaaac
1981    atatgatgca agtgatagaa ccccagtttc aacgagactt catttcattg ctccctaaag
2041    agttggcact ctatgtgctt tcattcctgg aacccaaaga cctgctacaa gcagctcaga
2101    catgtcgcta ctggagaatt ttggctgaag acaaccttct ctggagagag aaatgcaaag
2161    aagaggggat tgatgaacca ttgcacatca agagaagaaa agtaataaaa ccaggtttca
```

TABLE 1-continued

```
2221  tacacagtcc atggaaaagt gcatacatca dacagcacag aattgatact aactggaggc
2281  gaggagaact caaatctcct aaggtgctga aaggacatga tgatcatgtg atcacatgct
2341  tacagttttg tggtaaccga atagttagtg gttctgatga caacacttta aaagtttggt
2401  cagcagtcac aggcaaatgt ctgagaacat tagtgggaca tacaggtgga gtatggtcat
2461  cacaaatgag agacaacatc atcattagtg gatctacaga tcggacactc aaagtgtgga
2521  atgcagagac tggagaatgt atacacacct tatatgggca tacttccact gtgcgttgta
2581  tgcatcttca tgaaaaaaga gttgttagcg gttctcgaga tgccactctt agggtttggg
2641  atattgagac aggccagtgt ttacatgttt tgatgggtca tgttgcagca gtccgctgtg
2701  ttcaatatga tggcaggagg gttgttagtg gagcatatga ttttatggta aaggtgtggg
2761  atccagagac tgaaacctgt ctacacacgt tgcagggca tactaataga gtctattcat
2821  tacagtttga tggtatccat gtggtgagtg gatctcttga tacatcaatc cgtgtttggg
2881  atgtggagac agggaattgc attcacacgt taacagggca ccagtcgtta acaagtggaa
2941  tggaactcaa agacaatatt cttgtctctg ggaatgcaga ttctacagtt aaaatctggg
3001  atatcaaaac aggacagtgt ttacaaacat tgcaaggtcc caacaagcat cagagtgctg
3061  tgacctgttt acagttcaac aagaactttg taattaccag ctcagatgat ggaactgtaa
3121  aactatggga cttgaaaacg ggtgaattta ttcgaaacct agtcacattg gagagtgggg
3181  ggagtggggg agttgtgtgg cggatcagag cctcaaacac aaagctggtg tgtgcagttg
3241  ggagtcggaa tgggactgaa gaaaccaagc tgctggtgct ggactttgat gtggacatga
3301  agtgaagagc agaaaagatg aatttgtcca attgtgtaga cgatatactc cctgcccttc
3361  cccctgcaaa aagaaaaaaa gaaaagaaaa agaaaaaaat cccttgttct cagtggtgca
3421  ggatgttggc ttggggcaac agattgaaaa gacctacaga ctaagaagga aaagaagaag
3481  agatgacaaa ccataactga caagagaggc gtctgctgtc tcatcacata aaaggcttca
3541  cttttgactg agggcagctt tgcaaaatga gactttctaa atcaaaccag gtgcaattat
3601  ttctttattt tcttctccag tggtcattgg gcagtgttaa tgctgaaaca tcattacaga
3661  ttctgctagc ctgttctttt accactgaca gctagacacc tagaaaggaa ctgcaataat
3721  atcaaaacaa gtactggttg actttctaat tagagagcat ctgcaacaaa aagtcatttt
3781  tctggagtgg aaaagcttaa aaaaattact gtgaattgtt tttgtacagt tatcatgaaa
3841  agcttttttt ttttttttt tgccaaccat tgccaatgtc aatcaatcac agtattagcc
3901  tctgttaatc tatttactgt tgcttccata tacattcttc aatgcatatg ttgctcaaag
3961  gtggcaagtt gtcctgggtt ctgtgagtcc tgagatggat ttaattcttg atgctggtgc
4021  tagaagtagg tcttcaaata tgggattgtt gtcccaaccc tgtactgtac tcccagtggc
4081  caaacttatt tatgctgcta aatgaaagaa agaaaaaagc aaattatttt ttttttatttt
4141  ttttctgctg tgacgtttta gtcccagact gaattccaaa tttgctctag tttggttatg
4201  gaaaaagac ttttttgccac tgaaacttga gccatctgtg cctctaagag gctgagaatg
4261  gaagagtttc agataataaa gagtgaagtt tgcctgcaag taagaattg agagtgtgtg
4321  caaagcttat tttctttttat ctgggcaaaa attaaaacac attccttgga acagagctat
4381  tacttgcctg ttctgtggag aaacttttct ttttgagggc tgtggtgaat ggatgaacgt
4441  acatcgtaaa actgacaaaa tattttaaaa atatataaaa cacaaaatta aaataaagtt
4501  gctggtcagt cttagtgttt tacagtattt gggaaaacaa ctgttacagt tttattgctc
4561  tgagtaactg acaaagcaga aactattcag tttttgtagt aaaggcgtca catgcaaaca
```

TABLE 1-continued

```
4621    aacaaaatga atgaaacagt caaatggttt gcctcattct ccaagagcca caactcaagc 4681    tgaactgtga aagtggttta acactgtatc ctaggcgatc ttttttcctc cttctgttta 4741    ttttttttgtt tgttttattt atagtctgat ttaaaacaat cagattcaag ttggttaatt 4801    ttagttatgt aacaacctga catgatggag gaaaacaacc tttaaaggga ttgtgtctat 4861    ggtttgattc acttagaaat tttattttct tataacttaa gtgcaataaa atgtgttttt 4921    tcatgttaaa aaaaaaaaaa aaaaa
```

SEQ ID NO: 6 Homo sapiens F-box and WD repeat domain containing 7
(FBXW7) amino acid sequence, isoform 1 (NP_361014.1)
```
  1    mnqellsvgs krrrtggslr gnpsssqvde eqmnrvveee qqqqlrqqee ehtarngevv 61    gveprpggqn dsqqgqleen nnrfisvded ssgnqeeqee deehagegde edeeeeemdq 121    esddfdqsdd ssredehtht nsvtnsssiv dlpvhqlssp fytkttkmkr kldhgsevrs 181    fslgkkpckv seytsttglv pcsatpttfg dlraangqgq qrrritsvqp ptglgewlkm 241    fqswsgpekl laldelidsc eptqvkhmmq viepqfqrdf isllpkelal yvlsflepkd 301    llqaaqtcry wrilaednll wrekckeegi deplhikrrk vikpgfihsp wksayirqhr 361    idtnwrrgel kspkvlkghd dhvitclqfc gnrivsgsdd ntlkvwsavt gkclrtlvgh 421    tggvwssqmr dnillsgstd rtlkvwnaet gecihtlygh tstvrcmhlh ekrvvsgsrd 481    atlrvwdiet ggclhvlmgh vaavrcvqyd grrvvsgayd fmvkvwdpet etclhtlqgh 541    tnrvyslqfd gihvvsgsld tsirvwdvet gncihtltgh qsltsgmelk dnilvsgnad 601    stvkiwdikt gqclqtlqgp nkhqsavtcl qfknknfvits sddgtvklwd lktgefirnl 661    vtlesggsgg vvwrirasnt klvcavgsrn gteetkllvl dfdvdmk
```

SEQ ID NO: 7 Homo sapiens F-box and WD repeat domain containing 7
(FBXW7) amino acid sequence, isoform 2 (NP_060785.2)
```
  1    mcvprsglil sciclycgvl lpvllpnlpf ltclsmstle svtylpekgl ycqrlpssrt 61    hggteslkgk ntenmgfygt lkmifykmkr kldhgsevrs fslgkkpckv seytsttglv 121    pcsatpttfg dlraangqgq qrrritsvqp ptglgewlkm fqswsgpekl laldelidsc 181    eptqvkhmmq viepqfqrdf isllpkelal yvlsflepkd llqaaqtcry wrilaednll 241    wrekckeegi deplhikrrk vikpgfihsp wksayirqhr idtnwrrgel kspkvlkghd 301    dhvitclqfc gnrivsgsdd ntlkvwsavt gkclrtlvgh tggvwssqmr dniiisgstd 361    rtlkvwnaet gecihtlygh tstvrcmhlh ekrvvsgsrd atlrvwdiet ggclhvlmgh 421    vaavrcvqyd grrvvsgayd fmvkvwdpet etclhtlqgh tnrvyslqfd gihvvsgsld 481    tsirvwdvet gncihtltgh qsltsgmelk dnilvsgnad stvkiwdikt ggclqtlqgp 541    nkhqsavtcl qfknknfvits sddgtvklwd lktgefirnl vtlesggsgg vvwrirasnt 601    klvcavgsrn gteetkllvl dfdvdmk
```

SEQ ID NO: 8 Homo sapiens F-box and WD repeat domain containing 7
(FBXW7) amino acid sequence, isoform 3 (NP_001013433.1)
```
  1    mskpgkptln hglvpvdlks akeplphqtv mkifsislia qglpfcrrrm krkldhgsev 61    rsfslgkkpc kvseytsttg lvpcsatptt fgdlraangq gqqrrritsv qpptglgewl 121    kmfqswsgpe kllaldelid sceptqvkhm mqviepqfqr dfisllpkel alyvlsflep 181    kdllqaaqtc rywrilaedn llwrekckee gideplhikr rkvikpgfih spwksayirq 241    hridtnwrrg elkspkvlkg hddhvitclq fcgnrivsgs ddntlkvwsa vtgkclrtlv 301    ghtggvwssq mrdniiisgs tdrtlkvwna etgecihtly ghtstvrcmh lhekrvvsgs 361    rdatlrvwdi etggclhvlm ghvaavrcvq ydgrrvvsga ydfmvkvwdp etetclhtlq 421    ghtnrvyslq fdgihvvsgs ldtsirvwdv etgncihtlt ghqsltsgme lkdnilvsgn
```

TABLE 1-continued

```
481    adstvkiwdi ktggclqtlq gpnkhqsavt clqfnknfvi tssddgtvkl wdlktgefir 541    nlvtlesggs ggvvwriras ntklvcavgs rngteetkll vldfdvdmk
```

SEQ ID NO: 9 Homo sapiens F-box and WD repeat domain containing 7
(FBXW7) amino acid sequence, isoform 4 (NP_001243998.1)
```
  1    mnqellsvgs krrrtggslr gnpsssqvde eqmnrvveee qqqqlrqqee ehtarngevv 61    gveprpggqn dsqqgqleen nnrfisvded ssgneeeqee deehagegde edeeeeemdq 121    esddfdqsdd ssredehtht nsvtnsssiv dlpvhqlssp fytkttkvsi fnillt
```

SEQ ID NO: 10 Homo sapiens F-box and WD repeat domain containing 7
(FBXW7) amino acid sequence, isoform 1 (NP_001336727.1)
```
  1    mnqellsvgs krrrtggslr gnpsssqvde eqmnrvveee qqqqlrqqee ehtarngevv 61    gveprpggqn dsqqgqleen nnrfisvded ssgnqeeqee deehageqde edeeeeemdq 121    esddfdqsdd ssredehtht nsvtnsssiv dlpvhqlssp fytkttkmkr kldhgsevrs 181    fslgkkpckv seytsttglv pcsatpttfg dlraangqgq qrrritsvqp ptglgewlkm 241    fqswsgpekl laldelidsc eptqvkhmmq viepqfqrdf isllpkelal yvlsflepkd 301    llqaaqtcry wrilaednll wrekckeegi deplhikrrk vikpgfihsp wksayirqhr 361    idtnwrrgel kspkvlkghd dhvitclqfc gnrivsgsdd ntlkvwsavt gkclrtlvgh 421    tggvwssqmr dniiisgstd rtlkvwnaet gecihtlygh tstvrcmhlh ekrvvsgsrd 481    atlrvwdiet ggclhvlmgh vaavrcvqyd grrvvsgayd fmvkvwdpet etclhtlqgh 541    tnrvyslqfd gihvvsgsld tsirvwdvet gncihtltgh qsltsgmelk dnilvsgnad 601    stvkiwdikt ggclqtlqgp nkhqsavtcl qfnknfvits sddgtvklwd lktgefirnl 661    vtlesggsgg vvwrirasnt klvcavgsrn gteetkllvl dfdvdmk
```

SEQ ID NO: 11 Mus musculus F-box and WD repeat domain containing 7
(FBXW7) cDNA, transcript variant 1 (NM_001177774.1)
```
  1    atttcttctc tttatatctt ttgtgatccc tctacacatt gtgtctagac aatcagtttg 61    aattagtgct tggattttg cctagacaaa aggagtaact tggaatgaag aaaatggact 121    caaacttaaa gagctgcaca ctaatcaatc cttcgaacgc atggaaac cagagaccac 181    ccctactgtc ctcttagtta cacaagtggc tgagaatgtg aaacctttg catcttctga 241    tagtctagcc aaggtccaag aagtagcaag ctggcttttg gaaatgaatc aggaactgct 301    ctctgtgggc agcaaaagac gacgaactgg aggctctctg agagggaatg cttcctcaag 361    ccaggttgat gagggacaga tgaatcgcgt ggttgaggag atccacagc agcaagcgag 421    acatcaagag gaggagcaca ctgcgcggaa tggtgaactt gtgggtgcaa accctaggcc 481    tggagaccag aacgataccc agcaaggaca agtggaggaa ataataacc gctttatttc 541    agtagatgag gactcttcgg gaaatcagga agagcaagag gaagatgaag agcatgctgg 601    ggaacaggag gaggaagagg aggaagagga gaggaggag gagatggacc aggagagtga 661    tgattttgat ccgtctgatg acagtagcag agaagatgaa catacgcaca atagcaatgt 721    cacaaactgc agtagtgtct cggacctgcc cgctcaccag ctctcctctc cattctatac 781    aaagacaaca aaatgaaaa gaaagttgga ccatggttct gaagttcgtt ccttttcttt 841    gggaaagaaa ccatgcaaag tctcagatta taccagtacc actggccttg taccatgttc 901    agcaacacca acaacttttg gggacctgag agcagccaat ggcaagggc agcagcggcg 961    gaggattaca tctgtccaac cacccacagg ccttcaagag tggctgaaaa tgtttcagag 1021   ctggagcgga ccagagaagt tgctggcttt agatgagctc attgacagct gtgaaccaac 1081   acaagtgaag catatgatgc aagtgataga gccccagttc cagcgagact tcatctcctt 1141   gcttcctaaa gagttggcac tctatgtgct ttcattcctg gaacccaaag acctgctgca
```

TABLE 1-continued

```
1201  agcggctcag acttgtcgat actggagaat tttggctgag gataaccttc tctggagaga
1261  gaaatgtaaa gaagagggga ttgatgaacc gttgcacatc aagagaagaa aataataaa
1321  accaggtttc atacacagcc catggaagag tgcgtatatc agacagcaca gaattgatac
1381  aaactggaga cgaggagaac tcaaatctcc taaggtgctg aaagggcatg atgaccatgt
1441  gatcacatgc ctacagtttt gtggcaaccg catagttagt ggttctgatg acaacacttt
1501  aaaagtttgg tcagcggtca cgggcaagtg tctgagaacg ttagtgggac atacaggtgg
1561  agtgtggtca tcacagatga gagacaatat catcatcagt ggatcgactg accggactct
1621  caaagtgtgg aatgctgaaa ctggagagtg tatacatact ttatatgggc acacttctac
1681  tgtacggtgt atgcatctcc atgaaaaaag ggttgtaagc ggttctcgag atgccactct
1741  cagggtttgg gatattgaga ccggccagtg tttacacgtc ctgatgggtc acgtagcagc
1801  ggtccgctgc gttcagtatg atggcaggag ggttgttagt ggagcttatg attttatggt
1861  gaaggtgtgg gatccagaga ctgagacctg tctacacacg ttacagggac acactaatag
1921  agtctattca ttacagtttg atggcatcca tgtggtgagt ggatctcttg atacatcaat
1981  ccgagtctgg gatgtggaga cagggaattg tattcacacg ctaacaggac accagtcatt
2041  aacgagtgga atggaactca aagacaatat tcttgtctct gggaatgcag attctacagt
2101  taagatctgg gatatcaaaa caggacagtt tttacaaact ttgcaaggtc cagcaagca
2161  tcagagcgct gtgacctgct tacagttcaa caagaacttc gtaattacca gctcagacga
2221  cggaacggtc aaactctggg acttgaaaac gggtgaattt atccgaaacc tcgtcacatt
2281  ggagagtggg gggagcgggg gagttgtgtg gcggatcagg gcctcaaaca caaagctggt
2341  gtgtgcagtc gggagtcgga atggaactga ggaaaccaag ctcctggtgc tggactttga
2401  tgtggacatg aaatgaaaag cagacatgat gaattttgtc caactgtgta gacaatatac
2461  tccctaccct tcccctgcg caaaaaacaa aaacaaacaa acaaaaaaat gaaaaaaaa
2521  aacagaaaaa aaaaagaga aaaagaaaa ggaaaaaaat cccttgtact cagtggtgca
2581  ggatgttggc ttgggacaac agactgaaaa gacctacaga ctaagaaggc aagaagagac
2641  aagagaccgt aactgacagg aggcggcagc tgtcgcatct cgcaaaggcc tcacttgtga
2701  ctgaggggca gcttggcaag acgactctct aaatccaacc aggtgcaatt attctttgtt
2761  ttcttctcca gtggtcattg agcagagcta catcagcgtt gttaccgtca cctagaaagg
2821  agtggcagta atatccaaac acgggctgct tatcttctaa tcagagcatc tgcaacaaac
2881  cgtcattttt ctgaagtgga aaagcttaaa acaattactg tgaattgttt ttgtacagtt
2941  atcatgaagc tttctttttt ctcttttttcc tgtttctctt cttttctttt ttcttttttt
3001  ttttgccaa ccattgccaa tgtcaatcaa tcacagtatt agcctctgtt aatctatctc
3061  tttactgttg cttctactct tcaatgcata tgttgctcaa aggtggcaag ttgtcctggg
3121  ttgtgtgagt cctgagatgg atataattct tgatgctggt gctagaagta ggtcttcaaa
3181  tccggggtcg ttgtcccacc cctgtactgt actcccagtg gccaaactta tttatgctgc
3241  taaatgaaag aaagaaaaag caaattattt tttttttatt tttttctgc tgtgacgttt
3301  tagtcccaga ctgaattcca aatttgctct agtttggtta cagaaaaaaa agactttttt
3361  gccactgaaa cttgagccat ctgtgcctct aagaggctga gaatggaaaa gtttcagata
3421  ataaagagtg aagtttgcct gcaaataaag aattgagagt gtgtgcaaag cttatttct
3481  tttatctggg caaaaattaa aacacattcc ttgggacaga gcctgaggtg cctgttctgt
3541  ggagaaactt cttttttgagg gctgtggtga atggaagaac atacatagca aaactgacaa
```

TABLE 1-continued

```
3601    gatattttaa agatatataa aacacaaagg aaaaggaggt tgctggtcag tcgtagcatc
3661    ttacagtatt ggggaaaaca actgttacag tttcattgct ctgagtgact gacgtgagag
3721    gaattcgctc tgcagtgacg ctgtctgtca ctcgcctacc agctcgacga gcaagagagc
3781    gggagtcaga tggtccgcct cattcaccag gagccgtaac tcaagctgaa ctgtgaaagt
3841    ggttaacact gtatcctagg ccgtcttttt tttcctcctc ctgtttattt tttgtttgtt
3901    ttatttatag tctgatttaa aacaatcaga ttcaagttgg ttaattttag ttatgtaaca
3961    acctgacgtg atggaggaaa caacctgtaa agggattgtg tctatggttt gattcactta
4021    gaaattttat tttcttataa cttaagtgca ataaaatgtg tttttttcatg ttaaaaaaaa
4081    aaaaaaaaaa aa
```

SEQ ID NO: 12 *Mus musculus* F-box and WD repeat domain containing 7 (FBXW7) cDNA, transcript variant 2 (NM_001177773.1)

```
   1    gagcgagcgg ggccgccacc gccgcctcta tcccagcagc gcggaagaga cccgggtagc
  61    tgcttggtgg agcgacgcta gcaccgcttc ttcctcagtt ccgcgcctag ccagccttcc
 121    gcagctgccc gcctcagccc gaaggaggaa gggagccagc acattgtca gcgccaccgc
 181    tcgactctga agcgaaatct cagctatcaa ggagactttt aaaaggctct ctaaatattt
 241    ggtacgagaa tttcttctct ttatatcttt tgtgatccct ctacacattg tgtctagaca
 301    atcagaatgt gaaaaccttt gcatcttctg atagtctagc caaggtccaa gaagtagcaa
 361    gctggctttt ggaaatgaat caggaactgc tctctgtggg cagcaaaaga cgacgaactg
 421    gaggctctct gagagggaat gcttcctcaa gccaggttga tgagggacag atgaatcgcg
 481    tggttgagga ggatccacag cagcaagcga gacatcaaga ggaggagcac actgcgcgga
 541    atggtgaact tgtgggtgca aaccctaggc ctggagacca gaacgatacc cagcaaggac
 601    aagtggagga aaataataac cgctttattt cagtagatga ggactcttcg ggaaatcagg
 661    aagagcaaga ggaagatgaa gagcatgctg gggaacagga ggaggaagag gaggaagagg
 721    aagaggagga ggagatggac caggagagtg atgattttga tccgtctgat gacagtagca
 781    gagaagatga acatacgcac aatagcaatg tcacaaactg cagtagtgtc tcggacctgc
 841    ccgctcacca gctctcctct ccattctata caaagacaac aaaaatgaaa agaaagttgg
 901    accatggttc tgaagttcgt tccttttctt tgggaaagaa accatgcaaa gtctcagatt
 961    ataccagtac cactggcctt gtaccatgtt cagcaacacc aacaactttt ggggacctga
1021    gagcagccaa tgggcaaggg cagcagcggc ggaggattac atctgtccaa ccacccacag
1081    gccttcaaga gtggctgaaa atgtttcaga gctggagcgg accagagaag ttgctggctt
1141    tagatgagct cattgacagc tgtgaaccaa cacaagtgaa gcatatgatg caagtgatag
1201    agccccagtt ccagcgagac ttcatctcct tgcttcctaa agagttggca ctctatgtgc
1261    tttcattcct ggaacccaaa gacctgctgc aagcggctca gacttgtcga tactggagaa
1321    ttttggctga ggataacctt ctctggagag agaaatgtaa agaagagggg attgatgaac
1381    cgttgcacat caagagaaga aaaataataa aaccaggttt catacacagc ccatggaaga
1441    gtgcgtatat cagacagcac agaattgata caaactggag acgaggagaa ctcaaatctc
1501    ctaaggtgct gaaagggcat gatgaccatg tgatcacatg cctacagttt gtggcaacc
1561    gcatagttag tggttctgat gacaacactt taaaagtttg gtcagcggtc acgggcaagt
1621    gtctgagaac gttagtggga catacaggtg gagtgtggtc atcacagatg agagacaata
1681    tcatcatcag tggatcgact gaccggactc tcaaagtgtg gaatgctgaa actggagagt
1741    gtatacatac tttatatggg cacacttcta ctgtacggtg tatgcatctc catgaaaaaa
```

TABLE 1-continued

```
1801  gggttgtaag cggttctcga gatgccactc tcagggtttg ggatattgag accggccagt
1861  gtttacacgt cctgatgggt cacgtagcag cggtccgctg cgttcagtat gatggcagga
1921  gggttgttag tggagcttat gattttatgg tgaaggtgtg ggatccagag actgagacct
1981  gtctacacac gttacaggga cacactaata gagtctattc attacagttt gatggcatcc
2041  atgtggtgag tggatctctt gatacatcaa tccgagtctg ggatgtggag acagggaatt
2101  gtattcacac gctaacagga caccagtcat taacgagtgg aatggaactc aaagacaata
2161  ttcttgtctc tgggaatgca gattctacag ttaagatctg ggatatcaaa acaggacagt
2221  gtttacaaac tttgcaaggt cccagcaagc atcagagcgc tgtgacctgc ttacagttca
2281  acaagaactt cgtaattacc agctcagacg acggaacggt caaactctgg gacttgaaaa
2341  cgggtgaatt tatccgaaac ctcgtcacat tggagagtgg ggggagcggg ggagttgtgt
2401  ggcggatcag ggcctcaaac acaaagctgg tgtgtgcagt cgggagtcgg aatggaactg
2461  aggaaaccaa gctcctggtg ctggactttg atgtggacat gaaatgaaaa gcagacatga
2521  tgaattttgt ccaactgtgt agacaatata ctccctaccc ttcccctgc gcaaaaaaca
2581  aaaacaaaca aacaaaaaaa tgaaaaaaaa aaacagaaaa aaaaaagag aaaaagaaa
2641  aggaaaaaaa tcccttgtac tcagtggtgc aggatgttgg cttgggacaa cagactgaaa
2701  agacctacag actaagaagg caagaagaga caagagaccg taactgacag gaggcggcag
2761  ctgtcgcatc tcgcaaaggc ctcacttgtg actgaggggc agcttggcaa gacgactctc
2821  taaatccaac caggtgcaat tattctttgt tttcttctcc agtggtcatt gagcagagct
2881  acatcagcgt tgttaccgtc acctagaaag gagtggcagt aatatccaaa cacgggctgc
2941  ttatcttcta atcagagcat ctgcaacaaa ccgtcatttt tctgaagtgg aaaagcttaa
3001  aacaattact gtgaattgtt tttgtacagt tatcatgaag ctttcttttt tctcttttc
3061  ctgtttctct tcttttcttt ttcttttt ttttttgcca accattgcca atgtcaatca
3121  atcacagtat tagcctctgt taatctatct ctttactgtt gcttctactc ttcaatgcat
3181  atgttgctca aaggtggcaa gttgtcctgg gttgtgtgag tcctgagatg gatataattc
3241  ttgatgctgg tgctagaagt aggtcttcaa atccggggtc gttgtcccac ccctgtactg
3301  tactcccagt ggccaaactt atttatgctg ctaaatgaaa gaaagaaaaa gcaaattatt
3361  ttttttttat ttttttttctg ctgtgacgtt ttagtcccag actgaattcc aaatttgctc
3421  tagtttggtt acagaaaaaa aagactttt tgccactgaa acttgagcca tctgtgcctc
3481  taagaggctg agaatggaaa agtttcagat aataaagagt gaagtttgcc tgcaaataaa
3541  gaattgagag tgtgtgcaaa gcttattttc ttttatctgg gcaaaaatta aaacacattc
3601  cttgggacag agcctgaggt gcctgttctg tggagaaact tcttttgag ggctgtggtg
3661  aatggaagaa catacatagc aaaactgaca agatatttta aagatatata aaacacaaag
3721  gaaaaggagg ttgctggtca gtcgtagcat cttacagtat tggggaaaac aactgttaca
3781  gtttcattgc tctgagtgac tgacgtgaga ggaattcgct ctgcagtgac gctgtctgtc
3841  actcgcctac cagctcgacg agcaagagag cgggagtcag atggtccgcc tcattcacca
3901  ggagccgtaa ctcaagctga actgtgaaag tggttaacac tgtatcctag gccgtctttt
3961  ttttcctcct cctgtttatt ttttgtttgt tttatttata gtctgattta aaacaatcag
4021  attcaagttg gttaatttta gttatgtaac aacctgacgt gatggaggaa acaacctgta
4081  aagggattgt gtctatggtt tgattcactt agaaatttta ttttcttata acttaagtgc
4141  aataaaatgt gttttttcat gttaaaaaaa aaaaaaaaa aaa
```

TABLE 1-continued

SEQ ID NO: 13 Mus musculus F-box and WD repeat domain containing 7
(FBXW7) cDNA, transcript variant 3 (NM_080428.3)

```
   1 accctggact gcaccattct gtgttcaagg gaagatgtaa tctgatccct ctgctgctga
  61 gggaggaatc tgttcagtca aggctttgac agggcatagt ctcctccaat aatcttgtgg
 121 gttctcgctc attattcccc gagttctcct cagtggagct gcatgcgtgt gtgcgtcccg
 181 agcagcgttc tggttctgag ctgcgtctgc tggtgctggg gagttttgct gccggttccg
 241 ctgcctaatc ttcctttcct ggcgtgcctg agcatgtcca cgttagaatc tgtgacatac
 301 ctacctgaaa aggggttata ttgtcagaga ctgccaagca gccggacaca cggggggcaca
 361 gaatccctga aggggaaaaa tacagaaaat atgggtttct acggcacatt aaaaatgatt
 421 ttttacaaaa tgaaaagaaa gttggaccat ggttctgaag ttcgttcctt ttctttggga
 481 aagaaaccat gcaaagtctc agattatacc agtaccactg gccttgtacc atgttcagca
 541 acaccaacaa cttttgggga cctgagagca gccaatgggc aagggcagca gcggcggagg
 601 attacatctg tccaaccacc cacaggcctt caagagtggc tgaaaatgtt tcagagctgg
 661 agcggaccag agaagttgct ggctttagat gagctcattg acagctgtga accaacacaa
 721 gtgaagcata tgatgcaagt gatagagccc cagttccagc gagacttcat ctccttgctt
 781 cctaaagagt tggcactcta tgtgctttca ttcctggaac ccaaagacct gctgcaagcg
 841 gctcagactt gtcgatactg agaattttg gctgaggata accttctctg gagagagaaa
 901 tgtaaagaag aggggattga tgaaccgttg cacatcaaga aagaaaaat aataaaacca
 961 ggtttcatac acagcccatg gaagagtgcg tatatcagac agcacagaat tgatacaaac
1021 tggagacgag gagaactcaa atctcctaag gtgctgaaag gcatgatga ccatgtgatc
1081 acatgcctac agttttgtgg caaccgcata gttagtggtt ctgatgacaa cactttaaaa
1141 gtttggtcag cggtcacggg caagtgtctg agaacgttag tgggacatac aggtggagtg
1201 tggtcatcac agatgagaga caatatcatc atcagtggat cgactgaccg gactctcaaa
1261 gtgtggaatg ctgaaactgg agagtgtata catactttat atgggcacac ttctactgta
1321 cggtgtatgc atctccatga aaaagggtt gtaagcggtt ctcgagatgc cactctcagg
1381 gtttgggata ttgagaccgg ccagtgttta cacgtcctga tgggtcacgt agcagcggtc
1441 cgctgcgttc agtatgatgg caggagggtt gttagtggag cttatgattt tatggtgaag
1501 gtgtgggatc cagagactga gacctgtcta cacacgttac agggacacac taatagagtc
1561 tattcattac agtttgatgg catccatgtg gtgagtggat ctcttgatac atcaatccga
1621 gtctgggatg tggagacagg gaattgtatt cacacgctaa caggacacca gtcattaacg
1681 agtggaatgg aactcaaaga caatattctt gtctctggga atgcagattc tacagttaag
1741 atctgggata tcaaaacagg acagtgttta caaactttgc aaggtcccag caagcatcag
1801 agcgctgtga cctgcttaca gttcaacaag aacttcgtaa ttaccagctc agacgacgga
1861 acggtcaaac tctgggactt gaaaacgggt gaatttatcc gaaacctcgt cacattggag
1921 agtgggggga gcgggggagt tgtgtggcgg atcagggcct caaacacaaa gctggtgtgt
1981 gcagtcggga gtcggaatgg aactgaggaa accaagctcc tggtgctgga ctttgatgtg
2041 gacatgaaat gaaaagcaga catgatgaat tttgtccaac tgtgtagaca atatactccc
2101 tacccttccc cctgcgcaaa aaacaaaaac aaacaacaa aaaatgaaa aaaaaaaca
2161 gaaaaaaaaa aagagaaaaa agaaaaggaa aaaatccct tgtactcagt ggtgcaggat
2221 gttggcttgg gacaacagac tgaaaagacc tacagactaa gaaggcaaga agagacaaga
2281 gaccgtaact gacaggaggc ggcagctgtc gcatctcgca aaggcctcac ttgtgactga
```

TABLE 1-continued

```
2341  gggcagctt ggcaagacga ctctctaaat ccaaccaggt gcaattattc tttgttttct 2401  tctccagtgg tcattgagca gagctacatc agcgttgtta ccgtcaccta gaaaggagtg 2461  gcagtaatat ccaaacacgg gctgcttatc ttctaatcag agcatctgca caaaccgtc 2521  atttttctga agtggaaaag cttaaaacaa ttactgtgaa ttgttttgt acagttatca 2581  tgaagctttc ttttttctct ttttcctgtt tctcttcttt tcttttttct tttttttttt 2641  tgccaaccat tgccaatgtc aatcaatcac agtattagcc tctgttaatc tatctcttta 2701  ctgttgcttc tactcttcaa tgcatatgtt gctcaaaggt ggcaagttgt cctgggttgt 2761  gtgagtcctg agatggatat aattcttgat gctggtgcta gaagtaggtc ttcaaatccg 2821  gggtcgttgt cccacccctg tactgtactc ccagtggcca aacttattta tgctgctaaa 2881  tgaaagaaag aaaaagcaaa ttatttttt tttattttt ttctgctgtg acgttttagt 2941  cccagactga attccaaatt tgctctagtt tggttacaga aaaaaaagac tttttgcca 3001  ctgaaacttg agccatctgt gcctctaaga ggctgagaat ggaaaagttt cagataataa 3061  agagtgaagt ttgcctgcaa ataaagaatt gagagtgtgt gcaaagctta ttttctttta 3121  tctgggcaaa aattaaaaca cattccttgg gacagagcct gaggtgcctg ttctgtggag 3181  aaacttcttt ttgagggctg tggtgaatgg aagaacatac atagcaaaac tgacaagata 3241  ttttaaagat atataaaaca caaaggaaaa ggaggttgct ggtcagtcgt agcatcttac 3301  agtattgggg aaaacaactg ttacagtttc attgctctga gtgactgacg tgagaggaat 3361  tcgctctgca gtgacgctgt ctgtcactcg cctaccagct cgacgagcaa gagagcggga 3421  gtcagatggt ccgcctcatt caccaggagc cgtaactcaa gctgaactgt gaaagtggtt 3481  aacactgtat cctaggccgt ctttttttc ctcctcctgt ttatttttg tttgttttat 3541  ttatagtctg atttaaaaca atcagattca agttggttaa ttttagttat gtaacaacct 3601  gacgtgatgg aggaaacaac ctgtaaaggg attgtgtcta tggtttgatt cacttagaaa 3661  ttttattttc ttataactta agtgcaataa aatgtgtttt ttcatgttaa aaaaaaaaa 3721  aaaaaaaa
```

SEQ ID NO: 14 *Mus musculus* F-box and WD repeat domain containing 7 (FBXW7) amino acid sequence, isoform 1 (NP_001171245.1)

```
  1   mnqellsvgs krrrtggslr gnasssqvde gqmnrvveed pqqqarhgee ehtarngelv 61   ganprpgdqn dtqggqveen nnrfisvded ssgnqeeqee deehageqee eeeeeeeeee 121   mdqesddfdp sddssredeh thnsnvtncs svsdlpahql sspfytkttk mkrkldhgse 181   vrsfslgkkp ckvsdytstt glvpcsatpt tfgdlraang qgqqrrrits vqpptglgew 241   lkmfqswsgp ekllaldeli dsceptqvkh mmqviepqfq rdfisllpke lalyvlsfle 301   pkdllqaaqt crywrilaed nllwrekcke egideplhik rrklikpgfi hspwksayir 361   qhridtnwrr gelkspkvlk ghddhvitcl qfcgnrivsg sddntlkvws avtgkclrtl 421   vghtggvwss qmrdnilisg stdrtlkvwn aetgecihtl yghtstvrcm hlhekrvvsg 481   srdatlrvwd ietgqclhvl mghvaavrcv qydgrrvvsg aydfmvkvwd petetclhtl 541   qghtnrvysl qfdgihvvsg sldtsirvwd vetgncihtl tghqsltsgm elkdnilvsg 601   nadstvkiwd iktgqclqtl qgpskhqsav tclqfnknfv itssddgtvk lwdlktgefi 661   rnlvtlesgg sggvvwrira sntklvcavg srngteetkl lvldfdvdmk
```

SEQ ID NO: 15 *Mus musculus* F-box and WD repeat domain containing 7 (FBXW7) amino acid sequence, isoform 1 (NP_001171244.1)

```
  1   mnqellsvgs krrrtggslr gnasssqvde gqmnrvveed pqqqarhgee ehtarngelv 61   ganprpgdqn dtqggqveen nnrfisvded ssgnqeeqee deehageqee eeeeeeeeee
```

TABLE 1-continued

```
121     mdqesddfdp  sddssredeh  thnsnvtncs  svsdlpahql  sspfytkttk  mkrkldhgse 181     vrsfslgkkp  ckvsdytstt  glvpcsatpt  tfgdlraang  qgqqrrrits  vqpptglgew 241     lkmfqswsgp  ekllaldeli  dsceptqvkh  mmqviepqfq  rdfisllpke  lalyvlsfle 301     pkdllqaaqt  crywrilaed  nllwrekcke  egideplhik  rrkiikpgfi  hspwksayir 361     qhridtnwrr  gelkspkvlk  ghddhvitcl  qfcgnrivsg  sddntlkvws  avtgkclrtl 421     vghtggvwss  qmrdniiisg  stdrtlkvwn  aetgecihtl  yghtstvrcm  hlhekrvvsg 481     srdatlrvwd  ietggclhvl  mghvaavrcv  qydgrrvvsg  aydfmvkvwd  petetclhtl 541     qghtnrvysl  qfdgihvvsg  sldtsirvwd  vetgncihtl  tghqsltsgm  elkdnilvsg 601     nadstvkiwd  iktggclqtl  qgpskhqsav  tclqfnknfv  itssddgtvk  lwdlktgefi 661     rnlvtlesgg  sggvvwrira  sntklvcavg  srngteetkl  lvldfdvdmk
```

SEQ ID NO: 16 Mus musculu F-box and WD repeat domain containing 7
(FBXW7) amino acid sequence, isoform 2 (NP_536353.2)

```
  1     mrvcvpssvl  vlscvcwcwg  vllpvplpnl  pflaclsmst  lesvtylpek  glycqrlpss 61     rthggteslk  gkntenmgfy  gtlkmifykm  krkldhgsev  rsfslgkkpc  kvsdytsttg 121     lvpcsatptt  fgdlraangq  gqqrrritsv  qpptglgewl  kmfqswsgpe  kllaldelid 181     sceptqvkhm  mqviepqfqr  dfisllpkel  alyvlsflep  kdllqaaqtc  rywrilaedn 241     llwrekckee  gideplhikr  rkiikpgfih  spwksayirq  hridtnwrrg  elkspkvlkg 301     hddhvitclq  fcgnrivsgs  ddntlkvwsa  vtgkclrtlv  ghtggvwssq  mrdniiisgs 361     tdrtlkvwna  etgecihtly  ghtstvrcmh  lhekrvvsgs  rdatlrvwdi  etgqclhvlm 421     ghvaavrcvq  ydgrrvvsga  ydfmvkvwdp  etetclhtlq  ghtnrvyslq  fdgihvvsgs 481     ldtsirvwdv  etgncihtlt  ghqsltsgme  lkdnilvsgn  adstvkiwdi  ktgqclqtlq 541     gpskhqsavt  clqfnknfvi  tssddgtvkl  wdlktgefir  nlvtlesggs  ggvvwriras 601     ntklvcavgs  rngteetkll  vldfdvdmk
```

*Included in Table 1 are RNA nucleic acid molecules (e.g., thymines replaced with uridines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof. Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.
*Included in Table 1 are known Fbxw7 sequences, including those described herein and homologous sequences thereof, as well as Fbxw7 null mutations, missense mutations, nonsense mutations, frameshift mutations, insertion mutation, deletion mutations, and rearrangement mutations.

II. Subjects

In one embodiment, the subject for whom predicted likelihood of resistance to an immune checkpoint therapy, such as a PD-1 inhibitor is determined, is a mammal (e.g., mouse, rat, primate, non-human mammal, domestic animal, such as a dog, cat, cow, horse, and the like), and is preferably a human. In one embodiment, the subject for whom the immune checkpoint therapy in combination with an agent that increases the copy number, amount, and/or activity of Fbxw7 is administered, is a mammal (e.g., mouse, rat, primate, non-human mammal, domestic animal, such as a dog, cat, cow, horse, and the like), and is preferably a human. In another embodiment, the subject is an animal model of a cancer, such as melanoma, colorectal cancer, or uterine cancer. For example, the animal model can be an orthotopic xenograft animal model of a human-derived cancer, such as melanoma, colorectal cancer, or uterine cancer.

In another embodiment of the methods of the present invention, the subject has not undergone treatment, such as chemotherapy, radiation therapy, targeted therapy, and/or an immune checkpoint inhibitor therapy. In still another embodiment, the subject has undergone treatment, such as chemotherapy, radiation therapy, targeted therapy, and/or an immune checkpoint inhibitor therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the efficacy of an agent for treating many different cancers that are resistant to the immune checkpoint therapy in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be resistant to an immune checkpoint therapy, such as a PD-1 inhibitor, and/or evaluate a response to the combination of the immune checkpoint therapy, such as a PD-1 inhibitor, with an agent that increases the copy number, amount, and/or activity of Fbxw7. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising an immune checkpoint therapy, such as a PD-1 inhibitor, alone or in combination with other anti-cancer agents, such as an agent that increases the copy number, amount, and/or activity of Fbxw7.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement. In some embodiments of the present invention the change of biomarker amount and/or activity measurement(s) from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold or greater. In some embodiments, the fold change is less than about 1, less than about 5, less than about 10, less than about 20, less than about 30, less than about 40, or less than about 50. In other embodiments, the fold change in biomarker amount and/or activity measurement(s) compared to a predetermined level is more than about 1, more than about 5, more than about 10, more than about 20, more than about 30, more than about 40, or more than about 50.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray. Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids (e.g., Fbxw7 and/or SHP2/CD47/MYC) that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed.,

*Molecular Cloning: A Laboratory Manual,* 2nd ed., Cold Spring Harbor Laboratory Press, Cold Spring Harbor, NY, 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-i sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an a-anomeric nucleic acid molecule. An a-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., 51 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, CA (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol.185, Academic Press, San Diego, CA, 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, CA, 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast S. cerevisiae include pYepSecl (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, CA), and pPicZ (Invitrogen Corp, San Diego, CA).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, Science 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. The absence of at least one biomarker listed in Table 1 is predictive of poorer outcome of the immune checkpoint therapy, such as a PD-1 inhibitor, treatment. A copy number of at least 3, 4, 5, 6, 7, 8, 9, or 10 of at least one biomarker listed in Table 1 is predictive of likely responsive to the immune checkpoint therapy, such as a PD-1 inhibitor, treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.). In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) i Science 241:1077, and Barringer et al. (1990) Gene 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of cancer cells are obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos: 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}$P and $^{35}$S. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an immune checkpoint therapy, such as a PD-1 inhibitor, treatment. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques. Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ a of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify Fbxw7 protein that is overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et. al. (1990) Proc. Natl. Acad. Sci. USA 87:1874-1878), transcriptional amplification system (Kwoh, D. Y. et. al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad Sci. USA 74:5463. It is also contemplated that any of a variety of automated sequencing procedures can be utilized when performing the diagnostic assays (Naeve (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) Proc Natl. Acad. Sci USA 86:2766; see also Cotton (1993) Mutat. Res. 285:125-144 and Hayashi (1992) Genet. Anal. Tech. Appl. 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Anti-Cancer Therapies

The response of a cancer in a subject to an immune checkpoint therapy, such as a PD-1 inhibitor, treatment is predicted according to the methods described herein. In one embodiment, such immune checkpoint therapy, such as a PD-1 inhibitor, treatment or combinations of therapies (e.g., immune checkpoint therapy, such as a PD-1 inhibitor, treatment in combination with an agent that increases the copy number, amount, and/or activity of Fbxw7, anti-SHP2 therapy, anti-CD47 therapy, anti-MYC therapy, interferon-gamma therapy, IRF1 therapy, JAK/STAT therapy, and the like) can be administered once a subject is indicated as being a likely responder to an immune checkpoint therapy, such as a PD-1 inhibitor. In another embodiment, such immune checkpoint therapy, such as a PD-1 inhibitor, treatment can be avoided once a subject is indicated as not being a likely responder to an immune checkpoint therapy, such as a PD-1 inhibitor, and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with the immune checkpoint therapy, such as a PD-1 inhibitor. The immune checkpoint therapy, such as a PD-1 inhibitor, and exemplary agents useful for increasing the copy number, amount, and/or activity of Fbxw7 described herein, have been described above.

The term "targeted therapy" refers to administration of agents that selectively interact with a chosen biomolecule to thereby treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" referes to administration of agents that do not selectively interact with a chosen biomolecule yet treat cancer. Representative examples of untargeted therapies include, without limitation, chemotherapy, gene therapy, and radiation therapy.

In one embodiment, mitochondrial cofactor therapy is useful. For example, vitamin E is known to block cell death via ferroptosis such that mitochondrial cofactor therapy can alleviate or improve any toxicity associated with ISC biosynthesis pathway inhibition. Mitochondrial cofactor therapies are well known in the art and include, for example, coenzyme Q10 (ubiquinone), riboflavin, thiamin, niacin, vitamin K (phylloquinone and menadione), creatine, carnitine, and other antioxidants such as ascorbic acid and lipoic acid (see, for example, Marriage et al. (2003) *J. Am. Diet. Assoc.* 103:1029-1038 and Parikh et al. (2009) *Curr. Treat. Options Neurol.* 11:414-430).

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, pro-apoptotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; pro-apoptotic agents: venetoclax (ABT-199), navitoclax and Obatoclax; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside (cytarabine); purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of β-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 June 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. In addition to its use to destroy the cancer, laser surgery is also used to help relieve symptoms caused by cancer (palliative care). It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with an immune checkpoint therapy, such as a PD-1 inhibitor, in combination with an agent that increases the copy number, amount, and/or activity of Fbxw7 may vary according to the particular immune checkpoint therapy, such as a PD-1 inhibitor, inhibitor, agent, or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of the present invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of the present invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Feigner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

VII. Clincal Efficacy

Clinical efficacy can be measured by any method known in the art. For example, the response to a therapy, such as the combination of an immune checkpoint therapy, such as a PD-1 inhibitor, and an agent that increases the copy number, amount, and/or activity of Fbxw7, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular combination of an immune checkpoint therapy, such as a PD-1 inhibitor, and an agent that increases the copy number, amount, and/or activity of Fbxw7 regimen is at least 25%, 30%, 35%, 40%, 45%, 50%, 55%, 60%, 65%, 70%, 75%, 80%, 85%, or more.

Additional criteria for evaluating the response to the combination of an immune checkpoint therapy, such as a PD-1 inhibitor, and/or another agent, such as one that increases the copy number, amount, and/or activity of Fbxw7 is related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular combination of an immune checkpoint therapy, such as a PD-1 inhibitor, and/or another agent, such as one that increases the copy number, amount, and/or acticity of Fbxw7 therapeutic regimen can be administered to a population of subjects and the outcome can be correlated to biomarker measurements that were determined prior to administration of any combination therapy of an immune checkpoint therapy, such as a PD-1 inhibitor, and/or another agent, such as one that increases the copy number, amount, and/or acticity of Fbxw7. The outcome measurement may be pathologic response to therapy given in the neoadjuvant setting. Alternatively, outcome measures, such as overall survival and disease-free survival can be monitored over a period of time for subjects following the combination therapy of an immune checkpoint therapy, such as a PD-1 inhibitor, and/or another agent, such as one that increases the copy number, amount, and/or activity of Fbxw7 for whom biomarker measurement values are known. In certain embodiments, the same doses of immune checkpoint therapy, such as a PD-1 inhibitor, and/or another agent, such as one that increase the copy number, amount, and/or acticity of Fbxw7 are administered to each subject. In related embodiments, the doses administered are standard doses known in the art for immune checkpoint therapy, such as a PD-1 inhibitor, and/or another agent, such as one that increase the copy number, amount, and/or activity of Fbxw7. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an combination therapy of an immune checkpoint therapy, such as a PD-1 inhibitor, and/or another agent, such as one that increases the copy number, amount, and/or activity of Fbxw7 can be determined using methods such as those described in the Examples section.

VIII. Further Uses and Methods of the Present Invention

The methods described herein can be used in a variety of diagnostic, prognostic, and therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays. The compositions described herein can be used in a variety of diagnostic, prognostic, and therapeutic applications regarding biomarkers described herein, such as those listed in Table 1. Moreover, any method of diagnosis, prognosis, prevention, and the like described herein can be be applied to a therapy or test agent of interest, such as immune checkpoint therapy, such as a PD-1 inhibitor, treatment, combination therapy of an immune checkpoint therapy, such as a PD-1 inhibitor, and another agent, such as one that increases the copy number, amount, and/or activity of Fbxw7, and the like.

a. Screening Methods

One aspect of the present invention relates to screening assays, including non-cell based assays. In one embodiment, the assays provide a method for identifying whether a cancer is likely to respond to anti-cancer therapy (e.g., immune checkpoint therapy, such as a PD-1 inhibitor,) and/or whether an agent can inhibit the growth of or kill a cancer cell that is unlikely to respond to anti-cancer therapy (e.g., immune checkpoint therapy, such as a PD-1 inhibitor).

In one embodiment, the present invention relates to assays for screening test agents which have a cytotoxic or cytostatic effect on cancer cells that are resistant to an immune checkpoint therapy, such as a PD-1 inhibitor. In one embodiment, a method for identifying such an agent entails determining the ability of the agent to agent to increase the copy number, amount and/or activity of Fbxw7.

In one embodiment, an assay is a cell-free or cell-based assay, comprising contacting at least one biomarker listed in Table 1, with a test agent, and determining the ability of the test agent to modulate (e.g. upregulate) the enzymatic activity of the biomarker, such as by measuring direct binding of substrates or by measuring indirect parameters as described below.

In another embodiment, an assay is a cell-free or cell-based assay, comprising contacting at least one biomarker listed in Table 1, with a test agent, and determining the ability of the test agent to modulate (e.g. upregulate) the ability of the biomarker to regulate translation of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$, or $^{3}H$, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and its natural binding partner can be accomplished by determining the ability of the test agent to modulate the activity of a polypeptide or other product that functions downstream or upstream of its position within the same pathway of the biomarker.

The present invention further pertains to novel agents identified by the above-described screening assays. Accordingly, it is within the scope of the present invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby determine whether an individual afflicted with a cancer is likely to respond to an immune checkpoint therapy, such as a PD-1 inhibitor, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of the present invention.

In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of the present invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to an immune checkpoint therapy, such as a PD-1 inhibitor. In some embodiments, the present invention is useful for classifying a sample (e.g., from a subject) as associated with or at risk for responding to or not responding to an immune checkpoint therapy, such as a PD-1 inhibitor, using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to an immune checkpoint therapy, such as a PD-1 inhibitor, involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely immune checkpoint therapy, such as a PD-1 inhibitor, responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to an immune checkpoint therapy, such as a PD-1 inhibitor, treatment), a biological sample from the subject during remission, or a biological sample from the subject during treatment for developing a cancer progressing despite an immune checkpoint therapy, such as a PD-1 inhibitor, treatment.

d. Prognostic Assays

The diagnostic methods described herein can furthermore be utilized to identify subjects having or at risk of developing a cancer that is likely or unlikely to be responsive to an immune checkpoint therapy, such as a PD-1 inhibitor. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, immune checkpoint therapy, such as a PD-1 inhibitor, can be used to treat cancers determined to be responsive thereto.

Another aspect of the present invention pertains to methods of modulating the expression or activity of one or more biomarkers described herein (e.g., those listed in Table 1 and the Examples or fragments thereof) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Another aspect of the present invention pertains to methods of modulating the expression or activity of one or more biomarkers described herein (e.g., those listed in Table 1 and the Examples or fragments thereof,) for therapeutic purposes. The biomarkers of the present invention have been demonstrated to correlate with cancers. Accordingly, the activity and/or expression of the biomarker, as well as the interaction between one or more biomarkers or a fragment thereof and its natural binding partner(s) or a fragment(s) thereof, can be modulated in order to treat cancers.

Modulatory methods of the present invention involve contacting a cell with one or more biomarkers of the present invention, including one or more biomarkers of the present invention, including one or more biomarkers listed in Table 1 and the Examples or a fragment thereof or agent that modulates one or more of the activities of biomarker activity associated with the cell. An agent that modulates biomarker activity can be an agent as described herein, such as a nucleic acid or a polypeptide, a naturally-occurring binding partner of the biomarker, an antibody against the biomarker, a combination of antibodies against the biomarker and antibodies against other immune related targets, one or more biomarkers agonist or antagonist, a peptidomimetic of one or more biomarkers agonist or antagonist, one or more biomarkers peptidomimetic, other small molecule, or small RNA directed against or a mimic of one or more biomarkers nucleic acid gene expression product.

An agent that modulates the expression of one or more biomarkers of the present invention, including one or more biomarkers of the present invention, including one or more biomarkers listed in Table 1 and the Examples or a fragment thereof is, e.g., an antisense nucleic acid molecule, RNAi molecule, shRNA, mature miRNA, pre-miRNA, pri-miRNA, miRNA*, anti-miRNA, or a miRNA binding site, or a variant thereof, or other small RNA molecule, triplex oligonucleotide, ribozyme, or recombinant vector for expression of one or more biomarkers polypeptide. For example, an oligonucleotide complementary to the area around one or more biomarkers polypeptide translation initiation site can be synthesized. One or more antisense oligonucleotides can be added to cell media, typically at 200 µg/ml, or administered to a patient to prevent the synthesis of one or more biomarkers polypeptide. The antisense oligonucleotide is taken up by cells and hybridizes to one or more biomarkers mRNA to prevent translation. Alternatively, an oligonucleotide which binds double-stranded DNA to form a triplex construct to prevent DNA unwinding and transcription can be used. As a result of either, synthesis of biomarker polypeptide is blocked. When biomarker expression is modulated, preferably, such modulation occurs by a means other than by knocking out the biomarker gene.

Agents which modulate expression, by virtue of the fact that they control the amount of biomarker in a cell, also modulate the total amount of biomarker activity in a cell.

In one embodiment, the agent stimulates one or more activities of one or more biomarkers of the present invention, including one or more biomarkers listed in Table 1 and the Examples or a fragment thereof. Examples of such stimulatory agents include active biomarker polypeptide or a fragment thereof and a nucleic acid molecule encoding the biomarker or a fragment thereof that has been introduced into the cell (e.g., cDNA, mRNA, shRNAs, siRNAs, small RNAs, mature miRNA, pre-miRNA, pri-miRNA, miRNA*, anti-miRNA, or a miRNA binding site, or a variant thereof, or other functionally equivalent molecule known to a skilled artisan). In one embodiment, the agent inhibits or enhances the interaction of the biomarker with its natural binding partner(s). Examples of such inhibitory agents include antisense nucleic acid molecules, anti-biomarker antibodies, biomarker inhibitors, and compounds identified in the screening assays described herein.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a condition or disorder that would benefit from up- or down-modulation of one or more biomarkers of the present invention listed in Table 1 and the Examples or a fragment thereof, e.g., a disorder characterized by unwanted, insufficient, or aberrant expression or activity of the biomarker or fragments thereof. In one embodiment, the method involves administering an agent (e.g., an agent identified by a screening assay described herein), or combination of agents that modulates (e.g., upregulates or downregulates) biomarker expression or activity. In another embodiment, the method involves administering one or more biomarkers polypeptide or nucleic acid molecule as therapy to compensate for reduced, aberrant, or unwanted biomarker expression or activity.

Stimulation of biomarker activity is desirable in situations in which the biomarker is abnormally downregulated and/or in which increased biomarker activity is likely to have a beneficial effect. Likewise, inhibition of biomarker activity is desirable in situations in which biomarker is abnormally upregulated and/or in which decreased biomarker activity is likely to have a beneficial effect.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer, being treated, the extent of the disease and other factors familiar to the physician of skill in the art and can be determined by the physician.

IX. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in deg Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of the present invention.

Pharmaceutical compositions of the present invention suitable for parenteral administration comprise one or more therapeutic agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of the present invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

Other embodiments of the present invention are described in the following Examples. The present invention is further illustrated by the following examples which should not be construed as further limiting.

Exemplification

Example 1: Material and Methods for Examples 2-7

Cell Lines and Reagents

Murine melanoma D4M3A cells (a gift of David Fisher, Massachusetts General Hospital) were cultured in DMEM supplemented with 5% fetal bovine serum (FBS) and penicillin-streptomycin (PS). Murine colon carcinoma MC38 cells (gift of Robin Riley, National Institutes of Health), were grown in RPMI-1640 supplemented with 5% FBS, PS and glutamine. Cells were incubated at 37° C. at 5% $CO_2$.

Cells were routinely tested and found to be free of mycoplasma using PCR-based screening.

Generation of D4M3A-Cas9 (D4C9) and MC38-Cas9 (MCC9) Cells and Derivatives

The lentiviral Cas9-blast (pXPR_101; Broad Institute of Harvard and MIT) vector was co-transfected with packaging plasmids PAX2 and pMD2.G into Lenti-X cells (Clontech). Transfection was performed using TransIT-LT1 #MIR 2306) following the manufacturer's protocol. Virus was harvested at 48 and 72 hours post-transfection and stored at 4° C. D4M3A and MC38 cells were infected with Cas9-blast lentivirus for 24 hours, then selected with 10 µg/ml of blasticidin (InvivoGen, #ant-bl-1). D4C9 and MCC9 cells were infected with a lentivirus driving the expression of a specific Fbxw7 sgRNA or a non-targeting control sgRNA, followed by drug selection in 150 µg/ml hygromycin. gRNA oligos were annealed and cloned into LentiGuide-hygro (a derivative of LentiGuide-puro). An early passage pooled hygromycin-resistant population of cells were used for all experiments.

The murine wild-type Fbxw7 cDNA in the pENTR1A vector was purchased from GenScript (Piscataway, NJ). Site-directed mutagenesis was performed using In-Fusion HD (Clontech) using the following primers: mt_mFbxw7-505C-F, AGCGGTCTGCTGCGTTCAGTAT-GATGGCAGG; mt_mFbxw7-505C-R, ACGCAGCA-GACCGCTGCTACGTGACCC. Expression constructs in the pLX304 vector were generated using the Gateway cloning system (Reece-Hoyes & Walhout (2018) *Cold Spring Harb Protoc*). An empty vector control for viruses was generated pENTR4(no ccdB), a gift from Eric Campeau & Paul Kaufman (Addgene plasmid #17424). The IRF1 cDNA cloned in the pDONR vector was obtained from the GeneCopoeia, Inc (Rockville, MD). Gateway cloning was used to generate the lentiviral plasmid pLX304-zeo-IRF1 plasmid. All plasmids and their derivatives were verified by sequencing.

To establish stable cells ectopically expressing IRF1 or Fbxw7, D4C9 were infected with IRF1, Fbxw7(wild-type) or Fbxw7(R505C) lentiviruses, and selected with 400 µg/m1 zeocin. Ten days post-infection, the expression of Fbxw7 was determined by immunoprecipitation and Western blotting (below).

Cell Counting

Equal numbers of control (non-targeting sgRNA) and Fbxw7-deficient cells were seeded at day 0 and harvested at days 3, 6 and 9. Cell counting was performed using the Vi-Cell XR (Beckman Coulter). Cell viability was assessed by using Trypan Blue.

Animal Experiments $5\times10^5$ D4M3A cells (or derivatives) or $1.2\times10^5$ MC38 cells (or derivatives) were subcutaneously injected into both flanks of 6 week-old male C57BL/6 mice (Charles River Laboratories, #027). Nine days after implantation, mice were randomized into two groups and treated with 200 µg of either control Rat IgG2a (BioXCell, #BE0089) or anti-PD-1 (clone 29F.1A12) (Rodig et al. (2003) *Eur J Immunol* 33:3117-3126) by intraperitoneal injection at days 9, 12 and 15. Tumor volume was measured twice a week using a digital caliper. Mice were sacrificed when tumor volume reached 1000 mm$^3$ and overall survival was monitored. All experiments were performed in compliance with federal laws and institutional guidelines and were approved by the Animal Care and Use Committee of the Dana-Farber Cancer Institute.

Antibodies

The following antibodies were used for western blot: rabbit anti-Fbxw7 (Novus Biologicals, #NB100-88138), rabbit anti-phospho-STAT1 (Cell Signaling Technology, #7649), rabbit anti-STAT1 (Cell Signaling Technology, #9172), goat anti-PD-L1 (R&D Systems, #AF1019), rabbit anti-cMyc (Cell Signaling Technology, #5605), rabbit anti-COX IV (Cell Signaling Technology, #4844), rabbit anti-GAPDH (HRP conjugate) (Cell Signaling Technology, #3683), rabbit anti-IRF-1 (Cell Signaling Technology, #8478), rabbit anti-phospho-Jak1 (Cell Signaling Technology, #74129), and rabbit anti-Jak1 (Cell Signaling Technology, #3344). The following HRP-linked secondary antibodies were used: goat anti-rabbit-IgG (Cell Signaling Technology, #7074), donkey anti-goatIgG (Santa Cruz Biotechnology, #2020) and mouse anti-rabbit-IgG (conformation specific) (Cell Signaling Technology, #5127). The following antibodies were used for immunoprecipitation: rabbit anti-Fbxw7 (Bethyl Laboratories, #A301-720A) and mouse anti-Jak1 (Cell Signaling Technology, #50996). Parallel immunnoprecipitations using anti-rabbit IgG (Santa Cruz Biotechnology, sc-2027) were performed to confirm specificity.

The following antibodies were used for flow cytometry: anti-mouse H-2D$^b$ (BD Pharmingen, #553574), mouse IgG2b k isotype control (BD Pharmingen #555743), rat anti-mouse-PD-L1 (Biolegend, #124307), rat IgG2b k isotype control (Biolegend #400608), rat anti-mouse CD47 (BD Biosciences #563585), rat IgG2a k isotype control (BD Bisciences #553930).

Anti-CD3 and anti-CD8 antibodies (Dako, #A0452 (rabbit) and #M7103, clone C8/144B (mouse) respectively) were used for immunohistochemistry.

Western Blot Assay

Whole cell lysates were collected in Triton X-100 lysis buffer (Boston BioProducts, #BP117) supplemented with Complete ULTRA protease inhibitor (Roche) and Phospho-STOP phosphatase inhibitor (Roche). After protein quantities were normalized using BCA Protein Assay Kit (Thermo Scientific), samples were denatured with SDS loading dye at 95° C. for 5 min. Samples were resolved on a 4-20% Criterion TGX stain-free gel (Bio-Rad, #5678094) at 150V for 90 min. Proteins were transferred to 0.2 µm nitrocellulose membrane at 25V for 7 min. The membrane was blocked with 5% milk in TBST for 60 min, washed with TBST and incubated with primary antibodies overnight at 4° C. After washing with TBST, the membrane was incubated with secondary antibody at room temperature for one hour. Membranes were washed with TBST, and chemiluminescence reaction was performed using Pierce ECL Western Blotting Substrate, Supersignal West Dura or Supersignal West Femto (Thermo Scientific). Chemiluminescent films were exposed to the membrane in a darkroom and developed using a Kodak X-OMAT 2000A developer. Westerns shown are reflective of at least 3 biological independent experiments.

Immunoprecipitation

Whole cell lysates were collected in Triton X-100 lysis buffer (for Jak1) or RIPA lysis buffer (Boston BioProducts, #BP-115) (for Fbxw7) supplemented with Complete ULTRA protease inhibitor (Roche) and Phospho-STOP phosphatase inhibitor (Roche). Protein concentration was measured using BCA Protein Assay Kit. For each sample, 500 to 1000 µg protein was aliquoted into two 1.5 mL Eppendorf tubes. Antibodies for the protein of interest and control IgG were incubated with the samples overnight at 4° C. upon agitation. Protein A magnetic beads (New England Biolabs, #S1425) were added, and the samples were incubated for an additional hour at 4° C. upon agitation. The beads were precipitated three times using a magnetic stand apparatus and washed with fresh Triton X-100 or RIPA buffer after each precipitation. After the third wash, SDS loading dye was added, and the samples were boiled at 95° C. for 5 min. Samples were resolved by western blot, as described above.

Flow Cytometry

Control (non-targeting sgRNA) and Fbxw7-deficient cells were treated with murine IFNγ (Cell Signaling Technology, #5222) at the indicated concentration, or an equal volume of vehicle for 24 h. Cells were stained with antibodies for the proteins of interest or with a control IgG, followed by FACS analysis. BD FACSCanto II was used for data acquisition and FlowJo was used for data analysis. The median of fluorescence intensity (MFI) was calculated using FlowJo.

NanoString Assay $5 \times 10^5$ D4C9-sgCtrl or D4C9-sgFbxw7 were subcutaneously injected into both flanks of 6 weeks-old male C57BL/6 mice. Nine days after implantation, mice were randomized into two groups and either sacrificed (pre-treatment), or treated with 200 µg of anti-PD-1 at days 9, 12 and 15 prior to tumor harvest at day 16 (post-treatment). Tumors were harvested and total RNA was extracted using the RNeasy Plus Mini Kit (Qiagen, #74134) following the manufacturer's protocol. Total RNA was submitted to the CAMD Research Core at Brigham and Women's Hospital (BWH) for mRNA profiling using the nCounter Mouse PanCancer Immune Profiling Panel (NanoString Technologies). The analysis was done using the Advanced Analysis Module of nSolver.

Immunohistochemistry $5 \times 10^5$ D4C9-sgCtrl or D4C9-sgFbxw7 were subcutaneously injected into both flanks of 6 weeks-old male C57BL/6 mice. Nine days after implantation, mice were randomized into two groups and either sacrificed (pre-treatment), or treated with 200 µg of anti-PD-1 at days 9, 12 and 15 prior to sacrifice at day 16 (post-treatment). Harvested tumors were fixed in formalin 10%, stored in ethanol 70% and submitted to the BWH Pathology Core for paraffin embedding, sectioning, staining for CD3 and CD8, imaging and quantification. Analysis was performed by counting the number of CD3 and CD8 positive cells per mm² of tumor as previously described (Rodig et al. (2018) Sci Transl Med 10:eaar3342).

DNA Extraction and Sequencing

For samples newly sequenced from the Dana-Farber Cancer Institute, DNA extraction from formalin-fixed, paraffin-embedded (FFPE) tumor blocks were performed as previously described (Van Allen et al. (2014) Nat Med 20:682-688). Exome sequencing and data processing to produce a BAM file was performed using established analytical pipelines at the Broad Institute (George et al. (2017) Immunity 46:197-204). All samples with tumor and germline sequencing data and clinical annotations were processed through standard quality control pipelines (George et al. (2017) Immunity 46:197-204).

Whole Exome Analysis

Somatic nucleotide polymorphisms (SNPs) were identified by MuTect (Cibulskis et al. (2013) Nat Biotechnol 31:213-219), with computational filtering of artifacts introduced by DNA oxidation during sequencing (Costello et al. (2013) Nucleic Acids Res 41:e67) or FFPE-based DNA extraction using a filter-based method. Strelka (Saunders et al. (2012) Bioinformatics 28:1811-1817) was applied to detect small insertions and deletions (indels). Annotation of identified variants was done using Oncotator (http://www-.broadinstitute.org/cancer/cga/oncotator). Mutational clonality was estimated by ABSOLUTE, which uses allelic fraction of called mutations and allelic copy number information to determine mutational clonality and overall tumor purity and ploidy (Carter et al. (2012) Nat Biotechnol 30:413-421). Clonal mutations were defined as those with estimated cancer cell fraction (CCF) of 1 or those whose probability of being clonal exceeded the probability of being subclonal.

For copy number analysis, copy ratios were calculated for each captured target by dividing the tumor coverage by the median coverage obtained in a set of reference normal samples. The resulting copy ratios were segmented using the circular binary segmentation algorithm (Olshen et al. (2004) Biostatistics 5:557-572). To identify focal copy number events, we applied a previously described concept called focality (Brastianos et al. (2015) Cancer Discov 5:1164-15) to identify CNAs that were large outliers in copy ratio, representing either homozygous deletions expected to completely eliminate tumor expression of a given gene or amplifications expected to greatly over-express a gene. In this process, the rCN from ABSOLUTE was used as input. For each segment in a tumor genome, the focality was calculated by considering the fraction of a sample's genome with lower rCN than that segment (for amplified regions) or higher rCN (for deleted regions). Segments were considered deleted if their rCN was <0.25 and their focality was >0.995. Segments were considered amplified if focality exceeded $0.98-0.2 \times \log_2$ (rCN/5), and highly amplified if focality exceeded $0.98-(1/7) \times \log_2$ (rCN/7). Genes were considered amplified or deleted if all or part of the gene was in a segment with a called copy number alteration using this focality-based definition. All gene-level CNAs of interest were manually reviewed. A similar focality procedure was applied to allelic copy number calls from ABSOLUTE to determine heterozygous deletions and amplifications to identify loss-of-heterozygosity events.

Mutational signature deconvolution was conducted using a non-negative matrix factorization technique as previously described (Kim et al. (2016) Nat Genet 48:600-606). Mutational signatures were chosen from those previously described in COSMIC (http://cancer.sanger.ac.uk/cosmic/signatures). The vectors for the commonly observed mutational signatures for each cancer type were used as input for inference of their contribution to observed mutations. Thus, the signatures selected for melanoma pertained to UV exposure, prior alkylating agents, and other exposures.

For neoantigen prediction, the 4-digit HLA type for each sample was inferred using Polysolver (Shukla et al. (2015) Nat Biotechnol 33:1152-1158). Putative neoantigens were predicted for each patient by defining all novel amino acid 9-mers and 10-mers resulting from each somatic nonsynonymous point mutation and determining whether the predicted binding rank—a proxy for predicted binding affinity to the patient's germline HLA alleles—was <2%. Strong binders had 10 rank <0.5%, while weak binders had rank between 0.5% and 2% using NetMHCpan (v3.0) (Hoof et al. (2009) Immunogenetics 61:1-13; Nielsen & Andreatta (2016) Genome Med. 8:33; Nielsen et al. (2007) PLoS One 2:e796).

Association of FBXW7 Mutations with Immunotherapy Response and Gene Expression

To examine the association of clinically detected FBXW7 mutations with response to immune checkpoint blockade, it was identified herein a cohort of 62 patients with metastatic melanoma from 2 different institutions (Dana-Farber Cancer Institute, Vanderbilt) treated with immune checkpoint blockade (ICB) (pembrolizumab (n=24), ipilimumab (n=21), combined ipilimumab-nivolumab (n=13), combined ipilimumab-pembrolizumab (n=2), IL-2 (1), or combination ipilimumab/TVEC (n=1)) with at least 180 days of follow-up and a pre-ICB tumor biopsy that underwent sequencing. Sequencing was performed using a CLIA-certified gene panel with at least 280 cancer-related genes including FBXW7 on FFPE tumor blocks, and variants called as previously described (Garcia et al. (2017) Arch Pathol Lab Med 141:751-758).

The association of FBXW7 gene expression with survival was performed using TIMER (https://cistrome.shinyapps.io/timer/), which is based on the Cox Proportional Hazard Model. Levels of FBXW7 were equally divided into high and low expression (total N=429 with 209 dying). P-value of log-rank test for comparing survival curves of two group is showed in each plot.

For analyzing correlation of FBXW7 with cytotoxic T lymphocytes, it was calculated herein Spearman's correlation and estimated statistical significance using TIMER. To evaluate the correlation of FBXW7 mutations with gene expression, it was compared herein Gene Set enrichment analysis (hallmark gene set) on ranked list of genes correlated with FBXW7 mutant melanomas versus non-mutated melanomas.

RNA Sequencing Analysis

Control and Fbxw7-deficient cells were stimulated with mouse IFNγ 10 ng/ml or vehicle for 24 h. Total RNA was extracted using the RNeasy Plus Mini Kit (Qiagen, #74134) following the manufacturer's protocol. Total RNA was submitted to the Molecular Biology Core Facility at DFCI for sequencing. Raw reads were aligned using Gene counts to produce count tables for each gene. Differential gene analysis was performed on gene raw counts with edgeR package bioConductor. Read count table was filtered so that each gene had a minimum of 1 count across all conditions. Other analyses, including Gene Set Enrichment Analysis were performed using Bioconductor. Raw RNA sequencing will be deposited in the GEO database.

Statistical Analysis

The results are presented as the mean±s.e.m. Statistical significance was assessed using GraphPad Prism software. P<0.05 was considered statistically significant.

Example 2: Mutations in Fbxw7 Cause Resistance to Immune Checkpoint Therapy and are Associated with Decreased PD-L1 Expression and Increased C-Myc and CD47 Expression In order to discover genes that are associated with acquired resistance to immunotherapy, whole exome sequencing was performed from biopsies of 10 melanoma patients prior to treatment and upon therapy resistance. On average, more than 30 new somatic variants were found in the resistant tumor compared to the paired pre-treatment tumor. Specifically, paired tumor samples from 10 patients with diffusely metastatic melanoma who experienced near-complete responses to anti-PD-1 (alone or in conjunction with anti-CTLA-4) therapy were identified. For each patient, exome sequencing of a pre-treatment biopsy, a biopsy of the resistant tumor, and peripheral blood mononuclear cells (PBMCs), were conducted (FIG. 2A-FIG. 2D). When possible, cell lines were also generated from tumor biopsies. In terms of intra-patient resistance characterization, generally, no common predicted neoantigens, no major copy number variation, very limited overlap in somatic variation among patients, and ~30-50 somatic variants found exclusively in resistant tumor (per patient), were observed. Also, in all cases thus far, mutations in known immunotherapy resistance mechanisms, such as interferon-gamma or antigen presentation pathways, were not detected.

Figure 2A:
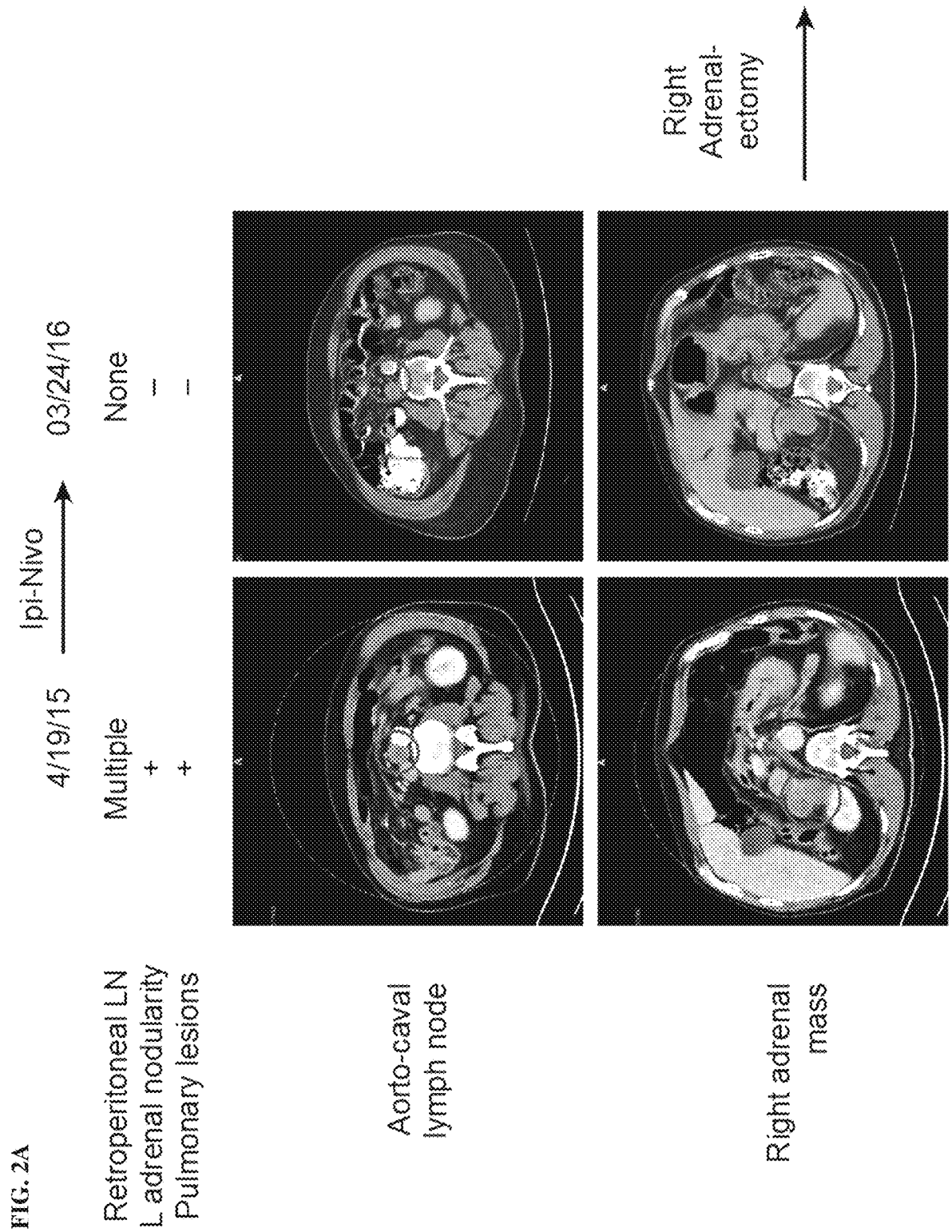
FIG. 2A-FIG. 2K show that inactivating mutations in FBXW7 are associated with resistance to immunotherapy.
Figure 2B:
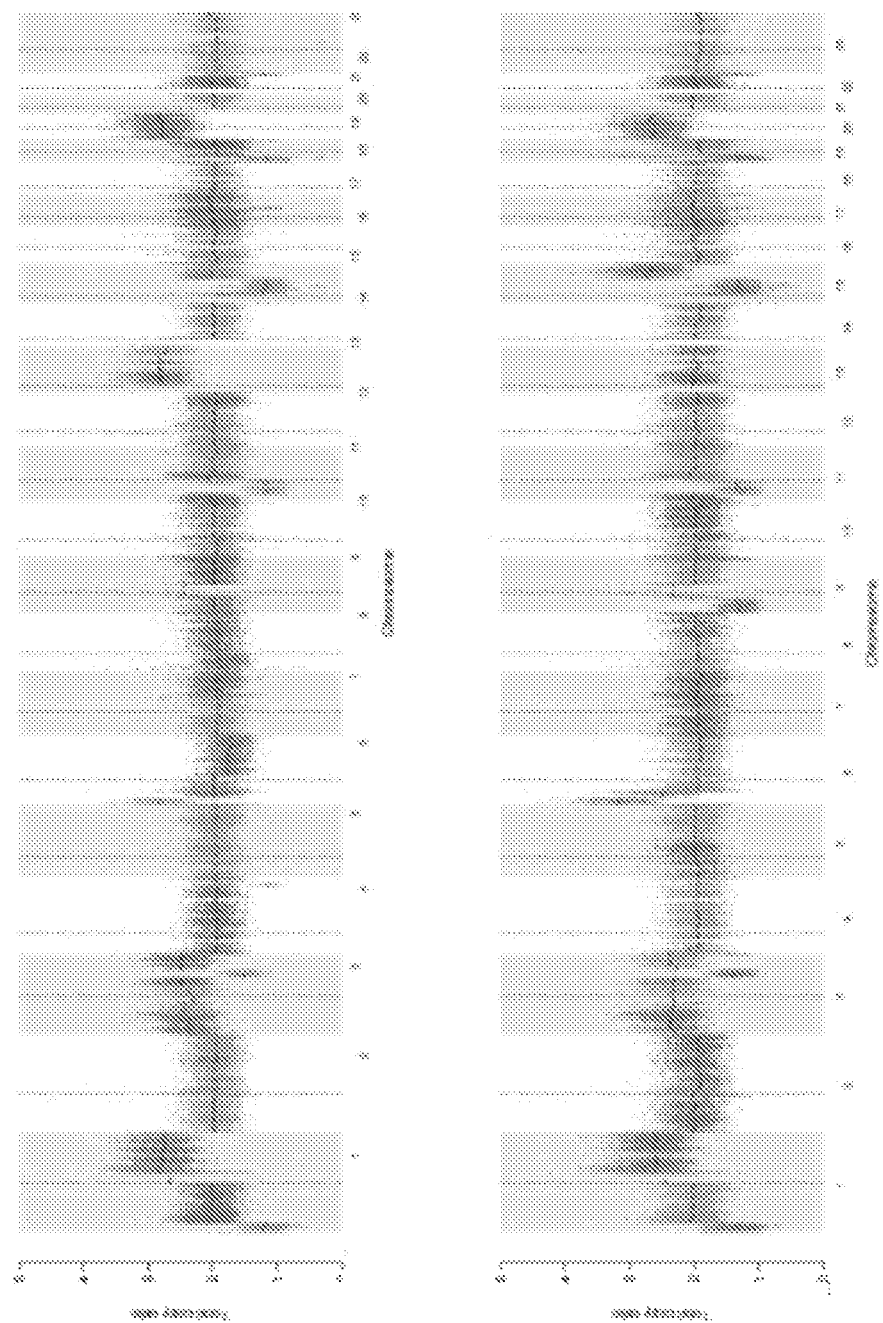
Figure 2C:
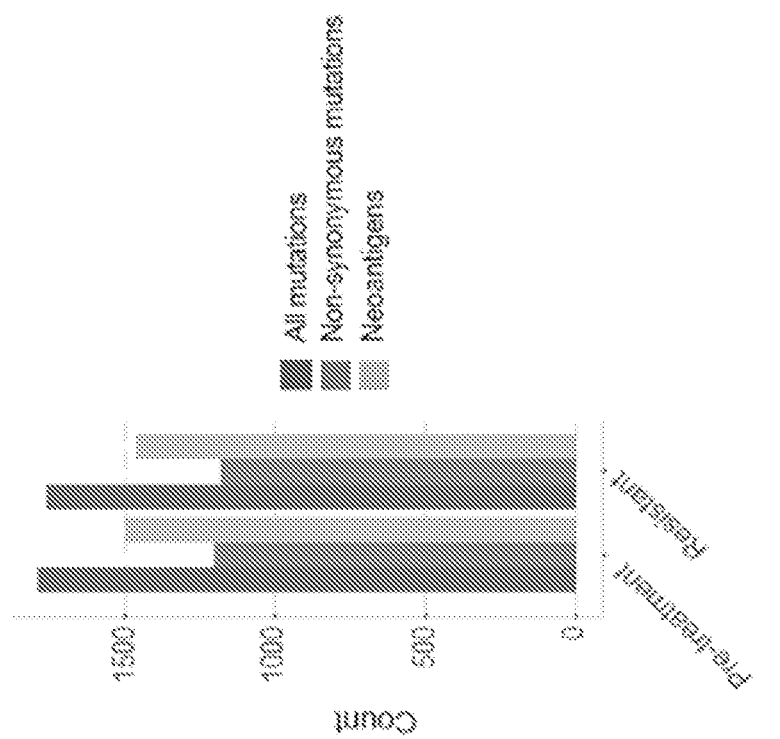
Figure 2C:
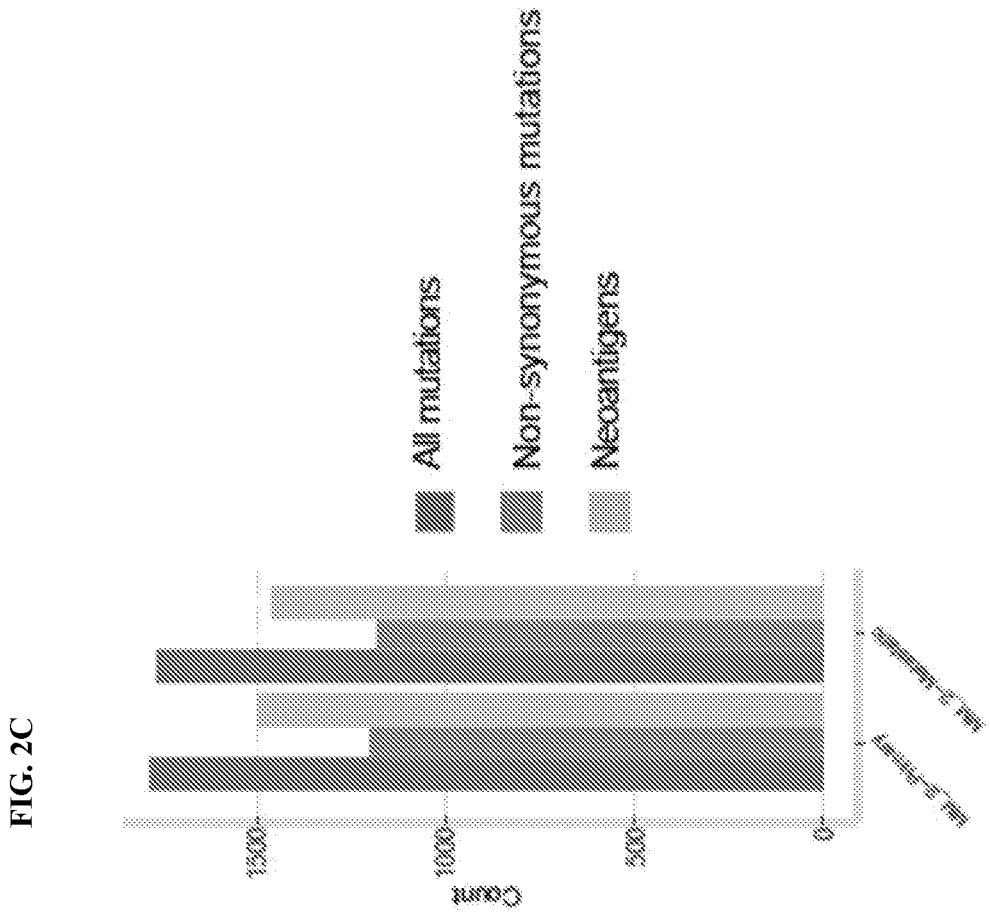
Figure 2D:
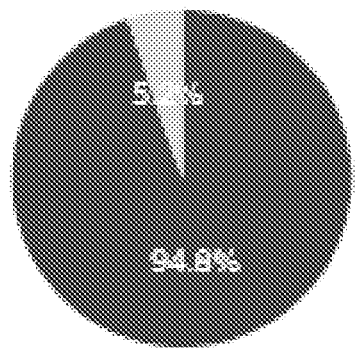
Figure 2D:
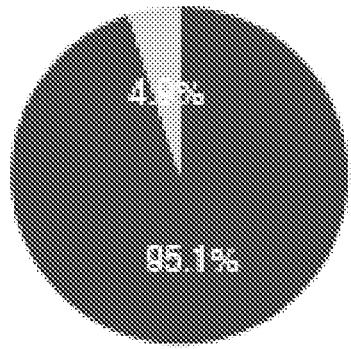
Figure 2E:
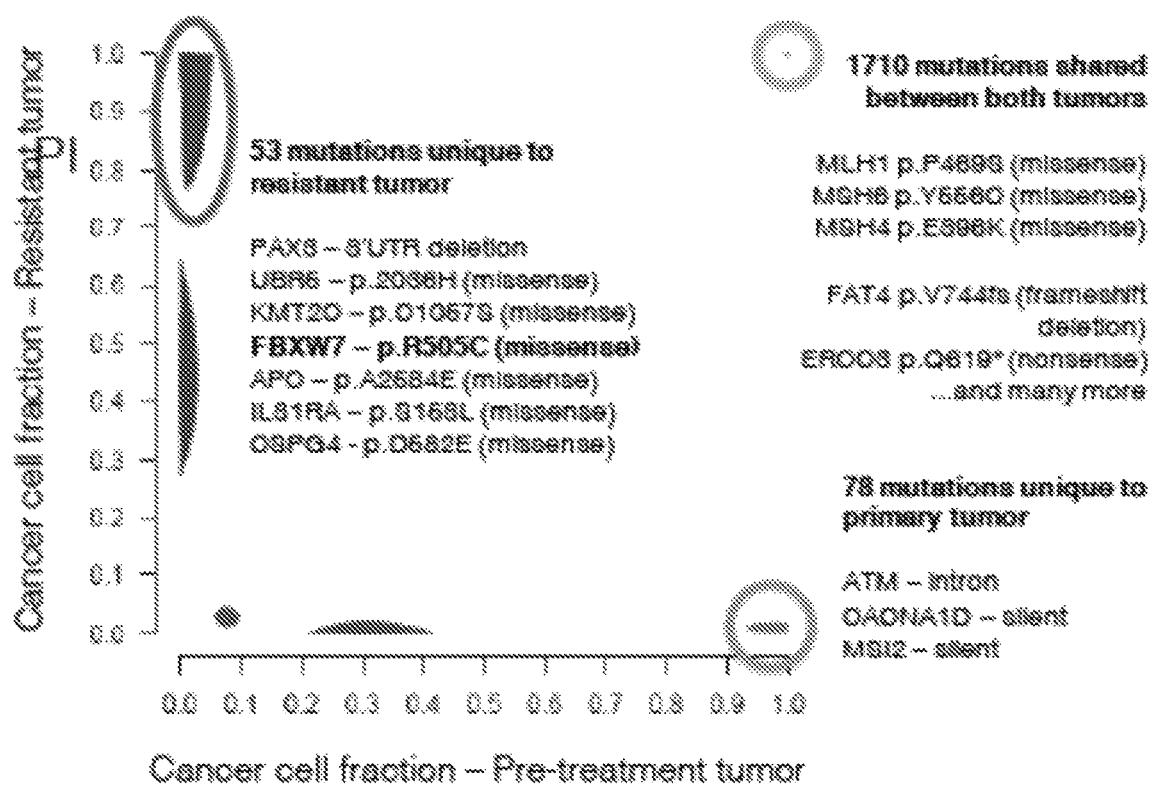
Figure 2F:
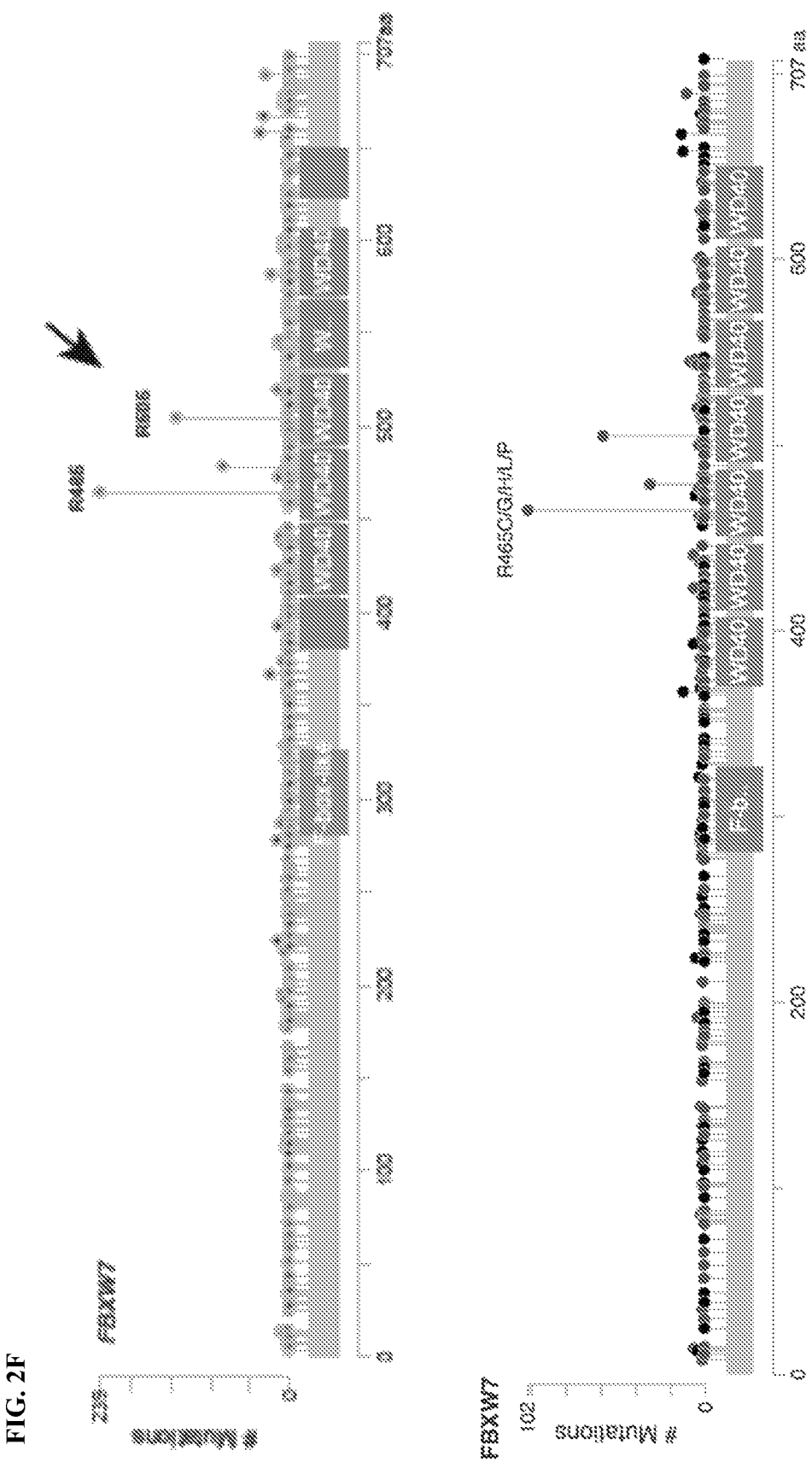
Figure 2G:
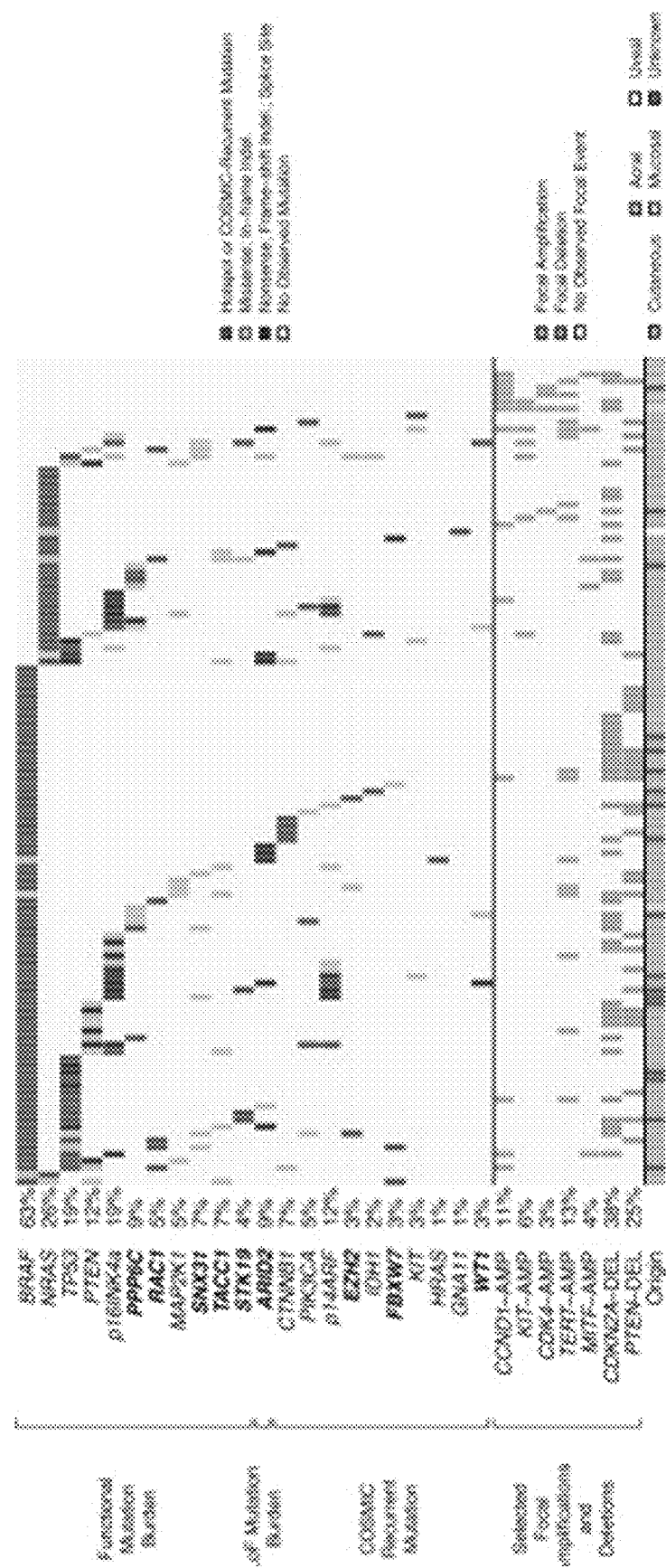
Figure 2H:
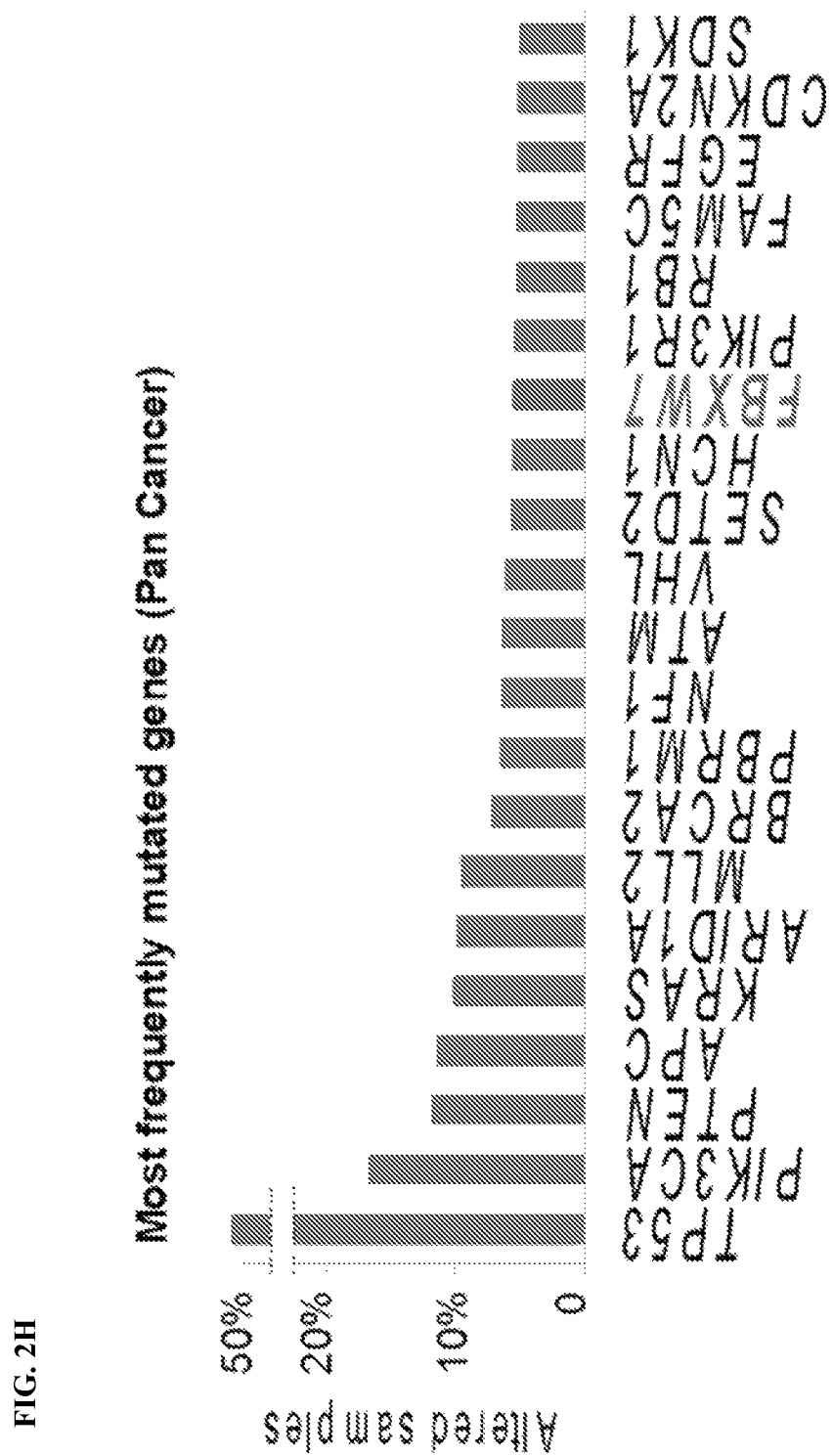

Two of the 10 patients had identical somatic mutations (R505→C) in the FBXW7 (F-box and WD repeat domain-containing 7) gene at the time of resistance, but not at the time of treatment (FIG. 2E and FIG. 2F). FBXW7 mutations are found in ~5% of melanoma patients (Cancer Genome Atlas N (2015) Cell 161:1681-1696) and are involved in tumor microenvironment processes (Mlecnik et al. (2016) Sci. Transl. Med. 8:327ra26). FBXW7 is the substrate recognition component of the evolutionary conserved SCF ubiquitin ligase complex (Welcker and Clurman (2008) Nat. Rev. Cancer 8:83-93) and is frequently mutated in cancers, although not in melanoma (FIG. 2G and FIG. 2H). In mammalian cells, FBXW7 degrades proto-oncogenes that function in cellular growth and division pathways, including c-Myc, Notch and c-Jun. The R505→C mutation has been described to increase the expression of FBXW7 substrates and lead to dominant negative phenotypes (Akhoondi et al. (2007) Cancer Res. 67:9006-9012; Davis et al. (2011) J. Pathol. 224:180-189; King et al. (2013) Cell 153:1552-1566; Welcker et al. (2013) Genes Dev. 27:2531-2536), suggesting immunotherapy resistance is associated with the loss of FBXW7 activity. FIG. 2F also shows many other Fbxw7 loss of function mutations, such as, without limitation, R465C, R465G, R465H, R465L, R465P, R465*, R486*, W244*, R278*, R479Q, R222*, and/or S282* mutations, wherein * represents any other amino acid.

In order to further evaluate the functional impact of candidate resistance genes, an immunocompetent mouse model of melanoma was established (FIG. 1) because current immunocompetent models to functionally test the importance of putative resistance mechanisms in melanoma are inadequate and have limited throughput (e.g., the most frequently used transplantable immunocompetent melanoma model is based on the B16 cell line which expresses low levels of major histocompatibility complex class I markers, cannot be recognized by cytotoxic CD8+ T-cells and is not responsive to PD-1 inhibitors (Becker et al. (2010) Exp. Dermatol. 19:157-164; Ashley and Kotlarski (1986) Cell Immunol. 101:156-167; Hoffman et al. (2014) Proc. Natl. Acad. Sci. U.S.A. 111:3128-3133; Leveson et al. (1979) Cancer Res. 39(2 Pt 2):582-586)).

This model consists of a BRAF(V600E)/PTEN-/- murine melanoma cell line, D4C9, which is >98% genetically identical (syngeneic) to C57BL/6 mice and could successfully engraft in C57BL/6 mice. The cell line is derived from a conditional mouse model of metastatic melanoma, Tyr::CreER; BrafCA; Ptenlox/lox (Jenkins et al. (2014) Pigment Cell Melanoma Res. 27:495-501). The cell line can be genetically manipulated ex vivo, then transplanted into C57BL/6 mice which have intact immune systems.

The D4C9 cells have been further modified to express Cas9, thereby enabling the deletion of genes by CRISPR (Cong et al. (2013) Science 339:819-823; Barbuddhe et al. (1998) Vet. Immunol. Immunopathol. 64:149-159) prior to transplantation into mice by transducing the cell line with a lentivirus carrying the Cas9 transgene. A clonal Cas9 cell line was selected to provide genetic and cellular homogeneity for subsequent screens. No significant difference between the growth or tumorigenicity of D4C9 cells in nude (nu/nu, immunodeficient) and C57BL/6 (immunocompetent) hosts were observed, indicating that this derivative is non-immunogenic. No effect of stable Cas9 expression, or transduction of sgRNAs on tumor growth in C57/B16 mice compared to nude mice have been observed. Also, in order to validate the ability of CRISPR to knockout functionally important genes in this model, D4C9 cells were transfected with various sgRNAs, such as those shown in Table 2 below.

TABLE 2

| | |
|---|---|
| sgPD-L1: | CTCCAAAGGACTTGTACG |
| sgFbxw7 #9: | TGAACATGGTACAAGGCCAG |
| sgFbxw7 #11: | GCAAAGTCTCAGATTATACC |
| sgFbxw7 #12: | CACCCACAGGCCTTCAAGAG |
| sgFbxw7 #10: | CCAGGTAACGTTGAATAGAG |

Figures 3A, 3B, 3C:
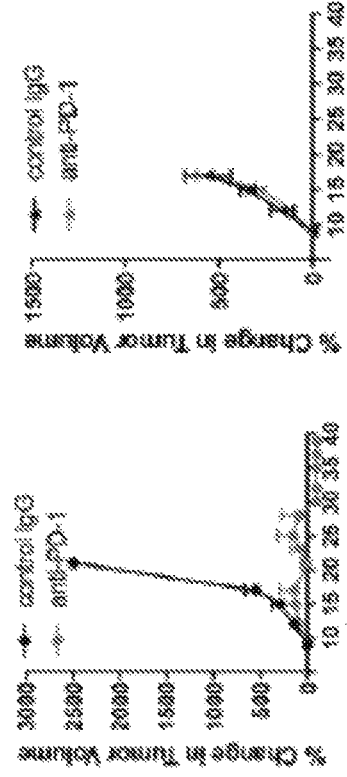
FIG. 3A-FIG. 3F show an evaluation of resistance to PD-1 inhibitor in a murine melanoma model and that tumor intrinsic PD-L1 is required for response of D4C9 melanoma cells to PD-1 inhibitor.
Figure 3D:
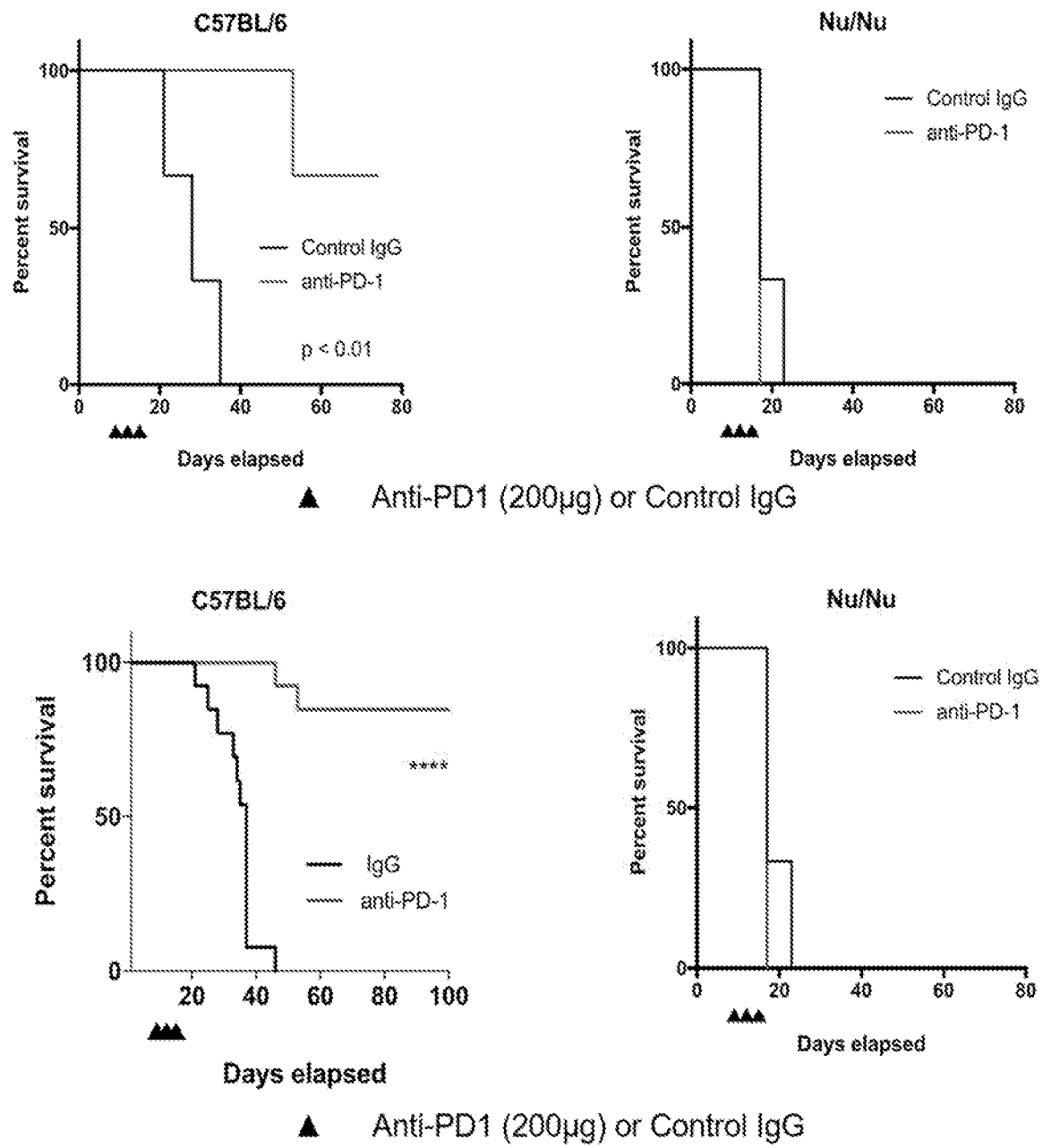
Figure 3E:
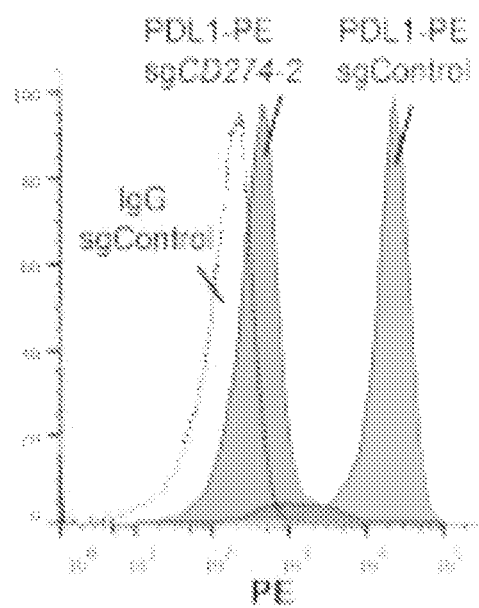
Figure 3F:
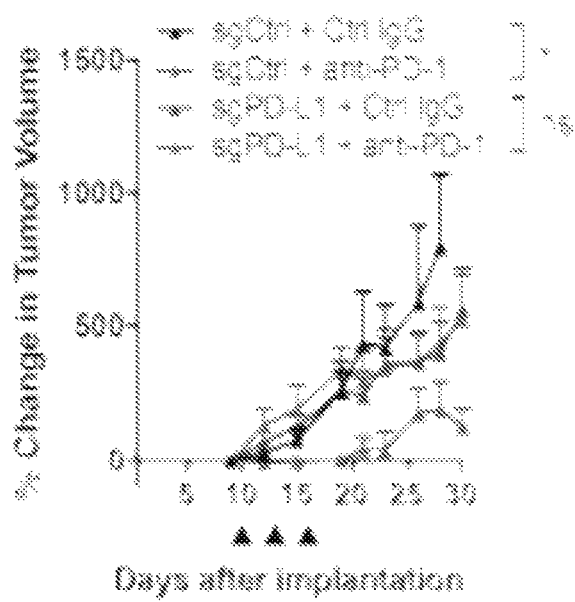

For example, sgRNA targeting the PD-1 ligand, PD-L1 (CD274), was used. PD-L1 expression is correlated with response to PD-1 inhibitors (Topalian et al. (2012) *N. Engl. J. Med.* 366:2443-2454). In particular, transfection of an sgRNA targeting the PD-1 ligand, PD-L1 (CD274), into D4C9 cells led to a dramatic loss of PDL1 surface expression (FIG. 3E). PD-L1 deletion also abolished response to an anti-PD-1 antibody (FIG. 3F), which is consistent with clinical observations (Topalian et al. (2012) *N. Engl. J. Med.* 366:2443-2454) and indicates that the response to the PD-1 inhibitor is dependent on tumor PD-L1 expression as described in patients (Shin et al. (2017) *Cancer Discov.* 7:188-201).

Unlike other syngeneic, transplantable melanoma mouse models (Becker et al. (2010) *Exp. Dermatol.* 19:157-164; Ashley and Kotlarski (1986) *Cell Immunol.* 101:156-167; Li et al. (2009) *Clin. Cancer Res.* 15:1623-1634; Leveson et al. (1979) *Cancer Res.* 39(2 Pt 2):582-586), implanted tumors in this model are responsive to PD-1 inhibitors in immunocompetent but not immunodeficient hosts (FIG. 3A-FIG. 3C) when tested for sensitivity to control and anti-PD1 antibodies (Cai et al. (2004) *Cell Immunol.* 230:89-98). The PD-1 inhibitor also significantly increased the survival of immunocompetent, but not immunodeficient animals harboring D4C9 tumors, even after discontinuing treatment (FIG. 3D). Thus, the pattern of responses to PD-1 inhibitor in this model parallel those observed in melanoma patients.

Although some heterogeneity exists amongst parental D4C9 cells with respect to tumor-forming capability, presumably partly due to epigenetic differences amongst subclones such that any individual subclone, such as generated during CRISPR gene editing, can be poorly tumorigenic, the heterogeneity can be overcome by analyzing and testing multiple individual subclones. Transplantable models have led to the identification of immune checkpoints such as PD-1 (Iwai et al. (2005) *Int. Immunol.* 17:133-144) and genetically engineered models can be readily adapted to validate effects described herein and allow analysis of, for example, human tumnor microenvironments. Thus, the model allows for the functional importance of each candidate resistance gene to be rapidly ascertained by its deletion prior to implantation and evaluating the response of formed tumors to PD-1 inhibitors. By enabling the deletion of individual genes, their importance in therapy resistance can be evaluated. For example, the contribution of antigen presentation to resistance can be evaluated by deletion of gene(s) involved in antigen presentation prior to implantation and drug treatment. Finally, conditions have been optimized for functional evaluation of ~1000 genes simultaneously using pooled in vivo screening with a CRISPR library (Bradley et al. (2015) *Cancer Immunol. Res.* 3:602-609).

Figure 4A:
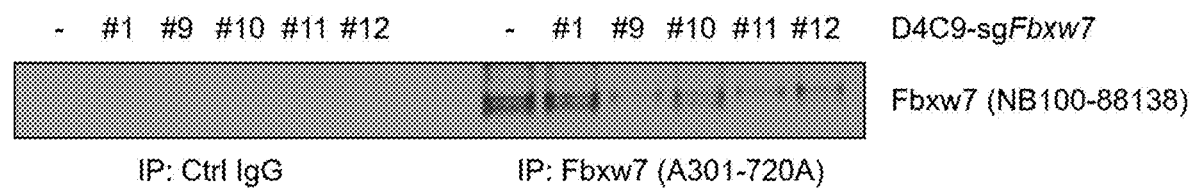
FIG. 4A-FIG. 4O show that Fbxw7 is required for PD-1 inhibitor efficacy and anti-tumor activity.
Figure 4B:
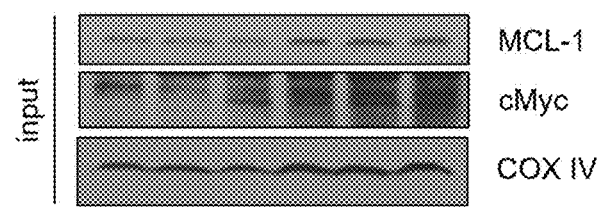
Figure 4C:
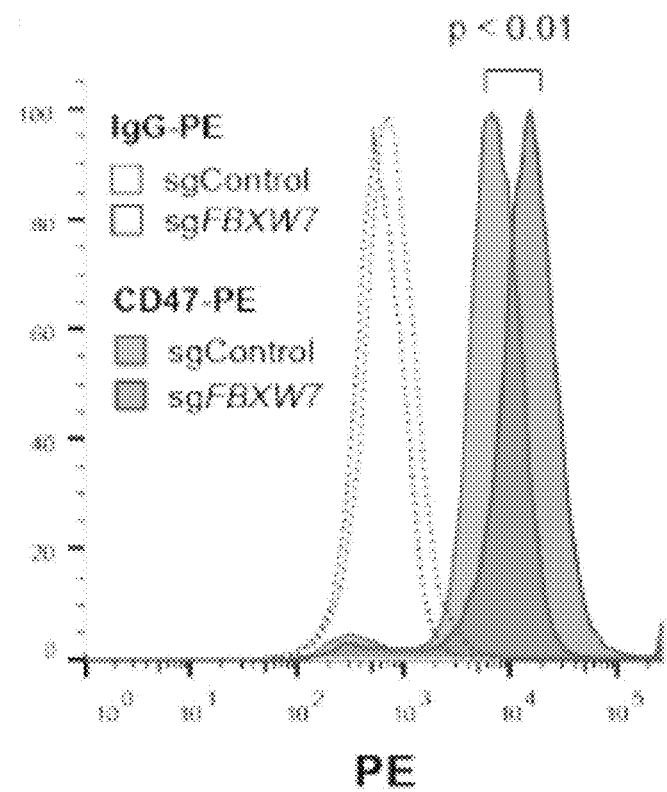
FIG. 4C shows CD47 surface expression in D4C9 control and FBXW7-deleted cells. *, $p<0.05$ compared to control IgG. Results with sgFBXW7 were confirmed with 3 additional sgRNAs.
Figure 4D:
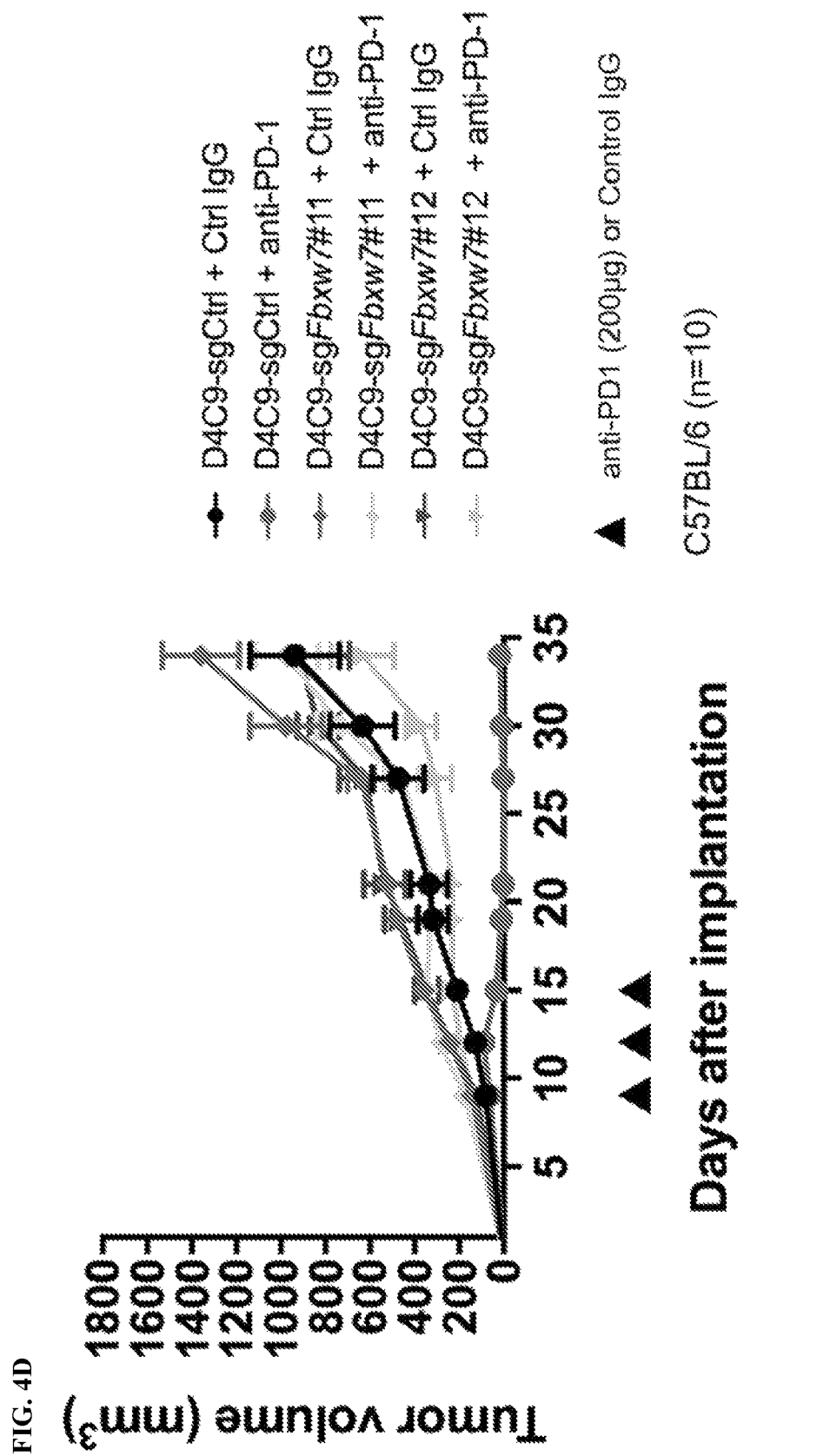
FIG. 4D shows growth of D4C9 control and sgFBXW7 cells following treatment with anti-PD-1 or control IgG antibodies at the indicated times (black arrows). Tumor growth was measured by calipers. Results with sgFBXW7 were confirmed with 3 additional sgRNAs.
Figure 4E:
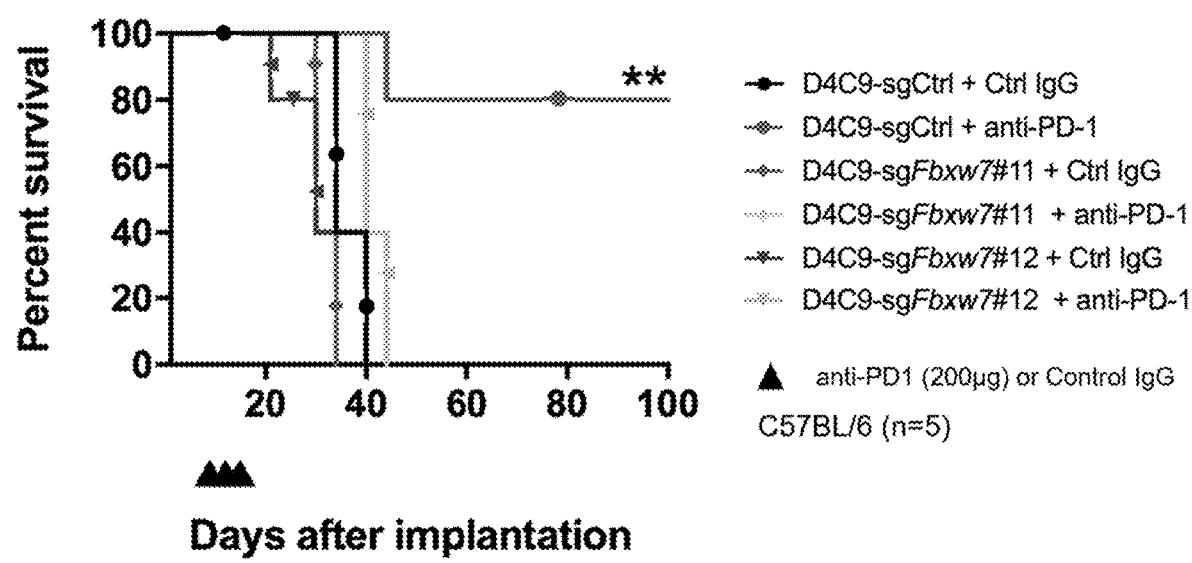
FIG. 4E shows overall survival of mice (right) with wild-type and Fbxw7-mutated D4C9 tumors treated with anti-PD-1 or control antibodies. $p<0.05$ comparing wild-type and Fbxw7-mutated D4C9 tumors.

After generating loss of function mutations (e.g., deletion) of candidate resistance genes in the murine melanoma model, it was found that loss of one gene, Fbxw7, conferred resistance to PD-1 inhibitors. In order to evaluate if Fbxw7 loss affects PD-1 inhibitor efficacy, this gene was knocked out in D4C9 cells using CRISPR and wild-type and Fbxwy-mutated cells were implanbted into C57BL/6 mice. Deletion of Fbxw7 significantly reduced tumor response to the PD-1 inhibitor (FIG. 4D) and increased overall survival (FIG. 4E). These results indicate that Fbxw7 is required for maximal response to PD-1 inhibitors. Similar results were seen using 3 other guide RNAs targeting Fbxw7.

A prominent known target of Fbxw7 is the oncogene c-Myc, which has recently been shown to regulate surface expression of CD47 (Casey et al. (2016) *Science* 352:227-231). Further, CD47 was shown to be required for c-Myc mediated immune suppression. Consistent with these observations, it was found that deletion of Fbxw7 using 4 independent guide RNAs increased protein levels of c-Myc (FIG. 4B) and to a 2.7-fold higher level of mean surface CD47 expression (FIG. 4C). This level of CD47 upregulation has been associated with significantly altered macrophage-mediated phagocytosis by two independent methods (Chao et al. (2010) *Cell* 142:699-713). Thus, loss of function mutations (e.g., deletion) of Fbxw7 were associated with the induction of the immunologic 'don't-eat-me' signal, CD47, indicating that programmed cell removal (PCR) (Chao et al. (2011) *Nat. Rev. Cancer* 12:58-67) is important for immunotherapy response and it was determined further determined that loss of Fbxw7 leads to increased levels of c-Myc.

Figure 5A:
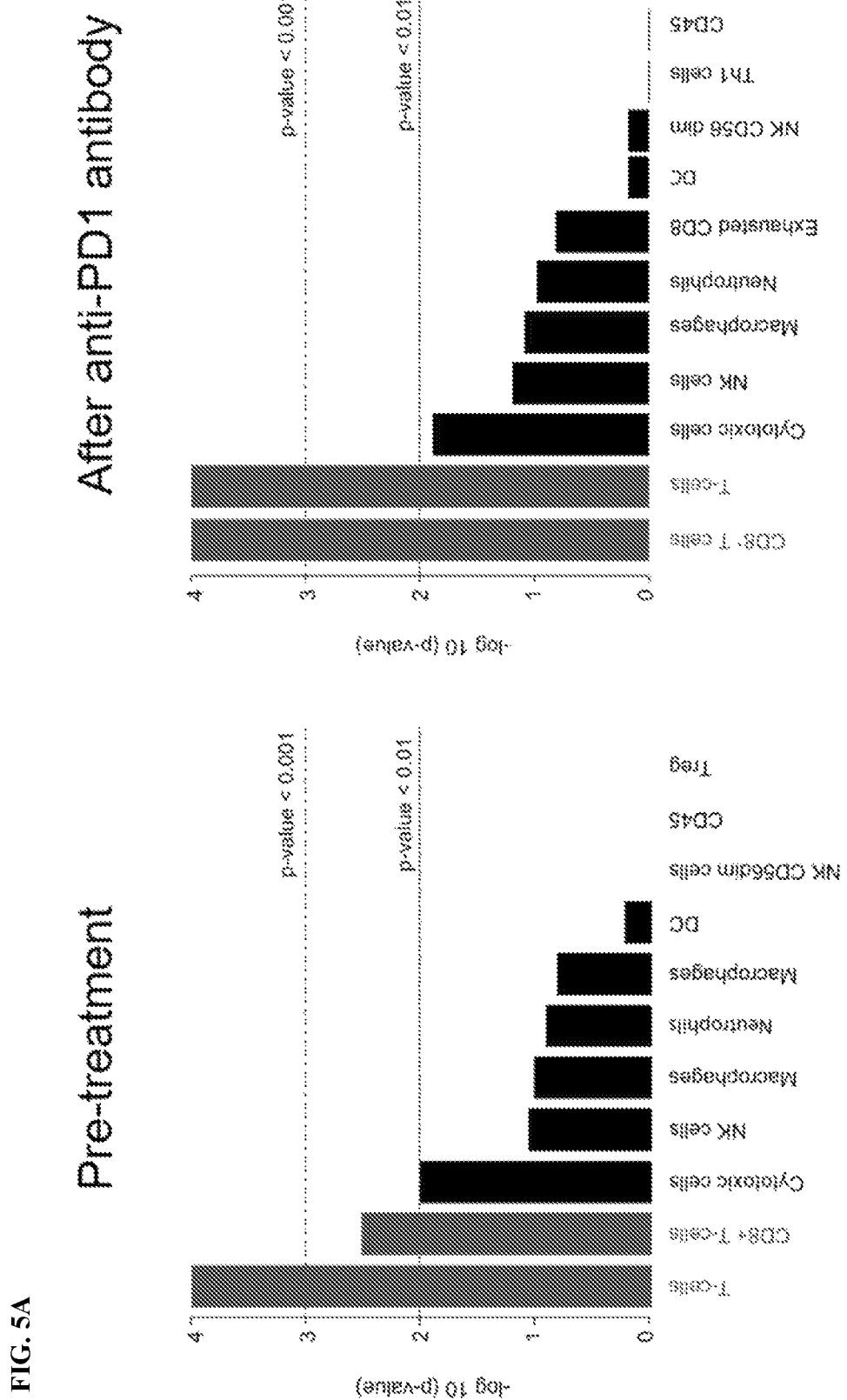
Figure 5B:
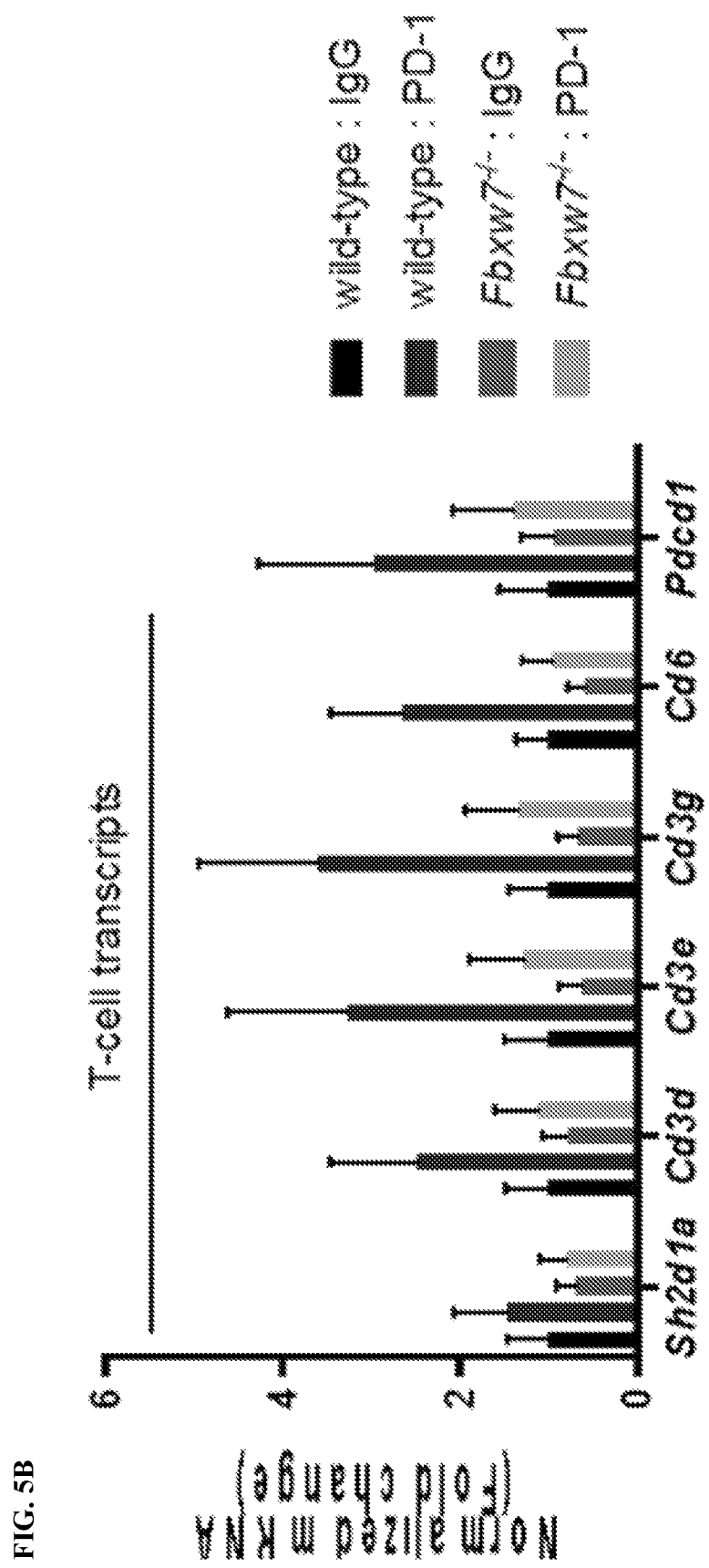
Figure 6A:
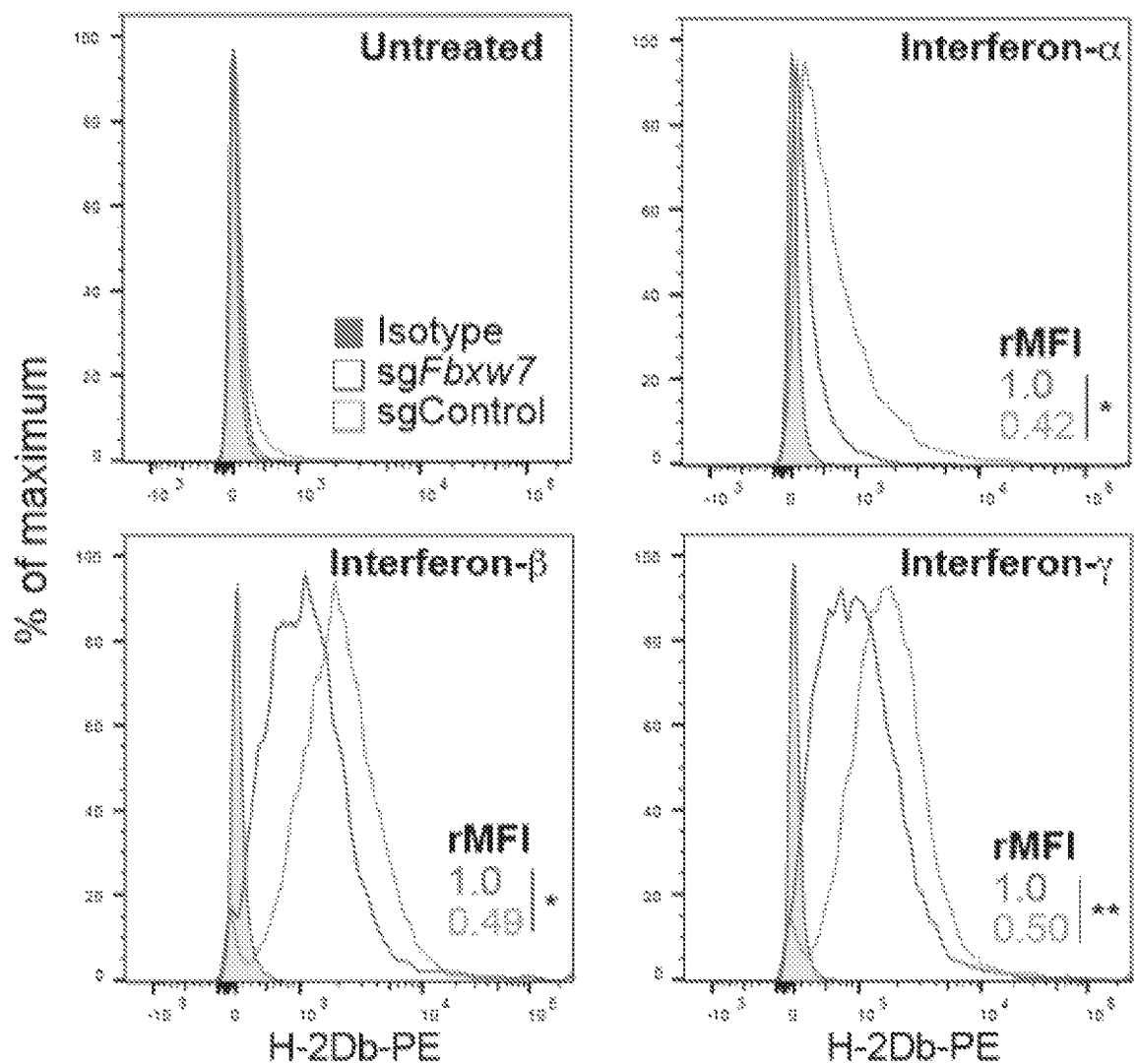
FIG. 6A-FIG. 6O show that Fbxw7 is required and sufficient for interferon gamma signaling.
Figure 6B:
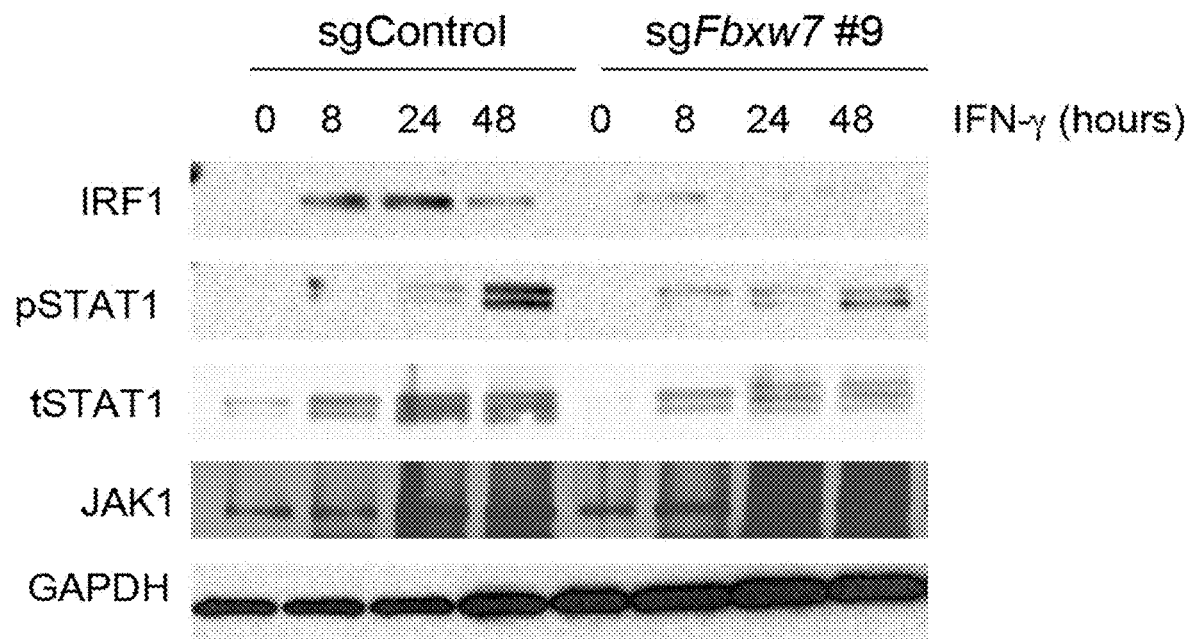
FIG. 6B and FIG. 6C show the effect of Fbxw7 deletion on induction of JAK/STAT signaling by interferon γ.
Figure 6C:
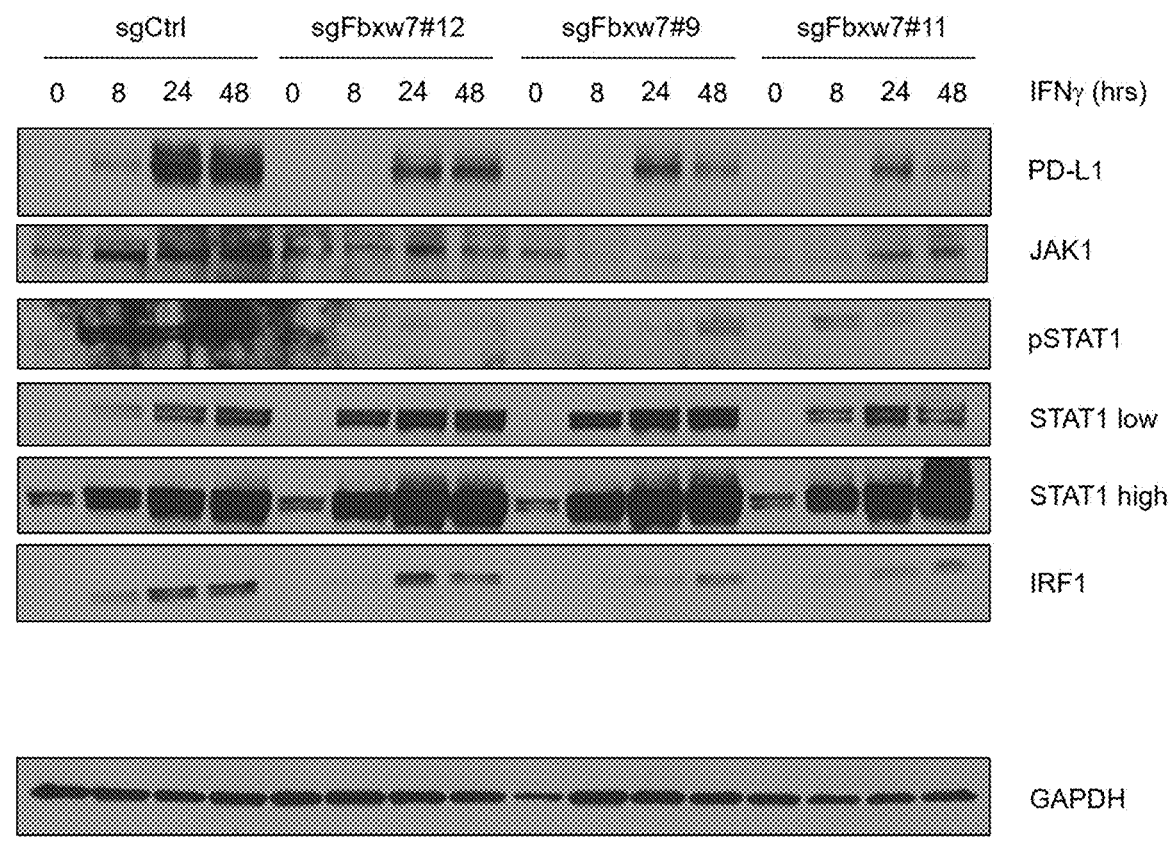

In addition, loss of Fbxw7 is associated with altered immune microenvironment. CD8+ T cells were significantly depleted in Fbxw7-mutant tumors (FIG. 5A and Fbxw7 is required for induction of T-cell signatures by PD-1 antibodies (FIG. 5B). Fbxw7 is also required and sufficient for interferon gamma signaling because Fbxw7 deletion affects induction of MHC Class I (H-2d$^b$) expression by interferon α, β and γ (FIG. 6A), as well induction of JAK/STAT signaling by interferon γ (FIG. 6B and FIG. 6C).

Example 3: Confirming Whether Defective Programmed Cell Removal (PCR) Confers Resistance to Immune Checkpoint Therapy It is believed that PCR is required for effective response to PD-1 inhibitors, and that Fbxw7 mutations confer resistance to immune checkpoint blockade by disabling PCR.

In order to evaluate if defective PCR confers resistance to immune checkpoint therapy, such as to PD-1 inhibitors, CD47 and/or 4 other genes required for PCR (Chao et al. (2011) *Nat. Rev. Cancer* 12:58-67) are knocked out in D4C9 cells. It is known that CD47 expression is sufficient to block phagocytosis that is essential for programmed cell removal (PCR) (Chao et al. (2011) *Nat. Rev. Cancer* 12:58-67). Target inactivation at the DNA and protein level is determined by surveyor mutation (Kim et al. (2009) *Genome Res* 19:1279-1288) and Western blot assays, respectively. To validate the functional consequences of deletion of PCR genes in vitro, the ability of the cells to resist phagocytosis is analyzed.

Cells are fluorescently labeled with the carboxyfluorescein succinimidyl ester (CF SE) dye and co-incubated with activated mouse bone marrow-derived macrophages in the presence of blocking CD47 mAb or isotype control (Jaiswal et al. (2009) *Cell* 138:271-28525). The number of macrophages containing at least one melanoma cell are calculated by inverted microscopy (Barbuddhe et al. (1998) *Vet. Immunol. Immunopathol.* 64:149-159; Majeti et al. (2009) *Cell* 138:286-299). After validation, wild-type and mutant cells are implated in C57/B16 mice. Response of the formed tumors to drug treatment are evaluated by measurement and by overall mouse survival.

Example 4: Confirming Whether Targeting Cd47 Overcomes Fbxw7 Loss of Function Mutation-Based Resistance to Immune Checkpoint Therapy It is believed that inhibition of PCR impairs efficacy of immune checkpoint therapy, such as PD-1 inhibitors, in vivo and that inhibition of CD47 or PCR by genetic or pharmacologic approaches enhances the efficacy of such immune checkpoint therapy on cancers having loss of function mutations in Fbxw7, such as Fbxw7-mutated melanomas, and that such cancers are resistant to macrophage phagocytosis in vitro. It is further believed that Fbxw7 mutation is associated with a diminished benefit to immunotherapies in melanoma patients.

In particular, it is believed that re-activation of PCR by suppression of c-Myc or CD47 can restore sensitivity of Fbxw7-mutant cancers, such as melanomas, to immune checkpoint therapy, such as PD-1 inhibitors.

In order to evaluate if CD47 limits PD-1 inhibitor activity, sgRNAs targeting CD47 are transduced into D4C9 cells. After implantation of these control or sgCD47 cells into C57BL/6 mice, mice are treated with control or anti-PD-1 antibodies. The response of transplanted tumors to the PD-1 inhibitor is measured as shown in FIG. 1.

Similarly, in order to evaluate if loss of Fbxw7 confers resistance to PD-1 inhibitor through the induction of CD47, sgRNAs targeting both Fbxw7 and CD47 are transduced into D4C9 cells. After implantation of these cells into C57/B16 mice, mice are treated with control IgG or anti-PD1 inhibitor. Response of transplanted tumors to PD-1 inhibitor is measured by tumor growth measurements, as well as the survival of recipient mice. These results are also corroborated pharmacologically. Wild-type and Fbxw7-mutant melanoma cells are injected in immunocompetent hosts. Animals are treated with control immunoglobulins, anti-PD-1 antibody alone, or combination therapy with anti-PD-1 and anti-CD47 antibodies. Responses are assessed as described above.

To confirm whether Fbxw7 loss increases CD47 via dysregulated c-Myc expression, c-Myc is knocked down using siRNA in wild-type or Fbxw7-mutant D4C9 cells in vitro. CD47 surface expression is evaluated by FACS. Upon any observed effects of c-Myc knockdown on CD47 expression, siRNA effects are rescued with an siRNA-resistant cDNA encoding c-Myc. In addition, siRNA findings are corroborated using the bromodomain inhibitor, JQ-1, which suppresses c-Myc (Filippakopoulos et al. (2010) *Nature* 468:1067-1073; Delmore et al. (2011) *Cell* 146:904-917) in Fbxw7-mutated leukemias (King et al. (2013) *Cell* 153: 1552-1566). CD47 expressed on the surface of tumor cells can interact with the SIRPα receptor on macrophages, leading to the inhibition of macrophage-mediated phagocytosis (Mathur et al. (2016) *Nat Genet.* 49:296-302; Okazawa et al. (2005) *J. Immunol.* 174:2004-2011).

To confirm whether whether Fbxw7 protects melanoma cells from phagocytosis, the ability of wild-type and Fbxw7-mutant D4C9 cells to resist phagocytosis in the presence and absence of CD47 blocking antibody is analyzed using the CFSE assay described above.

In addition, Fbxw7 is reported to be mutated in ~5% of melanoma patients (Cancer Genome Atlas N (2015) *Cell* 161:1681-169632). In order to confirm whether Fbxw7 mutation is associated with decreased response to immunotherapy, the exomes of 220 sequenced melanomas from 3 published cohorts (Van Allen et al. (2015) *Science* 350:207-211; Riaz et al. (2016) *Nat. Genet.* 48:1327-1329) and two melanoma clinical trials (Checkmate –064 and –038) (Weber et al. (2016) *Lancet Oncol.* 17:943-955) where exome sequencing is available are analyzed. Standardized pipelines for somatic variant calling, mutational signature deconvolution and correct for patient mutational burden by permutation, are used. Patients are stratified into clinical benefit versus no clinical benefit as described in Van Allen et al. (2015) *Science* 350:207-211. In addition, if Fbxw7 mutation is associated with CB to anti-PD1 and/or anti-CTLA-4 therapy is analyzed.

To characterize the effects of the Fbxw7 mutation on the immune microenvironment in melanoma patients, comprehensive immune profiling of pre-treatment and resistant Fbxw7-mutant tumors sections is performed by multi-parametric immunohistochemistry as described in Lizotte et al. (2016) *JCI Insight* 1:e89014. Immunoprofiling (such as surface marker profiles for M1 and M2 macrophages) is performed on tumors derived from D4C9 wild-type and Fbxw7-mutant cells, before and after drug treatments. Further in vitro characterization of the associatedion between Fbxw7 mutation and CD47 is carried out using patient-derived cell lines. The functional role of CD47 and macrophage phagocytosis in immune checkpoint therapy responses is evaluated by in vitro and in vivo phagocytosis assays, as well as the use of clodronate liposomes to deplete macrophages in the model. For example, engulfment of melanoma cells in vivo following drug treatment is done by staining for macrophages that contain melanocyte-specific markers as described in Zhang et al. (2016) PLoS One 11:e0153550.

Example 5: Confirming Whether Targeting S-HP2 Overcomes Fbxw7 Loss of Function Mutation-Based Resistance to Immune Checkpoint Therapy It has been determined herein that Fbxw7 is required for effective signaling through the interferon-gamma pathway. Fbxw7 is known to promote the degradation of target proteins, whereas the loss/mutation of Fbxw7 compromises this activity. One previously identified target of Fbxw7 is the protein SHP2 (PTPN11), a protein that negatively regulates the interferon/JAK/STAT signaling pathway (You et al. (1999) *Mol. Cell. Biol.* 19:2416-2424). Loss of Fbxw7 has been shown to stabilize SHP2 (Song et al. (2017) *Nat. Comm.* 8:14654). It is believed that Fbxw7 loss affects SHP2 protein levels and that Fbxw7-mutant cancers, such as melanomas, are resistant to immune checkpoint therapy (e.g., anti-PD-1 antibodies), whereas SHP2 inhibitors sensitize these tumors to the immune checkpoint therapy. To characterize the effects, SHP2 is genetically deleted in cells that lack Fbxw7 in order to determine that SHP2 is required for the effect of Fbxw7 loss on JAK/STAT signaling. In addition, mice harboring Fbxw7-mutant melanomas are treated with a SHP2 inhibitor (e.g., SHP099 (TN0155), sodium stibogluconate, and the like) with immune therapy, such as anti-PD1 antibodies.

It is also understood that in all experiments described above, PD-1 antibodies are a form of immune checkpoint therapy, but any immune checkpoint therapy, such as inhibition of one or more immune checkpoints, such as CTLA-4, LAG3, and the like, are applicable and contemplated.

Example 6: Inactivating Mutations in FBXW7 are Associated with Resistance to Immunotherapy The following examples further provide data that demonstrate that loss-of-function mutations in FBXW7 lead to acquired resistance to PD-1 blockade.

Figure 2I:
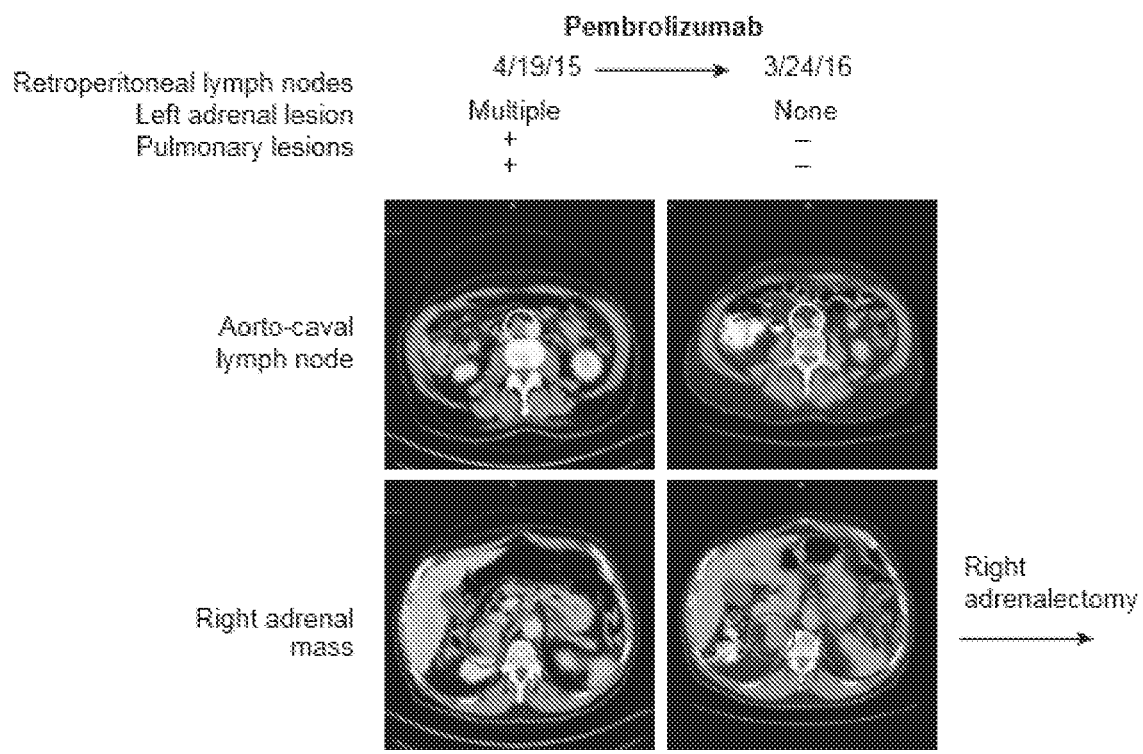
Figure 2K:
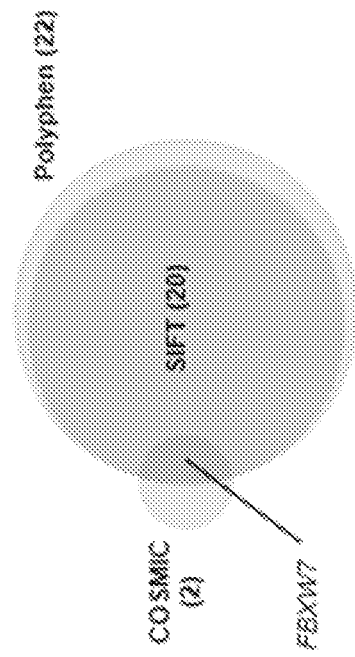
Figure 2J:
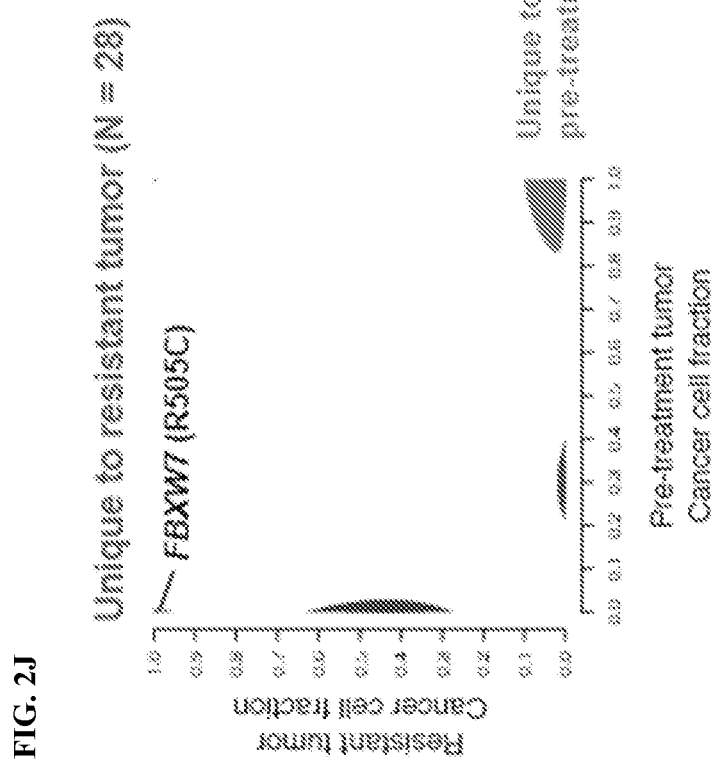

A 74-year old man with diffuse metastatic melanoma, including retroperitoneal lymph node involvement, left and right adrenal and pulmonary metastases (FIG. 2I) was treated with pembrolizumab. He exhibited a complete response in all lesions within 11 months, except for a right adrenal mass which did not respond. To identify genomic changes associated with resistance, it was performed herein whole exome sequencing and analysis on a pre-treatment lesion (a cervical lymph node), the right adrenal resistant lesion and a germline sample (peripheral blood mononuclear cells). ABSOLUTE (Carter et al. (2012) Nat Biotechnol 30:413-421; Brastianos et al. (2015) Cancer Discov 5:1164-15; Stachler et al. (2015) Nat Genet 47:1047-1055) was then used to determine allele fraction of called mutations and allelic copy number information in the pre-treatment and resistant samples. Overall, 1583 somatic variants were shared between both tumors (FIG. 2J). Twenty eight mutations were unique to the resistant adrenal tumor, whereas 26 mutations were unique to the pre-treatment tumor, indicating that the resistant lesion evolved from a precursor clone. As expected for melanoma, both the resistant and pre-treatment tumors had a mutational signature consistent with UV exposure (FIG. 2D). Both the pre-treatment and resistant lesion had similar numbers of total mutations, non-synonymous mutations and predicted neoantigens (FIG. 2C). The copy number profile between the pre-treatment and resistant lesions were also similar (FIG. 2B).

The large number of somatic changes between the pre-treatment and resistant lesion precluded a clear identification of the driver(s) mechanism of resistance. Since drivers of resistance are likely to be successful therapeutic targets, it was evaluated herein the resistant tumor for known genomic mechanisms of resistance to immunotherapy. However, no somatic mutations were found in antigen presentation, interferon, or beta-catenin signaling pathways, which are correlated with anti-PD-1 resistance (Zaretsky et al. (2016) N Engl J Med 375: 819-829; Sweis et al. (2016) Cancer Immunol Res 4:563-568; Spranger et al. (2015) Nature 523:231-235; Gao et al. (2016) Cell 167:397-404). COSMIC database (Forbes et al. (2010) Nucleic Acids Res 38:D652-657) and several variant discovery engines (Choi & Chan (2015) Bioinformatics 31:2745-2747; Kumar et al. (2009) Nat Protoc 4:1073-1081; Adzhubei et al. (2010) Nat Methods 7:248-249) were also used to predict oncogenic and deleterious mutations (FIG. 2K). The only known oncogenic mutation that distinguished the pre-treatment and resistant tumor was an arginine-to-cysteine mutation at amino acid 505 (R505C) in the tumor suppressor gene FBXW7 (F-box and WD repeat domain-containing 7; FIG. 2). FBXW7 is the substrate recognition component of the evolutionary conserved SCF ubiquitin ligase complex (Davis et al. (2014) Cancer Cell 26:455-464; Akhoondi et al. (2007) Cancer Res 67:9006-9012; King et al. (2013) Cell 153:1552-1566; Welcker & Clurman (2008) Nat Rev Cancer 8:83-93). In mammalian cells, FBXW7 activity leads to the degradation of protooncogenes that function in cellular growth and division pathways, including c-Myc, Notch and c-Jun. Mutations of FBXW7 are present in ~6% of all cancers (Welcker & Clurman (2008) Nat Rev Cancer 8:83-93) but its expression is diminished in up to 40% of melanomas (Aydin et al. (2014) J Natl Cancer Inst 106:dju107). The R505 mutation, the second most common mutation in FBXW7 observed in cancer (FIG. 2F), is associated with the increased expression of FBXW7 substrates and leads to dominant negative phenotypes, suggesting that immunotherapy resistance could be associated with the loss of FBXW7 activity.

Figure 4F:
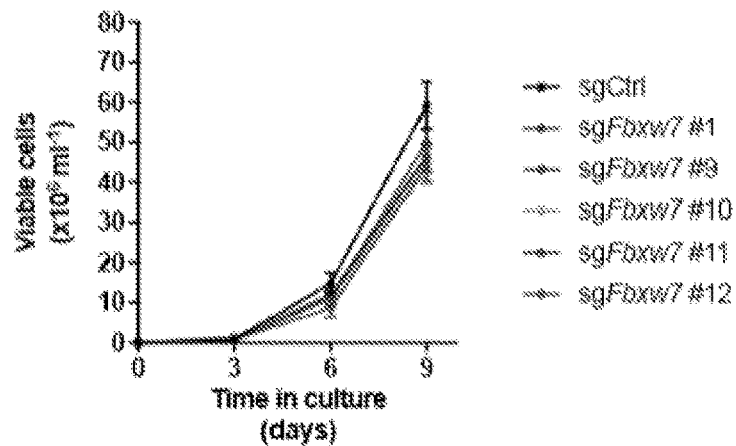
FIG. 4F-FIG. 4K show that Fbxw7 is required for PD-1 blockade anti-tumor activity.
Figure 4G:
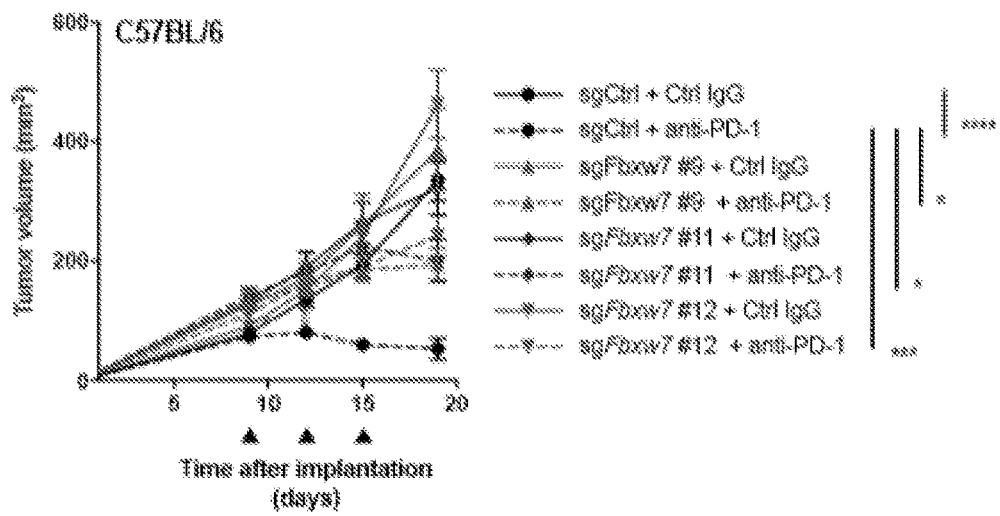
Figure 4H:
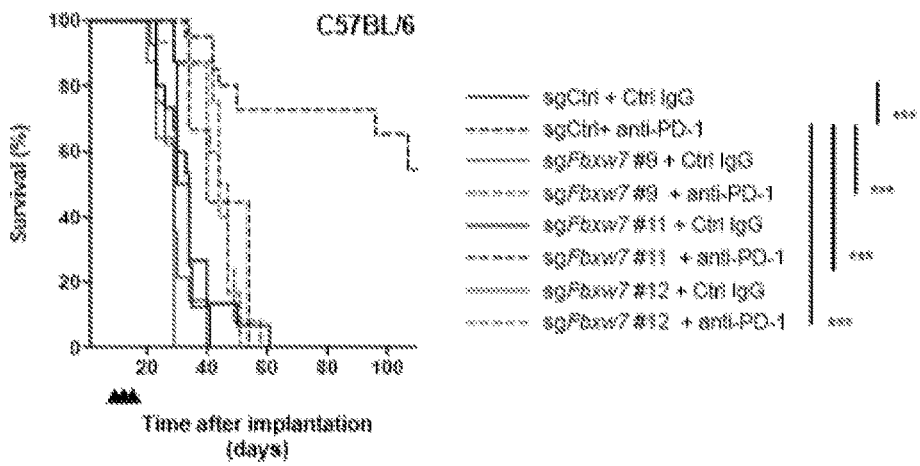
Figures 4I, 4J, 4K:
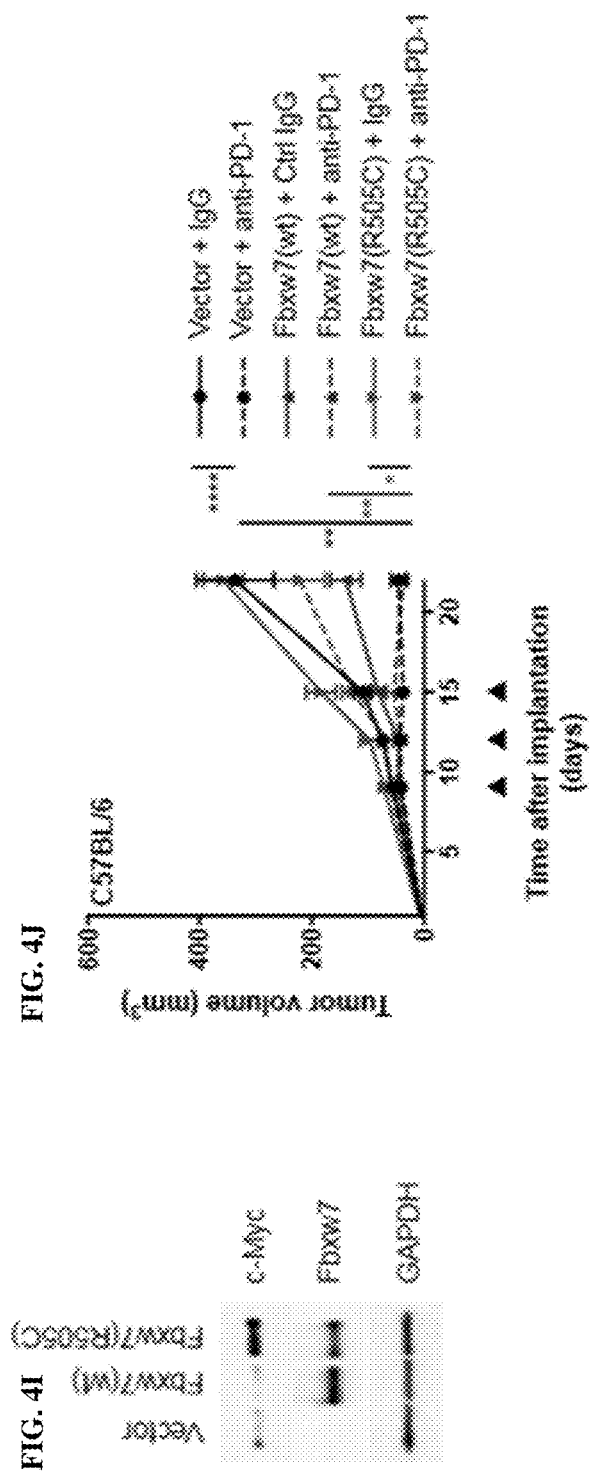
Figure 4L:
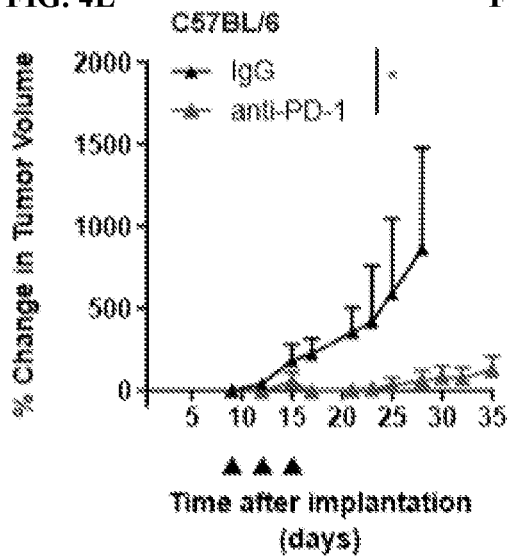
FIG. 4L and FIG. 4M show that Fbxw7 is required for PD-1 blockade anti-tumor activity.
Figure 4M:
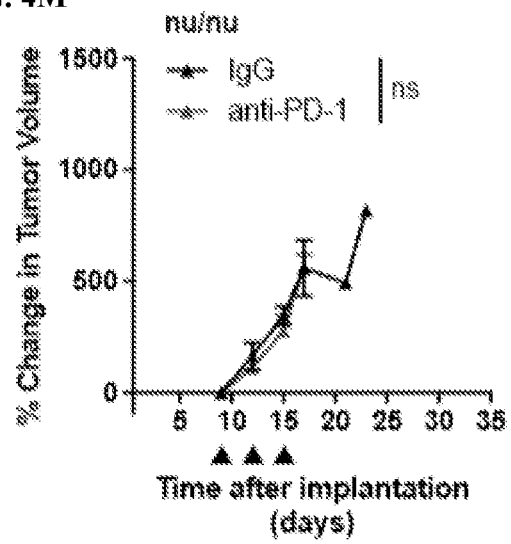

Example 7: Fbxw7 is Required for PD-1 Inhibitor Efficacy and Anti-Tumor Activity To test the possibility that FBXW7 inactivation leads to resistance to PD-1 inhibitor in melanoma, a melanoma murine model lacking Fbxw7 was developed. The model was based on D4M3A, a BRAF-mutant melanoma murine cell line that is 98% genetically identical to C57BL/6 mice (Jenkins et al. (2014) Pigment Cell Melanoma Res 27:495-501). D4M3A cells were modified ex vivo to express Cas9 (hereafter denoted D4C9), facilitating the rapid deletion of genes by CRISPR(Cong (2017) Anal Biochem 532:87-89). Cells transduced with a control sgRNA grew similarly in immunocompetent C57BL/6 and immunodeficient Nu/Nu mice (FIG. 4L and FIG. 4M). Anti-PD-1 treatment of immunocompetent mice with D4C9 tumors was associated with durable tumor control (>120 days), even after only three drug treatments (FIG. 3D). Anti-PD-1 treatment had no impact on survival of nude mice bearing D4C9 tumors (FIG. 3D).

Figure 4N:
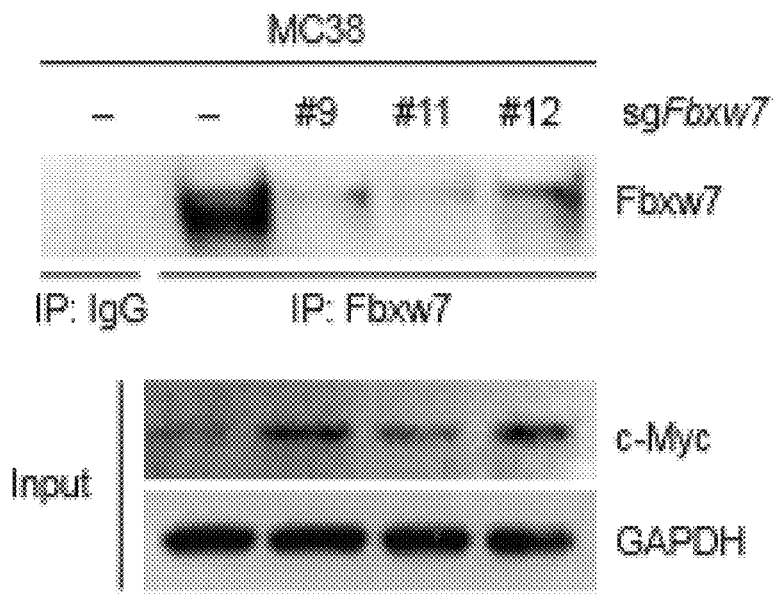
FIG. 4N shows Western blot of MC38-Cas9 cells transduced with control or Fbxw7 targeted sgRNAs #9, 11, 12. Fbxw7 was detected after immunoprecipitation with anti-Fbxw7 antibodies. c-Myc and GAPDH expression was determined by Western blot of whole cell lysates.
Figure 4O:
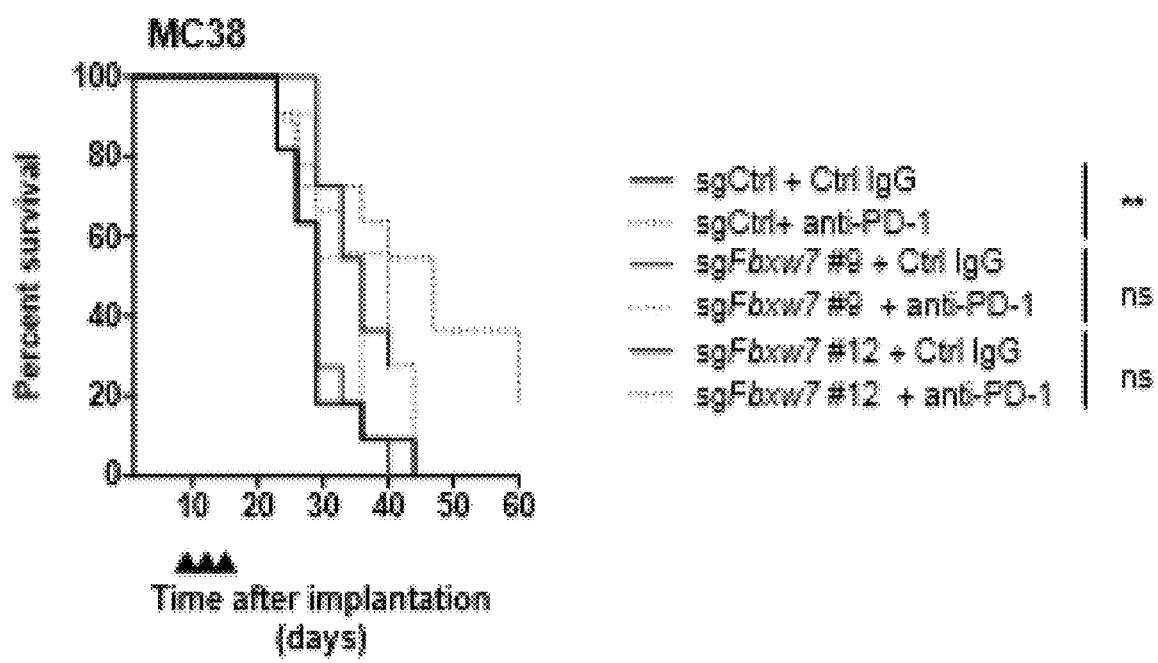

To specifically determine whether Fbxw7 is required for response to anti-PD-1 inhibitors, D4C9 derivatives lacking Fbxw7 were generated using CRISPR. Four sgRNAs (#9, #10, #11, and #12) decreased Fbxw7 protein with concomitant increases of the Fbxw7 target c-Myc (Welcker et al. (2004) Curr Biol 14:15) (FIG. 4A and FIG. 4B). There was no difference in the growth rate of Fbxw7-deficient and control D4C9 cells in vitro (FIG. 4F). However, Fbxw7-deficient tumors were resistant to anti-PD-1 treatment compared to isogenic matched wild-type tumors (FIG. 4G). Animals with Fbxw7-deficient tumors also had significantly poorer survival after anti-PD-1 treatment compared to mice with wild-type tumors (FIG. 4H). Fbxw7-deficient derivatives of MC38, a PD-1 sensitive colon carcinoma cell line syngeneic to C57BL/6 mice (Junej a et al. (2017) J Exp Med 214:895904) was similarly generated (FIG. 4N). Deletion of Fbxw7 in this model also significantly diminished the response to anti-PD-1 treatment (FIG. 4O).

To evaluate whether the Fbxw7(R505C) oncogenic mutation (rather than its deletion) also leads to resistance to anti-PD-1, D4C9 cells expressing wild-type Fbxw7 or Fbxw7 with the R505C mutation were generated. Fbxw7 (R505C) expression induced the expected increase in c-Myc expression (Welcker et al. (2004) Curr Biol 14:15), consistent with its known dominant negative effect23 (FIG. 4I). Whereas wild-type Fbxw7 tumors were sensitive to PD-1 blockade, Fbxw7(R505C) tumors were resistant to this treatment (FIG. 4J and FIG. 4K). Together, these data demonstrate that Fbxw7 loss-of-function leads to PD-1 blockade resistance.

Figure 5E:
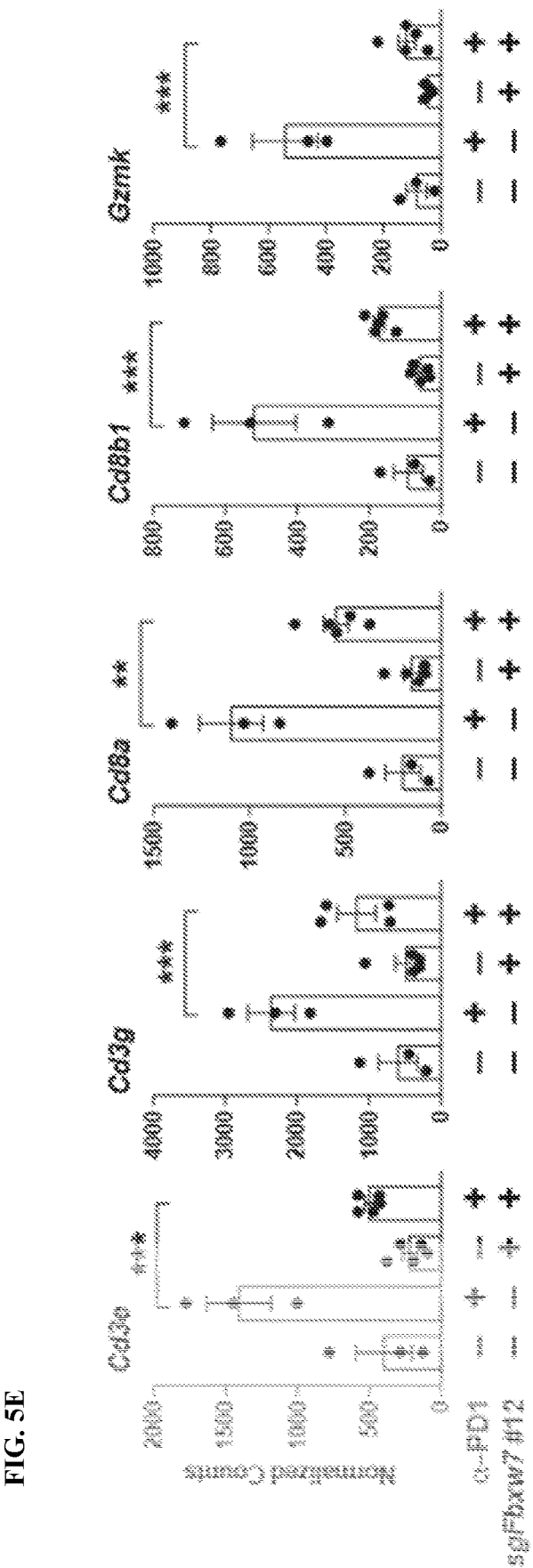
Figure 5F:
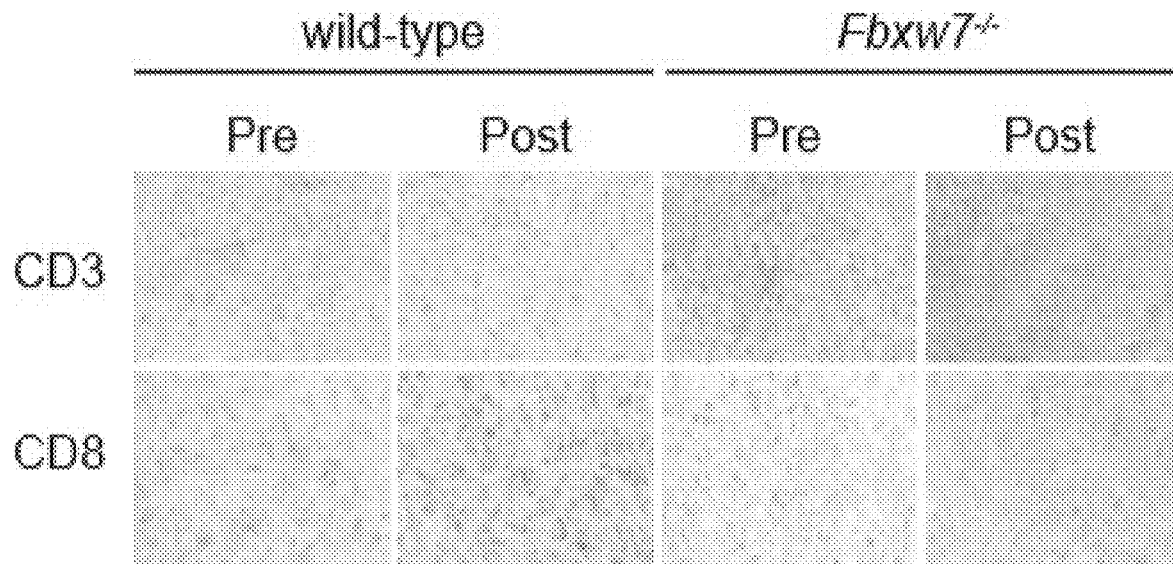
Figure 5G:
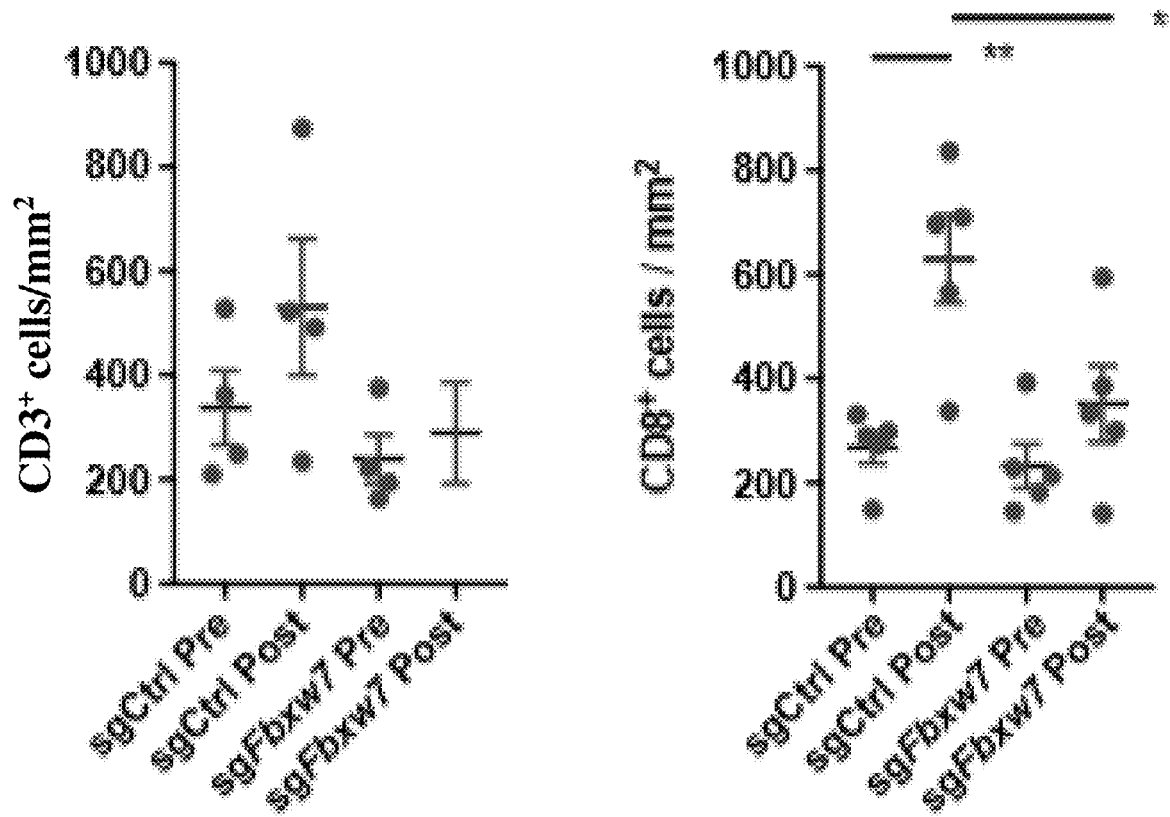

Example 8: Loss of Fbxw7 is Associated with Altered Immune Microenvironment, and Fbxw7 is Required and Sufficient for Interferon Gamma Signaling To identify the mechanism by which Fbxw7 deletion or loss of function impairs antitumor immunity, the Nanostring nCounter System (Danaher et al. (2017) *J Immunother Cancer* 5:18) was used to measure the intratumoral abundance of immune cell populations. Fbxw7-deficient and control tumors were harvested from C57BL/6 before and after treatment with anti-PD-1, and compared the expression of genes expressed by immune cell types. T-cells and CD8+ T-cells gene signatures were significantly decreased in Fbxw7-deficient tumors compared to control tumors, both before and after anti-PD-1 treatment (FIG. 5C and FIG. 5D). Loss of Fbxw7 significantly decreased PD-1 blockade-induced Cd3e, Cd3g, Cd8a and Cd8b1 T-cell receptor transcripts, as well as the cytotoxicity marker GzmK (FIG. 5E). Characterization of tumor infiltrating lymphocytes by immunohistochemistry confirmed that the loss of Fbxw7 abrogated PD-1-induced CD3+ and CD8+ T cell infiltration (FIG. 5F and FIG. 5G). These data are consistent with the association of intra-tumoral CD8+ T cell infiltration with response to PD-1 blockade (Tumeh et al. (2014) *Nature* 515:568-571; Daud et al. (2016) *J Clin Invest* 126:3447-3452; Gros et al. (2014) *J Clin Invest* 124:2246-2259; Tang et al. (2016) *Cancer Cell* 29:285-296).

Figure 5H:
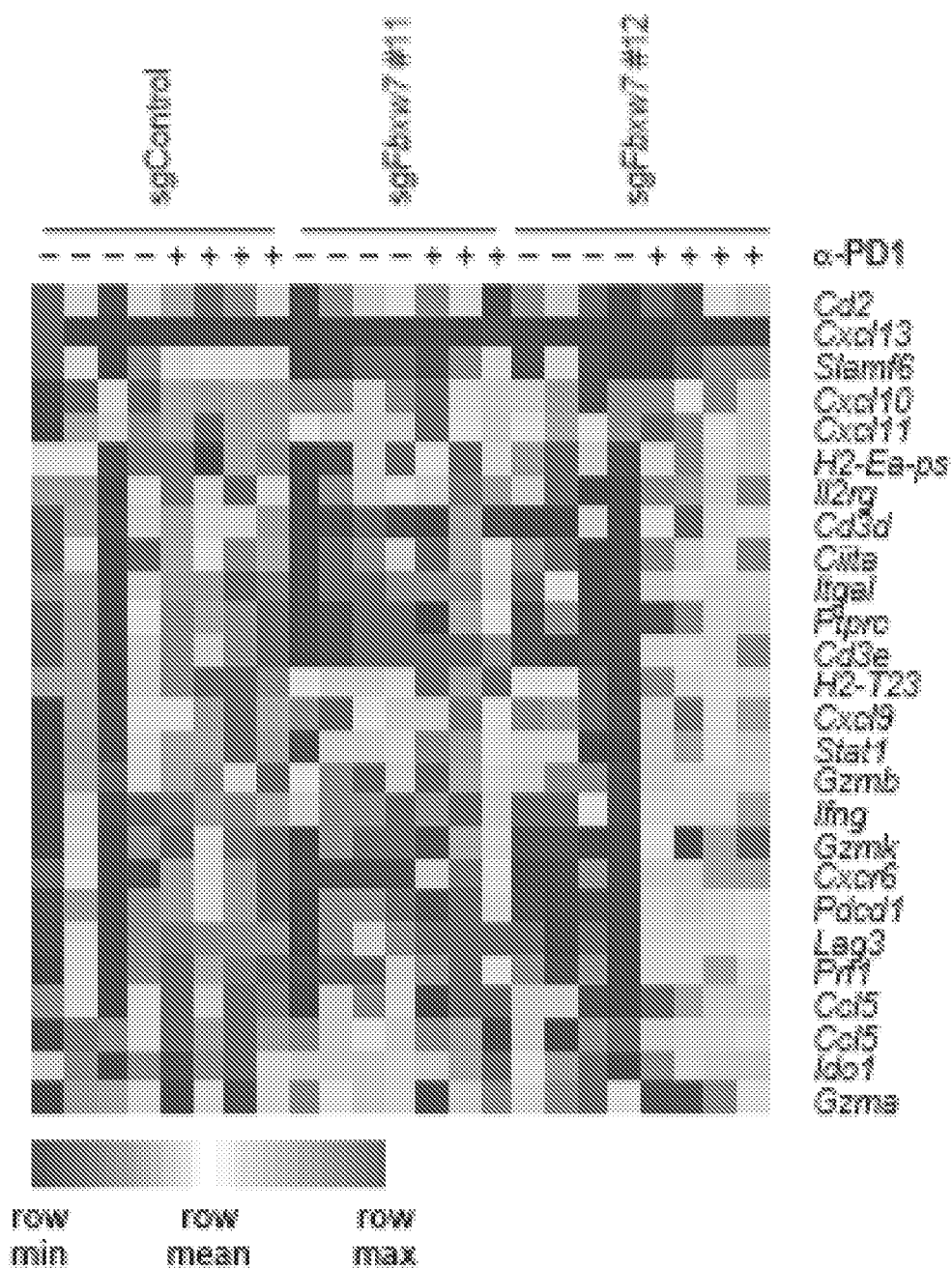

Recent studies suggest that interferon gamma (IFNγ) signaling enhances CD8+ T-cell infiltration of tumors (Lanitis et al. (2017) *Ann Oncol* 28:xii18-xii32) and predicts response to PD-1 blockade in patients (Ayers et al. (2017) *J Clin Invest* 127:2930-2940). It was therefore evaluated herein if diminished CD8+ T-cell infiltration in Fbxw7-deficient tumors was associated with an altered intratumoral IFNg gene expression signature. It was found that the expression of IFNγ-responsive genes was decreased in Fbxw7-deficient tumors compared to controls, both before and after anti-PD-1 treatment (FIG. 5H). Taken together, these results indicate that the loss of Fbxw7 alters the tumor immune microenvironment by decreasing lymphocyte infiltration and is associated with diminished IFNγ signaling.

Figure 6E:
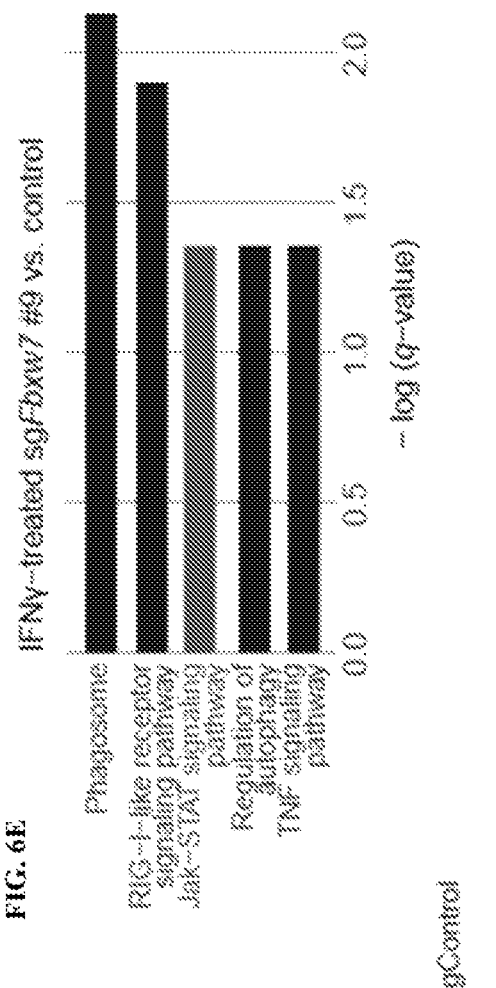
Figure 6D:
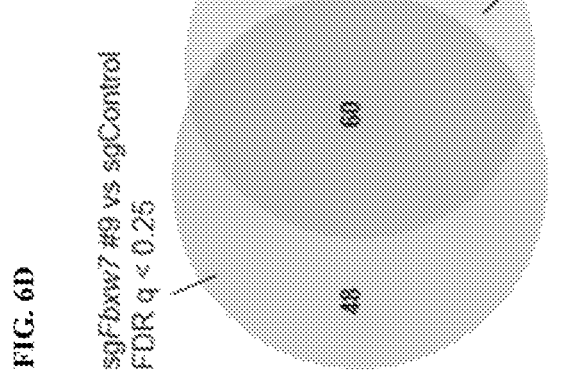
Figure 6F:
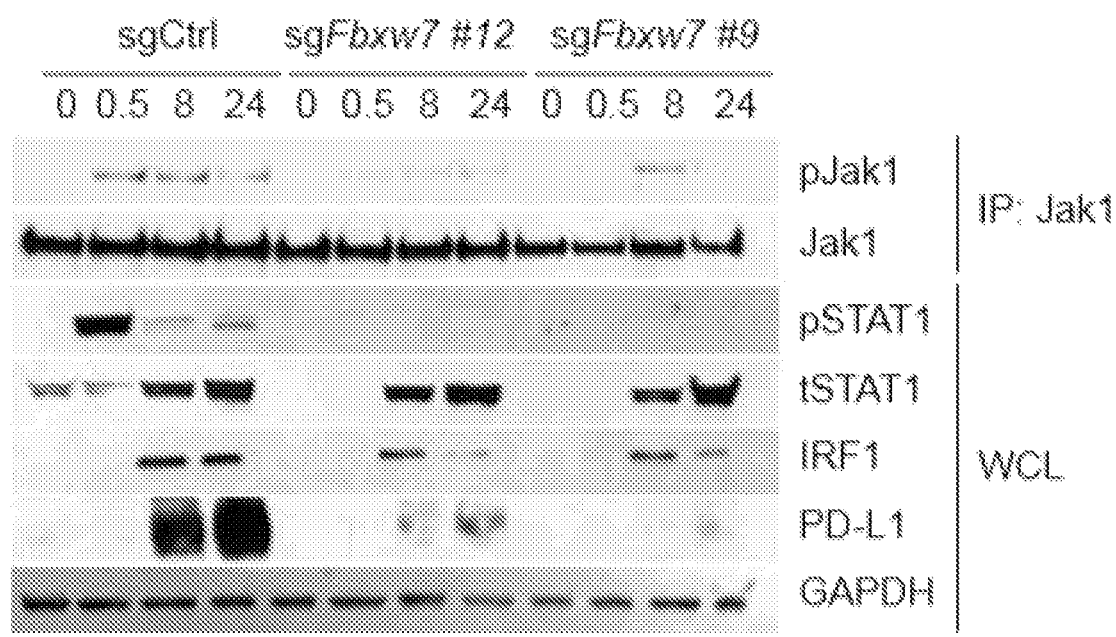
Figure 6H:
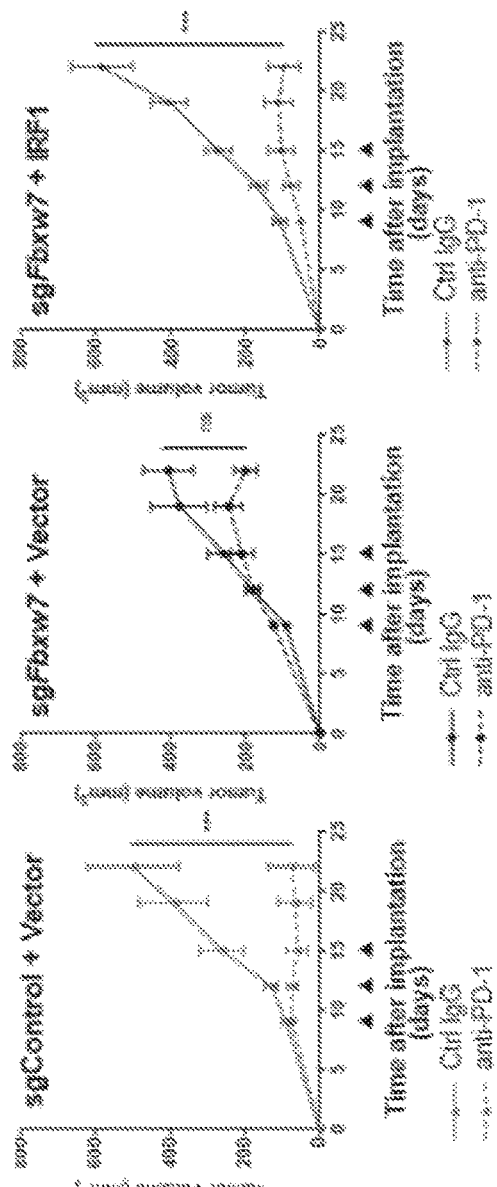
Figure 6G:
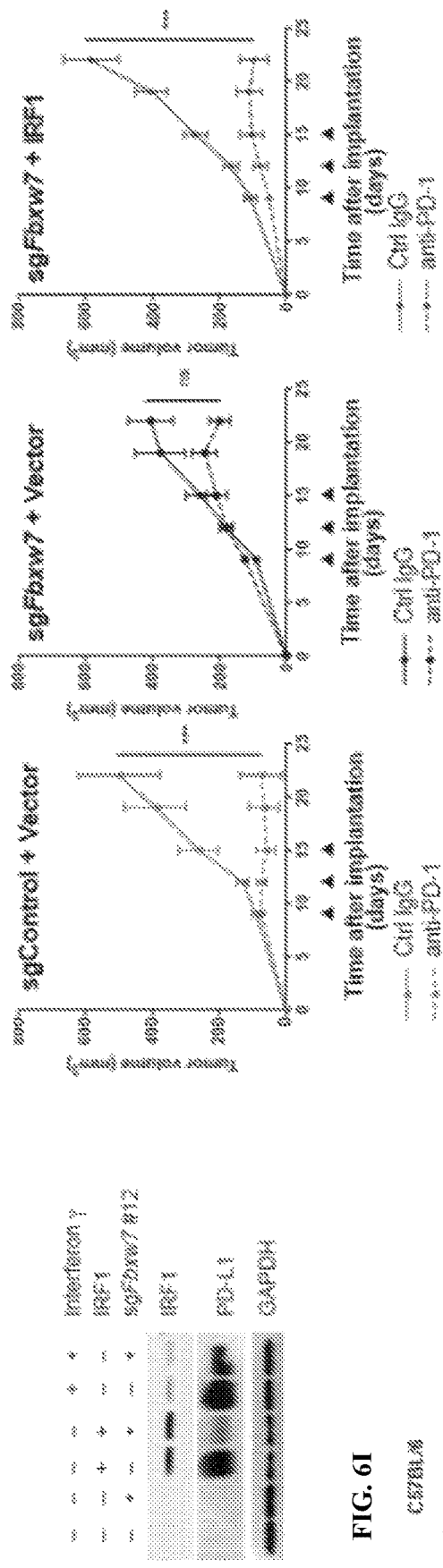
Figure 6I:
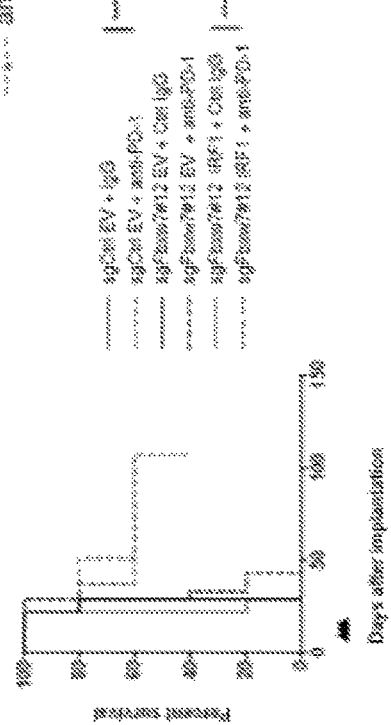
Figure 6J:
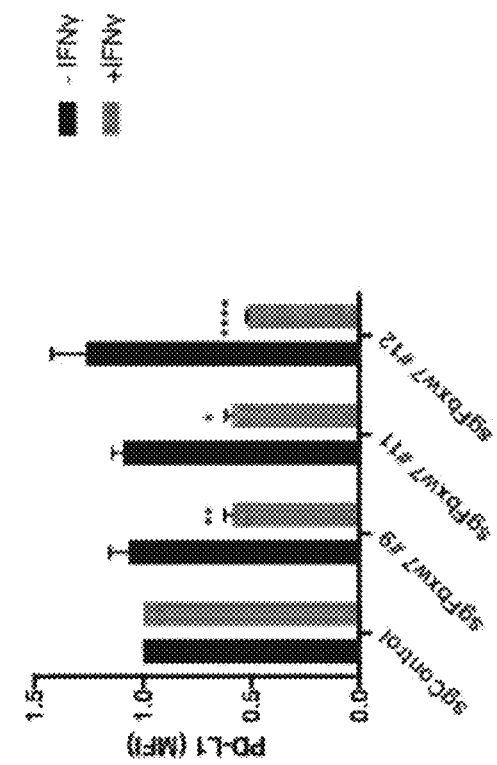
Figure 6K:
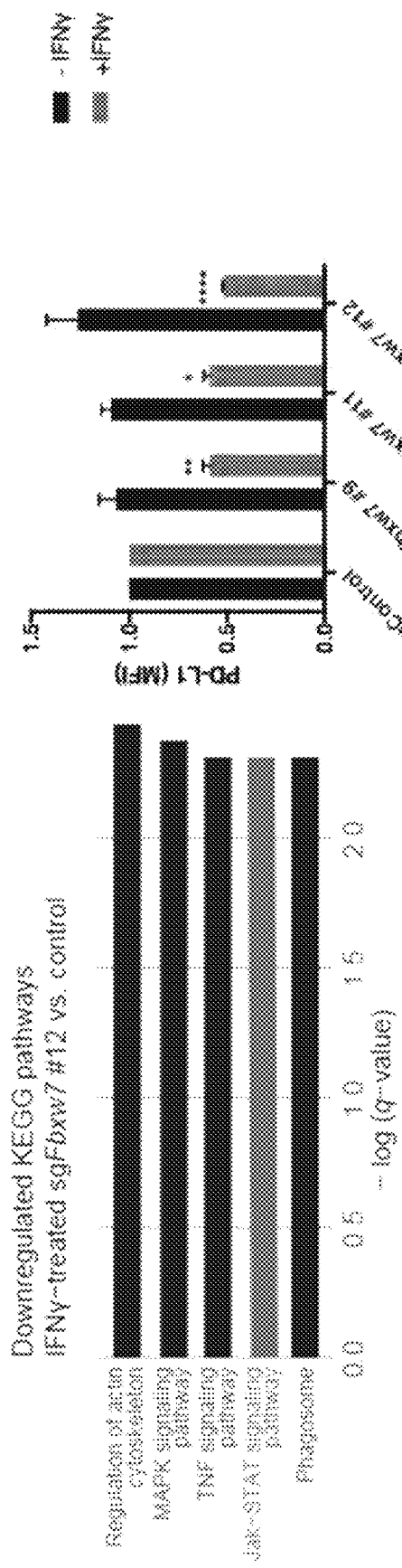

Example 9: A Mechanistic Role of Fbxw7 in Sensitizing Tumor Cells to Immunotherapy Next, it was evaluated herein if the immune effects observed were related to tumor intrinsic or extrinsic effects. Global gene expression of Fbxw7-deficient and control cells treated with IFNg treatment was compared using RNA-Seq. Gene set enrichment analysis (Subramanian et al. (2005) *Proc Natl Acad Sci USA* 102:15545-15550) was used to identify pathways enriched or depleted in Fbxw7-deficient cells. Two independent sgRNAs targeting Fbxw7 affected gene expression similarly (FIG. 6D). In both cases, diminished JAK-STAT signaling was observed in Fbxw7-deficient cells (FIG. 6E and FIG. 6J) among the most significantly altered changes. Since alterations of the JAK/STAT signaling pathway have been associated with resistance to anti-PD-1 (Cibulskis et al. (2013) *Nat Biotechnol* 31:213-219), these results provide an important molecular explanation of the resistance of Fbxw7-deficient tumors to anti-PD1 inhibitors. Therefore, the role of Fbxw7 in tumor cell-intrinsic responses to IFNγ was further examined by evaluating the expression and activation of individual components of the Jak-STAT signaling pathway. Inactivation of Fbxw7 suppressed IFNγ-induced Jak1 phosphorylation, as well as IFNγ-induced STAT1 phosphorylation (FIG. 6F), whereas the expression of total Jak1 and STAT1 were unchanged. Fbxw7 deletion or loss of function also decreased the expression of PD-L1, MHC class I and IRF1 (targets of JAK/STAT (Garcia-Diaz et al. (2017) *Cell Rep* 19:1189-1201)) at later time points (FIG. 6K).

Figure 6L:
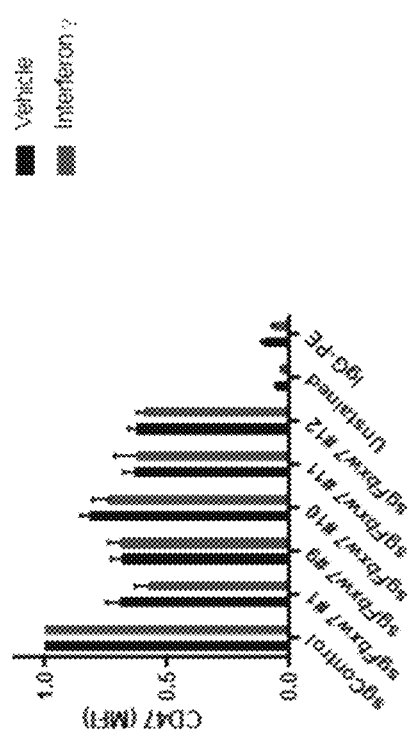
Figure 6M:
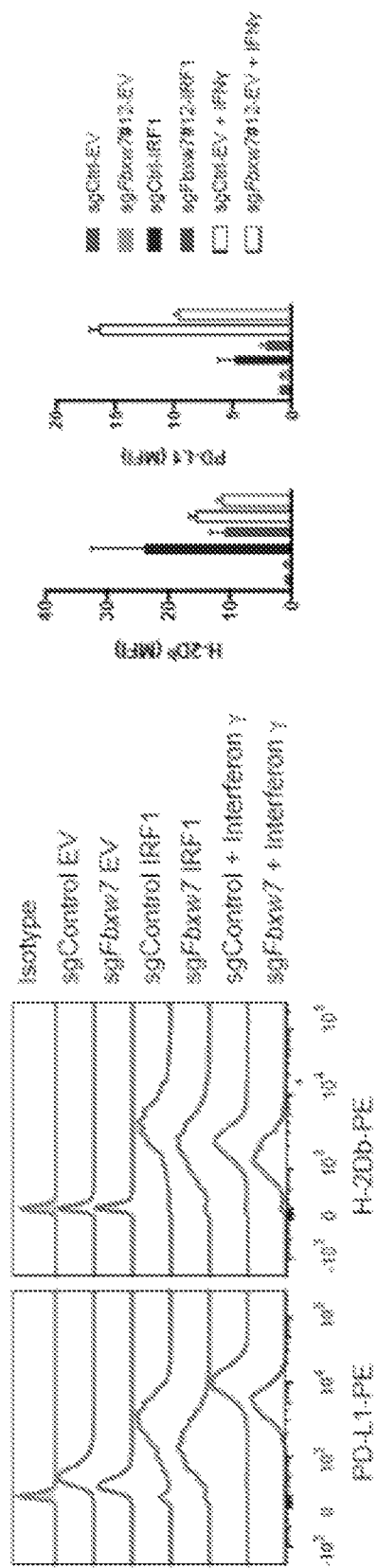
Figure 6O:
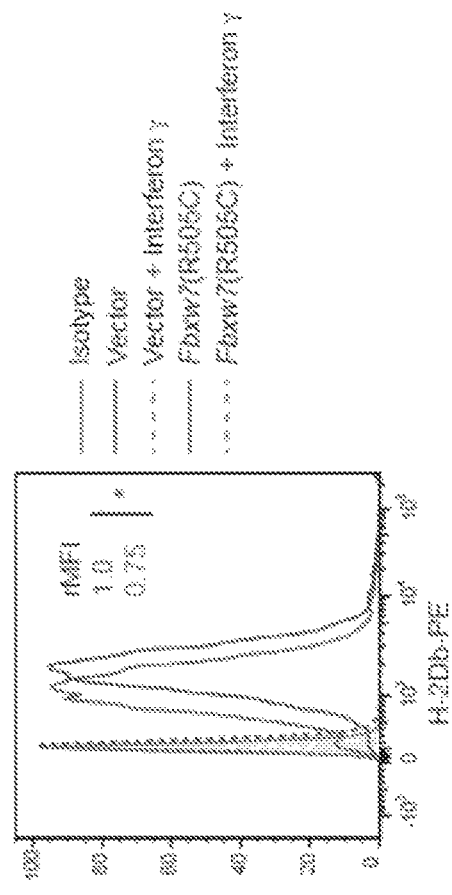
Figure 6N:
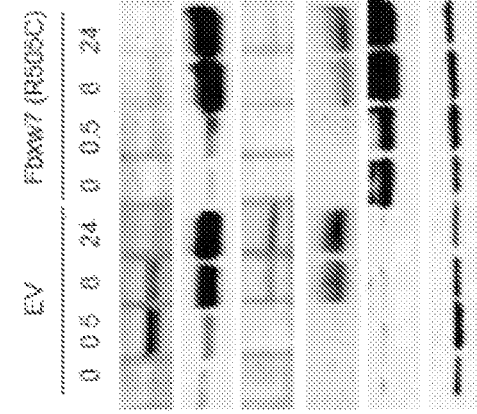

Antigen presentation is triggered by activation of the Jak-STAT pathway in response to IFNγ, and to a lesser extent by IFNα and IFNβ (Parker et al. (2016) *Nat Rev Cancer* 16:131-144). It was observed herein that the loss of Fbxw7 significantly decreased IFNα- and IFNβ-induced MHC-I surface expression (FIG. 6A). However, Fbxw7 depletion had no impact on CD47 (FIG. 6L), whose expression can be regulated by c-Myc in some cancers (Casey et al. (2016) *Science* 352:227-231). To determine if Jak-STAT signaling was sufficient to sensitize Fbxw7-deficient tumors to PD-1 blockade, the interferon regulatory factor 1 (IRF1) was expressed in Fbxw7-deficient and control cells. IRF1 expression was sufficient to increase the levels of Jak/STAT signaling (FIG. 6G), including the surface expression of levels of PD-L1 and MHC-I expression (FIG. 6M). Whereas Fbxw7-deficient tumors were resistant to PD-1 blockade, Fbxw7-deficient tumors overexpressing IRF1 responded to this treatment, similar to control tumors (FIG. 6H). IRF1 expression also led to the prolonged survival of Fbxw7-deficient tumor bearing mice treated with anti-PD-1 (FIG. 6I). It was confirmed herein that Fbxw7 mutations, rather than its genetic deletion, also impacted JAK/STAT signaling (FIG. 6N and FIG. 6O). These data demonstrate that Fbxw7 deficiency causes resistance to anti-PD-1 via the alteration of tumor-intrinsic IFN signaling, establishing Fbxw7 as a regulator of the Jak-STAT signaling pathway.

Figure 7A:
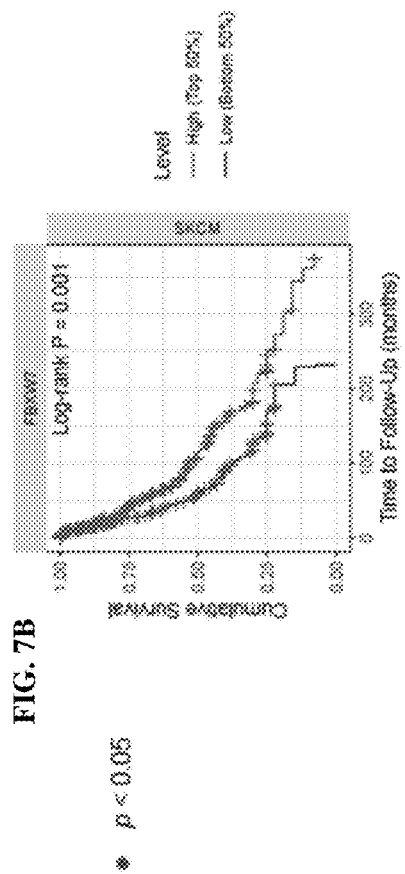
FIG. 7A-FIG. 7H show Fbxw7 mutations are associated with diminished interferon signaling and resistance to immunotherapy.
Figure 7B:
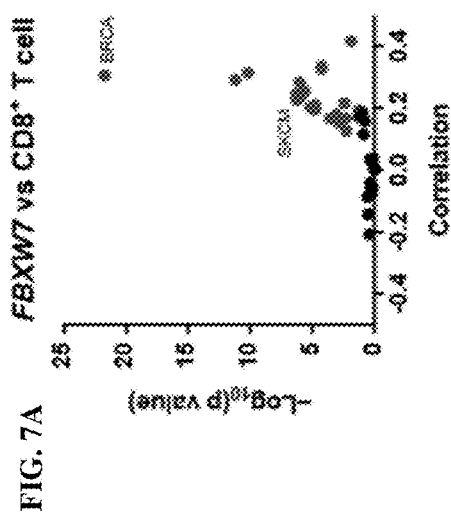
Figure 7C:
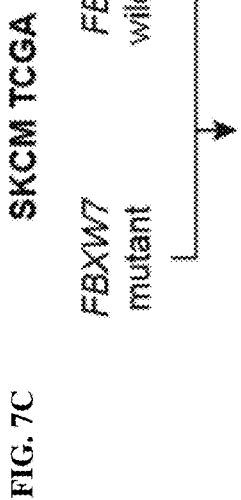
Figure 7D:
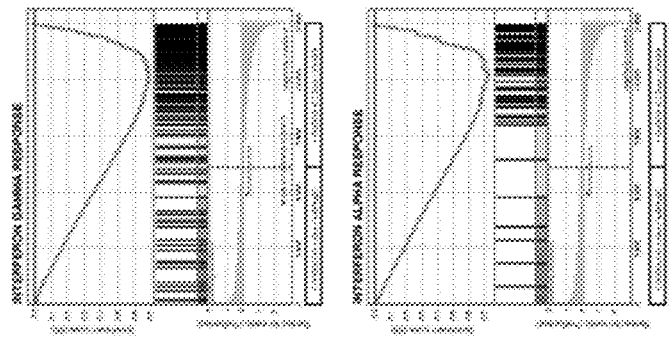
Figure 7E:
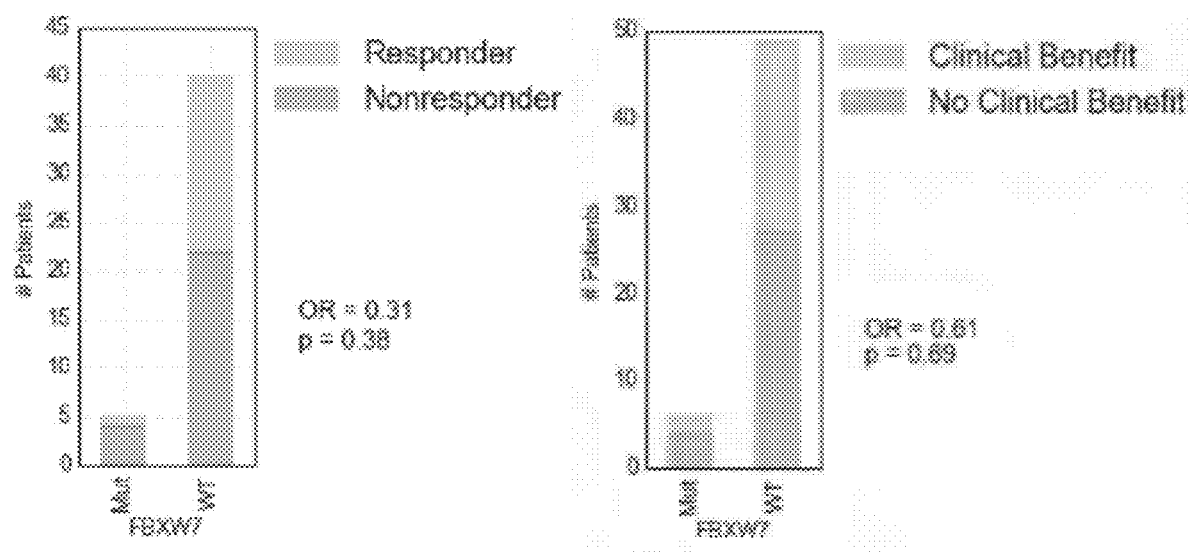
Figure 7F:
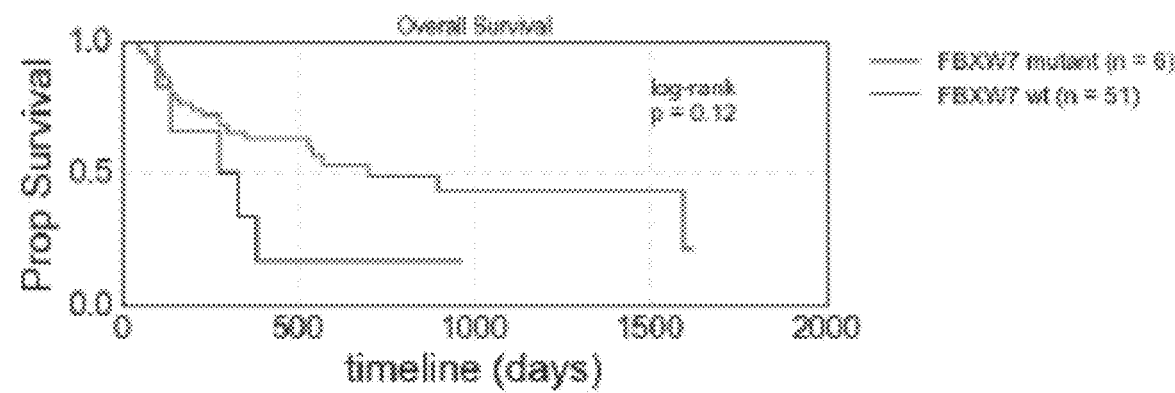
Figures 7G, 7H:
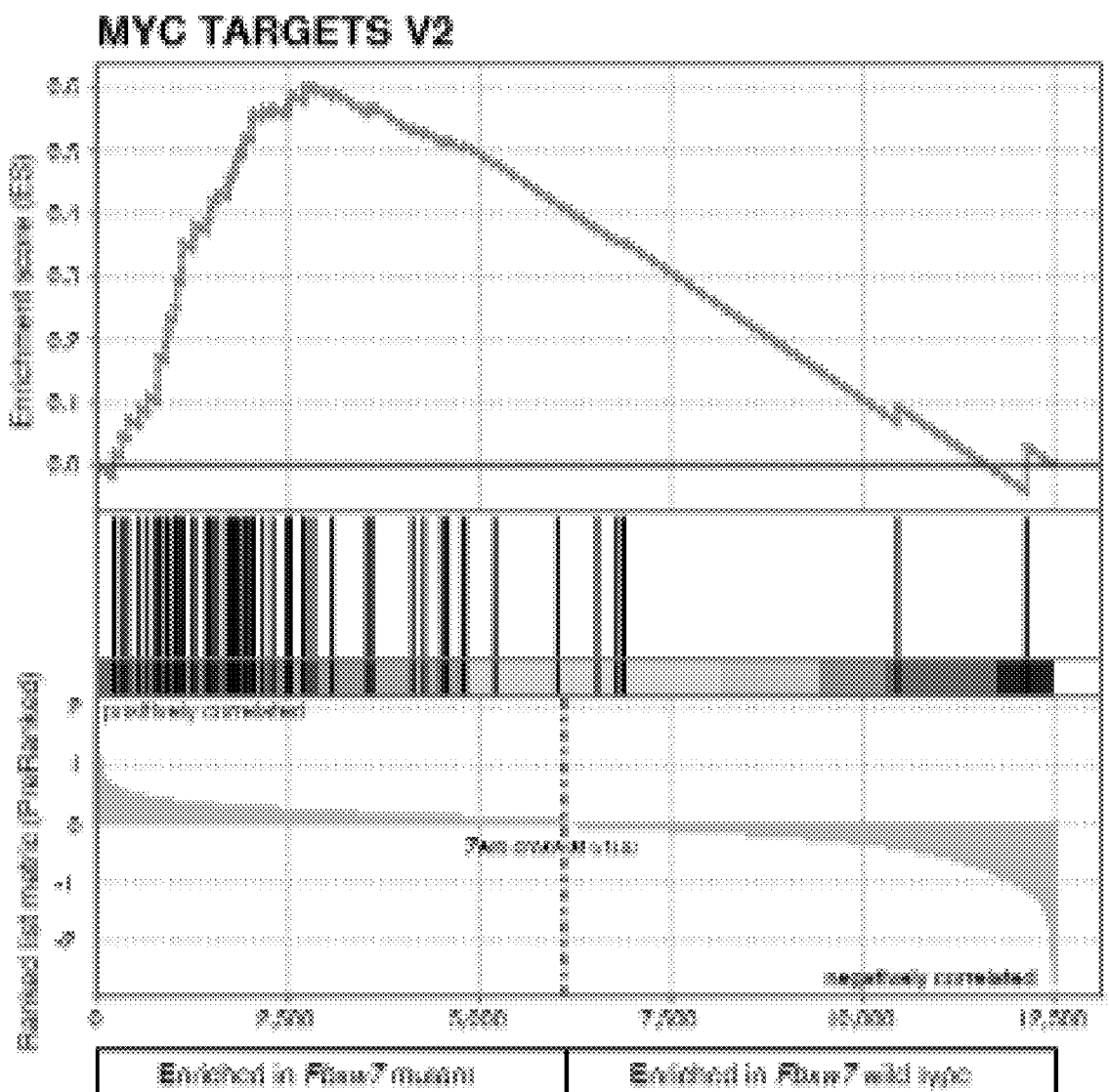

The Cancer Genome Atlas (TCGA) data sets were used to determine the relevance of above findings to human cancers. It was discovered herein that expression of FBXW7 correlated with CD8+ T-cell infiltration in many human cancer types, including melanoma (FIG. 7A). FBXW7 expression was also associated with a significant survival benefit (FIG. 7B). Next, gene set enrichment analysis was used to identify significantly dysregulated gene sets in mutant FBXW7 tumors compared to wild-type FBXW7 melanomas. Mutations in FBXW7 correlated with increased Myc signaling (FIG. 7G and FIG. 7H) and diminished IFN signaling (FIG. 7C and FIG. 7D). Finally, to evaluate the role of Fbxw7 in response to immunotherapy, a cohort of melanoma patients (n=62) treated at Dana-Farber Cancer Institute and Vanderbilt University were examined. It was found that a non-statistically significant trend towards poorer clinical responses (FIG. 7E) and decreased overall survival (FIG. 7F) to immunotherapy in patients with FBXW7 mutant tumors. These clinical data are consistent with the above preclinical findings and confirm a role for FBXW7 in anti-tumor immunity in human melanoma.

In summary, above data demonstrate that loss of Fbxw7 decreases tumor cell-intrinsic interferon signaling, diminishes CD8+ T-cell infiltration, and is sufficient to cause resistance to PD-1 blockade. Despite recent reports describing a role of the Fbxw7 target c-Myc in immune evasion through CD47(Casey et al. (2016) *Science* 352:227-231) and NK cells (Kortlever et al. (2017) *Cell* 171:1301-1315), the data presented herein indicate that Fbxw7 deletion did not significantly affect CD47 or NK cell abundance. In contrast, it was discovered herein that loss of Fbxw7 leads to dampened RIG-I signaling (FIG. 5E), consistent with recent observations demonstrating a role of FBXW7 for RIG-I stabilization during antiviral responses (Song et al. (2017) *Nat Commun* 8:14654). RIG-I and related viral sensing pathways are increasingly appreciated in regulating anti-tumor immune responses (Sheng et al. (2018) *Cell* 174:549-563). Another potentially relevant effector pathway downstream of Fbxw7, Notch, has also been associated with decreased immune cytolytic activity in tumors (Balli et al. (2017) *Clin Cancer Res* 23:3129-3138;

Li et al. (2018) *Immunity* 49:178-193). Interestingly, Fbxw7 regulates long non-coding RNAs (lncRNAs) associated with interferon responses (Snijders & Mao (2016) *Insights Cancer Res* 1:1-5) as well as circular RNAs, both previously linked to tumor immunity and immunotherapy (Xu et al. (2018) *Front Immunol* 9:9). Thus, multiple mechanisms may contribute to the regulation of the JAK/STAT pathway by FBXW7.

While this study primarily focused on FBXW7 mutations in melanoma, the observations presented herein will also extend to other cancer types, since Fbxw7 deletion reduced the response of a colorectal cancer cell line to anti-PD-1. It is noteworthy that mutations of FBXW7 are found in approximately 5-20% of cancers, whereas non-mutational mechanisms of FBXW7 inactivation are present in up to 40% of melanoma and nonmelanoma patients (Aydin et al. (2014) *J Natl Cancer Inst* 106:dju107). The prevalence of FBXW7 inactivation in cancer and the data presented herein indicate that FBXW7 is a powerful molecular tool for predicting immunotherapy responsiveness in melanoma and other cancers.

This study also has important implications for the development of precision approaches to immunotherapies. While large observational studies are typically required to nominate molecular markers of immunotherapy response, functional characterization of a single exceptional responder can simultaneously lead to biomarkers of response, and enable the development of rational approaches to overcome resistance in genomically defined populations. Such an approach is especially informative in patients whose tumors harbor a significant number of different mutations, such as the one described herein. Thus, integrating genomic biomarkers of response with other biomarkers such as PD-L1 staining or tumor mutational burden is believed to lead to rationally-based combination therapies to overcome resistance to immunotherapy and to improve patient outcome.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

Equivalents

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of identifying the likelihood of treating a colorectal or melanoma cancer in a subject likely to be resistant to an immune checkpoint therapy, wherein the immune checkpoint therapy comprises anti-PD-1 antibodies, anti-PD-L1 antibodies, and/or anti-PD-L2 antibodies, the method comprising:
   i) selecting the subject, the subject having been identified according to:
   a) obtaining or providing a sample comprising cancer cells from a subject having the cancer;
   b) measuring the presence, copy number, or amount of Fbxw7 in the subject sample; and
   c) comparing the presence, copy number, or amount of Fbxw7 in a control,
   wherein the presence of or a significantly increased amount of wild-type Fbxw7 in the subject sample and/or the absence of or a decreased amount of Fbxw7 having a loss of function mutation in the subject sample relative to the control identifies the cancer as being likely to be responsive to the immune checkpoint therapy; and
   ii) administering the immune checkpoint therapy to the selected subject.

2. The method of claim 1, wherein the sample comprises cells, serum, peritumoral tissue, and/or intratumoral tissue obtained from the subject;
   optionally the method further comprising determining responsiveness to the therapy and/or agent by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria;
   optionally wherein the cancer has an Fbxw7 loss of function mutation;
   optionally wherein the subject is an animal model of the cancer;
   optionally wherein the animal model is a mouse model;
   optionally wherein the subject is a mammal; and/or
   optionally wherein the mammal is a mouse or a human.

3. The method of claim 1, wherein the anti-PD-1 antibodies, anti-PD-L1 antibodies, and/or anti-PD-L2 antibodies are selected from the group consisting of pembrolizumab, nivolumab, pidilizumab, AMP-224, AMP-514, and PDR001.

4. The method of claim 1, wherein the anti-PD-1 antibodies, anti-PD-L1 antibodies, and/or anti-PD-L2 antibodies are selected from the group consisting of atezolizumab, avelumab, durvalumab, and BMS-936559.

5. The method of claim 1, wherein the control is determined from a cancerous or non-cancerous sample from the subject or a member of the same species to which the subject belongs or wherein the control is determined from a cancerous or non-cancerous sample from a member of the same species to which the subject belongs;
   optionally wherein the control does not comprise cells;
   optionally wherein the control is a sample that comprises cells or does not comprise cells; and/or
   optionally wherein the control sample comprises cancer cells that are resistant to the immune checkpoint therapy or are not resistant to the immune checkpoint therapy.

6. The method of claim 1, further comprising comparing the activity and/or phosphorylation of the JAK/STAT signaling pathway in the subject sample and control sample, optionally wherein the phosphorylation of the JAK/STAT signaling pathway is determined using phosphorylation of JAK1 and/or STAT1.

* * * * *